United States Patent [19]
Frechette et al.

[11] Patent Number: 5,696,117
[45] Date of Patent: Dec. 9, 1997

[54] BENZOXAZINE ANTIMICROBIAL AGENTS

[75] Inventors: Roger Frechette; Michele Ann Weidner-Wells, both of Somerville, N.J.

[73] Assignee: Ortho Pharmaceutical Corporation, Raritan, N.J.

[21] Appl. No.: 553,188

[22] Filed: Nov. 7, 1995

[51] Int. Cl.$^6$ .............. A61K 31/535; C07D 265/36; C07D 413/10; C07D 413/12

[52] U.S. Cl. .............. 514/230.5; 544/105; 549/313

[58] Field of Search ............. 544/105; 514/230.5

[56] References Cited

FOREIGN PATENT DOCUMENTS 43 04 806  8/1994  European Pat. Off. .

OTHER PUBLICATIONS

Kumonaka et al Chemical Abstract 121:280655j (1994).
Masuoka et al, Chem. Pharm. Bull 34(1), pp. 130–139 (1986).
McOmie, "Protecting Groups in organic Chemistry", Plenum Press, (1973), pp. 95, & 119–120.
Greene, "Protective Groups in Organic Synthesis", John Wiley & Sons, (1981), pp. 10–12.
M. J. Mahan, J. M. Slauch and J. J. Mekalanos, Science, 259, 686–688 (1993).
S. Roychoudhury et al., Proc. Nat. Acad. Sci., 90, 965–969 (1993) Inhibitors of Two–Component Signal Transduction Systems: Inhibition of Alginate Gene Activation in Pseudomonas Aeruginosa.

International Search Report—International Application No. PCT/US96/16669—International Filing Date Oct. 17, 1996.
Chemical Abstracts, vol. 82, No. 23, Jun. 9, 1975 No. 150506(b), p. 141, Takami.
Chemical Abstracts, vol. 105, No. 21, 24 Nov. 1986, No. 191020(a) p. 723, Mourin.
Chemical Abstracts, vol. 107, No. 17, 29 Oct., 1987, No. 154344(e) p. 704, Shridhar.
Chemical Abstracts, vol. 108, No. 25, 20 Jun. 1988, No. 221648(t) p. 569, Sastry.
Chemical Abstracts, vol. 114, No. 7, 17 Feb., 1991, No. 62024(s) p. 683, Jayamma.

*Primary Examiner*—Philip I. Datlow
*Attorney, Agent, or Firm*—Kenneth J. Dow

[57] ABSTRACT

The invention relates to benzoxazine and pyrido-oxazine antibacterial compounds of the general formula:

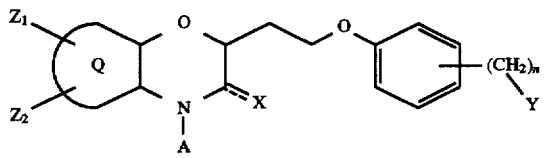

wherein the moiety Q is a fused phenyl or fused pyridyl moiety as herein described, pharmaceutical compositions containing the compounds, methods for their production and their use in treating bacterial infections.

26 Claims, No Drawings

BENZOXAZINE ANTIMICROBIAL AGENTS

FIELD OF THE INVENTION

The invention relates to benzoxazine and pyrido-oxazine antibacterial compounds, pharmaceutical compositions containing the compounds, and methods for their production and use. These compounds are effective in inhibiting the action of a bacterial histidine protein kinase and are thus useful as anti-infective agents against a variety of bacterial organisms, including organisms which are resistant to other known antibiotics.

BACKGROUND OF THE INVENTION

Prokaryotes regulate the transcription of many of their genes in response to changes in the organisms' environment (J. B. Stock, A. M. Stock, and J. M. Mottonen, Nature, 344, 395–400 (1990)). Such regulation is essential if the organism is to adapt itself to survival in a changing environment, and pathogenic bacteria rely on such regulatory systems to enable them to survive within their host's body (J. F. Miller, J. J. Mekalanos, S. Falkow, Science, 243, 1059 (1989)). Chemical compounds that interfere with the regulatory mechanisms would be expected to be useful anti-infective drugs, as they would prevent bacteria from making necessary adaptive changes in their patterns of gene expression.

Virulence, chemotaxis, toxin production, sporulation, and reproduction are examples of the bacterial processes that are under regulatory control, and which could be inhibited by such compounds. The inhibition of one or more of these processes is expected to lead to reduced virulence, a slowing or halting of bacterial growth and reproduction, and even to bacterial cell death if vital functions are interrupted.

For example, it has been shown that Salmonella species express certain proteins, under regulatory control and in response to the presence of intestinal epithelial cells, which enable them to adhere to and invade these cells. Bacteria unable to synthesize these proteins are avirulent: they cannot cause infection in mice (B. B. Finlay, F. Heffron, S. Falkow, Science, 243, 940–943 (1989)). A similar effect would be expected if the genes coding for these proteins were intact, but remained unexpressed.

To accomplish adaptive responses to the environment, bacteria rely on phosphorelay mechanisms, referred to in the art as "two-component switches." These switches have the net effect of transmitting information from the environment to the cell nucleus, where the information is responded to by the switching on or off of transcription of relevant genes. The first step of this phosphorelay scheme relies on numerous histidine protein kinase (HPK) enzymes. Most of these HPK enzymes are sensor molecules, and respond to stimulation by specific environmental signals by transferring phosphate from ATP to a histidine residue of the HPK protein. Some HPK enzymes are stimulated by the presence of acceptor proteins (described below), the concentration of which are modulated by environmental signals. In either case, this auto-phosphorylation is followed by transfer of the phosphate to an aspartyl residue of one or more acceptor proteins (the second components of the two-component switch), which are either regulators of gene expression (by binding to control regions on DNA, or to the RNA polymerase complex) or are themselves kinases for other acceptor molecules. These secondary acceptors may again be regulatory proteins, or kinases toward yet another protein. This cascade of phosphate from protein to protein eventually results in the phosphorylation of one or more regulatory proteins, which then control gene expression.

Mammalian cells do not, or at least are not presently known to, utilize HPK-driven phosphorelay systems for gene regulation. Thus, compounds which selectively inhibit either the autophosphorylation of the HPK protein, or the phosphotransfer step(s), or both, would not be expected to have undesirable effects on the host organism, and are promising candidates for antiinfective drugs. The emergence of drug-resistant pathogenic organisms that are resistant to one or more of the currently available drugs has created a need for novel antibiotics, that act by mechanisms unrelated to those of currently available agents, and inhibitors of HPK would fill this need. The presence of multiple HPK-driven systems (over fifty are currently known) in bacteria gives HPK inhibitors a potential advantage over current antibiotics, in that mutations of a single HPK enzyme are unlikely to confer drug resistance to an organism.

Recently, workers in this field reported a method for detecting bacterial "virulence" genes that are selectively expressed when bacteria infect a host (M. J. Mahan, J. M. Slauch, and J. J. Mekalanos, Science, 259, 686–688 (1993)). The potential use of this information in the design of new antibiotics was mentioned, but actual methods of reducing expression of these genes were not described. A preliminary report from another group of workers disclosed inhibitors of the two-component switch controlling alginate gene activation in Pseudomonas aeruginosa in an in vitro system (S. Roychoudhury et al., Proc. Nat. Acad. Sci., 90, 965–969 (1993)), but no anti-bacterial activity of the compounds was reported.

SUMMARY OF THE INVENTION

The invention comprises compounds of general structure 1 shown below:

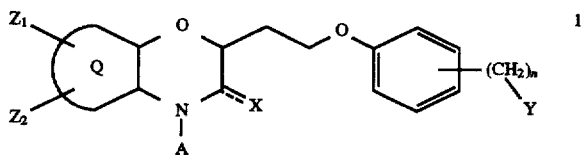

Wherein the moiety Q is a fused phenyl or fused pyridyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or a halogen;

X is hydrogen or oxygen;

A is $C_1$–$C_6$ alkyl, $C_1$–$C_6$ alkylaryl or $C_1$–$C_6$ alkylheterocyclyl wherein aryl is biphenyl, naphthyl or phenyl; and heterocyclyl is a 5 or 6 membered saturated or unsaturated heterocyclic group containing 1–4 nitrogen atoms, an oxygen or a sulfur atom;

wherein said aryl or heterocyclyl group is optionally substituted with ($C_1$–$C_6$) alkyl, benzyl, oxybenzyl, phenoxy, hydroxy, alkoxy, halogen, dihalogen, nitro, amino, carboxyl, carbo($C_1$–$C_4$)alkoxy or methylsulfonylamino;

n is an integer from 0–3;

Y is a moiety selected from:
(a) $NHR_1R_2$, $N+R_1R_2R_3$;

(b)

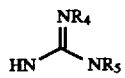

(c) $CO_2H$, CHO;
(d) $CH(R_6)CO_2H$, $CH(R_6)CO_2CH_3$, $CH=CHR_7$, $CH=C(CO_2H)_2$;
(e) a moiety of the formula:

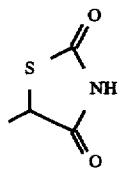

(f) 5-tetrazolyl;

wherein $R_1$, $R_2$ and $R_3$ are independently hydrogen, $C_1-C_6$ alkyl, or t-butoxycarbonyl;

$R_4$ and $R_5$ are independently t-butoxycarbonyl or hydrogen or $R_4$ and $R_5$ may be joined together to form an imidazoline, imidazolyl or pyrimidine ring;

$R_6$ is hydrogen, hydroxy or chloro;

$R_7$ is $CO_2H$ or $C(O)NH(CH_2)_pOH$ wherein p is an integer from 1-4;

and the pharmaceutically acceptable salts, esters and prodrug forms thereof.

Another aspect of the invention comprises a method of treating bacterial infections in mammals by administering to a mammal suffering from such infection a therapeutically effective amount of a compound selected from those of Formula 1 effective in inhibiting the action of a bacterial histidine protein kinase.

The compounds of the present invention inhibit the autophosphorylation of bacterial histidine kinases; they also inhibit the transfer of phosphate from phosphorylated histidine kinases to the aspartyl residues of the phosphate acceptor proteins involved in regulation of bacterial gene expression. The compounds of the present invention have been found to inhibit the growth of bacteria by the standard method, measurement of minimum inhibitory concentrations (MIC values). The compounds are useful as bacteriostatic and bactericidal agents, and as anti-infective agents in the treatment of infectious diseases. They may also have utility in increasing the sensitivity of bacteria to conventional antibiotics.

DETAILED DESCRIPTION

Relative to the above generic description, certain compounds of formula 1 are preferred.

Preferred embodiments are those compounds wherein Q is fused phenyl.

Preferred groups for A are $C_1-C_5$ alkyl, $CH_2$phenyl, $CH_2$thienyl, $CH_2$pyridyl, $CH_2$furyl, or ethyl piperidine.

Preferred groups for Y are:

(a) $NHR_1R_2$, $N+R_1R_2R_3$;

(b)

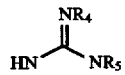

(c) $CO_2H$;
(d) $CH(R_6)CO_2H$,
(e) a moiety of the formula:

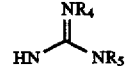

wherein $R_1$, $R_2$ and $R_3$ are independently hydrogen, $C_1-C_6$ alkyl or t-butoxycarbonyl;

$R_4$ and $R_5$ are independently t-butoxycarbonyl or hydrogen;

$R_6$ is hydrogen or hydroxy;

and the pharmaceutically acceptable salts, esters and prodrug forms thereof.

Most preferred are those compounds of formula 1 wherein: the moiety Q is a fused phenyl;

$Z_1$ is hydrogen, halogen, $C_1-C_6$ alkyl, $C_1-C_6$ alkoxy, phenyl, hydroxy, amino, nitro, sulfonylamino or trifluoromethyl;

$Z_2$ is hydrogen or, where $Z_1$ is a halogen, $Z_2$ is also a halogen;

X is oxygen;

A is $C_1-C_5$ alkyl, $CH_2$phenyl, $CH_2$thienyl, $CH_2$pyridyl, $CH_2$furyl, or ethyl piperidine; wherin said phenyl, thienyl, pyridyl, furyl or piperidine moiety is optionally substituted with ($C_1-C_6$)alkyl, benzyl, oxybenzyl phenoxy, hydroxy, alkoxy, halogen, dihalogen, nitro, amino, carboxyl or carbomethoxy;

n is an integer from 0-3;

Y is a moiety selected from:

(a) $NHR_1R_2$, $N^+R_1R_2R_3$;
(b)

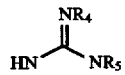

(c) $CO_2H$;
(d) $CH(R_6)CO_2H$,
(e) a moiety of the formula:

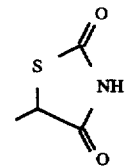

wherein $R_1$, $R_2$ and $R_3$ are independently hydrogen, $C_1-C_6$ alkyl or t-butoxycarbonyl;

$R_4$ and $R_5$ are independently t-butoxycarbonyl or hydrogen;

$R_6$ is hydrogen or hydroxy;
and the pharmaceutically acceptable salts, esters and prodrug forms thereof.

In another aspect of the present invention, certain novel intermediates useful in the preparation of the final compounds are contemplated. Thus the invention encompasses intermediates of the following formula:

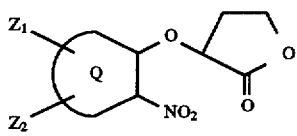

wherein the Q moiety is phenyl or pyridyl and $Z_1$ is hydrogen, halogen, $C_1$–$C_6$ alkyl, $C_1$–$C_6$ alkoxy, phenyl, hydroxy, amino, nitro, sulfonylamino or trifluoromethyl; and $Z_2$ is hydrogen or a halogen.

Also included are intermediates of the general formula:

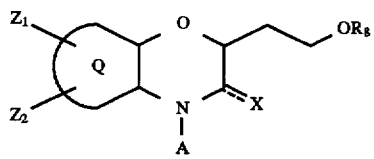

wherein the Q moiety is phenyl or pyridyl and $Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or a halogen, A is $C_1$–$C_6$ alkylaryl or $C_1$–$C_6$ alkylheterocyclyl, wherein aryl is biphenyl, naphthyl or phenyl; and heterocyclyl is a 5 or 6 membered saturated or unsaturated heterocyclic group containing 1–4 nitrogen atoms, an oxygen or a sulfur atom; wherein said aryl or heterocyclyl group is optionally substituted with ($C_1$–$C_6$) alkyl, benzyl, oxybenzyl, phenoxy, hydroxy, alkoxy, halogen, dihalogen, nitro, amino, carboxyl, carbo ($C_1$–$C_4$)alkoxy or methylsulfonylamino;

and $R_8$ is hydrogen or a hydroxy protecting group. A suitable hydroxy protecting group includes any conventional protecting groups for hydroxy moieties as routinely used by those skilled in the art such as those found in T. Greene, "Protecting Groups in Organic Synthesis", J. Wiley and Sons, 1981. These include silyl esters, aliphatic esters and aromatic esters such as trimethylsilyl, t-butyldimethylsilyl, acetyl, benzoyl and the like.

The compounds of the present invention are prepared in accordance with the methods described below and illustrated in the following Schemes. The first step in the synthesis involves a novel addition, cyclization reaction of the α-bromo-γ-butyrolactone shown in Scheme 1 with a suitably substituted 2-nitro or 2-aminophenol. The reaction may be carried out in two discrete steps, beginning with known, generally commercially available nitrophenols having most of the definitions for Z cited in the invention description. The solvent is usually DMF and a basic reagent such as $K_2CO_3$ is needed to drive the reaction to completion. The cyclization step occurs upon reduction of the nitro group with any of the reagent systems known to be useful for this reduction, including palladium catalyzed hydrogenation, nickel and sodium borohydride, and iron-acetic acid. Alternatively, especially in cases where Z is a nitro group or Q is a fused pyridyl, both the addition and cyclization steps may be carried out in a single procedure using a base, such as $K_2CO_3$ or NaH, in DMF with or without heating.

Having generated the benzoxazine heterocyclic ring system in this manner, the intermediate alcohol 2 may be prepared by a three step sequence of reactions. Protection of the alcohol group, with a known protecting group such as a t-butyldimethylsilyl derivative or equivalents thereof, is followed by reaction at the 4-position involving nucleophilic displacement of an alkyl or aryl halide under basic conditions: for example, NaH in DMF is highly effective. Alternatively, derivatization of the 4-position nitrogen may be carried out by Mitsunobu reaction of a suitably substituted alcohol. Deprotection of the alcohol with any of the usual fluoride anion reagents or under acidic conditions provides compound 2.

As is apparent, Scheme 1 depicts the preparation of benzoxazine compounds wherein the "Q" moiety is a fused phenyl. The pyrido-oxazine compounds where the "Q" moiety is a fused pyridyl may be prepared in accordance with the same procedure by substituting a suitably substituted 2-nitro- or 2-amino pyridoxyl moiety for the phenol starting material depicted in Scheme 1. In the remaining synthesis depicted in Schemes 2–10 hereinafter, the pyrido-oxazine compounds may likewise be conveniently substituted for the benzoxazine compounds illustrated in the Schemes.

Scheme 1

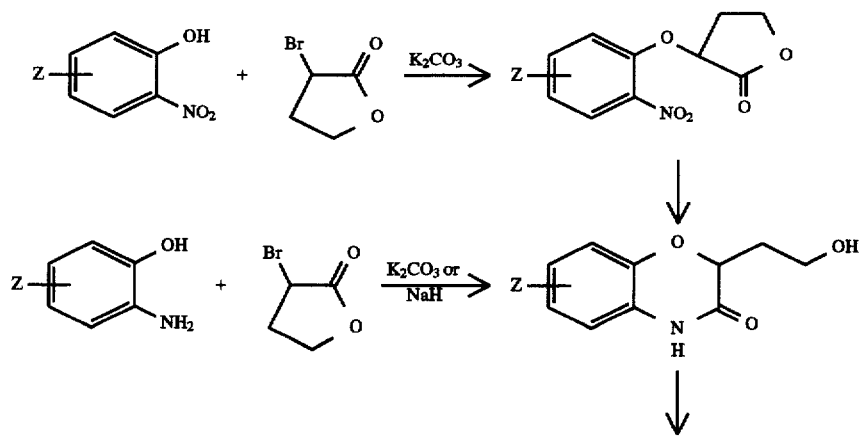

-continued
Scheme 1

P = t-butyldimethylsilyl

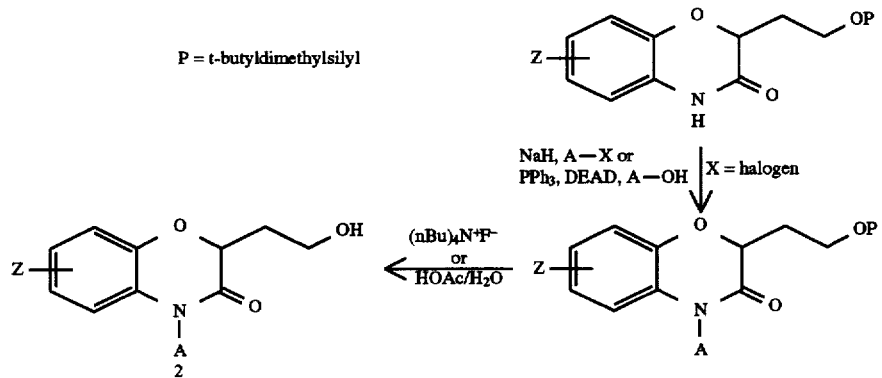

The key step of the synthesis is a coupling reaction of the alcohol 2 with a substituted phenol, by Mitsunobu reaction, oxazolidine. The chemical processes presented in the Scheme are in general applicable to all definitions of Y.

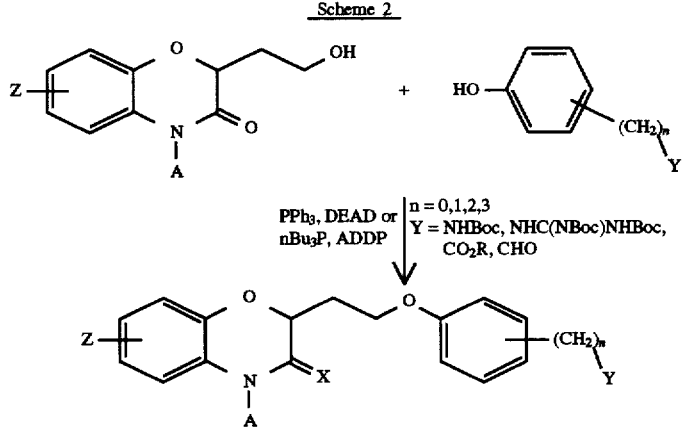

Scheme 2 as shown in Scheme 2. The Mitsunobu reaction may be one of several variants known in the art; the selection of the appropriate phosphine, azodicarbonyl reagent, and solvent will be at the discretion of the practitioner, based on published precedents and on empirical results with the particular combination of substrates to be coupled. Guidance can be found in the review article by D. L. Hughes, in *Organic Reactions*, 42, 335–656 (1992), and in the detailed examples below. In most cases triphenylphosphine ($Ph_3P$) and diethylazodicarboxylate (DEAD), or alternatively tributylphosphine ($Bu_3P$) and (azodicarbonyl)dipiperidine (ADDP), will suffice.

At the time of the Mitsunobu reaction, the group Y will in most cases have to be in a protected form of a more potent compound, or else (for instance when the desired compound is a heterocycle) Y will be a precursor functional group convertible into the desired heterocycle. Once the linkage of the two portions has been established, the group Y is converted, if necessary, into the preferred functional group, as shown in the Schemes below. Suitable protecting groups for guanidines and amines include, but are not limited to, trifluoroacetyl, t-butoxycarbonyl (Boc), and benzyloxycarbonyl. Suitable protecting groups for carboxylic acids include, but are not limited to, lower alkyl esters or benzyl esters; suitable precursor groups include olefin, nitrile, or To obtain those compounds where X=hydrogen, the Mitsunobu coupling reaction is carried out on a reduced derivative of compound 2. The reduction is most easily carried out on the protected precursor of 2 as illustrated in Scheme 3 by using a commercially available borane reagent such as borane-THF complex. After reduction, deprotection as shown in Scheme 1 affords the alcohol which undergoes the Mitsunobu reaction as before.

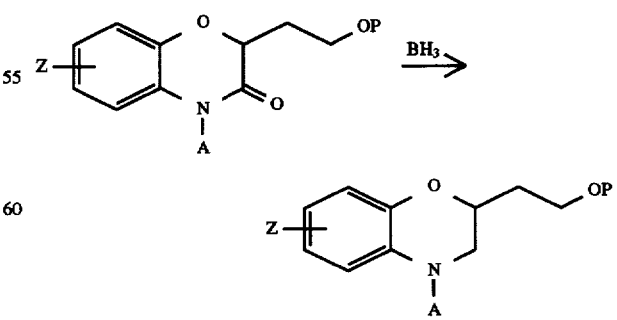

Scheme 3

In Scheme 4, reaction of 2-(4-hydroxyphenyl)ethylamine with di-t-butyldicarbonate, to afford a protected phenolic coupling component for the Mitsunobu reaction, is illustrated. A variety of (hydroxyphenyl)alkylamines are commercially available or are known compounds; they can be synthesized by common methods such as reductive amination of benzaldehydes, hydrogenation of arylacetonitriles or aryloxyacetonitriles, reduction of cinnamides or cinnamylamines, etc. Methods for their preparation can be chosen from, but are not limited to, the examples presented herein.

Also in Scheme 4, the generation of a protected guanidine from the corresponding amine is illustrated, again providing a phenolic component for the Mitsunobu coupling. The illustrated use of N,N'-bis(t-butoxycarbonyl)-S-methylisothiourea for this purpose is a known procedure (R. J. Bergeron, J. S. McManis, *J. Org. Chem.*, 52, 1700–1703 (1987); it is in some cases improved by the addition of silver acetate to the reaction mixture. (See also M. S. Bernatowicz, Y. Wu, G. R. Matsueda, *Tetrahedron Letters*, 34, 3389 (1993)). These methods are in general applicable to all amines with the various definitions of Ar, X, W, and n.

Alternatively, one can prepare I (see description of invention) with Y=$NH_2$ and then convert the amino group into a guanidino group by the above or by other known methods (e.g., M. S. Bernatowicz, Y. Wu, G. R. Matsueda, *J. Org. Chem.*, 57, 2497–2502 (1992) and references therein).

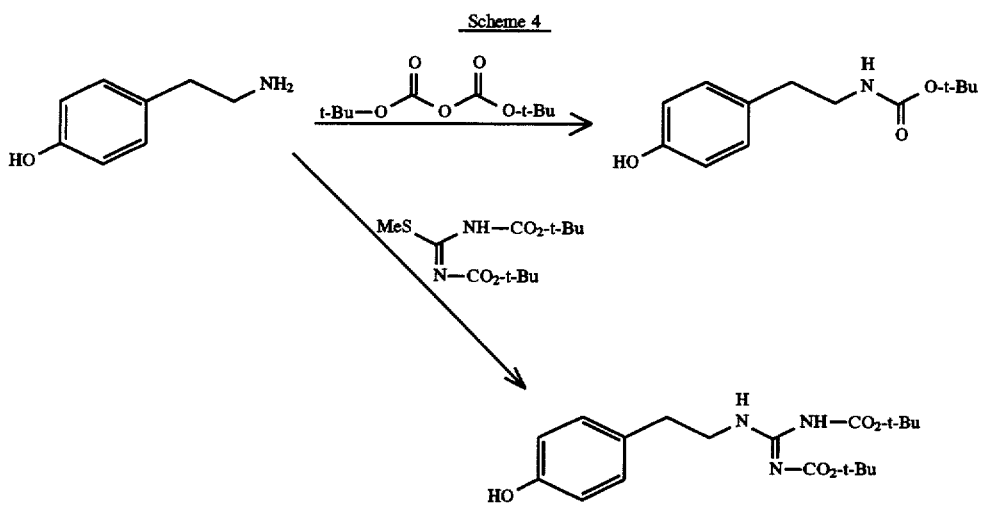

Scheme 4

For compounds where Y is a carboxylic acid (see definition), the starting phenols with the appropriate substitution are known compounds and are commercially available as either the carboxylic acids or the corresponding alkanoic esters. The acids are first protected as the alkanoic esters prior to Mitsunobu coupling in the usual manner as shown in Scheme 5. After coupling, saponification with NaOH provides the final products.

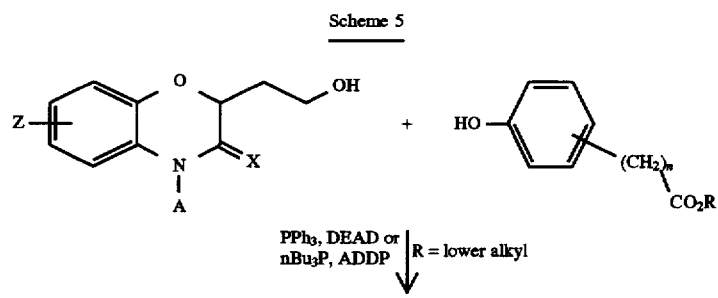

Scheme 5

-continued
Scheme 5

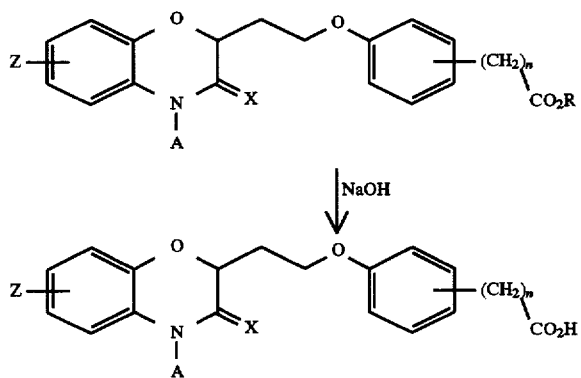

Where n is 0 and Y is CHO (Scheme 6), reaction with bromoform and KOH followed by methylation of the crude product provides hydroxy ester 3. Hydrolysis of the ester thus formed, affords the corresponding hydroxy acid 4. The acid 4, may be treated with reagents such as thionyl chloride to generate the chloro derivative, followed by reaction with thiourea to produce the thiazolidinedione also shown in Scheme 6.

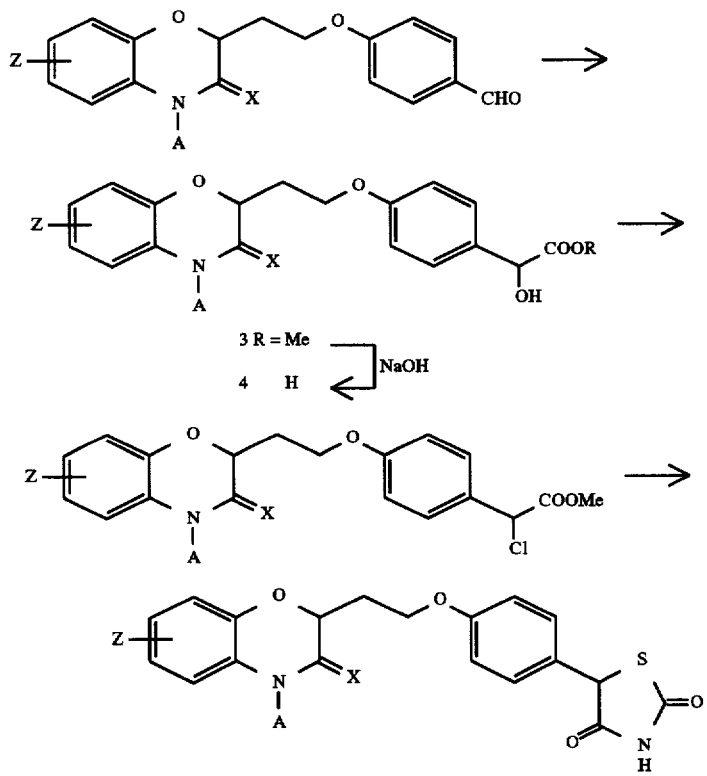

For compounds where Y is, in effect, a protected amine or guanidine (Scheme 7), reaction under acidic conditions, for example, trifluoroacetic acid or hydrochloric acid in isopropanol, affords the amine and guanidine salts, respectively.

Scheme 7

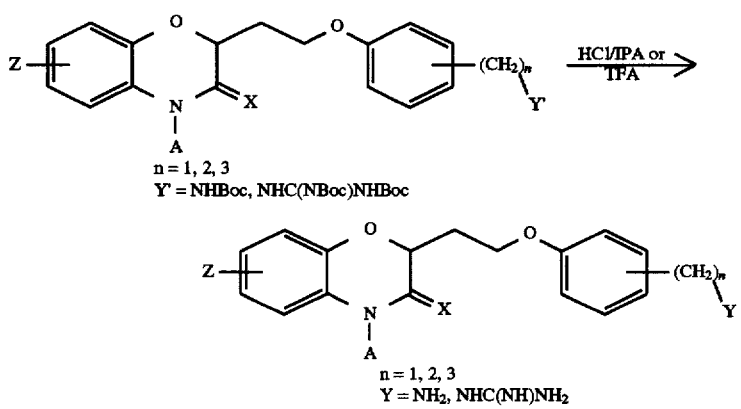

n = 1, 2, 3
Y' = NHBoc, NHC(NBoc)NHBoc n = 1, 2, 3
Y = NH₂, NHC(NH)NH₂

In the cases where A (see description of invention), is a carboxylic acid substituted benzyl group, the alcohol shown in Scheme 8 may be prepared by the method outlined in Scheme 1, using known benzylic halides bearing a carboxylic ester substituent. The previously described transformations are carried out with the ester in place, followed by hydrolysis of the ester to generate the acid, usually in the final step of the sequence.

Scheme 8

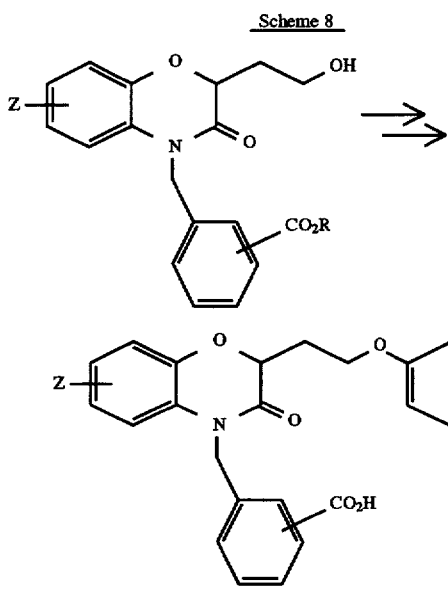

The transformations outlined in Scheme 1, for preparation of alcohol 2 and the coupling reaction described in Scheme 2 may be carried out on nitro substituted starting materials to afford the products shown in Scheme 9. Reduction of the nitro group with reagents such as iron/acetic acid or palladium catalyzed hydrogenation, can be carried out on, for example, compounds originating from the protected amino or guanidino phenols shown in Scheme 2. Alternatively, the reduction may be effected on the unprotected compounds, provided that no further manipulations are needed. With the protected species, the resulting amine may be further functionalized with electrophilic reagents to afford the products shown in Scheme 9. Similar transformations can be carried out on compounds derived from 2 bearing a nitrobenzyl substituent, as shown in Scheme 10.

Scheme 9

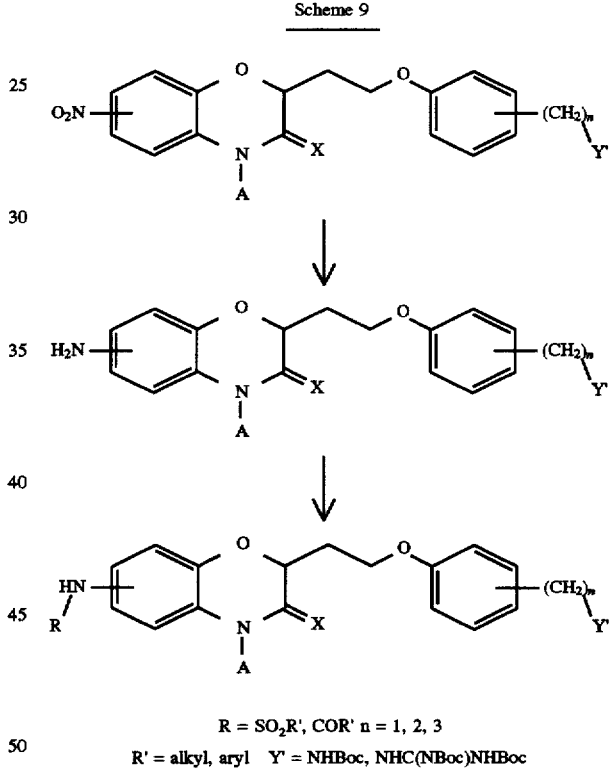

R = SO₂R', COR'  n = 1, 2, 3
R' = alkyl, aryl   Y' = NHBoc, NHC(NBoc)NHBoc

Scheme 10

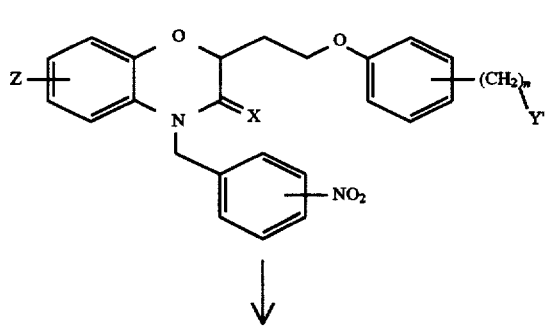

-continued
Scheme 10

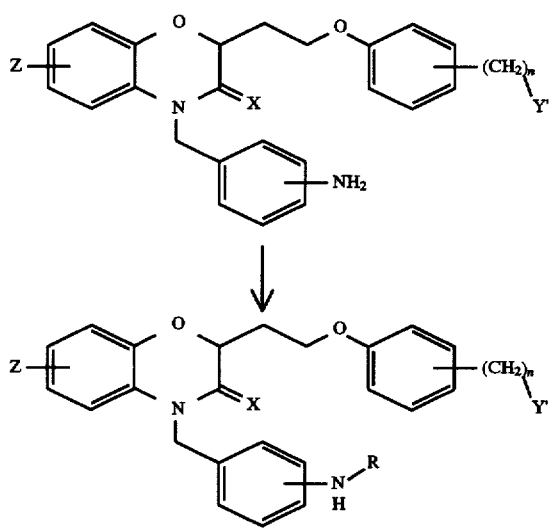

R = SO₂R', COR' n = 1, 2, 3
R' = alkyl, aryl  Y' = NHBoc, NHC(NBoc)NHBoc

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From formula I it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastere omeric salts with optically active acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, Ca(OH)₂, Al(OH)₃, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The ability of bacteria to quickly respond to changes in the environment is of utmost importance for their survival. Bacteria are capable of rapidly responding and adapting to such diverse stimuli as changes in nutrients, osmolarity, temperature, light, or host environment. These responses may be transient, such as those required for changes in motility or for entry into a host cell. Alternatively, the responses may require major shifts in gene expression and cell morphology, such as those required for sporulation, or for survival within a macrophage. The mechanism by which bacteria are able to sense cues from the physical environment (or from within the cytoplasm) and process these signals into appropriate responses often involves the so-called "two-component" systems.

As stated above, the treatment method of the present invention is based on the inhibition of this "two-component switch" system. All bacteria use this mechanism to control various adaptive/virulence factors to facilitate establishment of a bacterial population in the environment (for example, a bacterial infection in a host). The system invariably consists of a sensor which either activates a kinase or is a part of the kinase, and which upon stimulation, autophosphorylates. This phosphorylated species is a highly active phosphodonor which immediately transfers its phosphate to a "regulatory" component, which in turn initiates the biological response such as transcription or further phosphotransfer in a cascade which eventually ends in regulation of bacterial gene expression. Although each of the kinases and response regulators has a unique sequence (in fact, even functionally identical proteins have slightly different sequences in different species) they share a homologous biochemical mechanism and they share significant homology in the active site.

As stated, the present invention provides compounds which exhibit antibiotic activity by inhibiting the autophosphorylation of bacterial histidine kinases. They also inhibit the transfer of phosphate from phosphorylated histidine kinases to the aspartyl residues of the phosphate acceptor proteins involved in regulation of bacterial gene expression.

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The compounds of the present invention have antibacterial activity as determined by the following tests. First, the compounds were tested for their activity in inhibiting the autophosphorylation of Kinase A and the transphosphorylation of SpoOF, two proteins involved in one of the above described signal transduction systems controlling gene expression in bacteria. Representative compounds were then tested for antibacterial activity against selected organisms by the standard MIC method. The results are set forth below.

Table 1 lists examples of compounds of the invention, along with their $IC_{50}$ values in the HPK in vitro assay described below, and MIC value ranges for the selected microorganisms identified below. These examples are merely illustrative of the invention, and are not intended to limit the scope of the claims in any way. In Table 1, benzoxazine compounds are listed in accordance with the following formula:

TABLE 1

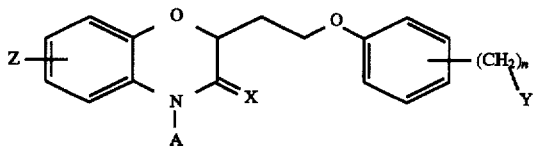

KEY: Bz = benzyl T = $NH_2$ G = $NHC(NH)NH_2$ napMe = naphthylmethyl pyrMe = pyridylmethyl Cl-Thi = 2-Chloro-4-thienylmethyl Thi = thienylmethyl BoB = benzyloxybenzyl PBz = phenylbenzyl Thia = 2,4 dioxodihydrothiazole

| Cpd # | A | Z | X | pos. (n)-Y | $IC_{50}$ | MIC ($G^+/G^-$) |
|---|---|---|---|---|---|---|
| 1 | 3-Cl-Bz | H | O | 4(1)-T-Boc | 253 | |
| 2 | 3-Cl-Bz | H | O | 4(1)-T | 55 | 8–32/32→128 |
| 3 | 4-Cl-Bz | H | O | 4(1)-T-Boc | 283 | |
| 4 | 4-Cl-Bz | H | O | 4(1)-T | 47 | 8–16/8→128 |
| 6 | 4-Cl-Bz | H | O | 4(2)-T | 61 | 1–2/2–64 |
| 7 | 4-Cl-Bz | H | O | 3(2)-T-Boc | 308 | |
| 8 | 4-Cl-Bz | H | O | 3(2)-T | 89 | 8–16/8–128 |
| 10 | 4-Cl-Bz | H | O | 3(1)-T | 122 | |
| 12 | 2-Cl-Bz | H | O | 3(1)-T | 140 | |
| 13 | 2-Cl-Bz | H | O | 4(1)-T-Boc | 272 | |
| 14 | 2-Cl-Bz | H | O | 4(1)-T | 172 | |
| 15 | 2-Cl-Bz | H | O | 3(2)-T-Boc | 165 | |
| 16 | 2-Cl-Bz | H | O | 3(2)-T | 74 | 8–16/8→128 |
| 17 | 2-Cl-Bz | H | O | 4(2)-T-Boc | 352 | |
| 18 | 2-Cl-Bz | H | O | 4(2)-T | 264 | |
| 19 | 2-Cl-Bz | H | O | 4(1)-G | 16 | 1–4/4→128 |
| 20 | 2-Cl-Bz | H | O | 4(2)-G | 16 | |
| 21 | 4-Cl-Bz | H | O | 4(1)-G | 26 | |

TABLE 1-continued

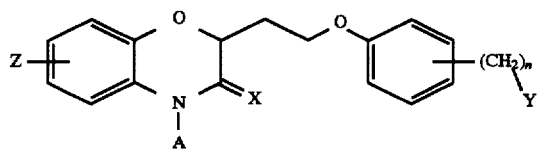

KEY: Bz = benzyl  T = NH₂  G = NHC(NH)NH₂  napMe = naphthylmethyl
pyrMe = pyridylmethyl  Cl-Thi = 2-Chloro-4-thienylmethyl  Thi = thienylmethyl
BoB = benzyloxybenzyl  PBz = phenylbenzyl  Thia = 2,4 dioxodihydrothiazole

| Cpd # | A | Z | X | pos. (n)-Y | IC₅₀ | MIC (G⁺/G⁻) |
|---|---|---|---|---|---|---|
| 22 | 4-Cl-Bz | H | H,H | 4(2)-G | 41 | 2–4/8→64 |
| 23 | 3-Cl-Bz | H | H,H | 4(2)-G | 17 | 1–2/4→128 |
| 24 | 3-Cl-Bz | 6-Me | O | 4(2)-G | 56 | |
| 145 | 2-Cl-Bz | H | H,H | 4(1)-G | 23 | 1–2/8→64 |
| 26 | 4-Cl-Bz | H | O | 4(2)-G | 68 | 2–4/4→128 |
| 27 | Bz | H | O | 4(2)-G-diBoc | 340 | |
| 28 | Bz | H | O | 4(2)-G | 44 | |
| 29 | 2-OMe-Bz | H | O | 4(2)-G | 54 | |
| 31 | 3-F-Bz | H | O | 4(2)-G | 46 | |
| 33 | 3-OMe-Bz | H | O | 4(2)-G | 145 | |
| 35 | 3-BoB | H | O | 4(2)-G | 24 | |
| 36 | 3-OH-Bz | H | O | 4(2)-G | 72 | |
| 37 | 4-OMe-Bz | H | O | 4(2)-G | 51 | |
| 38 | 4-PBz | H | O | 4(2)-G | 34 | |
| 39 | 3,5-diCl-Bz | H | O | 4(1)-T | 46 | 4–16/4→128 |
| 40 | 3,5-diCl-Bz | H | O | 4(2)-G | 24 | 2/8→128 |
| 42 | 4-pyrMe | H | O | 4(2)-G | 444 | |
| 43 | 1-napMe | H | O | 4(2)-G | 13 | |
| 45 | 2-napMe | H | O | 4(2)-G | 17 | |
| 46 | Thi | H | O | 4(2)-G | 68 | |
| 47 | 4-Cl-Thi | H | O | 4(2)-G-diBoc | 398 | |
| 48 | 4-Cl-Thi | H | O | 4(2)-G | 26 | |
| 50 | 3-Cl-Bz | 6-Cl | O | 4(2)-G | 9 | 2/4→128 |
| 52 | 3-Cl-Bz | 6-Ph | O | 4(2)-G | 36 | |
| 53 | 3-Cl-Bz | 7-CF₃ | O | 4(2)-G-diBoc | 84 | |
| 54 | 3-Cl-Bz | 7-CF₃ | O | 4(2)-G | 14 | |
| 55 | 3-Cl-Bz | 7-F | O | 4(2)-G | 28 | |
| 57 | 3-Cl-Bz | 6,8-diCl | O | 4(2)-G | 17 | |
| 58 | 3-Cl-Bz | 7-Me | O | 4(2)-G | 17 | 2/4→128 |
| 59 | Me | H | O | 4(2)-G-diBoc | 473 | |
| 60 | Me | H | O | 4(2)-G | 55 | 16–34/16→64 |
| 61 | n-pentyl | H | O | 4(2)-G | 41 | 4–8/4–64 |
| 64 | 3,5-diCl-Bz | H | O | 3(2)-T | 32 | 4–8/4→128 |
| 66 | 4-Me-Bz | H | H,H | 4(2)-G | 19 | |
| 68 | 2,4-diCl-Bz | H | H,H | 4(2)-G | 17 | |
| 69 | 3-Cl-Bz | H | O | 3(2)-T-Boc | 358 | |
| 70 | 3-Cl-Bz | H | O | 3(2)-T | 65 | 8–16/8→128 |
| 71 | 3-Cl-Bz | H | O | 4(2)-G-diBoc | 300 | |
| 72 | 3-Cl-Bz | H | O | 4(2)-G | 30 | 2–4/4→128 |
| 73 | 3-Cl-Bz | H | O | 3(1)-T-Boc | 354 | |
| 74 | 3-Cl-Bz | H | O | 3(1)-T | 81 | 8–16/≦16→128 |
| 76 | 3-Cl-Bz | H | O | 4(3)-T | 32 | 8/8→128 |
| 77 | 3-Cl-Bz | H | O | 4(1)-G-diBoc | 51 | |
| 78 | 3-Cl-Bz | H | O | 4(1)-G | 32 | 1–4/4→128 |
| 79 | 3-Cl-Bz | H | O | 4(2)-T | 78 | 8–16/8→128 |
| 80 | 3-Cl-Bz | 7-NO₂ | O | 4(2)-G-diBoc | 162 | |
| 82 | 3-Cl-Bz | 7-NO₂ | O | 4(2)-T | 27 | |
| 84 | 3-Cl-Bz | 7-NO₂ | O | 4(2)-G | 30 | |
| 87 | 2-Cl-Bz | 7-NO₂ | O | 4(1)-G | 11 | |
| 89 | 2-Cl-Bz | 6-NO₂ | O | 4(2)-G | 17 | 1–4/2→128 |
| 91 | 3-NO₂Bz | 7-NO₂ | O | 4(2)-G | 33 | |
| 92 | 3-Cl-Bz | 6-A | O | 4(2)-G | 34 | 2–16/4→128 |
| 95 | 3-NO₂-Bz | H | O | 4(2)-G | 32 | |
| 97 | 4-NO₂-Bz | 7-NO₂ | O | 4(2)-G | 53 | |
| 99 | 3-NO₂Bz | 7-OMe | O | 4(2)-G-diBoc | 343 | |
| 100 | 3-NO₂-Bz | 7-OMe | O | 4(2)-G | 32 | |
| 104 | 4-CO₂Me-B | H | O | 4(2)-T | 24 | |
| 106 | 3-CO₂Me-B | H | O | 4(2)-T | 166 | |
| 110 | 4-CO₂H-Bz | H | O | 4(2)-T | 324 | |
| 111 | 3-CO₂H-Bz | H | O | 4(2)-T-Boc | 113 | |
| 112 | 3-CO₂H-Bz | H | O | 4(2)-T | 254 | |
| 127 | 3-Cl-Bz | H | O | 3(2)-CO₂H | 251 | |
| 134 | 3-Cl-Bz | H | O | 4(0)-Thia | 23 | |
| 139 | 4-NO₂-Bz | H | O | 4(2)-G | 24 | |

TABLE 1-continued

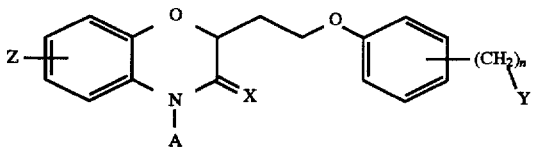

KEY: Bz = benzyl T = NH₂ G = NHC(NH)NH₂ napMe = naphthylmethyl
pyrMe = pyridylmethyl Cl-Thi = 2-Chloro-4-thienylmethyl Thi = thienylmethyl
BoB = benzyloxybenzyl PBz = phenylbenzyl Thia = 2,4
dioxodihydrothiazole

| Cpd # | A | Z | X | pos. (n)-Y | IC$_{50}$ | MIC (G⁺/G⁻) |
|---|---|---|---|---|---|---|
| 140 | 4-OMe-Bz | H | O | 4(2)-G-diBoc | 343 | |
| 141 | 2,4-diCl-Bz | H | O | 4(2)-G | 37 | |
| 142 | 4-Cl-Bz | H | O | 3(3)-T | 42 | |
| 143 | 2-NO₂-Bz | 7-NO₂ | O | 4(2)-G-diBoc | 73 | |
| 144 | 3-Cl-Bz | H | O | 4(2)-T-Boc | 348 | |

In Table 2, activities for pyrido-oxazine compounds of the following formula where Q is a fused pyridyl moiety are listed:

TABLE 2

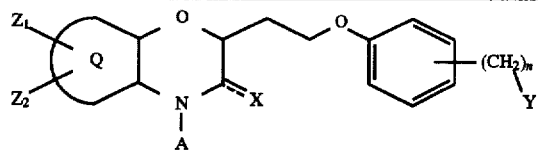

KEY: Bz = benzyl T = NH₂ G = NHC(NH)NH₂ napMe = naphthyl-
methyl pyrMe = pyridylmethyl Cl-Thi = 2-Chloro-4-thienylmethyl
Thi = thienylmethyl BoB = benzyloxybenzyl PBz = phenylbenzyl
Thia = 2,4 dioxodihydrothiazole

| Cpd # | A | Z₁Z₂ | X | pos. (n)-Y | IC$_{50}$ | MIC (G⁺/G⁻) |
|---|---|---|---|---|---|---|
| 25 | 3-Cl-Bz | H,H | O | 4(2)-G | 41 | |
| 62 | 3-Cl-Bz | H,H | O | 4(2)-G | 174 | |

The protocols for the above referenced assays are as follows.

1. Autophosphorylation of Kinase A and Transphosphorylation of SpoOF Assay

To study the effect of the compounds of the present invention on the signal transduction process in bacteria, the inhibiting effect of the compounds on the sporulation operon proteins Kinase A and SpoOF was examined. Specifically, the inhibition of autophosphorylation of Kinase A and the transphosphorylation of SpoOF was determined in the following assays. The SpoOF response regulator is the primary substrate for phosphorylation by the protein kinase, Kin A, involved in the sporulation process in bacteria. See D. Burbulys, K. A. Trach, J. A. Hoch, Cell, 64, 545–552 (1991). SpoOF and KinA were prepared from recombinant E. coli overexpressing the proteins (J. Cavanagh et al, Amino Acids, 6, 131–140 (1994) and references therein).

The following stock reagents were either prepared and used promptly or stored at the indicated temperature:

8× Salts: 2M KCl (5 mL), 1M MgCl₂ (800 mL), 1M CaCl₂ (100 mL), 10 mg/mL phenylmethylsulfonyl fluoride (200 mL), 1M dithioreitol (50 mL), 0.25M Na₂EDTA (32 mL) and H₂O 3.82 mL (-20° C.)

5× Loading Dye: 0.5M TRIS-HCl-pH 6.8 (7.5 mL), 10% SDS (2 mL) 0.1% bromophenol blue (0.5 mL), 100% glycerol (3 mL) and 12.5M 2-mercaptoethanol (0.3 mL)

1–1.3 mg/mL KinA:15 mM TRIS-HCl, pH 8.0, 6 mM KCl; 4 mM 2-mercaptoethanol; 40% glycerol (-20° C.)

1 mg/mL SpoOF: 17.5 mM TRIS-HCl, pH 8.0; 0.7 mM KCl; 0.7 mM MgCl₂; 0.7 mM CaCl₂; 5mM 2-mercaptoethanol; 30% Glycerol (-20° C.)

5% Stacking Gel: 40% 29:1 acrylamide:bis acrylamide (1.25 mL), 0.5M TRIS-HCl, pH 6.8 (2.5 mL), 10% SDS (0.1 mL), D-H₂O (6.15 mL) 10% ammonium persulfate (100 mL) and TEMED (25 mL)

SDS Running Buffer: TRIS-BASE (3.02 g), glycine (14.4 g) SDS (1 g), D-H₂O (to 1 L)

The reaction mixture was prepared from 8× Salts (87 μL), 1M TRIS, pH 8 (118 μL), 50% glycerol (63 μL), SpoOF (14.1 μL) and KinA (7.0 μL). Microcentrifuge tubes were charged with the reaction mixture (18.5 μL) and a 1.0 mM solution of the test compound in 5% DMSO (18.5 μL), and incubated for 15 min on ice. 100 mM ATP solution (3.0 μl, containing 625 μCi [³²P]ATP) was added, and the mixture left for 10 minutes at room temperature. The reaction was quenched with 5× loading dye (10 μL per tube) and the samples were loaded on a prepared 5% Stacking Gel, or stored on dry ice until ready for use. The prepared wells were filled with SDS Running Buffer, samples were loaded into the wells, and 80 volts were applied to the gel until the dye front reached the bottom of the stacking gel. The voltage was then increased to 250 volts until electrophoresis was complete. Radioactive bands in the gel corresponding to phosphorylated KinA and SpoOF were imaged and quantitated with a phosphoimager.

If either enzyme was inhibited (as evidenced by the absence of labelled protein in the developed gel), an IC$_{50}$ was calculated by running the assay with a range of inhibitor concentrations from 1 to 500 μM. After electrophoresis of the reaction mixtures, percent inhibition was determined by measuring the concentration of radioactive phosphorus with a phosphoimager and calculating the values using a software program (BioRad Molecular Analyst). IC$_{50}$ values of less than 500 μM are considered active.

2. MIC Anitimicrobial Assay

The in vitro antimicrobial activity of the compounds was determined by the microdilution broth method following the test method from the National Committee for Laboratory Standards (NCCLS). This method is described in the NCCLS Document M7-A2, Vol. 10, No. 8 "Methods for Dilution Antimicrobial Susceptibility Test for Bacteria that Grow Aerobically—Second Edition."

In this method two-fold serial dilutions of drug in cation supplemented Mueller-Hinton broth are added to wells in microdilution trays. The test organisms are prepared by adjusting the turbidity of actively growing broth cultures so that the final concentration of test organism after it is added to the wells is approximately $5 \times 10^4$ CFUs/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Tables 1 and 2, compounds of the present invention were tested against a variety of Gram+ and Gram- pathogenic bacteria resulting in a range of activities, from 1→128 µg/mL depending on the organism tested. The following test organisms were utilized in the assay:

gram positive bacteria
*Enterococcus faecalis* ATCC 29212
*Enterococcus faecalis* oc 3041
*Enterococcus faecium* oc 2993
Methicillin resistant *Staphylococcus aureus* oc 2089
Methicillin resistant *Staphylococcus aureus* oc667
*Staphylococcus aureus* ATCC 29213
*Staphylococcus aureus* ATCC 6538
*Staphylococcus epidermidis* oc 2603
gram negative bacteria
*Escherichia coli* oc 2605
*Escherichia coli* oc 2530 ss
*Klebsiella pneumoniae* oc 1943
*Pseudomonas aeroginosa* oc 161
*Pseudomonas aeroginosa* ATCC 27853

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

Methods of preparing the exemplified compounds of the invention are presented below. These examples are intended to illustrate the methods of synthesis, and are not intended to limit the scope of the claims in any way. Abbreviations used: DEAD, diethyl azodicarboxylate; Ph$_3$P, triphenylphosphine; Bu$_3$P, tri-n-butylphosphine; THF, tetrahydrofuran; DMF, N,N-dimethylformamide; ADDP, 1,1'-(azodicarbonyl)dipiperidine.

REFERENCE EXAMPLE 1

Intermediate 9086-181-1

Dihydro-3-(2-nitrophenoxy)-2-(3H)-furanone

Method A: 2-nitrophenol (20.2 g, 1 eq) was dissolved in DMF (250 ml) and treated with K$_2$CO$_3$ (30 g, 1.3 eq), followed by addition of α-bromo-γ-butyrolactone (14.4 ml, 1.2 eq) at room temperature under nitrogen. After stirring 18 h, an additional amount of K$_2$CO$_3$ (5g, 0.25 eq) was added. After a total reaction time of 48 h, the reaction was cooled in an ice bath and acetic acid (13.7 ml, 1.65 eq) was added. The crude reaction mixture was poured into water and extracted with EtOAc. The combined extract was concentrated under vacuum and crystallized from ethanol/water to afford white needles (22.4 g 70% yield), mp 112°–113° C.; IR (KBr) 2939, 1771, 1607, 1586, 1524, 1481, 1356, 1275, 1221, 1194, 1019, 745 cm$^{-1}$; $^1$H NMR (CDCl$_3$) δ7.84 (dd, J=8.1, 1.6 Hz, 1H), 7.62–7.48 (m, 2H), 7.16 (m, 1H), 5.02 (apparent t, J=7.4 Hz, 1H), 4.62–4.52 (m, 1H), 4.45–4.35 (m, 1H), 2.83–2.55 (m, 3H). Anal. Calc'd for C$_{10}$H$_9$NO$_5$: C 53.82, H 4.06, N 6.28. Found: C 53.65, H 3.84, N 6.05.

REFERENCE EXAMPLE 2

Intermediate 10353-186-A

Dihydro-3-(4-methyl-2-nitrophenoxy)-2-(3H)-furanone

Prepared from 4-methyl-2-nitrophenol by method A in 33% yield as a white solid, MS (CI) 238 (MH$^+$); IR (KBr) 3523, 3072, 3005, 1770, 1623, 1577, 1530, 1496, 1463, 1392, 1357, 1282, 1270, 1225, 1194, 1184, 1095, 1020, 992, 804 cm$^{-1}$; $^1$H NMR (CDCl$_3$) ,δ7.66 (s, 1H), 7.38 (m, 2H), 4.93 (apparent t, J=7.4 Hz, 1H), 4.59 (m, 1H), 4.39 (apparent q, J=7.3 Hz, 1H), 2.78–2.61 (m, 2H), 2.38 (s, 3H). Anal. Calc'd for C$_{11}$H$_{11}$NO$_5$: C 55.70 H 4.67, N 5.90. Found: C 55.62, H 4.66, N 5.82.

REFERENCE EXAMPLE 3

Intermediate 12168-2-1

Dihydro-3-(4-methoxy-2-nitrophenoxy)-2-(3H)-furanone

Prepared from 4-methoxy-2-nitrophenol by method A to afford yellow needles in 52% yield, MS (CI) 254 (MH$^+$); IR (KBr) 3519, 3102, 3023, 2984, 1765, 1726, 1581, 1532, 1496, 1463, 1442, 1274, 1265, 1229, 1218, 1178, 1145, 1092, 1068, 1018, 992, 942, 859, 839, 806, 791, 755 cm$^{-1}$; $^1$H NMR (CDCl$_3$) δ7.52 (d, J=9.1 Hz, 1H), 7.39, (d, J=3.1 Hz, 1H), 7.31 (dd, J=9.1, 3.0 Hz, 1H), 4.87 (apparent t, J=7.5 Hz, 1H), 4.55 (m, 1H), 4.36 (m, 1H), 3.87 (s, 3H), 2.82–2.69 (m, 1H), 2.68–2.53 (m, 1H). Anal. Calc'd for C$_{11}$H$_{11}$NO$_6$: C 52.18, H 4.38, N 5.53. Found: C 52.19, H 4.50, N 5.43.

REFERENCE EXAMPLE 4

Intermediate 11653-187

Dihydro-3-(5-methoxy-2-nitrophenoxy)-2-(3H)-furanone

Prepared from 5-methoxy-2-nitrophenol by method A in 53% yield, mp 109°–110° C.; MS (CI) MH$^+$254; IR (KBr) 3517, 3100, 3075, 2994, 2955, 2931, 2852, 1484, 1258, 1079, 714 cm$^{-1}$; $^1$H NMR (DMSO-d$_6$) δ7.98 (d, 1H, J=9.1 Hz), 7.02 (d, 1H, J=2.5 Hz), 6.76 (dd, 1H, J=2.5, 9.2 Hz), 5.62 (t, 1H, J=8.7 Hz), 4.48 (dt, 1H, J=2.4, 8.8 Hz), 4.28 (m, 1H), 3.88 (s, 3H), 2.89–2.73 (m, 1H), 2.38–2.29 (m, 1H). Anal. Calc'd for C$_{11}$H$_{11}$NO$_6$: C 52.18, H 4.38, N 5.53. Found: C 51.97, H 4.18, N 5.45.

REFERENCE EXAMPLE 5

Intermediate 11578-25

Dihydro-3-(3-methyl-2-nitrophenoxy)-2(3H)-furanone

Prepared from 3-methyl-2-nitrophenol by method A in 41% yield. A portion of this material was crystallized from CH$_2$Cl$_2$/ether to afford a white solid, mp 82°–84° C.; IR (KBr) 2946, 1792, 1530, 1294, 1275, 1182, 1118, 1014, 994, 777, 638 cm$^{-1}$; $^1$H NMR (CDCl$_3$) δ2.32 (s, 3H), 2.45–2.57 (m, 1H), 2.63–2.74 (m, 1H), 4.32–4.40 (m, 1H), 4.48–4.55 (m, 1H), 4.96 (t, J=7.4 Hz, 1H), 6.97 (dd, J=7.1, 0.6 Hz, 1H), 7.24–7.36 (m, 2H); MH$^+$ at m/z=238; Anal. Calc'd for C$_{11}$H$_{11}$NO$_5$: C, 55.70; H, 4.67; N, 5.90. Found: C, 55.61; H, 4.62; N, 5.87.

REFERENCE EXAMPLE 6

Intermediate 11578-61

Dihydro-3-(4-chloro-2-nitrophenoxy)-2(3H)-furanone

Prepared from 4-chloro-2-nitrophenol by Method A in 60% yield and isolated as a yellow solid, mp 136°–140° C.; IR (KBr) 3110, 1786, 1771, 1608, 1527, 1488, 1359, 1276, 1193, 1180, 1020, 825, 734 cm$^{-1}$; $^1$H NMR (CDCl$_3$) δ2.57–2.83 (m, 2H), 4.35–4.45 (m, 1H), 4.54–4.63 (m, 1H), 4.98 (t, J=7.4 Hz, 1H), 7.48–7.56 (m, 2H), 7.85 (d, J=2.3 Hz, 1H); MH$^+$ at m/z=258; Anal. Calc'd for C$_{10}$H$_8$ClNO$_5$: C, 46.62; H, 3.13; N, 5.44. Found: C, 46.61; H, 3.11; N, 5.20.

REFERENCE EXAMPLE 7

Intermediate 11578-62

Dihydro-3-(4-carbomethoxy-2-nitrophenoxy)-2(3H)-furanone

Prepared from 4-carbomethoxy-2-nitrophenol by Method A in 30% yield using equal portions of reagents. This material was isolated directly from the aqueous workup as a beige solid, mp 99°–101° C.; IR (KBr) 2958, 1780, 1726, 1618, 1531, 1348, 1300, 1270, 1179, 1127, 756 cm$^{-1}$; $^1$H NMR (CDCl$_3$) δ2.62–2.85 (m, 2H), 3.95 (s, 3H), 4.44 (dt, J=9.3, 7.2 Hz, 1H), 4.58–4.65 (m, 1H), 5.14 (t, J=7.3 Hz, 1H), 7.53 (d, J=8.8 Hz, 1H), 8.24 (dd, J=8.8, 2.1 Hz, 1H), 8.52 (d, J=2.1 Hz, 1H); MH$^+$ at m/z=282; Anal. Calc'd for C$_{12}$H$_{11}$NO$_7$·0.3H$_2$O: C, 50.29; H, 4.08; N, 4.89. Found: C, 50.03; H, 3.85; N, 4.68.

REFERENCE EXAMPLE 8

Intermediate 11578-32

Dihydro-3-(4-phenyl-2-nitrophenoxy)-2(3H)-furanone

Prepared from 4-benzyl-2-nitrophenol by Method A in 54% yield as a yellow crystalline solid, mp 117°–119° C.; IR (KBr) 2931, 1785, 1625, 1535, 1346, 1334, 1279, 1261, 1156, 1022, 756 cm$^{-1}$; $^1$H NMR (CDCl$_3$) δ2.64–2.85 (m, 2H), 4.42 (q, J=7.3 Hz, 1H), 4.57–4.65 (m, 1H), 5.05 (t, J=7.3 Hz, 1H), 7.40–7.59 (m, 6H), 7.78 (dd, J=8.7, 2.4 Hz, 1H), 8.07 (d, J=2.4 Hz, 1H); Anal. Calc'd for C$_{16}$H$_{13}$NO$_5$: C, 64.21; H, 4.38; N, 4.68. Found: C, 64.00; H, 4.20; N, 4.59.

REFERENCE EXAMPLE 9

Intermediate 11578-50

Dihydro-3-(4-trifluoromethyl-2-nitrophenoxy)-2(3H)-furanone

Prepared from 4-trifluoromethyl-2-nitrophenol by Method A in 51% yield using equal portions of reagents. This material was isolated as a white solid, mp 128°–129° C.; IR (KBr) 3100, 2995, 1782, 1626, 1537, 1358, 1329, 1283, 1159, 1131, 1098, 998, 822 cm$^{-1}$; $^1$H NMR (CDCl$_3$) δ2.63–2.86 (m, 2H), 4.40–4.48 (m, 1H), 4.58–4.65 (m, 1H), 5.14 (t, J=7.4 Hz, 1H), 7.63 (d, J=8.8 Hz, 1H), 7.83 (dd, J=8.8, 1.9 Hz, 1H), 8.14 (d, J=1.9 Hz, 1H); MH$^+$ at m/z=292; Anal. Calc'd for C$_{11}$H$_8$F$_3$NO$_5$: C, 45.22; H, 3.10; N, 4.79. Found: C, 45.37; H, 2.77; N, 4.81.

REFERENCE EXAMPLE 10

Intermediate 11578-40

Dihydro-3-(5-fluoro-2-nitrophenoxy)-2(3H)-furanone

Prepared from 5-fluoro-2-nitrophenol by Method A in 65% yield using equal portions of reagents. This material was isolated as an off-white solid after crystallization from CH$_2$Cl$_2$/ether, mp 98°–100° C.; IR (KBr) 3055, 1773, 1619, 1591, 1508, 1350, 1284, 1024, 750 cm$^{-1}$; $^1$H NMR (CDCl$_3$) δ2.62–2.85 (m, 2H), 4.38–4.46 (m, 1H), 4.57–4.65 (m, 1H), 5.01 (t, J=7.3 Hz, 1H), 7.23–7.27 (m, 1H plus CHCl$_3$), 7.96 (dd, J=9.1, 5.8 Hz, 1H); MH$^+$ at m/z=242; Anal. Calc'd for C$_{10}$H$_8$FNO$_5$: C, 49.80; H, 3.34; N, 5.81. Found: C, 49.85; H, 3.24; N, 5.78.

REFERENCE EXAMPLE 11

Intermediate 11578-38

Dihydro-3-(5-methyl-2-nitrophenoxy)-2(3H)-furanone

Prepared from 5-methyl-2-nitrophenol by Method A in 22% yield using equal portions of reagents. This material was crystallized from CH$_2$Cl$_2$/ether to afford a white solid, mp 68°–70° C.; IR (KBr) 3003, 2950, 2928, 1774, 1516, 1355, 1189, 1023, 947 cm$^{-1}$; $^1$H NMR (CDCl$_3$) δ2.43 (s, 3H), 2.58–2.81 (m, 2H), 4.35–4.43 (m, 1H), 4.55–4.62 (m, 1H), 4.99 (t, J=7.4 Hz, 1H), 6.95 (d, J=8.4 Hz, 1H), 7.28 (s, 1H), 7.79 (d, J=8.3 Hz, 1H); MH+ at m/z=238; Anal. Calc'd for C$_{11}$H$_{11}$NO$_5$: C, 55.70; H, 4.67; N, 5.90. Found: C, 55.68; H, 4.62; N, 5.85.

REFERENCE EXAMPLE 12

Intermediate 11578-22-Precursor

Dihydro-3-(4,6-dichloro-2-nitrophenoxy)-2(3H)-furanone

Prepared from 4,6-dichloro-2-nitrophenol by Method A in 20% yield as an orange solid and used without further purification; IR (KBr) 3086, 1779, 1542, 1457, 1353, 1250, 1222, 1152, 1066, 995, 877 cm$^{-1}$; $^1$H NMR (CDCl$_3$) δ2.62–2.81 (m, 2H), 4.35–4.42 (m, 1H), 4.59–4.66 (m, 1H), 5.02 (t, J=6.6 Hz, 1H), 7.67 (d, J=2.6 Hz, 1H), 7.86 (d, J=2.6 Hz); MH$^+$ at m/z 292.

REFERENCE EXAMPLE 13

Intermediate 9086-183-1

3,4-Dihydro-2-(2-hydroxyethyl)-3-oxo-2H-1,4-benzoxazine

Method B: Intermediate 9086-181-1, (11.9 g, 1 eq, Reference Example 1) was reacted with H$_2$ at 50 psi in a Parr shaker bottle containing 10% Pd/C (1.8 g, 15% w/w) in EtOH (200 ml) for 13 h. The catalyst was removed by filtration and the filtrate concentrated under vacuum. The crude product was triturated with hot Et$_2$O to afford the benzoxazinone in 87% yield as a white powder, mp 65°–69° C.; IR (KBr) 3298, 3076, 2993, 2917, 1677, 1613, 1505, 1439, 1410, 1312, 1275, 1231, 1119, 1104, 1059, 805, 745, 689 cm$^{-1}$; $^1$H NMR (CDCl$_3$) δ8.29 (br s, 1H), 7.01–6.95 (m, 3H), 6.82 (m, 1H), 4.76 (dd, J=7.6, 5.5 Hz, 1H), 3.91 (m, 2H), 2.35–2.13 (m, 3H). Calc'd for C$_{10}$H$_{11}$NO$_3$: C 62.17, H 5.74, N 7.25. Found: C 62.01, H 5.48, N 6.95.

REFERENCE EXAMPLE 14

Intermediate 11653-189A 3,4-Dihydro-2-(2-hydroxyethyl)-7-methoxy-3-oxo-2H-1,4-benzoxazine Method C: NaBH$_4$ (2.7 g, 6 eq.) was gradually added to a stirring mixture of intermediate 11653-187 (3.0 g, 11.8 mmol, Reference Example 4) and NiCl$_2$.6H$_2$O (11.2g, 4 eq.) in methanol (75 ml) at 0° C. The resulting dark reaction was allowed to return to room temperature slowly. After 2 days, 2N HCl was carefully added to the reaction mixture until gas evolution stopped. The resulting mixture was diluted with water and extracted with EtOAc. The combined EtOAc layers were washed with saturated NaHCO$_3$ then concentrated in vacuo to afford a 66% yield of a pale yellow solid, mp 123°–126° C.; MS (CI) MH$^+$224; IR (KBr) 3475, 3307, 3188, 3066, 2931, 2892, 2835, 1769, 1664, 1450, 1327, 1258, 1224, 925 cm$^{-1}$; $^1$H NMR (DMSO-d$_6$) δ10.15 (brs, 1H), 6.80 (d, 1H, J=8.5 Hz), 6.52 (d, 1H, J=2.6 Hz), 6.46 (dd, 1H, J=2.6, 8.5 Hz), 4.67 (dd, 1H, J=4.6, 8.8 Hz), 4.05 (t, 1H, J=5.4 Hz), 3.79 (m, 2H), 3.74 (s, 3H), 2.16 (m, 1H), 2.01 (m, 1H). Anal. Calc'd for C$_{11}$H$_{13}$NO$_4$: C 59.19, H 5.87, N 6.27. Found: 58.87, 5.80, N 6.09.

REFERENCE EXAMPLE 15

Intermediate 11653-29A 3,4-Dihydro-2-(2-hydroxyethyl)-7-nitro-3-oxo-2H-1,4-benzoxazine Method D: 2-amino-5-nitrophenol (13.5 g, 87.6 mmol, 1 eq.) and α-bromo-γ-butyrolactone (8.0 ml, 96.3 mmol, 1.1 eq.) were added to a stirring mixture of DMF (80 ml) and potassium carbonate (12.1 g, 87.6 mmol). After refluxing 5 hours and returning to room temperature, the reaction was poured into an equal volume of ice water and was stirred 15 minutes before being filtered. The resulting brown solid was dried in vacuo at 65° C. to afford a 45% yield of the product, mp 177°–178° C.; MS (FAB) MH$^+$ 239; IR (KBr) 3541, 3204, 3095, 3037, 2929, 2888, 1699, 1599, 1508, 1480, 1417, 1389, 1342, 1299, 1136, 1034, 798, 617, 499 cm$^{-1}$; $^1$H NMR (DMSO-d$_6$) δ11.32 (br s, 1H), 7.91 (dd, 1H, J=2.4, 8.7 Hz), 7.79 (s, 1H), 7.05 (d, 1H, J=8.7 Hz), 4.82 (dd, 1H, J=3.8, 9.0 Hz), 4.70 (br s, 1H), 3.59 (m, 2H), 1.98 (m, 1H), 1.90 (m, 1H). Anal. Calc'd for C$_{10}$H$_{10}$N$_2$O$_5$: C 50.42, H 4.23, N 11.76. Found: C 50.37, H 4.20, N 11.43.

REFERENCE EXAMPLE 16

Intermediate 12168-6-1

3,4-Dihydro-2-(2-hydroxyethyl)-6-methoxy-3-oxo-2H-1,4-benzoxazine

Prepared from intermediate 12168-2-1 (Reference Example 3) as a light grey solid in 76% yield by method B, mp 111°–113° C.; MS (CI) 224 (MH$^+$); IR (KBr) 3472, 3337, 3196, 3113, 3055, 2996, 2898, 2832, 1684, 1626, 1611, 1520, 1501, 1466, 1403, 1312, 1292, 1264, 1229, 1192, 1162, 1082, 796, 785 cm$^{-1}$; $^1$H NMR (CDCl$_3$) δ7.99 (br s, 1H), 6.91 (d, J=8.8 Hz, 1H), 6.52 (dd, J=8.8, 2.8 Hz, 1H), 6.37 (d, J=2.8 Hz, 1H), 4.70 (dd, J=7.5, 5.4 Hz, 1H), 3.90 (m, 2H), 3.77 (s, 3H), 2.21 (m, 2H). HRMS Calc'd for C$_{11}$H$_{13}$NO$_4$ (MH$^+$): 224.0922. Found: 224.0974.

REFERENCE EXAMPLE 17

Intermediate 10353-189-1

3,4-Dihydro-2-(2-hydroxyethyl)-6-methyl-3-oxo-2H-1,4-benzoxazine

Prepared by method B from intermediate 10353-186-A (Reference Example 2) and isolated in 70% yield as a white solid. MS (CI) 208 (MH$^+$); IR (KBr) 3337, 3196, 3099, 2919, 1681, 1609, 1523, 1498, 1409, 1365, 1232, 1058, 806cm$^{-1}$; $^1$H NMR (CDCl$_3$) 87.96 (br s, 1H), 6.90 (d, J=9.1 Hz, 1H), 6.80 (d, 9.1 Hz, 1H), 6.61 (s, 1H), 4.72 (apparent t, J=7.3 Hz, 1H), 3.90 (apparent q, J=5.4 Hz, 2H), 2.32–2.15 (m, 3H), 2.30 (s, 3H). Anal. Calc'd for C$_{11}$H$_{13}$NO$_3$: C 63.76, H 6.32, N 6.76. Found: C 63.54, H 6.20, N 6.76.

REFERENCE EXAMPLE 18

Intermediate 10353-184-B 3,4-Dihydro-2-(2-hydroxyethyl)-3-oxo-6-trifluoromethyl-2H-1,4-benzoxazine Prepared from intermediate 11578-50 (Reference Example 9 by method B and isolated in 54% yield as a fluffy white solid. MS (CI) 262 (MH$^+$); IR (KBr) 3468, 3202, 3113, 3044, 2962, 2888, 1696, 1622, 1496, 1402, 1336, 1215, 1159, 1124, 1111, 1058, 878, 827, 807 cm$^{-1}$; $^1$H NMR (CDCl$_3$) δ8.01 (br s, 1H), 7.28 (m, 1H), 7.09 (d, J=8.4 Hz, 1H), 7.05 (s, 1H), 4.86 (dd, J=8.2, 5.2 Hz, 1H), 3.92 (apparent dd, J=12.7, 5.6 Hz, 2H), 2.38–2.17(m, 1H), 1.92(t, J=5.6 Hz, 1H). Calc'd for C$_{11}$H$_{10}$F$_3$NO$_3$: C 50.58, H 3.86, N 5.36. Found: C 50.52, H 3.86, N 5.28. HRMS Calc'd for C$_{11}$H$_{10}$F$_3$NO$_3$ (MH$^+$): 262.0691. Found: 262.0740.

REFERENCE EXAMPLE 19

Intermediate 11578-28

3,4-Dihydro-2-(2-hydroxyethyl)-5-methyl-3-oxo-2H-1,4-benzoxazine

Prepared from intermediate 11578-25 (Reference Example 5) by Method C using 3 eq of NiCl$_2$.6H$_2$O and 6 eq of NaBH$_4$, and isolated by flash chromatography (ether elution) in 39% yield as a white solid, mp 147°–149° C.; IR (KBr) 3221, 1683, 1502, 1480, 1266, 1225, 1099, 1057, 770, 723 cm$^{-1}$; $^1$H NMR (CDCl$_3$) δ2.14–2.32 (m, 3H), 2.27 (s, 3H), 4.71 (q, J=5.3 Hz, 2H), 4.71 (dd, J=5.5, 7.4 Hz, 1H), 6.82–6.94 (m, 3H), 8.01 (br s, 1H); MH+ at m/z=208; Anal. Calc'd for C$_{11}$H$_{13}$NO$_3$: C, 63.76; H, 6.32; N, 6.76. Found: C, 63.38; H, 6.24; N, 6.72.

REFERENCE EXAMPLE 20

Intermediate 11578-68

6-Chloro-3,4-dihydro-2-(2-hydroxyethyl)-3-oxo-2H-1,4-benzoxazine

Prepared from intermediate 11578-61 (Reference Example 6) by Method C using 3 eq of NiCl$_2$.6H$_2$O and 6 eq of NaBH$_4$. Isolated in 66% yield as a white solid, mp 135°–138° C.; IR (KBr) 3475, 2956, 1690, 1498, 1385, 1059, 809 cm$^{-1}$; $^1$H NMR (DMSO-d$_6$) δ1.95–2.08 (m, 1H), 2.12–2.23 (m, 1H), 3.33 (br s, 1H plus DHO), 3.77–3.82 (m, 2H), 4.69 (dd, J=8.9, 4.4 Hz, 1H), 6.87 (s, H), 6.92 (s, 1H), 10.5 (br s, 1H); MH$^+$ at m/z=228; Anal. Calc'd for C$_{10}$H$_{10}$ClNO$_3$: C, 52.76; H, 4.43; N, 6.15. Found: C, 53.15; H, 4.50; N, 6.16.

REFERENCE EXAMPLE 21

Intermediate 11578-72

6-Carbomethoxy-3,4-dihydro-2-(2-hydroxyethyl)-3-oxo-2H-1,4-benzoxazine

Prepared from intermediate 11578-62 (Reference Example 7) by Method C using 3 eq of NiCl$_2$.6H$_2$O and 6 eq of NaBH$_4$, and isolated from EtOAc extraction in 51% yield as a white solid, mp 167°–169° C.; IR (KBr) 3428, 1729, 1688, 1494, 1400, 1305, 1214, 1049, 764 cm$^{-1}$; $^1$H NMR (DMSO-d$_6$) δ1.93–2.05 (m, 1H), 2.10–2.16 (m, 1H), 3.34 (v brs, 1H), 3.75–3.78 (m, 2H), 3.86 (s, 3H), 4.77 (dd, J=9.1, 4.1 Hz, 1H), 7.00 (d, J=8.2 Hz, 1H), 7.57–7.62 (m, 2H), 10.65 (s, 1H); Anal. Calc'd for C$_{12}$H$_{13}$NO$_5$.0.2H$_2$O: C, 56.56; H, 5.30; N, 5.50. Found: C, 56.71; H, 5.18; N, 5.35.

REFERENCE EXAMPLE 22

Intermediate 11578-36

3,4-Dihydro-2-(2-hydroxyethyl)-6-phenyl-3-oxo-2H-1,4-benzoxazine

Prepared by intermediate 11578-32 (Reference Example 8) by Method C in 55% yield and was isolated as a white crystalline solid, mp 170°–171° C.; IR (KBr) 3428, 1682, 1605, 1489, 1403, 1237, 1030, 863, 762 cm$^{-1}$; $^1$H NMR (DMSO-d$_6$) δ1.81–1.90 (m, 1H), 1.92–2.01 (m, 1H), 3.53–3.63 (m, 2H), 4.69 (dd, J=9.2, 3.9 Hz, 1H), 7.04 (d, J=8.3 Hz, 1H), 7.13 (d, J=2.0 Hz, 1H), 7.21 (dd, J=8.4, 2.1 Hz, 1H), 7.31–7.36 (m, 1H), 7.45 (t, J=7.5 Hz, 2H), 7.54 (d, J=7.3 Hz, 2H), 10.78 (s, 1H); MH$^+$at m/z=270; Anal. Calc'd for C$_{16}$H$_{15}$NO$_3$: C, 71.36; H, 5.61; N, 5.20. Found: C, 71.06; H, 5.53; N, 5.16.

REFERENCE EXAMPLE 23

Intermediate 11578-42

3,4-Dihydro-7-fluoro-2-(2-hydroxyethyl)-3-oxo-2H-1,4-benzoxazine

Prepared from intermediate 11578-40 (Reference Example 10) by Method C (reaction time of 3 days) in 43% yield to afford a white solid, mp 136°–138° C.; IR (KBr) 3474, 3199, 3087, 1676, 1514, 1425, 1150, 1113, 1054, 845 cm$^{-1}$; $^1$H NMR (DMSO-d$_6$) δ1.95–2.07 (m, 1H), 2.12–2.23 (m, 1H), 3.79 (q, J=5.2 Hz, 2H), 4.01 (t, J=5.4 Hz, 1H), 4.71 (dd, J=8.8, 4.5 Hz, 1H), 6.59–6.70 (m, 2H), 6.85 (dd, J=8.6, 5.5 Hz, 1H), 10.34 (br s, 1H); MH$^+$at m/z=121; Anal. Calc'd for C$_{10}$H$_{10}$FNO$_3$: C, 56.87; H, 4.77; N, 6.63. Found: C, 56.75; H, 4.74; N, 6.56.

REFERENCE EXAMPLE 24

Intermediate 11578-45

3,4-Dihydro-2-(2-hydroxyethyl)-7-methyl-3-oxo-2H-1,4-benzoxazine

Prepared from intermediate 11578-38 (Reference Example 11) by Method C to afford a white crystalline solid in 49% yield after crystallization from EtOAc, mp 143°–144° C.; IR (KBr) 3468, 3069, 1664, 1520, 1421, 1260, 1154, 1135, 1057, 931, 802 cm$^{-1}$; $^1$H NMR (DMSO-d$_6$) δ1.72–1.86 (m, 1H), 1.87–2.00 (m,1H), 2.21 (s, 3H), 3.54–3.60 (m, 2H), 4.59 (dd, J=9.4, 3.9 Hz, 1H), 4.65 (t, J=5.3 Hz, 1H), 6.72–6.78 (m, 3H), 10.58 (s, 1H); MH+ at m/z=208; Anal. Calc'd for C$_{11}$H$_{13}$NO$_3$: C, 63.76; H, 6.32; N, 6.76. Found: C, 63.73; H, 6.30; N, 6.67.

REFERENCE EXAMPLE 25

Intermediate 11578-22

6,8-Dichloro-3,4-dihydro-2-(2-hydroxyethyl)-3-oxo-2H-1,4-benzoxazine

Prepared from dihydro-3-(3,5-dichloro-2-nitrophenoxy)-2-(3H)-furanone by Method C to afford the product as a white solid in 72% yield, mp 174°–176° C.; IR (KBr) 3056, 1702, 1598, 1478, 1386, 1227, 1055, 853 cm$^{-1}$; $^1$H NMR (DMSO-d$_6$) δ1.77–1.87 (m, 1H), 1.89–1.95 (m, 1H), 3.55–3.63 (m, 2H), 4.72 (t, J=5.2 Hz, 1H), 4.82 (dd, J=9.6, 3.7 Hz, 1H), 6.86 (d, J=2.3 Hz, 1H), 7.22 (d, J=2.5 Hz, 1H), 11.00 (br s, 1H); MH+ at m/z=262; Anal. Calc'd for C$_{10}$H$_9$Cl$_2$NO$_3$: C, 45.83; H, 3.46; N, 5.34. Found: C, 45.82; H, 3.49; N, 5.29.

REFERENCE EXAMPLE 26

Intermediate 11653-20A

3,4-Dihydro-2-(2-hydroxyethyl)-6-nitro-3-oxo-2H-1,4-benzoxazine

Prepared from 2-amino-4-nitrophenol by method D in 35% yield, mp 173.5°–175° C.; MS (FAB) MH$^+$239; IR (KBr) 3401, 3092, 2932, 1595, 1536, 1499, 1323, 1213, 1144, 1100, 945, 474 cm$^{-1}$; $^1$H NMR (DMSO-d$_6$) δ11.06 (br s, 1H), 7.85 (dd, 1H, J=2.59, 8.90 Hz), 7.74 (d, 1H, J=2.54 Hz), 7.17 (d, 1H, J=8.90 Hz), 4.88 (dd, 1H, J=3.88, 8.90 Hz), 4.71 (m, 1H), 3.56 (m, 2H), 2.03 (m, 1H), 1.90 (m, 1H). Anal. Calc'd for C$_{10}$H$_{10}$N$_2$O$_5$: C 50.42, H 4.23, N 11.76. Found: C 50.48, H 4.21, N 11.44.

REFERENCE EXAMPLE 27

Intermediate 11653-156-A

3,4-Dihydro-6-fluoro-2-(2-hydroxyethyl)-3-oxo-2H-1,4-benzoxazine

Prepared from 2-amino-4-fluorophenol by method D in 22% yield, mp 126°–129.5° C.; MS (CI) MH$^+$ 212; IR (KBr) 3349, 3199, 3109, 3054, 2981, 2893, 1621, 1517, 1500, 1364, 1105, 1009, 946 cm$^{-1}$; $^1$H NMR (DMSO-d$_6$) δ10.78 (brs, 1H), 6.98 (dd, 1H, J=5.1, 8.8 Hz), 6.77 (d, 0.5H, J=3.0 Hz), 6.74 (d, 0.5H, J=3.0 Hz), 6.70 (m, 0.5H), 6.67 (d, 0.5H, J=3.0 Hz), 4.65 (m, 2H), 3.59 (m, 2H), 1.96 (m, 1H), 1.79 (m, 1H). Anal. Calc'd for C$_{10}$H$_{10}$FNO$_3$: C 56.87, H 4.77, N 6.63 .Found: C 56.55, H 4.91, N 6.54.

REFERENCE EXAMPLE 28

Intermediate 12168-5-1

3,4-Dihydro-2-(2-t-butyldimethylsilyloxyethyl)-6-methyl-3-oxo-2H-1,4-benzoxazine Method E: Intermediate 10353-189-1 (1.6 g, 1 eq, Reference Example 17), was dissolved in DMF (4 ml) and treated, sequentially, with chloro t-butyldimethylsilane (1.4 g, 1.2 eq) and imidazole (1.3 g, 2.5 eq) while stirring in a nitrogen atmosphere. After 18 h, the reaction mixture was diluted with $CH_2Cl_2$ and washed with water. The organic layer was concentrated and the product isolated in 93% yield, as a white powder by crystallization from MeOH/water, MS (CI) 322 (MH$^+$); IR (KBr) 2953, 2927, 2883, 2856, 1698, 1609, 1523, 1496, 1360, 1234, 1119, 1093, 842, 832, 811, 778 cm$^{-1}$; $^1$H NMR (CDCl$_3$) δ8.27 (br s, 1H), 6.86 (d, J=8.1 Hz, 1H), 6.76 (dd, J=8.1, 1.7 Hz, 1H), 6.61 (d, J=1.7 Hz, 1H), 4.72, (dd, J=9.7, 3.7 Hz, 1H), 3.95–3.78 (m, 2H), 2.28 (s, 3H), 2.20 (m, 1H), 2.00 (m, 1H), 0.90 (s, 9H), 0.70 (s, 3H). Anal. Calc'd for $C_{17}H_{27}NO_3Si$: C 63.51, H 8.47, N 4.36. Found: C 63.90, H 8.44, N 4.28.

REFERENCE EXAMPLE 29

Intermediate 12168-8-1

3,4-Dihydro-2-(2-t-butyldimethylsilyloxyethyl)-3-oxo-6-trifluoromethyl-2H-1,4-benzoxazine Prepared from intermediate 10353-184-B (Reference Example 18) by method E in 90% yield, as a white solid, MS (CI) 376 (MH$^+$); IR (KBr) 3027, 3076, 2956, 2931, 2883, 2859, 1698, 1615, 1495, 1390, 1335, 1257, 1222, 1164, 1125, 1095, 1069, 956, 833, 777 cm$^{-1}$; $^1$H NMR (CDCl$_3$) δ8.59 (br s, 1H), 7.25, (m, 1H), 7.06 (m, 2H), 4.85 (dd, J=9.2, 3.8 Hz, 1H), 3.85 (m, 2H), 2.23 (m, 1H), 2.02 (m, 1H), 0.89 (s, 9H), 0.07 (s, 3H), 0.06 (s, 3H). Calc'd for $C_{17}H_{24}F_3NO_3Si$: C 54.38, H 6.44, N 3.73. Found: C 54.34, H 6.45, N 3.73. HRMS Calc'd for $C_{17}H_{24}F_3NO_3Si$ (MH$^+$): 376.1556. Found: 376.1570.

REFERENCE EXAMPLE 30

Intermediate 10353-188-A 3,4-Dihydro-2-(2-t-butyldimethylsilyloxyethyl)-3-oxo-2H-pyrido[2,3-b]-1,4-oxazine Prepared from 3,4-dihydro-2-(2-hydroxyethyl)-3-oxo-2H-pyrido[2,3-b]-1,4-oxazine by method E in 91% yield as off-white flakes MS (CI) 309 (MH$^+$); IR (KBr) 3053, 2955, 2884, 2857, 1699, 1610, 1510, 1463, 1375, 1357, 1278, 1256, 1092, 836, 775 cm$^{-1}$; $^1$H NMR (CDCl$_3$) δ10.40 (br s, 1H), 8.04 (dd, J=5.4, 1.4 Hz, 1H), 7.26 (d, J=7.7 Hz, 1H), 7.00 (dd, J=7.7, 5.4 Hz, 1H), 4.83 (dd, J=9.5, 4.1 Hz, 1H), 3.84 (m, 2H), 2.25 (m, 1H), 2.03 (m, 1H), 0.89 (s, 9H), 0.07 (s, 3H), 0.06 (s, 3H). HRMS Calc'd for $C_{15}H_{24}N_2O_3Si$ (MH$^+$): 309.1634. Found: 309.1608.

REFERENCE EXAMPLE 31

Intermediate 11653-23

2-(2-tert-Butyldimethylsiloxyethyl)-3,4-dihydro-7-nitro-3-oxo-2H-1,4-benzoxazine Prepared from intermediate 11653-29A (Reference Example 15) by method E and isolated by recrystallization from Et$_2$O/hexane, mp 152°–157° C.; MS (FAB) MH$^+$ 353; IR (KBr) 3548, 3209, 3094, 2936, 2889, 1702, 1600, 1529, 1509, 1483, 1418, 1390, 1344, 1229, 1133, 1035 cm$^{-1}$; $^1$H NMR (CDCl$_3$) δ9.45 (br s, 1H), 7.95 (dd, 1H, J=2.4 8.6 Hz), 7.91 (d, 1H, J=2.3 Hz), 6.98 (d, H, J=8.6 Hz), 4.93 (dd, 1H, J=3.9, 9.0 Hz), 3.90 (m, 2H), 2.28 (m, 1H), 2.04 (m, 1H), 0.93 (s, 9H), 0.12 (s, 3H), 0.10 (s, 3H). Anal. Calc'd for $C_{16}H_{24}N_2O_5Si$: C 54.52, H 6.86, N 7.95. Found: C 54.14, H 6.64, N 8.18.

REFERENCE EXAMPLE 32

Intermediate 11653-33A 2-(2-tert-Butyldimethylsiloxyethyl)-3,4-dihydro-6-nitro-3-oxo-2H-1,4-benzoxazine Prepared from intermediate 11653-20A (Reference Example 26) by method E in 92% yield, mp 121.5°–124.5° C.; MS (FAB) MH$^+$353; IR (KBr) 3190, 3125, 3055, 2952, 2884, 2426, 1921, 1623, 1446, 1296, 1281, 1209, 1004, 925, 682, 512 cm$^{-1}$; $^1$H NMR (CDCl$_3$) δ7.10 (dd, 1H, J=2.65, 8.79 Hz), 7.75 (d, 1H, J=2.56 Hz), 6.96 (dd, 1H, J=4.99, 8.68 Hz), 4.80 (dd, 1H, J=3.88, 9.30 Hz), 3.78 (m, 2H), 2.18 (m, 1H), 1.95 (m,1H), 0.82 (s, 9H), 0.01 (d, 6H, J=3.51 Hz). Anal. Calc'd for $C_{16}H_{24}N_2O_5$: C 54.52, H 6.86, N 7.95. Found: C 54.18, H 6.51, N 8.29.

REFERENCE EXAMPLE 33

Intermediate 11653-163-A1

2-(2-tert-Butyldimethylsiloxyethyl)-3,4-dihydro-6-fluoro-3-oxo-2H-1,4-benzoxazine Prepared from intermediate 11653-156-A (Reference Example 27) by method E in 77% yield mp 84°–86° C.; MS (CI) MH$^+$326; IR (KBr) 3101, 3066, 2951, 2931, 2893, 2857, 1692, 1622, 1518, 1499, 1469, 1386, 1292, 1248, 1108, 1006, 812 cm$^{-1}$; $^1$H NMR (CDCl$_3$) δ8.86 (br s, 1H), 6.92 (dd, 1H, J=4.9, 8.8 Hz), 6.67 (m, 1H), 6.60 (dd, 1H, J=2.9, 8.5 Hz), 4.73 (dd, 1H, J=3.7, 9.5 Hz), 3.91–3.78 (m, 2H), 2.26 (m, 1H), 1.98 (m, 1H), 0.89 (s, 9H), 0.08 (s, 3H), 0.07 (s, 3H). Anal. Calc'd for $C_{16}H_{24}FNO_3Si$: C 59.05, H 7.43, N 4.30. Found: C 59.01, H 7.54, N 4.16.

REFERENCE EXAMPLE 34

Intermediate 11578-31

2-(2-tert-Butyldimethylsiloxyethyl)-3,4-dihydro-5-methyl-3-oxo-2H-1,4-benzoxazine Prepared from 11578-28 (Reference Example 19) by Method E and isolated directly from the reaction mixture in 24% yield as a white solid, by adding water and collecting the precipitate, mp 90°–92° C.; IR (KBr) 2953, 2927, 2855, 1693, 1502, 1482, 1390, 1360, 1250, 1119, 1093, 959, 837, 780, 769 cm$^{-1}$; $^1$H NMR (CDCl$_3$) δ0.07 (s, 3H), 0.08 (s, 3H), 0.90 (s, 9H), 1.92–2.03 (m, 1H), 2.17–2.26 (m, 1H), 2.26 (s, 3H), 3.78–3.93 (m, 2H), 4.72 (dd, J=3.7, 9.7 Hz, 1H), 6.81–6.92 (m, 3H), 8.04 (br s, 1H); Anal. Calc'd for $C_{17}H_{27}NO_3Si$: C, 63.51; H, 8.47; N, 4.36. Found: C, 63.50; H, 8.53; N, 4.24.

REFERENCE EXAMPLE 35

Intermediate 11578-70

2-(2-tert-Butyldimethylsiloxyethyl)-6-chloro-3,4-dihydro-3-oxo-2H-1,4-benzoxazine Prepared from 11578-68 (Reference Example 20) by Method E using 1 eq of imidazole and t-butyldimethylsilylchloride and isolated in 44% yield as a white solid after trituration with hexane, mp 86°–89° C.; MH$^+$ at m/z=342; IR (KBr) 2955, 2928, 2881, 2857, 1700, 1496, 1400, 1360, 1231, 1124, 1094, 954, 834 cm$^{-1}$; $^1$H NMR (CDCl$_3$) δ0.07 (s, 3H), 0.08 (s, 3H), 0.89 (s, 9H), 1.96–2.05 (m, 1H), 2.16–2.24 (m, 1H), 3.81–3.89 (m, 2H), 4.76 (dd, J=9.4, 3.7 Hz, 1H), 6.83 (d, J=2 Hz, 1H), 6.89–6.98 (m, 2H), 8.80 (br s, 1H). Anal. Calc'd for $C_{16}H_{24}ClNO_3Si$: C, 56.21; H, 7.08; N, 4.10. Found: C, 56.59; H, 7.17; N, 4.04.

REFERENCE EXAMPLE 36

Intermediate 11578-44

2-(2-tert-Butyldimethylsiloxyethyl)-3,4-dihydro-7-fluoro-3-oxo-2H-1,4-benzoxazine Prepared from 11578-42 (Reference Example 23) by Method E and isolated directly from the reaction mixture in 80% yield as a white solid, by adding water and collecting the precipitate, mp 100°–102° C.; IR (KBr) 2958, 2928, 2888, 2854, 1697, 1667, 1517, 1428, 1367, 1252, 1150, 1112, 1084, 833, cm$^{-1}$; $^1$H NMR (CDCl$_3$) δ0.07 (s, 3H), 0.08 (s, 3H), 0.90 (s, 9H), 1.96–2.05 (m, 1H), 2.16–2.27 (m, 1H), 3.80–3.91 (m, 2H), 4.77 (dd, J=9.5, 3.8), 6.64–6.80 (m, 3H), 9.05 (br s, 1H); Anal. Calc'd for $C_{16}H_{24}FNO_3Si$: C, 59.05; H, 7.43; N, 4.30. Found: C, 58.98; H, 7.39; N, 4.27.

REFERENCE EXAMPLE 37

Intermediate 11578-30

2-(2-tert-Butyldimethylsiloxyethyl)-6,8-dichloro-3,4-dihydro-3-oxo-2H-1,4-benzoxazine Prepared from 11578-22 (Reference Example 25) by Method E and isolated directly from the reaction mixture in 90% yield as a white solid, by adding water and collecting the precipitate, mp 118°–120° C.; IR (KBr) 2954, 2931, 2885, 2857, 1702, 1480, 1404, 1254, 1085, 838, 778 cm$^{-1}$; $^1$H NMR (CDCl$_3$) δ0.07 (s, 3H), 0.08 (s, 3H), 0.90 (s, 9H), 1.94–2.03 (m, 1H), 2.15–2.21 (m, 1H), 3.77–3.89 (m, 1H), 3.93 (td, J=9.7, 4.4 Hz, 1H), 4.89 (dd, J=9.8, 3.5 Hz, 1H), 6.78 (d, J=2.3 Hz, 1H), 7.05 (d, J=2.3 Hz, 1H), 9.39 (br s, 1H); Anal. Calc'd for $C_{16}H_{23}Cl_2NO_3Si$: C, 51.06; H, 6.16; N, 3.72. Found: C, 50.72; H, 5.87; N, 3.82.

REFERENCE EXAMPLE 38

Intermediate 11578-77-Precursor 2-(2-tert-Butyldimethylsiloxyethyl)-6-carbomethoxy 3,4-dihydro-3-oxo-2H-1,4-benzoxazine Prepared from intermediate 11578-72 (Reference Example 21 ) by Method E in 80% yield. The crude product was used without purification, MH$^+$ at m/z=366.

REFERENCE EXAMPLE 39

Intermediate 12168-10-1

4-(3-Chlorobenzyl)-3,4-dihydro-2-(2-hydroxyethyl)-3-oxo-6-methyl-2H-1,4-benzoxazine Prepared in two steps beginning from intermediate 12168-5-1 (Reference Example 28).

Method F: A solution of the silylated alcohol (2.17 g, 1 eq) in DMF (20 ml), was treated with NaH (60% oil dispersion, 0.27 mg, 1 eq) in one portion and stirred at room temperature in an nitrogen atmosphere for 20 min, followed by addition of 3-chlorobenzyl bromide (0.89 ml, 1 eq). After 14 h, the crude reaction mixture was poured into cold water and extracted with EtOAc. The combined organic extract was washed with brine and concentrated under vacuum. The crude product was carried on to the next step without further purification.

Method G: The product from Method F was dissolved in THF (15 ml) and tetrabutylammonium fluoride (1M solution in THF, 13 ml, 2 eq) was added. After stirring at room temperature for 8 h, the reaction mixture was concentrated under vacuum. The crude product was subjected to flash chromatography, eluting with EtOAc, and additionally purified by trituration with hot hexanes to afford the product in 93% overall yield, as a white solid, mp 75°–78° C.; MS (CI) 332 (MH$^+$); IR (KBr) 3501, 3451, 3062, 1969, 2937, 2874, 1660, 1610, 1598, 1575, 1513, 1473, 1432, 1387, 1321, 1280, 1258, 1106, 1067, 1061, 934, 775, 698 cm$^{-1}$; $^1$H NMR (CDCl$_3$) ,δ7.27 (m, 3H), 7.17 (m, 1H), 6.90 (d, J=8.1 Hz, 1H), 6.79 (d, J=7.0 Hz, 1H), 6.63 (s, 1H), 5.17 (d, J=16.3 Hz, 1H), 5.08 (d, J=16.3 Hz, 1H), 4.80 (dd, J=7.6, 5.5 Hz, 1H), 3.92 (apparent q, J=5.8 Hz, 2H), 2.29–2.17 (m, 3H), 2.23 (s, 3H). HRMS Calc'd for $C_{18}H_{18}ClNO_3$ (MH$^+$): 332.1053. Found: 332.1041.

REFERENCE EXAMPLE 40

Intermediate 10353-191-1

4-(3-Chlorobenzyl)-3,4-dihydro-2-(2-hydroxyethyl)-3-oxo-6-methyl-2H-pyrido[2,3-b]-1,4-oxazine Prepared from intermediate 10353-188-A (Reference Example 30) by methods F and G, alkylating with 3-chlorobenzyl bromide, in 69% overall yield as an off-white powder mp 80°–81° C.; MS (CI) 319 (MH$^+$); IR (KBr) 3525, 3446, 2928, 2874, 1667, 1600, 1574, 1465, 1411, 1362, 1325, 1285, 1230, 1205, 1121, 1096, 1064, 797, 750 cm$^{-1}$; $^1$H NMR (CDCl$_3$) δ8.04 (dd, J=4.8, 1.5 Hz, 1H), 7.42 (s, 1H), 7.37–7.18 (m, 4H), 6.96 (dd, J=7.9, 4.8 Hz, 1H), 5.31 (s, 2H), 4.85 (dd, J=7.5, 5.4 Hz, 1H), 3.90 (m, 2H), 2.35–2.16 (m, 2H), 2.04 (t, 5.6 Hz, 1H). HRMS Calc'd for $C_{16}H_{15}ClN_2O_3$ (MH$^+$): 319.0849. Found: 319.0857.

REFERENCE EXAMPLE 41

Intermediate 10353-28-1

4-(4-Chlorobenzyl)-3,4-dihydro-2-(2-hydroxyethyl)-3-oxo-2H-1,4-benzoxazine

Prepared from 2-(2-tert-butyldimethylsiloxyethyl)-3,4-dihydro-3-oxo-2H-1,4-benzoxazine by methods F and G, alkylating with 4-chlorobenzyl chloride, in 63% overall yield as a white solid mp 86°–88° C.; MS (CI) 300 (MH$^+$ —H$_2$O); IR (KBr) 3496, 2977, 2890, 1656, 1607, 1501, 1466, 1401, 1297, 1250, 1088, 1061, 1018, 795, 747 cm$^{-1}$; $^1$H NMR (CDCl$_3$) δ7.28 (d, J=8.5 Hz, 2H), 7.18 (d, J=8.5 Hz, 2H), 7.05–6.87 (m, 3H), 6.83 (d, J=8.0 Hz, 1H), 5.12 (s, 2H), 4.83 (dd, J=7.5, 5.5 Hz, 1H), 3.92 (apparent t, J=5.7 Hz, 2H), 2.38–2.15 (m, 3H). Calc'd for $C_{17}H_{16}ClNO_3$: C 64.26, H 5.08, N 4.41. Found: C 64.01, H 5.08, N 4.37.

REFERENCE EXAMPLE 42

Intermediate 9086-189-1

4-(2-Chlorobenzyl)-3,4-dihydro-2-(2-hydroxyethyl)-3-oxo-2H-1,4-benzoxazine

Prepared from 2-(2-tert-butyldimethylsiloxyethyl)-3,4-dihydro-3-oxo-2H-1,4-benzoxazine by methods F and G, alkylating with 2-chlorobenzyl chloride, in 65% overall yield as white powder mp 90°–91.5° C.; MS (CI) 318 (MH$^+$—H$_2$O); IR (KBr) 3482, 2935, 2881, 1663, 1607, 1594, 1505, 1466, 1443, 1407, 1320, 1306, 1283, 1252, 1063, 749 cm$^{-1}$; $^1$H NMR (CDCl$_3$) δ7.42 (dd, J=7.6, 1.5 Hz, 1H), 7.30–7.13 (m, 2H), 7.08–9.88 (m, 4H), 6.73 (dd, J=7.9, 1.3 Hz, 1H), 5.25 (d, J=17.2 Hz, 1H), 5.23 (d, J=17.3 Hz, 1H), 4.88 (dd, J=7.5, 5.5 Hz, 1H), 3.95 (apparent q, J=5.9 Hz, 2H), 2.40–2.20 (m, 2H), 2.19 (t, J=5.9 Hz, 1H). Anal. Calc'd for $C_{17}H_{16}ClNO_3$: C 64.26, H 5.08, N 4.41. Found: C 64.41, H 5.00, N 4.47.

REFERENCE EXAMPLE 43

Intermediate 12168-25-1

4-(3-Chlorobenzyl)-3,4-dihydro-2-(2-hydroxyethyl)-3-oxo-6-methoxy 2H-1,4-benzoxazine Prepared from 2-(2-tert-butyldimethylsiloxyethyl)-3,4-dihydro-6-methoxy-3-oxo-2H-1,4-benzoxazine by methods F and G, alkylating with 3-chlorobenzyl bromide, in 80% overall yield. Isolated by crystallization from EtOH/water to afford a white powder. MS (CI) 348 (MH$^+$); IR (KBr) 3501, 3053, 3021, 2959, 2933, 2876, 2838, 1664, 1618, 1600, 1575, 1512, 1466, 1445, 1435, 1390, 1361, 1337, 1313, 1272, 1237, 1201, 1173, 1107, 1078, 1049, 1030 cm$^{-1}$; $^1$H NMR (CDCl$_3$) δ7.27–7.20 (m, 3H), 7.13 (m, 1H), 6.94 (d, J=8.8 Hz, 1H), 6.52 (dd, J=9.1, 2.7 Hz, 1H), 6.41 (d, J=2.7 Hz, 1H), 5.12 (d, J=16.2 Hz, 1H), 4.79 (dd, J=8.2, 5.4 Hz, 1H), 3.92 (m, 2H), 3.68 (s, 3H), 3.39–2.16 (m, 2H), 2.17 (t, J=5.9 Hz, 1H). Anal. Calc'd for $C_{18}H_{18}ClNO_4 \cdot 0.25\,H_2O$: C 61.37, H 5.29, N 3.98. Found: C 61.35, H 5.14, N 3.95.

REFERENCE EXAMPLE 44

Intermediate 11578-41

4-(3-Chlorobenzyl)-3,4-dihydro-2-(2-hydroxyethyl)-3-oxo-6-phenyl-2H-1,4-benzoxazine Prepared from 2-(2-tert-butyldimethylsiloxyethyl)-3,4-dihydro-3-oxo-6-phenyl-2H-1,4-benzoxazine by Methods F and G, alkylating with 3-chlorobenzyl bromide, to afford a white crystalline solid in 27% overall yield, mp 119°–121° C.; IR (KBr) 3517, 1659, 1487, 1435, 1387, 1282, 1260, 1060, 760 cm$^{-1}$; $^1$H NMR (CDCl$_3$) δ2.22–2.38 (m, 3H), 3.95 (v br s, 2H), 4.90 (dd, J=7.6, 5.5 Hz, 1H), 5.18 (ABq, J$_{AB}$=17.1 Hz, 2H), 7.04 (d, J=1.9 Hz, 1H), 7.08 (d, J=8.3 Hz, 1H), 7.15–7.42 (m, 10H); MH$^+$ at m/z=394; Anal. Calc'd for $C_{23}H_{20}ClNO_3$: C, 70.14; H, 5.12; N, 3.56. Found: C, 70.10; H, 5.11; N, 3.51.

REFERENCE EXAMPLE 45

Intermediate 10508-24-A 4-(3-Fluorobenzyl)-3,4-dihydro-2-(2-hydroxyethyl)-3-oxo-2H-1,4-benzoxazine Prepared from 2-(2-tert-butyldimethylsiloxyethyl)-3,4-dihydro-3-oxo-2H-1,4-benzoxazine by Methods F and G, alkylating with 3-flourobenzyl chloride, in 49% overall yield and isolated as a gummy solid; IR (KBr) 3425, 1683, 1501, 1401, 1252, 1061, 751 cm$^{-1}$; $^1$H NMR (CDCl$_3$) δ2.16–2.38 (m, 3H), 3.92 (t, J=5.8 Hz, 2H), 4.85 (dd, J=7.6, 5.5 Hz, 1H), 5.14 (s, 2H), 6.82–6.85 (m, 1H), 6.90–7.08 (m, 6H), 7.26–7.33 (m, 1H); MH+ at m/z=302; Anal. Calc'd for $C_{17}H_{16}FNO_3$: C, 67.76; H, 5.35; N, 4.65. Found: C, 67.48; H, 5.34; N, 4.57.

REFERENCE EXAMPLE 46

Intermediate 10840-33

3,4-Dihydro-2-(2-hydroxyethyl)-4-(4-methylbenzyl)-3-oxo-2H-1,4-benzoxazine

Prepared from 2-(2-tert-butyldimethylsiloxyethyl)-3,4-dihydro-3-oxo-2H-1,4-benzoxazine by Methods F and G alkylating with 4-methylbenzyl chloride, in 50% overall yield. This material was crystallized from ether to afford a white solid, mp 92°–94° C.; IR (KBr) 3496, 1659, 1503, 1405, 1304, 1283, 1248, 1063, 801 cm$^{-1}$; $^1$H NMR (CDCl$_3$) δ2.18–2.36 (m, 5H), 3.91 (q, J=5.7, 2H), 4.83 (dd, J=7.4, 5.7, 1H), 5.12 (s, 2H), 6.90–7.00 (m, 4H), 7.13 (s, 4H); MH$^+$ at m/z=298; Anal. Calc'd for $C_{18}H_{19}NO_3$: C, 72.71; H, 6.44; N, 4.71. Found: C, 72.71; H, 6.48; N, 4.65.

REFERENCE EXAMPLE 47

Intermediate 10508-19

3,4-Dihydro-2-(2-hydroxyethyl)-4-(4-methoxybenzyl)-3-oxo-2H-1,4-benzoxazine

Prepared from 2-(2-tert-butyldimethylsiloxyethyl)-3,4-dihydro-3-oxo-2H-1,4-benzoxazine by Methods F and G, alkylating with 4-methoxybenzyl chloride, in 48% overall yield after flash chromatography eluting with EtOAc/hexane, mp 80°–82° C.; IR (KBr) 3496, 1660, 1515, 1501, 1412, 1250, 1057, 754 cm$^{-1}$; $^1$H NMR (CDCl$_3$) δ 2.00 (v br s, 1H), 2.16–2.37 (m, 2H), 3.77 (s, 3H), 3.91 (t, J=6.1 Hz, 2H), 4.82 (dd, J=7.5, 5.6 Hz, 1H), 5.09 (s, 2H), 6.85 (d, J=8.7 Hz, 2H), 6.91–7.00 (m, 4H), 7.18 (d, J=8.7 Hz, 2H); MH+ at m/z=314; Anal. Calc'd for $C_{18}H_{19}NO_4$: C, 68.99; H, 6.11; N, 4.47. Found: C, 69.22; H, 6.10; N, 4.35.

REFERENCE EXAMPLE 48

Intermediate 10005-181-1

4-(3,5-Dichlorobenzyl)-3,4-dihydro-2-(2-hydroxyethyl)-3-oxo-2H-1,4-benzoxazine

Prepared from 2-(2-tert-butyldimethylsiloxyethyl)-3,4-dihydro-3-oxo-2H-1,4-benzoxazine by Methods F and G, alkylating with 3,5-dichlorobenzyl chloride, in 89% overall yield. A sample was crystallized from CH$_2$Cl$_2$/hexane/ether to afford a white solid, mp 104°–106° C.; IR (KBr) 3525, 1680, 1570, 1505, 1398, 1063, 760 cm$^{-1}$; $^1$H NMR (CDCl$_3$) δ1.92 (brs, 1H), 2.17–2.37 (m, 2H), 3.93 (t, J=5.7 Hz, 2H), 4.87 (q, J=5.4 Hz, 1H), 5.13 (ABq, J$_{AB}$=16.3 Hz, 2H), 6.78 (d, J=7.3 Hz, 1H), 6.93–7.05 (m, 2H), 7.12 (br d, J=1.7 Hz, 2H), 7.26–7.28 (m, 2H); Anal. Calc'd for $C_{17}H_{15}Cl_2NO_3$: C, 57.97; H, 4.29; N, 3.98. Found: C, 57.96; H, 4.17; N, 3.87.

REFERENCE EXAMPLE 49

Intermediate 11578-71

6-Chloro-4-(3-chlorobenzyl)-3,4-dihydro-2-(2-hydroxyethyl)-3-oxo-2H-1,4-benzoxazine Prepared from intermediate 11578-70 (Reference Example 35) by Methods F and G, alkylating with 3-chlorobenzyl bromide, and isolated in 43% overall yield as a white solid, mp 90°–92° C.; IR (KBr) 3499, 1663, 1601, 1497, 1433, 1386, 1324, 1267, 1091, 1050, 933, 783 cm$^{-1}$; $^1$H NMR (CDCl$_3$) δ2.05 (br s, 1H), 2.18–2.30 (m, 2H), 3.89–3.97 (m, 2H), 4.86 (dd, J=7.7, 5.5 Hz, 1H), 5.1 (s, 2H), 6.81 (s, 1H), 6.96 (d, J=1.4 Hz, 2H), 7.12–7.30 (m, 4H); MH$^+$ at m/z=352; Anal. Calc'd for $C_{17}H_{15}Cl_2NO_3$: C, 57.95; H, 4.29; N, 3.98. Found: C, 58.26; H, 4.32; N, 3.89.

REFERENCE EXAMPLE 50

Intermediate 11578-56

4-(3-Chlorobenzyl)-6-trifluoromethyl-3,4-dihydro-2-(2-hydroxyethyl)-3-oxo-2H-1,4-benzoxazine 0.2 Hydrate Prepared from intermediate 12168-8-1 (Reference Example 29) by methods F and G, alkylating with 3-chlorobenzyl bromide, in 96% yield as a white crystalline solid, mp 92°–94° C.; IR (KBr) 3520, 1671, 1454, 1330, 1299, 1269, 1120, 868, 712 cm$^{-1}$; $^1$H NMR (CDCl$_3$) δ2.20–2.40 (m, 2H), 3.92 (t, J=6.3 Hz, 2H), 4.93 (t, J=7.6 Hz, 1H), 5.14 (s, 2H), 7.07–7.16 (m, 3H), 7.23–7.30 (m, 4H); MH$^+$ at m/z=386; Anal. Calc'd for C$_{18}$H$_{15}$ClF$_3$NO$_3$.0.2H$_2$O: C, 55.52; H, 3.99; N, 3.60. Found: C, 55.49; H, 3.77; N, 3.53.

REFERENCE EXAMPLE 51

Intermediate 11578-77

6-Carbomethoxy-4-(3-chlorobenzyl)-3,4-dihydro-2-(2-hydroxyethyl)-3-oxo-2H-1,4-benzoxazine Prepared from 2-(2-tert-butyldimethylsiloxyethyl)-6-carbomethoxy-3,4-dihydro-3-oxo-2H-1,4-benzoxazine by Methods F and G, alkylating with 3-chlorobenzyl bromide, in 70% overall yield as a white solid, after trituration with hexane, IR (KBr) 3468, 2952, 1688, 1452, 1285, 1260, 765 cm$^{-1}$; $^1$H NMR (CDCl$_3$) δ1.61 (br s, 1H plus HDO), 2.17–2.39 (m, 2H), 3.86 (s, 3H), 3.93 (t, J=5.7 Hz, 2H), 4.94 (dd, J=7.6, 5.5 Hz, 1H), 5.16 (s, 2H), 7.04 (d, J=8.4, 1H), 7.15–7.33 (m, 4H), 7.59 (d, J=1.8 Hz, 1H), 7.71 (dd, J=8.4, 1.8 Hz, 1H); MH$^+$ at m/z=376; Anal. Calc'd for C$_{19}$H$_{18}$ClNO$_5$.0.1H$_2$O: C, 60.44; H, 4.86; N, 3.71. Found: C, 60.26; H, 4.60; N, 3.58.

REFERENCE EXAMPLE 52

Intermediate 11578-47

4-(3-Chlorobenzyl)-3,4-dihydro-7-fluoro-2-(2-hydroxyethyl)-3-oxo-2H-1,4-benzoxazine Prepared from intermediate 11578-44 (Reference Example 36) by Methods F and G, alkylating with 3-chlorobenzyl bromide, in 76% overall yield. This material was isolated as an off-white solid, mp 79°–82° C.; IR (KBr) 3487, 1662, 1508, 1412, 1320, 1155, 1115, 1053, 854, 799 cm$^{-1}$; $^1$H NMR (CDCl$_3$) δ2.10 (t, J=4.3 Hz, 1H), 2.18–2.40 (m, 2H), 3.92 (q, J=6.0 Hz, 2H), 4.88 (t, J=5.5 Hz, 1H), 5.10 (ABq, J$_{AB}$=15.4 Hz, 2H), 6.64 (td, J=7.9, 2.7 Hz, 1H), 6.72–6.79 (m, 2H), 7.11 (br s, 1H), 7.22–7.28 (m, 3H plus CHCl$_3$); MH$^+$ at m/z=336; Anal. Calc'd for C$_{17}$H$_{15}$ClFNO$_3$: C, 60.81; H, 4.50; N, 4.17. Found: C, 60.74; H, 4.69; N, 4.28.

REFERENCE EXAMPLE 53

Intermediate 11578-113

7-Fluoro-3,4-dihydro-4-(3-fluorobenzyl)-2-(2-hydroxyethyl)-3-oxo-2H-1,4-benzoxazine Prepared from intermediate 11578-44 (Reference Example 36) by Methods F and G, alkylating with 3-fluorobenzyl chloride, to afford a white solid in 67% yield, mp 78°–79° C.; IR (KBr) 3497, 1661, 1509, 1415, 1252, 1159, 1119, 1057, 937, 857, 801 cm$^{-1}$; $^1$H NMR (CDCl$_3$) δ2.11 (t, J=5.1 Hz, 1H), 2.17–2.39 (m, 2H), 3.92 (q, J=5.5 Hz, 2H), 4.87 (dd, J=7.6, 5.5 Hz, 1H), 5.13 (s, H), 6.64 (td, J=8.0, 2.7 Hz, 1H), 6.73–6.79 (m, 2H), 6.94 (t, J=8.5 Hz, 2H), 7.01 (s, J=7.7 Hz, 1H), 7.27–7.35 (m, 1H); MH$^+$at m/z=320; Anal. Calc'd for C$_{17}$H$_{15}$F$_2$NO$_3$: C, 63.95; H, 4.74; N, 4.39. Found: C, 63.91; H, 4.70; N, 4.30.

REFERENCE EXAMPLE 54

Intermediate 11578-114

7-Fluoro-3,4-dihydro-2-(2-hydroxyethyl)-4-(2-nitrobenzyl)-3-oxo-2H-1,4-benzoxazine Prepared from intermediate 11578-44 (Reference Example 36) by Methods F and G, alkylating with 2-nitrobenzyl chloride, to afford a white solid after column chromatography, eluting with ether, in 76% yield. A portion of this material was crystallized from hexane, mp 123°–124° C.; IR (KBr) 3510, 1655, 1527, 1509, 1357, 1157, 1127, 1063, 801 cm$^{-1}$; $^1$H NMR (CDCl$_3$) δ2.01 (t, J=5.1 Hz, 1H), 2.22–2.38 (m, 2H), 3.93 (q, J=5.6 Hz, 2H), 4.92 (dd, J=7.54, 5.63 Hz, 1H), 5.23 (ABq, J$_{AB}$=16.5 Hz, 2H), 6.63–6.75 (m, 2H), 6.80 (dd, J=8.7, 2.6 Hz, 1H), 7.51–7.60 (m, 2H), 8.12 (s, 1H), 8.15 (d, J=7.1 Hz, 1H); MH$^+$ at m/z=347; Anal. Calc'd for C$_{17}$H$_{15}$FN$_2$O$_5$: C, 58.96; H, 4.37; N, 8.09. Found: C, 58.81; H, 4.37; N, 8.01.

REFERENCE EXAMPLE 55

Intermediate 11578-52

4-(3-Chlorobenzyl)-3,4-dihydro-2-(2-hydroxyethyl)-7-methyl-3-oxo-2H-1,4-benzoxazine Prepared from 2-(2-tert-butyldimethylsiloxyethyl)-3,4-dihydro-7-methyl-3-oxo-2H-1,4-benzoxazine by Methods F and G, alkylating with 3-chlorobenzyl bromide, in 76% yield as a white solid after crystallization from ether/hexane, mp 72°–74° C.; IR (KBr) 3418, 1679, 1512, 1402, 1292, 1061, 763 cm$^{-1}$; $^1$H NMR (CDCl$_3$) δ2.20–2.36 (m, 3H), 2.27 (s, 3H), 3.92 (q, J=5.6 Hz, 2H), 4.83 (dd, J=7.6, 5.5 Hz, 1H), 5.10 (ABq, J$_{AB}$=17.0 Hz, 2H), 6.68–6.75 (m, 2H), 6.84 (s, 1H), 7.10–7.14 (m, 1H), 7.22–7.29 (m, 3H); MH$^+$at m/z=332; Anal. Calc'd for C$_{18}$H$_{18}$ClNO$_3$.0.2H$_2$O: C, 64.46; H, 5.53; N, 4.18. Found: C, 64.48; H, 5.51; N, 4.06.

REFERENCE EXAMPLE 56

Intermediate 11578-33

4-(3-Chlorobenzyl)-6,8-dichloro-3,4-dihydro-2-(2-hydroxyethyl)-3-oxo-2H-1,4-benzoxazine Prepared from intermediate 11578-30 (Reference Example 37) by Methods F and G, alkylating with 3-chlorobenzyl bromide, in 80% yield. This material was isolated as a white foam after flash chromatography using ether/CH$_2$Cl$_2$ (¼); IR (KBr) 3430, 1694, 1592, 1480, 1434, 1380, 1285, 1059, 933, 843, 755 cm$^{-1}$; $^1$H NMR (CDCl$_3$) 2.00 (t, J=5.4 Hz, 1H), 2.15–2.40 (m, 2H), 3.92–4.03 (m, 2H), 4.97 (dd, J=8.8, 4.7 Hz, 1H), 5.09 (s, 2H), 6.72 (d, J=2.3 Hz, 1H), 7.08 (d, J=2.2 Hz, 2H), 7.20 (s, 1H), 7.26–7.30 (m, 2H plus CHCl$_3$); Anal. Calc'd for C$_{17}$H$_{14}$Cl$_3$NO$_3$: C, 52.81; H, 3.65; N, 3.62. Found: C, 52.90; H, 3.73; N, 3.46.

REFERENCE EXAMPLE 57

Intermediate 10840-18

3,4-Dihydro-2-(2-hydroxyethyl)-3-oxo-4-(2-picolyl)-2H-1,4-benzoxazine 2-(2-tert-Butyldimethylsiloxyethyl)-3,4-dihydro-3-oxo-2H-1,4-benzoxazine was alkylated with 2-chloromethylpyridine by method F and the crude product was deprotected by method H without purification.

Method H: The t-butyldimethylsiloxy intermediate was dissolved in methanol and an excess of 6N HCl. The solution was stirred at room temperature 1 h and then concentrated under vacuum. The aqueous residue was extracted with dichloromethane and the combined extract was washed with brine and dried over Na$_2$SO$_4$. Removal of solvent produced the crude product which was purified by flash chromatography in 42% yield and was isolated as a white solid after crystallization from ether/hexane, mp 108°–111° C.; IR (KBr) 2881, 1675, 1505, 1401, 1279, 1115, 1070, 749 cm$^{-1}$; $^1$H NMR (CDCl$_3$) δ2.18–2.38 (m, 2H), 2.44 (br s, 1H), 3.92 (br d, J=3.8 Hz, 2H), 4.86 (dd, J=7.2, 5.8 Hz, 1H), 5.27 (ABq, J$_{AB}$=16.3 Hz, 2H), 6.89–7.03 (m, 4H), 7.17–7.24 (m, 2H), 7.64 (td, J=7.7, 1.7 Hz, 1H), 8.56 (br d, J=4.3 Hz, 1H); MH$^+$ at m/z=285; Anal. Calc'd for C$_{16}$H$_{16}$N2O3: C, 67.59; H, 5.67; N, 9.85. Found: C, 67.55; H, 5.83; N, 9.83.

REFERENCE EXAMPLE 58

Intermediate 10840-22

3,4-Dihydro-2-(2-hydroxyethyl)-3-oxo-4-(4-picolyl)-2H-1,4-benzoxazine

Prepared from 2-(2-tert-butyldimethylsiloxyethyl)-3,4-dihydro-3-oxo-2H-1,4-benzoxazine by Methods F and H, alkylating with 4-chloromethylpyridine, in 12% yield and isolated as a beige solid, mp 153°–154° C.; IR (KBr) 3204, 1679, 1505, 1407, 1283, 1256, 1077, 1065, 750 cm$^{-1}$; $^1$H NMR (CDCl$_3$) δ2.18–2.38 (m, 3H), 3.93 (br q, J=3.9 Hz, 2H), 4.88 (dd, J=7.7, 5.4 Hz, 1H), 5.15 (s, 2H), 6.73 (d, J=7.6 Hz, 1H), 6.92 (td, J=6.7, 3.2 Hz, 1H), 6.98–7.06 (m, 2H), 7.15 (d, J=5.9 Hz, 2H), 8.56 (dd, J=4.5, 1.5 Hz, 2H); MH$^+$ at m/z=285; Anal. Calc'd for C$_{16}$H$_{16}$N$_2$O$_3$: C, 67.59; H, 5.67; N, 9.85. Found: C, 67.67; H, 5.78; N, 9.79.

REFERENCE EXAMPLE 59

Intermediate 11578-99

3,4-Dihydro-2-(2-hydroxyethyl)-4-(4-phenylbenzyl)-3-oxo-2H-1,4-benzoxazine

Prepared from 2-(2-tert-butyldimethylsiloxyethyl)-3,4-dihydro-3-oxo-2H- 1,4-benzoxazine by Methods F and G, alkylating with 4-phenylbenzyl chloride, in 98% yield as a yellow crystalline solid, mp 110°–113° C.; IR (KBr) 3350, 1683, 1500, 1400, 1304, 1275, 1247, 1051, 908, 758 cm$^{-1}$; $^1$H NMR (CDCl$_3$) δ2.21–2.38 (m, 2H), 3.94 (q, J=5.48 Hz, 2H), 4.87 (dd, J=7.5, 5.61 Hz, 1H), 5.20 (ABq, J$_{AB}$=17.1 Hz, 2H), 6.93–7.04 (m, 4H), 7.30–7.40 (m, 3H), 7.43 (t, J=7.0 Hz, 2H), 7.55 (d, J=8.1 Hz, 4H); MH$^+$ at m/z=360; Anal. Calc'd for C$_{23}$H$_{21}$NO$_3$: C, 76.86; H, 5.89; N, 3.90. Found: C, 76.61; H, 5.88; N, 3.74.

4-Phenylbenzyl chloride was prepared by treating a CH$_2$Cl$_2$ solution of the corresponding alcohol (1 eq) with methanesulfonyl chloride (1.1 eq) and TEA (1.1 eq) at 0° C. This solution was stirred for 16 h, treated with 3N HCl and the organic layer was isolated. After drying, the solvent was evaporated to afford the 4-phenylbenzyl chloride in 64% yield, MH$^+$ at m/z=202.

REFERENCE EXAMPLE 60

Intermediate 10840-185

3,4-Dihydro-2-(2-hydroxyethyl)-3-oxo-4-pentyl-2H-1,4-benzoxazine

Prepared from 2-(2-tert-butyldimethylsiloxyethyl)-3,4-dihydro-3-oxo-2H-1,4-benzoxazine by Methods F and G, alkylating with 1-chloropentane in 32% yield and isolated as a colorless oil; IR (KBr) 3424, 2956, 2932, 1680, 1500, 1272, 1062, 749 cm$^{-1}$; $^1$H NMR (CDCl$_3$) δ0.91 (t, J=6.8 Hz, 3H), 1.31–1.38 (m, 4H), 1.66 (br t, J=5.5 Hz, 2H), 2.08–2.29 (m, 2H), 2.59 (br s, 1H), 3.87–3.94 (m, 2H), 4.69 (dd, J=7.3, 5.8 Hz, 1H), 6.92–7.08 (m, 4H); Anal. Calc'd for C$_{15}$H$_{21}$NO$_3$: C, 68.42; H, 8.04; N, 5.32. Found: C, 68.10; H, 7.88; N, 5.32.

REFERENCE EXAMPLE 61

Intermediate 11653-180

3,4-Dihydro-2-(2-hydroxyethyl)-4-(3-nitrobenzyl)-3-oxo-2H-1,4-benzoxazine

The intermediate silyl protected alcohol was prepared from 2-(2-tert-butyldimethylsiloxyethyl)-3,4-dihydro-3-oxo-2H-1,4-benzoxazine by Method F, alkylating with 3-nitrobenzyl chloride. Deprotection to the indicated product was carried out by method I.

Method I: The TBDMS-protected benzoxazine (3.1 mmol) was stirred into a milky mixture with AcOH (12 mL), THF (2 mL) and H$_2$O (5 mL). This mixture was stirred for 18 h to give a clear solution. The addition of water gave a white solid precipitate which was filtered and dried in vacuo at 80° C: mp 103°–104° C.; MS (CI) MH$^+$329; IR (KBr) 3490, 3087, 2947, 2879, 1685, 1663, 1607, 1593, 1466, 1280, 1168, 976 cm$^{-1}$; $^1$H NMR (CDCl$_3$) δ8.15 (s, 1H), 8.13 (s, 1H), 7.54 (m, 2H), 7.04 (m, 2H), 6.95 (m, 1H), 6.79 (d, 1H, J=7.6 Hz), 5.28 (d, 1H, J=16.5 Hz), 5.21 (d, 1H, J=16.5 Hz), 4.90 (dd, 1H, J=5.5, 7.6 Hz), 3.93 (m, 2H), 2.29 (m, 2H), 2.13 (t, 1H, J=5.6 Hz). Anal. Calc'd for C$_{17}$H$_{16}$N$_2$O$_5$: C 62.19, H 4.91, N 8.53. Found: C 61.99, H 4.91, N 8.43.

REFERENCE EXAMPLE 62

Intermediate 12279-11

3,4-Dihydro-2-(2-hydroxyethyl)-7-nitro-4-(4-nitrobenzyl)-3-oxo-2H-1,4-benzoxazine Prepared from intermediate 11653-23 (Reference Example 31) by methods F and I and isolated as a yellow-orange solid in 42% yield, mp 100°–104° C.; MS (CI) MH$^+$ 374; IR (KBr) 3395, 3113, 3089, 2939, 1683, 1598, 1432, 1395, 1142, 991, 914, 800, 544, 455 cm$^{-1}$; $^1$H NMR (CDCl$_3$) δ8.23 (d, 2H, J=8.70 Hz), 7.92 (d, 1H, J=2.42 Hz), 7.85 (dd, 1H, J=8.85, 2.54 Hz), 7.41 (d, 2H, J=8.60 Hz), 6.85 (d, 1H, J=8.93), 5.30 (d, 2H, J=4.56 Hz), 5.01 (dd, 1H, J=7.76, 5.11 Hz), 3.96 (t, 2H, J=6.45 Hz), 2.30 (m, 2H), 1.79 (br.s, 1H). Anal. Calc'd for C$_{17}$H$_{15}$N$_3$O$_7$.0.7 H$_2$O: C 52.91, H 4.28, N 10.89. Found: C 53.17, H 4.36, N 10.53.

REFERENCE EXAMPLE 63

Intermediate 12279-18-A 3,4-Dihydro-2-(2-hydroxyethyl)-7-methoxy-4-(3-nitrobenzyl)-3-oxo-2H-1,4-benzoxazine Prepared from 2-(2-tert-butyldimethylsiloxyethyl)-3,4-dihydro-7-methoxy-3-oxo-2H-1,4-benzoxazine by methods F and I, alkylating with 3-nitrobenzyl chloride, in 30% yield, mp 116°–118° C.; MS (CI) MH$^+$ 359; IR (KBr) 3306, 3086, 2926, 2872, 1628, 1595, 1476, 1309, 1290, 1255, 1087, 999, 713, 458 cm$^{-1}$; $^1$H NMR (DMSO-d$_6$) δ8.14 (s, 1H), 8.11 (s, 1H), 7.63 (m, 2H), 6.97 (d, 1H, J=8.93 Hz), 6.66 (d, 1H, J=2.42 Hz), 6.53 (d, 1H, J=8.87 Hz), 5.26 (s, 2H), 4.87 (dd, 1H, J=8.98, 3.76 Hz), 4.72 (t, 1H, J=5.23 Hz), 3.68 (s, 3H), 3.61 (m, 2H), 2.01 (m, 1H), 1.90 (m, 1H). Anal. Calc'd for C$_{18}$H$_{18}$N$_2$O$_6$: C 60.33 H 5.06, N 7.82. Found: C 59.96, H 5.08, N 7.62.

REFERENCE EXAMPLE 64

Intermediate 12279-21

3,4-Dihydro-6-fluoro-2-(2-hydroxyethyl)-4-(3-nitrobenzyl)-3-oxo-2H-1,4-benzoxazine Prepared from intermediate 11653-163-A1 (Reference Example 33) by methods F and I, alkylating with 3-nitrobenzyl chloride, in 35% yield, mp 110°–112° C.; MS (CI) MH⁺ 347; IR (KBr) 3483, 3077, 2945, 2872, 1620, 1603, 1453, 1297, 1210, 1098, 979, 791, 742, 685, 470 cm⁻¹; ¹H NMR (CDCl₃) δ8.16 (d, 1H, J=6.87 Hz), 8.10 (s, 1H), 7.54 (m, 2H), 6.90 (dd, 1H, J=3.73, 5.12 Hz), 6.71 (m, 1H), 6.51 (dd, 1H, J=9.35, 2.76 Hz), 5.20 (d, 2H, J=5.46 Hz), 4.87 (dd, 1H, J=7.60, 5.41 Hz), 3.93 (t, 2H, J=5.78 Hz), 2.29 (m, 2H), 2.00 (m, 1H). Anal. Calc'd for $C_{17}H_{15}FN_2O_5$: C 58.96, H 4.37, N 8.09. Found: C 58.57, H 4.43, N 7.89.

REFERENCE EXAMPLE 65

Intermediate 12279-13-A 4-(3-Aminobenzyl)-3,4-dihydro-2-(2-hydroxyethyl)-3-oxo-2H-1,4-benzoxazine Prepared by dissolving the intermediate t-butyldimethylsiloxy compound from example 11653-180 (1.58 g, Reference Example 61) in ethanol (25 ml). Fe powder (1.3 g) was added with stirring, followed by conc. HCl (12 ml). The reaction was stirred at room temperature for 16 hrs. The reaction was filtered directly into ice water, and extracted with EtOAc. The extract was washed with brine, and concentrated under vacuum. The resulting brown oil was rinsed in ether. After decanting the ether, the oil was scratched to produce the product as a light brown solid in 50% yield, mp 79° C.—darkens, 85°–90° C.—melts; MS (CI) MH. 299; IR (KBr) 3470, 3373, 3215, 3031, 2930, 2877, 1657, 1605, 1590, 1465, 1441, 1356, 1251, 1183, 1165, 1101, 1016, 995, 898, 688, 560 cm⁻¹; ¹H NMR (CDCl₃) 257.10 (t, 1H, J=7.70 Hz), 7.10–6.20(v br.s, 2H), 6.98 (m, 2H), 6.93 (m, 2H), 6.63 (d, 1H, J=7.8 Hz), 6.56 (d, s, 2H, J=8.6 Hz), 5.10 (d, 1H, J=16.0 Hz), 5.00 (d, 1H, J=16.0 Hz), 4.83 (dd, 1H, J=5.61, 7.45 Hz), 3.91 (q, 2H, J=5.4 Hz), 3.85–3.20(v br.s, 1H), 2.23 (m, 2H). Anal. Calc'd for $C_{17}H_{18}N_2O_3 \cdot 0.1 H_2O$: C 68.03, H 6.11, N 9.33. Found: C 67.93, H 6.05, N 9.05.

REFERENCE EXAMPLE 66

Intermediate 10488-22

4-(3-Chlorobenzyl)-3,4-dihydro-2-(2-hydroxyethyl)-3-oxo-2H-1,4-benzoxazine

Prepared by methods F and G, alkylating with 3-chlorobenzyl bromide, in 55% yield. The product was isolated as an oil which could be crystallized from Et₂O/Hexane, mp 63°–67° C.; MS (CI) MH⁺318; IR (KBr) 3477, 2927, 2863, 1688, 1599, 1576, 1503, 1466, 1217, 1109, 931, 903 cm⁻¹; ¹H NMR (CDCl₃) 7.26 (m, 3H), 7.12 (m, 1H), 7.01 (m, 2H), 6.94 (m, 1H), 6.82 (m, 1H), 5.15 (d, 1H, J=16.3 Hz), 5.08 (d, 1H, J=16.2 Hz), 4.85 (dd, 1H, J=5.5, 7.6 Hz), 3.92 (d, 2H, J=4.9 Hz), 2.39–2.14 (br. m, 3H). Anal. Calc'd for $C_{17}H_{16}ClNO_3$: C 64.26, H 5.08, N 4.44. Found: C 63.89, H 5.00, N 4.13.

REFERENCE EXAMPLE 67

Intermediate 11653-85-B-1

3,4-Dihydro-2-(2-hydroxyethyl)-7-nitro-4-(3-nitrobenzyl)-3-oxo-2H-1,4-benzoxazine Prepared from intermediate 11653-23 (Reference Example 31) by methods F and G, alkylating with 3-nitrobenzyl chloride, in 66% yield, mp 157°–160° C.; MS (CI) MH⁺374; IR (KBr) 3592, 3433, 3087, 2926, 2892, 1671, 1598, 1525, 1482, 1433, 1219, 1168, 1097, 838 cm⁻¹; ¹H NMR (DMSO-d₆) δ8.17 (s, 1H), 8.13 (s, 1H), 7.86 (s, 1H), 7.83 (d, 1H, J=2.5 Hz), 7.65 (d, 1H, J=7.8 Hz), 7.58 (t, 1H, J=7.8 Hz), 7.08 (d, 1H, J=9.2 Hz), 5.40 (d, 1H, J=16.5 Hz), 5.31 (d, 1H, J=16.6), 5.07 (dd, 1H, J=4.0, 9.0 Hz), 4.57 (t, 1H, J=5.2 Hz), 3.80 (m, 2H), 2.23 (m, 1H), 2.10 (m, 1H). Anal. Calc'd for $C_{17}H_{15}N_3O_7$: C 54.69, H 4.05, N 11.26. Found: C 54.57, H 4.04, N 11.08.

REFERENCE EXAMPLE 68

Intermediate 11653-58C 4-(3-Chlorobenzyl)-3,4-dihydro-2-(2-hydroxyethyl)-6-nitro-3-oxo-2H-benzoxazine Prepared from intermediate 11653-33A (Reference Example 32) by methods F and G, alkylating with 3-chlorobenzyl bromide, in 77% yield, mp >38° C. (dec); MS (CI) MH⁺363; IR (KBr) 3855, 3745, 3423, 1686, 1590, 1522, 1448, 1389, 1343, 1267, 1056, 875, 778, 680 cm⁻¹; ¹H NMR (CDCl₃) δ7.93 (dd, 1H, J=2.5, 8.8 Hz), 7.78 (d, 1H, J=2.5 Hz), 7.30 (m, 3H), 7.19 (m, 1H), 7.10 (d, 1H, J=8.8 Hz), 5.20 (d, 1H, J=16.3 Hz), 5.14 (d, 1H, J=16.2 Hz), 5.03 (dd, 1H, J=5.3, 7.6 Hz), 3.93 (t, 2H, J=6.2 Hz), 2.41–2.19 (m, 2H), 1.71 (br s, 1H). Anal. Calc'd for $C_{17}H_{15}Cl N_2O_5$: C 56.29, H 4.17, N 7.72. Found: C 56.19, H 4.22, N 7.55.

REFERENCE EXAMPLE 69

Intermediate 11653-142

3,4-Dihydro-2-(2-hydroxyethyl)-7-nitro-4-(2-nitrobenzyl)-3-oxo-2H-1,4-benzoxazine Prepared from intermediate 11653-23 (Reference Example 31) by methods F and I, alkylating with 2-nitrobenzyl chloride, in 52% yield, mp 139°–143° C.; MS (CI) MH⁺ 374; IR (KBr) 3569, 3122, 3088, 2942, 2892, 1693, 1600, 1530, 1501, 1420, 1390, 1254, 1059, 888, 727 cm⁻¹; ¹H NMR (DMSO-d₆) δ8.24 (dd, 1H, J=1.2, 8.0 Hz), 7.90 (d, 1H, J=2.5 Hz), 7.83 (dd, 1H, J=2.6, 8.9 Hz), 7.62 (m, 2H), 7.20 (d, 2H, J=8.9 Hz), 5.59 (d, 1H, J=18.2 Hz), 5.49 (d, 1H, J=18.2 Hz), 5.16 (dd, 1H, J=4.4, 8.5 Hz), 4.79 (t, 1H, J=5.2 Hz), 3.66 (m, 2H), 2.05 (m, 2H). Anal. Calc'd for $C_{17}H_{15}N_3 O_7$: C 54.69, H 4.05, N 11.26. Found: C 54.81, H 4.03, N 11.07.

REFERENCE EXAMPLE 70

Intermediate 11653-44A 4-(2-Chlorobenzyl)-3,4-dihydro-2-(2-hydroxyethyl)-6-nitro-3-oxo-2H-benzoxazine Prepared from intermediate 11653-33A (Reference Example 32) by methods F and G, alkylating with 2-chlorobenzyl chloride, in 23% yield, mp 108°–110° C.; MS (CI) MH⁺363; IR (KBr) 3520, 3092, 2984, 2938, 2889, 1906, 1775, 1588, 1474, 1446, 1316, 1253, 1185, 1127, 1112, 926, 680 cm⁻¹; ¹H NMR (DMSO-d₆) δ7.94 (dd, 1H, J=2.5, 8.8 Hz), 7.62 (d, 1H, J=2.5 Hz), 7.56 (d, 1H, J=7.6 Hz), 7.31 (m, 3H), 7.15 (d, 1H, J=7.3 Hz), 5.25 (s, 2H), 5.16 (dd, 1H, J=4.2, 8.5 Hz), 4.78 (t, 1H, J=5.2 Hz), 3.63 (m, 2H), 2.09 (m, 2H). Anal. Calc'd for $C_{17}H_{15}ClN_2O_5$: C 56.29, H 4.17, N 7.72. Found: C 56.19, H 4.10, N 7.58.

REFERENCE EXAMPLE 71

Intermediate 11653-173

3,4-Dihydro-2-(2-hydroxyethyl)-4-(4-nitrobenzyl)-3-oxo-2H-1,4-benzoxazine

Prepared from 2-(2-tert-butyldimethylsiloxyethyl)-3,4-dihydro-3-oxo-2H-1,4-benzoxazine by methods F and I, alkylating with 4-nitrobenzyl chloride, in 89% yield, mp 124°–127° C.; MS (CI) MH+ 329; IR (KBr) 3498, 3076, 2930, 2863, 1656, 1605, 1500, 1466, 1302, 1279, 1184, 1126, 982, 613 cm$^{-1}$; $^1$H NMR (CDCl$_3$) δ8.20 (dd, 2H, J=2.0, 6.9 Hz), 7.40 (d, 2H, J=8.8 Hz), 7.03 (m, 2H), 6.93 (m, 1H), 6.75 (d, 1H, J=7.6 Hz), 5.25 (s, 2H), 4.88 (dd, 1H, J=5.4, 7.6 Hz), 3.93 (m, 2H), 2.38–2.17 (m, 2H), 2.10 (m, 1H). Anal. Calc'd for C$_{17}$H$_{16}$N$_2$O$_5$: C 62.19, H 4.91, N 8.54. Found: C 62.05, H 4.87, N 8.39.

REFERENCE EXAMPLE 72

Intermediate 11653-170-A2

4-Benzyl-3,4-dihydro-2-(2-hydroxyethyl)-7-nitro-3-oxo-2H-1,4-benzoxazine

Prepared from intermediate 11653-23 (Reference Example 31) by methods F and G, alkylating with benzyl bromide, in 98% yield, mp 102°–105° C.; MS (CI) MH+ 329; IR (KBr) 3561, 3086, 3062, 2970, 2932, 2873, 1698, 1598, 1500, 1452, 1075, 985 cm$^{-1}$; $^1$NMR (CDCl$_3$) δ7.88 (d, 1H, J=2.5 Hz), 7.82 (dd, 1H, J=2.5, 8.9 Hz), 7.34 (m, 3H), 7.23 (m, 2H), 6.96 (d, 1H, J=8.9 Hz), 5.23 (d, 1H, J=16.4 Hz), 5.17 (d, 1H, J=16.4 Hz), 4.80 (dd, 1H, J=5.1, 7.9 Hz), 3.94 (m, 2H), 2.34 (m, 1H), 2.28 (m, 1H), 1.98 (t, 1H, J=5.5 Hz). Anal. Calc'd for C$_{17}$H$_{16}$N$_2$O$_5$: C 62.19, H 4.91, 8.53. Found: C 61.81, H 4.63, N 8.36.

REFERENCE EXAMPLE 73

Intermediate 11653-174-A 3,4-Dihydro-2-(2-hydroxyethyl)-4-(3-nitrobenzyl)-3-oxo-2H-1,4-benzoxazine Prepared from 2-(2-tert-butyldimethylsiloxyethyl)-3,4-dihydro-3-oxo-2H-1,4-benzoxazine by methods F and I, alkylating with 2-nitrobenzyl chloride, in 3% yield, mp 128.5°–130° C.; MS (CI) MH+ 329; IR (KBr) 3850, 3495, 3074, 2974, 2949, 2896, 1658, 1605, 1576, 1515, 1503, 1468, 1426, 1362, 1218, 1163, 902 cm$^{-1}$; $^1$H NMR (DMSO-d$_6$) δ8.20 (dd, 1H, J=1.3, 8.1 Hz), 7.67 (t, 1H, J=7.6 Hz), 7.56 (t, 1H, J=7.0 Hz), 7.15 (d, 1H, J=7.0 Hz), 7.08 (d, 1H, J=7.7 Hz), 6.99 (m, 1H), 6.92 (d, 2H, J=3.7 Hz), 5.49 (d, 1H, J=18.2 Hz), 5.42 (d, 1H, J=18.1 Hz), 4.94 (dd, 1H, J=4.1, 9.0 Hz), 4.72 (t, 1H, J=5.2 Hz), 3.63 (m, 2H), 2.00 (m, 2H). Anal. Calc'd for C$_{17}$H$_{16}$N2O$_5$: C 62.19, H 4.91, N 8.53. Found: C 61.85, H 4.89, N 8.37.

REFERENCE EXAMPLE 74

Intermediate 10508-23-A

4-Benzyl-3,4-dihydro-2-(2-hydroxyethyl)-3-oxo-2H-1,4-benzoxazine

Prepared from 2-(2-tert-butyldimethylsiloxyethyl)-3,4-dihydro-3-oxo-2H-1,4-benzoxazine by Methods F and G, alkylating with benzyl chloride, in 49% overall yield and crystallized from ether/hexane to produce a white solid, mp 83°–85.5° C.; IR (KBr) 3213, 1680, 1505, 1399, 1250, 1050, 753 cm$^{-1}$; $^1$H NMR (CDCl$_3$) δ2.17–2.38 (m, 3H), 3.92 (q, J=5.7 Hz, 2H), 4.84 (dd, J=7.5, 5.6 Hz, 1H), 5.16 (s, 2H), 6.86–7.03 (m, 4H), 7.21–7.37 (m, 5H); MH+ at m/z=284; Anal. Calc'd for C$_{17}$H$_{17}$NO$_3$: C, 72.07; H, 6.05; N, 4.94. Found: C, 72.08; H, 6.20; N, 4.87.

REFERENCE EXAMPLE 75

Intermediate 10508-25-A 3,4-Dihydro-2-(2-hydroxyethyl)-4-(2-methoxybenzyl)-3-oxo-2H-1,4-benzoxazine Prepared from 2-(2-tert-butyldimethylsiloxyethyl)-3,4-dihydro-3-oxo-2H-1,4-benzoxazine by methods F and G, alkylating with the methanesulfonate ester of 2-methoxybenzyl alcohol, in 47% overall yield as a light yellow gum after flash chromatography, eluting with EtOAc/hexanes, IR (Neat) 3436, 2941, 1583, 1683, 1501, 1466, 1403, 1281, 1246, 1113, 1052, 751 cm$^{-1}$; $^1$H NMR (CDCl$_3$) δ2.18–2.36 (m, 2H), 2.39 (br t, J=6.0 Hz, 1H), 3.90 (s, 3H), 3.92 (br q, J=5.5 Hz, 2H), 4.85 (dd, J=7.4, 5.7 Hz, 1H), 5.15 (s, 2H), 6.81–7.03 (m, 7H), 7.23 (td, J=8.3, 1.7 Hz, 1H); MH+ at m/z=314; Anal. Calc'd for C$_{18}$H$_{19}$NO$_4$.0.2 H$_2$O: C, 68.21; H, 6.17; N, 4.42. Found: C, 68.36; H, 6.18; N, 4.36.

REFERENCE EXAMPLE 76

Intermediate 10508-22-A 3,4-Dihydro-2-(2-hydroxyethyl)-4-(3-methoxybenzyl)-3-oxo-2H-1,4-benzoxazine Prepared by Methods F and G, alkylating with 3-methoxybenzyl chloride, in 49% overall yield as a clear viscous gum, after flash chromatography eluting with 25–50% EtOAc in hexane, IR (Neat) 3433, 2941, 1683, 1583, 1501, 1466, 1403, 1262, 1152, 1052, 753 cm$^{-1}$; $^1$H NMR (CDCl$_3$) δ2.17–2.37 (m, 3H), 3.77 (s, 3H), 3.91 (br q, J=5.3 Hz, 2H), 4.84 (dd, J=7.5, 5.6 Hz, 1H), 5.12 (ABq, J$_{AB}$=17 Hz, 2H), 6.76–7.03 (m, 7H), 7.24 (td, J=7.6, 0.98 Hz, 1H); MH+ at m/z=31 4; Anal. Calc'd for C$_{18}$H$_{19}$NO$_4$: C, 68.99; H, 6.11; N, 4.47. Found: C, 68.54; H, 6.14; N, 4.33.

REFERENCE EXAMPLE 77

Intermediate 10508-82-A 4-(3-Benzyloxybenzyl)-3,4-dihydro-2-(2-hydroxyethyl)-3-oxo-2H-1,4-benzoxazine Prepared from 2-(2-tert-butyldimethylsiloxyethyl)-3,4-dihydro-3-oxo-2H-1,4-benzoxazine by Methods F and G, alkylating with the methanesulfonate ester of 3-benzyloxybenzyl alcohol, in 67% overall yield as a viscous liquid, after flash chromatography eluting with 30–100% EtOAc in hexane, IR (CHCl$_3$) 3434, 2933, 1681, 1500, 1401, 1256, 1054, 751 cm$^{-1}$; $^1$H NMR (CDCl$_3$) δ1.77 (br s, 1H plus HDO), 2.20–2.34 (m, 2H), 3.91 (t, J=5.5 Hz, 2H), 4.82 (dd, J=7.5, 5.7 Hz, 1H), 5.02 (s, 2H), 5.11 (ABq, J$_{AB}$=16.0 Hz, 2H), 6.85–7.01 (m, 7H), 7.22–7.41 (m, 6H); MH+ at m/z=390; Anal. Calc'd for C$_{24}$H$_{23}$NO$_4$: C, 74.02; H, 5.95; N, 3.60. Found: C, 73.61; H, 6.03; N, 3.55.

REFERENCE EXAMPLE 78

Intermediate 10508-84-A1

3,4-Dihydro-2-(2-hydroxyethyl)-4-(1-naphthylmethyl)-3-oxo-2H-1,4-benzoxazine

Prepared from 2-(2-tert-butyldimethylsiloxyethyl)-3,4-dihydro-3-oxo-2H-1,4-benzoxazine by Methods F and G, alkylating with 1-chloromethylnaphthalene, in 42% overall yield. the crude product was crystallized from ether/EtOAc/hexane to afford a white solid, mp 100°–104° C.; IR (KBr) 3435, 2896, 1668, 1504, 1414, 1253, 1132, 1068, 768, 758 cm$^{-1}$; $^1$H NMR (CDCl$_3$) δ1.92 (br s, 1H plus HDO), 2.26–2.44 (m, 2H), 3.96 (t, J=5.6 Hz, 2H), 4.94 (dd, J=7.5, 5.6 Hz, 1H), 5.62 (ABq, J$_{AB}$=16.9 Hz, 2H), 6.72 (dd, J=8.0, 1.1 Hz, 1H), 6.84 (td, J=8.1, 1.5 Hz, 1H), 6.96–7.11 (m, 3H), 7.36 (t, J=7.4 Hz, 1H), 7.54–7.64 (m, 2H), 7.78 (d, J=8.2 Hz, 1H), 7.92 (d, J=7.8 Hz, 1H), 8.04 (d, J=8.1 Hz, 1H); MH+ at m/z=334; Anal. Calc'd for C$_{21}$H$_{19}$NO$_3$: C, 75.66; H, 5.74; N. 4.20. Found: C, 75.56; H, 5.80; N, 4.14.

REFERENCE EXAMPLE 79

Intermediate 10508-80-1

3,4-Dihydro-2-(2-hydroxyethyl)-4-(2-naphthylmethyl)-3-oxo-2H-1,4-benzoxazine

Prepared from 2-(2-tert-butyldimethylsiloxyethyl)-3,4-dihydro-3-oxo-2H-1,4-benzoxazine by Methods F and G, alkylating with 2-chloromethyl naphthalene, in 81% overall yield. the crude product was crystallized from ether/hexane to afford a white solid, mp 81°–87° C.; IR (KBr) 3459, 2940, 1665, 1500, 1403, 1277, 1242, 1066, 746 cm$^{-1}$; $^1$H NMR (CDCl$_3$) δ2.23–2.40 (m, 3H), 3.95 (t, J=5.4 Hz, 2H), 4.90 (dd, J=7.6, 5.6 Hz, 1H), 5.32 (ABq, J$_{AB}$=16.1 Hz, 2H), 6.87–7.03 (m, 4H), 7.38 (d, J=8.5 Hz, 1H), 7.43–7.48 (m, 2H), 7.67 (s, 1H), 7.75–7.84 (m, 3H); MH$^+$ at m/z=334; Anal. Calc'd for C$_{21}$H$_{19}$NO$_3$: C, 75.66; H, 5.74; N, 4.20. Found: C, 75.65; H, 5.71; N, 4.02.

REFERENCE EXAMPLE 80

Intermediate 10508-79

4-(5-Chloro-2-thienylmethyl)-3,4-dihydro-2-(2-hydroxyethyl)-3-oxo-2H-1,4-benzoxazine Prepared from 2-(2-tert-butyldimethylsiloxyethyl)-3,4-dihydro-3-oxo-2H-1,4-benzoxazine by Methods F and G, alkylating with 5-chloro-2-(chloromethyl)thiophene and was isolated in 83% overall yield as a light yellow viscous oil after flash chromatography using 30–50% EtOAc in hexane; IR (CHCl$_3$) 3418, 2943, 1677, 1500, 1400, 1278, 1062, 750 cm$^{-1}$; $^1$H NMR (CDCl$_3$) δ2.11–2.32 (m, 3H), 3.89 (q, J=5.4 Hz, 2H), 4.78 (dd, J=7.6, 5.5 Hz, 1H), 5.15 (ABq, J$_{AB}$=16.0 Hz, 2H), 6.74 (d, J=3.7 Hz, 1H), 6.84 (d, J=3.7 Hz, 1H), 7.01–7.08 (m, 4H); MH$^+$at m/z=324; Anal. Calc'd for C$_{15}$H$_{14}$ClNO$_3$S.0.25 H$_2$O: C, 54.88; H, 4.45; N, 4.27; S, 9.77. Found: C, 54.86; H, 4.41; N, 4.04; S, 9.87.

REFERENCE EXAMPLE 81

Intermediate 11758-71-2

Methyl 4-[3,4-dihydro-2-(2-hydroxyethyl)-3-oxo-2H-1,4-benzoxazin-4-yl]methylbenzoate Prepared from 2-(2-tert-butyldimethylsiloxyethyl)-3,4-dihydro-3-oxo-2H-1,4-benzoxazine by methods F and G, alkylating with 4-(methoxycarbonyl)benzyl chloride, to afford the alcohol as a white solid in 65% yield, mp=94°–95° C.; $^1$H NMR (CDCl$_3$) δ8.00 (d, J=8.4 Hz, 2H), 7.30 (d, J=8.4 Hz, 2H), 6.95–7.04 (m, 2H), 6.89 (dt, J=2.1, 8.0 Hz, 1H), 6.77 (dd, J=7.8, 1.5 Hz, 1H), 5.20 (s, 2H), 4.86 (dd, J=5.4, 7.7 Hz, 1H), 3.82–3.96 (m, 5H with 3H singlet at δ3.89), 2.16–2.37 (m, 3H, one of which is exchangeable). $^{13}$C NMR (CDCl$_3$) δ166.8, 166.5, 144.1, 141.1, 130.1 (CH), 129.4, 128.4, 126.3 (CH), 124.2 (OH), 122.8 (OH), 117.3 (OH), 115.2 (OH), 75.1 (OH), 58.7 (OH$_2$), 52.0 (CH$_3$), 45.1 (CH$_2$), 33.1 (CH$_2$). IR 3450–3500 (br), 1719, 1660 cm$^{-1}$. MS 342 (MH$^+$), 324 (M-OH)$^+$, 310 (M-OMe)$^+$. Anal. Calc'd. for C$_{19}$H$_{19}$NO$_5$: C, 66.85; H, 5.61; N, 4.10. Found: C, 66.48; H, 5.47; N, 3.97.

REFERENCE EXAMPLE 82

Intermediate 11758-93-2A

Methyl 3-[3,4-dihydro-2-(2-hydroxyethyl)-3-oxo-2H-1,4-benzoxazin-4-yl]methylbenzoate Prepared from 2-(2-tert-butyldimethylsiloxyethyl)-3,4-dihydro-3-oxo-2H-1,4-benzoxazine by methods F and G, alkylating with 3-(methoxycarbonyl)benzyl chloride, and isolated as a white powder in 87% yield, mp 73°–75° C.; $^1$H NMR (CDCl$_3$) δ7.92–7.95 (m, 2H), 7.38–7.43 (m, 2H), 6.96–7.03 (m, 2H), 6.91 (dt, J=2.3, 7.3 Hz, 1H), 6.81 (dd, J=1.4, 7.7 Hz, 1H), 5.23 (d, J=16.3 Hz, 1H), 5.16 (d, J=16.3 Hz, 1H), 4.87 (dd, J=5.7, 7.4 Hz, 1H), 3.92–3.95 (m, 2H), 3.91 (s, 3H), 2.21–2.37 (m, 3H containing one exchangeable hydrogen). $^{13}$C NMR (CDCl$_3$) δ166.9, 166.7, 144.2, 136.5, 130.9 (CH), 130.7, 129.1 (CH), 128.7 (CH), 128.5, 127.7 (CH), 124.3 (CH), 122.9 (CH), 117.4 (CH), 115.4 (CH), 75.3 (CH), 58.9 (CH$_2$), 52.2 (CH$_2$), 45.1 (CH$_2$), 33.3 (CH$_2$). IR 3569, 2948, 1709, 1676, 1502 cm$^{-1}$. MS 342 (MH$^+$). Anal. Calc'd. for C$_{19}$H$_{19}$NO$_5$: C, 66.85; H, 5.61; N, 4.10. Found: C, 66.37; H, 5.62; N, 3.97.

REFERENCE EXAMPLE 83

Intermediate 11758-82-2

Ethyl 2-[3,4-Dihydro-2-(2-hydroxyethyl)-3-oxo-2H-1,4-benzoxazin-4-yl]methylbenzoate Prepared from 2-(2-tert-Butyldimethylsiloxyethyl)-3,4-dihydro-3-oxo-2H-1,4-benzoxazine by methods F and G, alkylating with 2-(methoxycarbonyl)benzyl chloride, and isolated as a white solid in 38% yield overall, mp 114°–115.5° C. (EtOAc/Hexanes). $^1$H NMR (CDCl$_3$) δ8.08 (dd, J=1.4, 7.8 Hz, 1H), 7.40 (dr, J=1.3, 7.5 Hz, 1H), 7.33 (br t, J=7.6 Hz, 1H), 6.97–7.06 (m, 3H), 6.89 (dt, J=1.9, 7.5 Hz, 1H), 6.74 (d, J=8.0 Hz, 1H), 5.63 (d, J=18.0 Hz, 1H), 5.54 (d, J=18.0 Hz, 1H), 4.88 (dd, J=5.7, 7.4 Hz, 1H), 4.41 (q, J=7.1 Hz, 2H), 3.90–3.95 (m, 2H), 2.23–2.35 (m, 2H), 1.43 (t, J=7.1 Hz, 3H). IR 3450–3550 (br), 1675, 1502 cm$^{-1}$. MS 356 (MH$^+$). Anal. Calc'd. for C$_{20}$H$_{21}$NO$_5$: C, 67.59; H, 5.96; N, 3.94. Found: C, 67.29; H, 5.97; N, 3.83.

REFERENCE EXAMPLE 84

Intermediate 11578-190

4-(3-Chlorobenzyl)-3,4-dihydro-2-(2-hydroxyethyl)-3-oxo-2H-pyrido[4,3-b]-1,4-oxazine Freshly prepared 4-hydroxypyridine nitrate was nitrated by the procedure of D. Rasala and R. Gawinecki, Org. Prep. Proc. Int., 1985, 17, 409–423. An EtOH solution of this nitropyridine (1 eq) and NaOAc (1 eq) was reduced with 10% Pd/C (10% w/w) under a hydrogen atmosphere at 50 psig for 4 h. The crude 3-amino-4-hydroxypyridine was dissolved in DMF (5 mL) and treated with NaH (1.2 eq). This mixture was then treated with α-bromo-γ-butyrolactone (1.2 eq) at room temperature under nitrogen. After stirring at room temperature for 24 h, the DMF solution was treated with imidazole (1.2 eq) and t-butyldimethylsilyl chloride (1.2 eq). This solution was stirred for 16 h and then quenched with H$_2$O. The aqueous solution was extracted with EtOAc and the combined extract was washed with H$_2$O and dried over MgSO$_4$. The EtOAc solution was filtered through SiO$_2$ and concentrated under vacuum to afford the intermediate silyloxy compound in 14% yield. This material was alkylated by Method F, with 3-chlorobenzyl bromide, and then deprotected with TFA (20% v/v) in CHCl$_3$ to afford the alcohol in 41% yield as a white crystalline solid; IR (KBr) 3519, 1664, 1393, 1320, 1192, 1082, 1054, 868 cm$^{-1}$; $^1$H NMR (DMSO-d$_6$) δ1.97–2.09 (m, 2H), 3.58–3.62 (m, 2H), 4.75 (t, J=5.0, 1H), 5.10 (dd, J=8.5, 4.2 Hz, 1H), 5.21 (s, 2H), 7.07 (d, J=5.3 Hz, 1H), 7.25 (br d, J=6.8 Hz, 1H), 7.35–7.43 (m, 3H), 8.13 (d, J=5.8 Hz, 1H), 8.20 (s, 1H); MH+ at m/z=319.

REFERENCE EXAMPLE 85

Intermediate 11721-108-1

3,4-dihydro-2-(2-hydroxyethyl)-[4-(3-thienylmethyl)]-3-oxo-2H-1,4-benzoxazine

Tributyl phosphine (1.5 eq) and 1,1'-(azodicarbonyl)dipiperidine (1.5 eq) were added to a solution of 2-(2-tert-butyldimethylsiloxyethyl)-3,4-dihydro-3-oxo-2H-1,4-benzoxazine (1 eq) in $CH_2Cl_2$ at room temperature. 3-thiophenemethanol (1.5 eq) was added dropwise and the mixture was stirred for 16 hours at room temperature. Hexane was added and this mixture was filtered and concentrated in vacuo. The oily residue was purified by column chromatography using 1–2% $EtOAc/CH_2Cl_2$ as an eluent to give the alkylated intermediate as yellow oil; MH+ at m/z=404. The alkylated intermediate was treated following the procedure of method G to give the title compound as a clear oil. IR (neat) 3427, 3101, 1681, 1500, 1060, 750 cm$^{-1}$; $^1$H NMR (CDCl$_3$) δ2.1–2.4 (m, 2H), 3.8–4.0 (m, 2H), 4.15 (q, 1H), 4.80 (t, 1H), 5.21 (s, 2H), 7.07 (m, 5H), 7.1 (m, 1H), 7.25–7.3 (m, 1H); MH+ at m/z=289.

REFERENCE EXAMPLE 86

Intermediate 11653-24A 4-(2-Chlorobenzyl)-3,4-dihydro-2-(2-hydroxyethyl)-3-oxo-7-nitro-2H-1,4-benzoxazine Prepared from 2-(2-tert-butyldimethylsiloxyethyl)-3,4-dihydro-3-oxo-2H-1,4-benzoxazine by methods F and G, alkylating with 2-chlorobenzyl bromide, to give a yellow solid: mp 106°–108° C.; MS (CI) 363 (MH$^+$); IR (KBr) 3268, 3122, 3088, 3068, 2969, 2937, 2881, 1888, 1794, 1571, 1478, 1210, 1148, 1135, 1116, 972, 926, 864, 705, 626, 475 cm$^{-1}$; $^1$H NMR (CDCl$_3$/TMS) δ7.90 (d,1H, J=2.42 Hz), 7.84 (dd, 1H, J=2.51, 8.91 Hz), 7.45 (d, 1H, J=7.77 Hz), 7.20 (m, 2H), 6.95 (d, 1H, J=7.52 Hz), 6.81 (d, 1H, J=8.90 Hz), 5.29 (s, 2H), 5.00 (dd, 1H, J=5.13, 7.90 Hz), 3.95 (q, 2H, J=5.51 Hz), 2.30 (brm, 2H), 1.86 (t, 1H, J=5.47); Anal. Calc'd for $C_{17}H_{15}ClN_2O_5$: C 56.29, H 4.17, N 7.72,. Found: C 56.25, H 4.24, N 7.60.

REFERENCE EXAMPLE 87

Intermediate 11653-358

4-(3-Chlorobenzyl)-3,4-dihydro-2-(2-hydroxyethyl)-3-oxo-7-nitro-2H-1,4-benzoxazine Prepared from 2-(2-tert-butyldimethylsiloxyethyl)-3,4-dihydro-3-oxo-2H-1,4-benzoxazine by methods F and G, alkylating with 3-chlorobenzyl bromide, to give a yellow solid: mp 100°–102.5° C.; MS (CI) 363 (MH$^+$); IR (KBr) 3512, 3092, 3058, 2980, 2939, 2886, 1888, 1600, 1518, 1498, 1475, 1443, 1431, 1278, 1204, 1107, 1080, 1020, 863, 681, 602, 452 cm$^{-1}$; $^1$H NMR (CDCl$_3$/TMS) δ7.89(d, 1H, J=2.46 Hz), 7.84(dd, 1H, J=2.53, 8.84 Hz), 7.27(m, 3H), 7.10(m, 1H), 6.90(d,1H, J=8.85 Hz), 5.17(s, 2H), 4.99(dd, 1H, J=5.13, 7.85 Hz), 3.94(m, 2H), 2.35(m, 1H), 2.24(m, 1H), 1.92(t, 1H, J=5.40 Hz); Anal. Calc'd for $C_{17}H_{15}ClN_2O_5$: C 56.29, H 4.17, N 7.72, Found: C 56.25, H 4.09, N 7.63.

REFERENCE EXAMPLE 88

Intermediate 10840-117-1

3,4-Dihydro-2-(2-hydroxyethyl)-4-methyl-7-nitro-3-oxo-2H-1,4-benzoxazine

Prepared from intermediate 11653-23 (Reference Example 31) by methods F and G, alkylating with methyl iodide, to give an oil: Anal. Calc'd for $C_{11}H_{13}NO_3 \cdot \%_{10} H_2O$: C 62.14, H 6.41, N 6.59, Found: C 62.21, H 6.27, N 6.42

Compound 1

2-[2-[4-(t-Butoxycarbonylaminomethyl)phenoxy]ethyl]-4-(3-chlorobenzyl)-3,4-dihydro-3-oxo-2H-1,4-benzoxazine

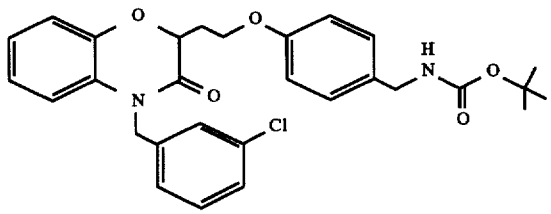

Method J: Intermediate 10488-22 (7.65 g, 1 eq, Reference Example 66), was dissolved in THF. Triphenylphosphine (0.5 g, 1.1 eq) and 4-(N-t-butoxycarbonyl)aminomethylphenol (0.38 g, 1 eq) were added, followed by dropwise addition of diethyl azodicarboxylate (0.303 ml, 1.1 eq). The reaction was stirred at reflux temperature for 48 h and concentrated under vacuum. The residue was triturated with $Et_2O$ and the precipitate removed by filtration. The product was isolated from the filtrate by flash chromatography, eluting with EtOAc/hexanes. Fractions containing product were crystallized from EtOAc/hexanes to afford a 50% yield of a white powder, mp 99°–100° C.; IR (KBr) 3386, 2981, 1692, 1613, 1501, 1393, 1366, 1248, 1171, 1053, 862, 752, 388 cm$^{-1}$; $^1$H NMR (CDCl$_3$) δ7.29–7.2 (m, 3H), 7.21 (d, J=8.6 Hz, 2H), 7.13 (m, 1H), 7.04–6.91 (m, 3H), 6.88 (d, J=8.6 Hz, 2H), 6.82 (dd, J=8, 1.4 Hz), 5.17 (d, J=16 Hz, 1H), 5.08 (d, J=16 Hz, 1H), 4.94 (dd, J=9.2, 4.0 Hz, 1H), 4.75 (br s, 1H), 4.24 (m, 4H), 2.56 (m, 1H), 2.34 (m, 1H), 1.46 (s, 9H). Anal. Calc'd for $C_{29}H_{31}ClN_2O_5$: C 66.60, H 5.97, N 5.36. Found: C 66.41, H 6.00, N 5.34.

Compound 2

2-[2-[4-(Aminomethyl)phenoxy]ethyl]-4-(3-chlorobenzyl)-3,4-dihydro-3-oxo-2H-1,4-benzoxazine

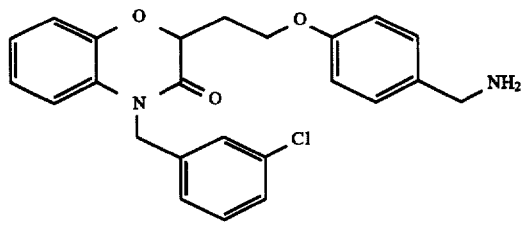

Method K: Compound 1 was dissolved in isopropyl alcohol containing an excess of HCl (g) (0.2–0.3 g/ml) and stirred at room temperature 2 h. The product was filtered from the reaction mixture and the solid was washed with $Et_2O$ to afford an 87% yield of a white solid, mp 194°–200 (dec); MS (CI) MH$^+$422; IR (KBr) 2930, 1609, 1503, 1404, 1306, 1283, 1248, 1182, 1111, 1051, 833 cm$^{-1}$; $^1$H NMR (DMSO-d$_6$) δ8.45–8.24 (brs, 2H), 7.42 (d, 2H, J=8.6 Hz), 7.35 (m, 2H), 7.22 (d, 1H, J=6.8 Hz), 7.05 (m, 5H), 5.23 (d, 1H, J=16.5 Hz), 5.13 (d, 1H, J=16.5 Hz), 5.00 (dd, 1H, J=4.2, 8.6 Hz), 4.22 (m, 2H), 3.94 (br t, 2H, J=2.5 Hz), 3.39

(br s, 2H), 2.40 (m, 1H), 2.25 (m, 1H). Anal. Calc'd for C$_{24}$H$_{22}$Cl N$_2$ O$_3$.HCl: C 62.89, H 5.06, N 6.11. Found: C 62.49, H 5.21, N 6.03.

Compound 3

2-[2-[4-(t-Butoxycarbonylaminomethyl)phenoxy]ethyl]-4-(4-chlorobenzyl)-3,4-dihydro-3-oxo-2H-1,4-benzoxazine

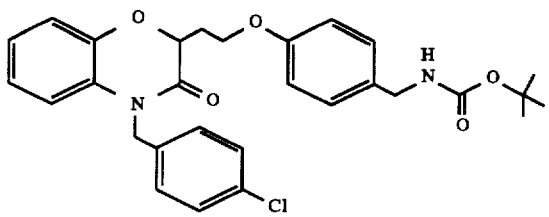

Prepared by method J, using intermediate 10353-28-1, (Reference Example modified by stirring at room temperature for 48 h, in 54% yield as a white solid, mp121°–122.5° C.; IR (KBr) 3400, 2977, 2931, 1690, 1613, 1516, 1503, 1468, 1436, 1395, 1366, 1301, 1277, 1248, 1171, 1094, 1053, 1014, 753 cm$^{-1}$; $^1$H NMR (CDCl$_3$) δ7.33–7.22 (m, 2H), 7.22–7.15 (m, 4H), 7.03–6.8 (m, 6H), 5.16 (d, J=16.6 Hz, 1H), 5.08 (d, J=16.6 Hz, 1H), 4.92 (dd, J=9.4, 4.1 Hz, 1H), 4.76 (br s, 1H), 4.25 (m, 4H), 2.57 (m, 1H), 2.33 (m, 1H), 1.47 (s, 9H). Anal. Calc'd for C$_{29}$H$_{31}$ClN$_2$O$_5$: C 66.60, H 5.97, N 5.36. Found: C 66.48, H$_{5.86}$, N 5.32.

Compound 4

2-[2-[4-(Aminomethyl)phenoxy]ethyl]-4-(4-chlorobenzyl)-3,4-dihydro-3-oxo-2H-1,4-benzoxazine

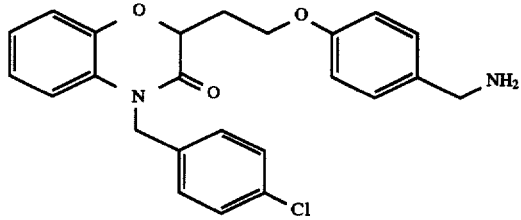

Prepared by method K using Compound 3. The HCl/isopropanol solution was evaporated under vacuum and the product isolated by crystallization from CH$_2$Cl$_2$/Et$_2$O in 76% yield as white solid, mp 200°–201° C.; IR (KBr) 3480, 3360, 3235, 2910, 2878, 1681, 1609, 1519, 1503, 1465, 1401, 1281, 1243, 1183, 1110, 1023, 913, 830, 797, 749, 569, 529 530 cm$^{-1}$; $^1$H NMR (DMSO-d$_6$) δ8.18 (br s, 3H), 7.40 (m, 4H), 7.30 (d, J=8.6 Hz, 2H), 7.02 (m, 6H), 5.21 (d, J=16.8 Hz, 1H), 5.12 (d, J=16.8 Hz, 1H), 4.98 (dd, J=9.2, 4.4 Hz, 1H), 4.23 (m, 2H), 3.96 (m, 2H), 2.39 (m, 1H), 2.25 (m, 1H). Anal. Calc'd for C$_{24}$H$_{23}$ClN$_2$O$_3$.HCl.0.5 H$_2$O: C 61.54, H 5.38, N 5.98. Found: C 61.30, H 5.33, N 5.90.

Compound 5

2-[2-[4-(2-(t-Butoxycarbonylamino)ethyl)phenoxy]ethyl]-4-(4-chlorobenzyl)-3,4-dihydro-3-oxo-2H-1,4-benzoxazine

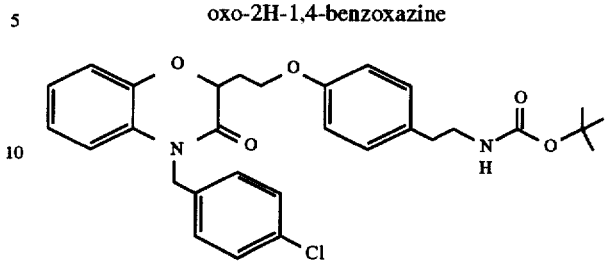

Method L: The alcohol intermediate 10353-28-1 (0.6 g, 1 eq Reference Example 41) was dissolved in dry benzene (6 ml) and treated with tributylphosphine (0.63 ml, 1.5 eq) and boc-protected 4-(2-aminoethyl)phenol (0.66 g, 1.5 eq). The resulting solution was cooled in an ice bath and 1,1'-(azodicarbonyl)dipiperidine (ADDP, 0.71 g, 1.5 eq) was added in one portion. The reaction was warmed to room temperature after 10 min. After 20 h, diluted with Et$_2$O and the white precipitate was filtered off. The filtrate was washed with 2N NaOH and concentrated. The product was isolated by flash chromatography eluting with acetone/hexanes. Recrystallization from EtOAc/hexanes afforded a 72% yield of the product as a white solid 108°–109° C.; MS (CI) 537 (MH$^+$); IR (KBr) 3378, 2979, 1798, 1609, 1515, 1500, 1395, 1368, 1246, 1171, 1061, 816, 749 cm$^{-1}$; $^1$H NMR (CDCl$_3$) δ7.39 (d, J=8.5 Hz, 2H), 7.18 (d, J=8.5 Hz, 2H), 7.11 (d, J=8.7 Hz, 2H), 7.04–6.80 (m, 4H), 6.86 (d, J=8.7 Hz, 2H), 5.14 (d, J=16.4 Hz, 1H), 5.11 (d, J=16.4 Hz, 1H), 4.93 (dd, J=9.5, 4.1 Hz, 1H), 4.52 (brs, 1H), 4.23 (m, 2H), 3.34 (m, 2H), 2.74 (apparent t, J=7.1 Hz, 2H), 2.56 (m, 1H), 2.33 (m, 1H), 1.44 (s, 9H). Anal. Calc'd for C$_{30}$H$_{33}$ClN$_2$O$_5$: C 67.09, H 6.19, N 5.22. Found: C 66.88, H 6.07, N 5.22.

Compound 6

2-[2-[4-(2-Aminoethyl)phenoxy]ethyl]-4-(4-chlorobenzyl)-3,4-dihydro-3-oxo-2H-1,4-benzoxazine

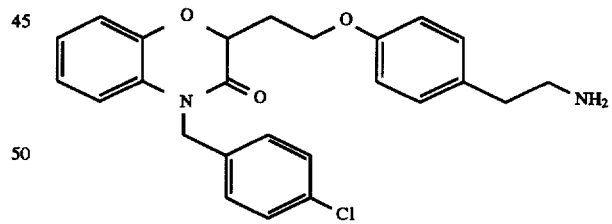

Prepared by method K using Compound 5. The HCl/isopropanol solution was evaporated under vacuum after 18 h and the product isolated by crystallization from CH$_2$Cl$_2$/Et$_2$O in 43% yield as white solid, mp 174°–176° C.; IR (KBr) 3415, 2933, 1681, 1609, 1503, 1465, 1401, 1279, 1241, 1065, 824, 789, 488, 428, 415 cm$^{-1}$; $^1$H NMR (DMSO-d$_6$) δ7.74 (br s, 3H), 7.39 (d, J=8.5 Hz, 2H), 7.30 (d, J=8.5 Hz, 2H), 7.28 (d, J=8.8 Hz, 2H), 7.1 (m, 4H), 6.93 (d, J=8.8 Hz, 2H), 5.20 (d, J=16.8 Hz, 1H), 5.13 (d, J=16.8 Hz, 1H), 4.97 (dd, J=9.2, 4.1 Hz, 1H), 4.19 (m, 2H), 2.99 (m, 2H), 2.80 (m, 2H), 2.38 (m, 1H), 2.24 (m, 1H). Anal. Calc'd for C$_{25}$H$_{25}$ClN$_2$O$_3$.HCl: C 63.43, H 5.54, N 5.92. Found: C 63.17, H 5.47, N 5.82.

Compound 7

2-{2-[3-(2-t-Butoxycarbonylaminoeth-
yl)phenoxy]ethyl}-4-(4-chlorobenzyl)-3,4-dihydro-
3-oxo-2H-1,4-benzoxazine

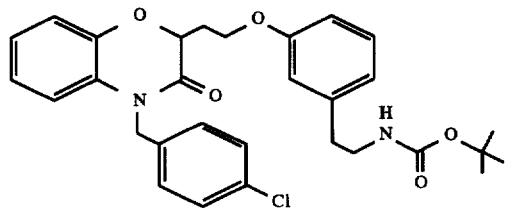

Prepared by method J using intermediate 10353-28-1 (Reference Example 41), modified by stirring at room temperature for 20 h, in 30% yield as a white solid; mp 97°–98.5° C.; IR (KBr) 3368, 3066, 3050, 2981, 2940, 1680, 1602, 1594, 1522, 1503, 1466, 1447, 1399, 1364, 1267, 1175, 1113, 1052, 1013 cm$^{-1}$; $^1$H NMR (CDCl$_3$) δ7.32–7.16 (m, 5H), 7.05–6.89 (m, 3H), 6.86–6.73 (m, 4H), 5.16 (d, J=17.6 Hz), 5.09 (d, J=17.6 Hz), 4.93 (dd, J=6.7, 5.0 Hz), 4.55 (m, 1H), 4.23 (m, 2H), 3.38 (m, 2H), 2.78 (apparent t, J=7.2 Hz, 2H), 2.58 (m, 1H), 2.33 (m, 1H), 1.43 (s, 9H). Anal. Calc'd for C$_{30}$H$_{33}$ClN$_2$O$_5$: C 67.09, H 6.19, N 5.22. Found: C 67.14, H 6.21, N 5.16.

Compound 9

2-[2-[3-(t-Butoxycarbonylaminometh-
yl)phenoxy]ethyl]-4-(4-chlorobenzyl)-3,4-dihydro-3-
oxo-2H-1,4-benzoxazine

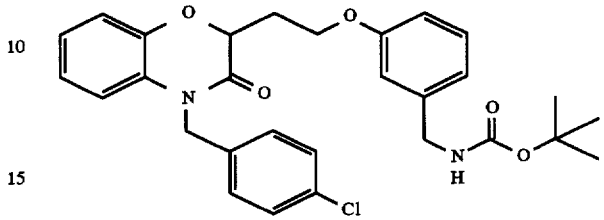

Prepared by method J, using intermediate 10353-28-1 (Reference Example 41) and modified by stirring at room temperature for 24 h, in 50% yield. Trituration with hot Et$_2$O afforded a white solid, mp 114°–116° C.; IR (KBr) 3365, 2985, 1686, 1600, 1526, 1503, 1451, 1395, 1366, 1268, 1173, 1129, 1067, 1052, 843, 787, 760 cm$^{-1}$; $^1$H NMR (CDCl$_3$) δ7.29 (d, J=8.9 Hz, 2H), 7.23 (d, J=8.4 Hz, 1H), 7.19 (d, J=8.9 Hz, 2H), 7.15–6.78 (m, 7H), 5.15 (d, J=16.8 Hz, 1H), 5.1 (d, J=16.8 Hz, 1H), 4.93 (dd, J=9.2, 4.2 Hz, 1H), 4.82 (br s, 1H), 4.37–4.13 (m, 4H), 2.57 (m, 1H), 2.34 (m, 1H), 1.46 (s, 9H). Anal. Calc'd for C$_{29}$H$_{31}$ClN$_2$O$_5$: C 66.60, H 5.97, N 5.36. Found: C 66.62, H 5.90, N 5.33.

Compound 8

2-[2-[3-(2-Aminoethyl)phenoxy]ethyl]-4-(4-
chlorobenzyl)-3,4-dihydro-3-oxo-2H-1,4-
benzoxazine

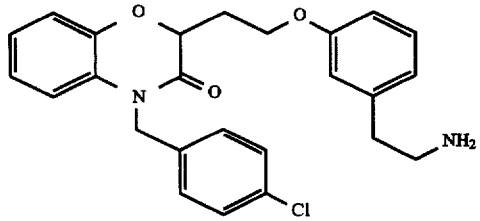

Prepared by method K using Compound 7. The HCl/isopropanol solution was evaporated under vacuum after 2.5 h and the product isolated by crystallization from CH$_2$Cl$_2$/Et$_2$O in ~72% yield as a white solid, mp 155°–156° C.; IR (KBr) 3400, 3052, 2940, 1683, 1605, 1501, 1399, 1301, 1248, 1162, 1094, 1053, 751 cm$^{-1}$; $^1$H NMR (DMSO-d$_6$) δ7.40 (d, J=8.4 Hz, 2H), 7.35–7.23 (m, 3H), 7.02 (m, 4H), 6.86 (m, 3H), 5.2 (d, J=17.0 Hz, 1H), 5.14 (d, J=17 Hz, 1H), 5.15–3.30 (v brs, 4H), 4.22 (m, 2H), 3.05 (m, 2H), 2.83 (m, 2H), 2.40 (m, 1H), 2.25 (m, 1H). Calc'd for C$_{25}$H$_{25}$ClN$_2$O$_3$·C$_2$H$_2$O$_4$·0.75 H$_2$O: C 60.00, H 5.32, N 5.18. Found: C 60.11, H 5.08, N 5.06.

Compound 10

2-[2-[3-(Aminomethyl)phenoxy]ethyl]-4-(4-
chlorobenzyl)-3,4-dihydro-3-oxo-2H-1,4-
benzoxazine

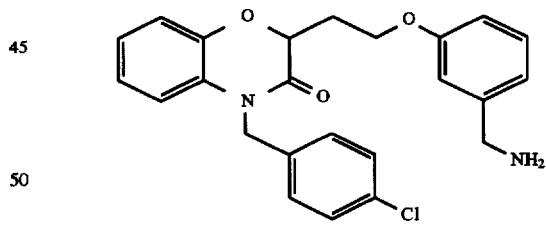

Prepared by method K, using Compound 9. The HCl/isopropanol solution was evaporated under vacuum after 24 h and the product isolated in 30% yield by conversion to the oxalate salt followed by trituration with hot CH$_2$Cl$_2$. mp 127°–129° C.; IR (KBr) 3446, 3053, 1501, 1466, 1401, 1248, 797, 747, 700, 486, 428 cm$^{-1}$; $^1$H NMR (DMSO-d$_6$) δ8.20 (br s, 1H), 7.40 (d, J=8.4 Hz, 2H), 7.36 (d, J=8.0 Hz, 1H), 7.31 (d, J=8.4 Hz, 2H), 5.21 (d, J=17.2 Hz, 1H), 5.13 (d, J=17.2 Hz, 1H), 4.98 (dd, J=9.2, 4.2, 1H), 5.15–4.10 (v br s, 3H), 4.22 (m, 2H), 4.01 (s, 2H), 2.45 (m, 1H), 2.27 (m, 1H). Calc'd for C$_{24}$H$_{23}$ClN$_2$O$_3$·C$_2$H$_2$O$_4$·1.5 H$_2$O: C 57.83, H 5.23, N 5.19. Found: C 58.06, H 4.85, N 5.20.

Compound 11

2-[2-[3-(t-Butoxycarbonylaminomethyl)phenoxy]ethyl]-4-(2-chlorobenzyl)-3,4-dihydro-3-oxo-2H-1,4-benzoxazine

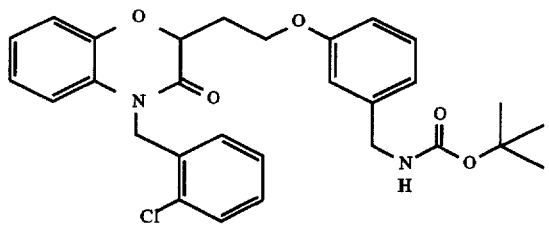

Prepared by method J, using intermediate 9086-189-1 (Reference Example 42), without chromatography. The product was isolated by precipitation from aqueous methanol and made basic by dropwise addition of 2N NaOH, followed by recrystallization from MeOH/water, in 84% yield mp 115°–116° C.; MS (CI) 523 (MH$^+$); IR (KBr) 3357, 2979, 1686, 1611, 1586, 1526, 1505, 1466, 1449, 1395, 1368, 1285, 1252, 1165, 1052, 749 cm$^{-1}$; $^1$H NMR (CDCl$_3$) δ7.43 (dd, J=7.6, 1.7 Hz, 1H), 7.27–7.13 (m, 4H), 7.16–6.96 (m, 3H), 6.95–6.81 (m, 3H), 6.73 (dd, J=8.4, 1.3 Hz, 1H), 5.28 (d, J=17.8 Hz, 1H), 5.21 (d, J=17.8 Hz, 1H), 4.97 (dd, J=9.4, 4.2 Hz, 1H), 4.82 (br s, 1H), 4.35–4.17 (m, 4H), 2.59 (m, 1H), 2.37 (m, 1H), 1.47 (s, 9H). Anal. Calc'd for C$_{29}$H$_{31}$ClN$_2$O$_5$: C 66.60, H 5.97, N 5.36. Found: C 66.59, H 5.87, N 5.30.

Compound 12

2-[2-[3-(Aminomethyl)phenoxy]ethyl]-4-(2-chlorobenzyl)-3,4-dihydro-3-oxo-2H-1,4-benzoxazine

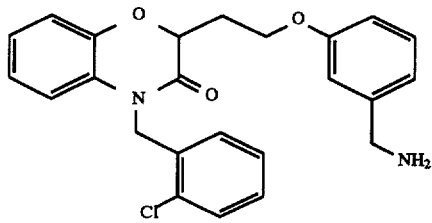

Prepared by method K, using Compound 11. The HCl/isopropanol solution was evaporated under vacuum after 20 h and the product isolated by crystallization from CH$_2$Cl$_2$ in 50% yield as a white powder; mp 191°–193° C.; MS (CI) 423 (MH$^+$); IR (KBr) 3419, 2889, 2624, 1683, 1605, 1505, 1466, 1443, 1403, 1324, 1279, 1181, 1110, 1086, 1038, 951, 930, 893, 791, 749, 695, 627, 567, 452 cm$^{-1}$; $^1$H NMR (DMSO-d$_6$) δ8.35 (br s, 3H), 7.53 (dd, J=7.7, 1.2 Hz, 1H), 7.32 (m, 3H), 7.17 (s, 1H), 7.13–6.95 (m, 6H), 6.85 (dd, J=8.7.7, 1.2 Hz, 1H), 5.22 (d, J=17.3 Hz, 1H), 5.13 (d, J=17.3 Hz, 1H), 5.04 (dd, J=8.8, 4.2 Hz, 1H), 4.25 (m, 2H), 4.0 (s, 2H), 2.44 (m, 1H), 2.30 (m, 1H). Anal. Calc'd for C$_{24}$H$_{23}$ClN$_2$O$_3$.HCl.0.5 H$_2$O: C 61.54, H 5.38, N 5.98. Found: C 61.35, H 5.08, N 5.87.

Compound 13

2-[2-[4-(t-Butoxycarbonylaminomethyl)phenoxy]ethyl]-4-(2-chlorobenzyl)-3,4-dihydro-3-oxo-2H-1,4-benzoxazine

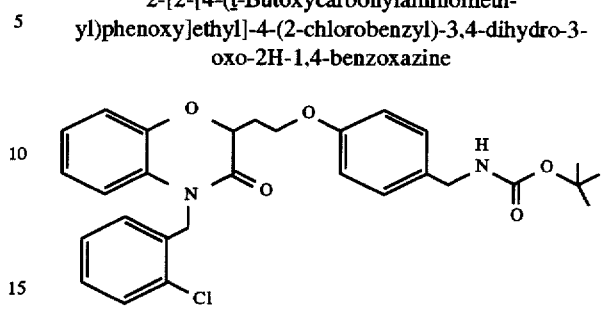

Prepared by method J using intermediate 9086-189-1 (Reference Example 42), in 50% yield as a white solid, mp 121°–123° C.; IR (KBr) 3345, 2979, 2925, 1683, 1611, 1503, 1466, 1401, 1248, 1171, 749 cm$^{-1}$; $^1$H NMR (CDCl$_3$) δ7.42 (dd, J=7.8, 1.4 Hz, 1H), 7.27–7.12 (m, 2H), 7.21 (d, J=8.4 Hz, 2H), 7.05–6.87 (m, 4H), 6.88 (d, J=8.4 Hz, 2H), 6.71 (d, J=7.8 Hz, 1H), 5.27 (d, J=17.6 Hz, 1H), 5.21 (d, J=17.6 Hz, 1H), 4.96 (dd, J=9.4, 4.1 Hz, 1H), 4.76 (br s, 1H), 4.25 (m, 4H), 2.58 (m, 1H), 2.36 (m, 1H), 1.46 (s, 9H). Anal. Calc'd for C$_{29}$H$_{31}$ClN$_2$O$_5$: C 66.60, H 5.97, N 5.36. Found: C 66.35, H 5.82, N 5.72.

Compound 14

2-[2-[4-(Aminomethyl)phenoxy]ethyl]-4-(2-chlorobenzyl)-3,4-dihydro-3-oxo-2H-1,4-benzoxazine

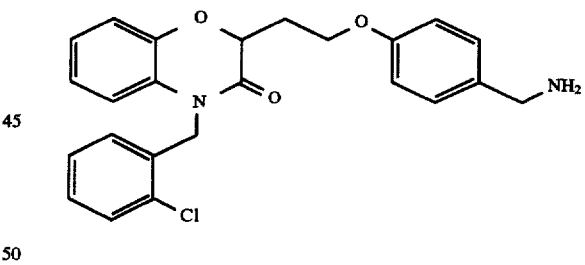

Prepared by method K from Compound 13. The isopropanol was removed under vacuum and the product isolated by crystallization from CHCl$_3$/EtOAc in 69% yield as a white solid; mp 200°–205° C.; MS (CI) 423 (MH$^+$); IR (KBr) 3430, 2960, 2890, 2600, 1690, 1611, 1517, 1501, 1468, 1401, 1279, 1250, 1183, 1050, 749, 407 cm$^{-1}$; $^1$H NMR (DMSO-d$_6$) δ8.22 (br s, 3H), 7.53 (dd, J=7.6, 1.3 Hz, 1H), 7.40 (d, J=8.7 Hz, 2H), 7.37–7.23 (m, 3H), 7.12–6.95 (m, 4H), 7.02 (d, J=8.7 Hz, 2H), 6.83 (dd, J=7.9, 1.6 Hz, 1H), 5.2 (d, J=17.2 Hz, 1H), 5.13 (d, J=17.2 Hz, 1H), 5.04 (dd, 8.4, 4.2 Hz, 1H), 4.25 (m, 2H), 3.95 (s, 2H), 2.42 (m, 1H), 2.39 (m, 1H). Anal. Calc'd for C$_{24}$H$_{23}$ClN$_2$O$_3$.HCl.0.3 H$_2$O: C 62.02, H 5.34, N 6.03. Found: C 61.99, H 5.20, N 5.87.

Compound 15

2-[2-[3-(2-(t-Butoxycarbonylamino)ethyl)phenoxy]ethyl]-4-(2-chlorobenzyl)-3,4-dihydro-3-oxo-2H-1,4-benzoxazine

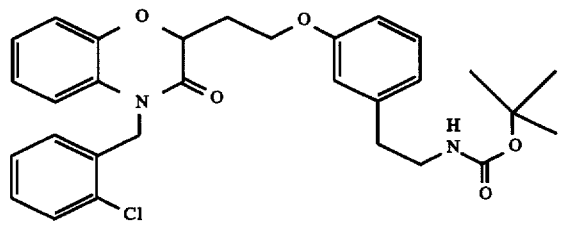

Prepared by method J using intermediate 9086-189-1 (Reference Example 42), in 48% yield as a white powder, mp 61°–65° C. (softens) 68°–70° C.; MS (CI) 537 (MH⁺); IR (KBr) 3365, 2998, 2935, 1690, 1607, 1503, 1447, 1401, 1366, 1254, 1171, 1050, 751 cm⁻¹; ¹H NMR (CDCl₃) δ7.42 (dd, J=7.6, 1.2 Hz, 1H), 7.35–7.13 (m, 3H), 7.08–6.87 (m, 4H), 6.85–6.68 (m, 4H), 5.28 (d, J=17.6 Hz, 1H), 5.21 (d, J=1H), 4.97 (dd, J=9.2, 4.1 Hz, 1H), 4.54 (br s, 1H), 4.25 (m, 2H), 3.37 (m, 2H), 2.66 (m, 2H), 2.59 (m, 1H), 2.38 (m, 1H), 1.44 (s, 9H). Anal. Calc'd for $C_{30}H_{33}ClN_2O_5$: C 67.09, H 6.19, N 5.22. Found: C 67.08, H 6.15, N 5.17.

Compound 17

2-[2-[4-(2-(t-Butoxycarbonylamino)ethyl)phenoxy]ethyl]-4-(2-chlorobenzyl)-3,4-dihydro-3-oxo-2H-1,4-benzoxazine

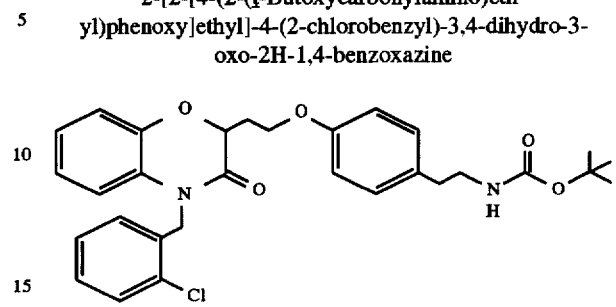

Prepared by method J using intermediate 9086-189-1 (Reference Example 42) in 33% yield as a white powder, mp 108°–111° C.; IR (KBr) 3378, 2978, 2920, 1692, 1611, 1515, 1503, 1397, 1366, 1248, 1175, 1056, 751 cm⁻¹; ¹H NMR (CDCl₃) δ7.43 (dd, J=8.0, 1.3 Hz, 1H), 7.26–7.13 (m, 2H), 7.11 (d, J=8.5 Hz, 2H), 7.06–6.88 (m, 4H), 6.88 (d, J=8.5 Hz, 2H), 6.71 (d, J=8.0 Hz, 1H), 5.28 (d, J=17.8 Hz, 1H), 5.22 (d, J=17.9 Hz, 1H), 4.97 (dd, J=9.7, 4.2 Hz, 1H), 4.52 br s, 1H), 4.25 (m, 2H), 3.35 (m, 2H), 2.74 (apparent t, J=7.1 Hz, 2H), 2.05 (m, 1H), 2.36 (m, 1H), 1.44 (s, 9H). Anal. Calc'd for $C_{30}H_{33}ClN_2O_5$: C 67.09, H 6.19, N 5.22. Found: C 66.71, H 6.00, N 5.58.

Compound 16

2-[2-[3-(2-Aminoethyl)phenoxy]ethyl]-4-(2-chlorobenzyl)-3,4-dihydro-3-oxo-2H-1,4-benzoxazine

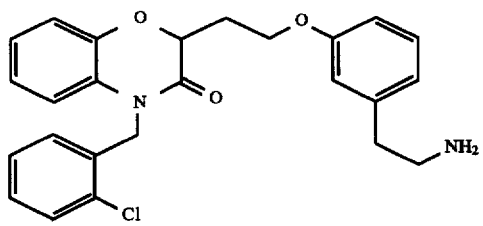

Prepared by method K using Compound 15. The isopropanol was removed under vacuum after 3 h and the product isolated by crystallization from CHCl₃/EtOAc in 91% yield to afford a white solid, mp 173°–175° C.; MS (CI) 437 (MH⁺); IR (KBr) 3420, 2932, 1687, 1603, 1501, 1466, 1445, 1401, 1326, 1252, 1160, 1050, 748, 695 cm⁻¹; ¹H NMR (DMSO-d₆) δ7.94 (br s, 3H), 7.53 (d, J=7.9 Hz, 1H), 7.37–7.23 (m, 3H), 7.15–6.95 (m, 5H), 6.86 (m, 3H), 5.22 (d, J=17.5 Hz, 1H), 5.13 (d, J=17.5 Hz, 1H), 5.04 (dd, J=9.2, 2.2 Hz, 1H), 4.23 (m, 2H), 3.04 (m, 2H), 2.35 (m, 2H), 2.4 (m, 1H), 2.29 (m, 1H). Anal. Calc'd for $C_{25}H_{25}ClN_2O_3·HCl·0.2\ H_2O$: C 62.95, H 5.58, N 5.87. Found: C 62.83, H 5.29, N 5.62.

Compound 18

2-[2-[4-(2-Aminoethyl)phenoxy]ethyl]-4-(2-chlorobenzyl)-3,4-dihydro-3-oxo-2H-1,4-benzoxazine

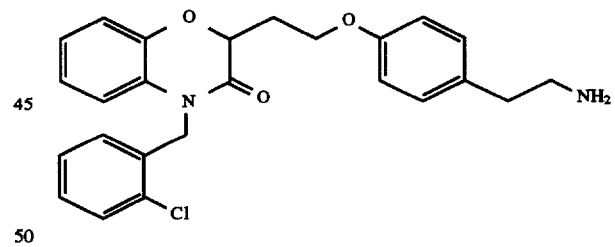

Prepared by method K using Compound 18. The isopropanol was removed under vacuum after 1 h and the product isolated, by trituration with Et₂O, in 49% yield as an off white powder mp 143°–148° C.; MS (CI) 437 (MH⁺—H₂O); IR (KBr) 3365, 2930, 1686, 1609, 1515, 1503, 1468, 1445, 1401, 1252, 1111, 1050, 826, 747 cm⁻¹; ¹H NMR (DMSO-d₆) δ7.97 (br s, 3H), 7.54 (dd, J=7.7, 1.4 Hz, 1H), 7.37–7.22 (m, 2H), 7.19 (d, J=8.6 Hz, 2H), 7.12–6.95 (m, 4H), 6.94 (d, J=8.6 Hz, 2H), 6.83 (dd, J=7.6, 1.5 Hz, 1H), 5.20 (d, J=17.3 Hz, 1H), 5.13 (d, J=17.3 Hz, 1H), 5.04 (dd, J=9.1, 4.0 Hz, 1H), 4.21 (m, 2H), 2.99 (m, 2H), 2.82 (m, 2H), 2.40 (m, 1H), 2.27 (m, 1H). Anal. Calc'd for $C_{25}H_{25}ClN_2O_3·HCl·0.5H_2O$: C 62.24, H 5.64, N 5.81. Found: C 62.17, H 5.31, N 6.13.

Compound 19

4-(2-Chlorobenzyl)-2-[2-[4-(guanidinomethyl)phenoxy]ethyl]-3,4-dihydro-3-oxo-2H-1,4-benzoxazine

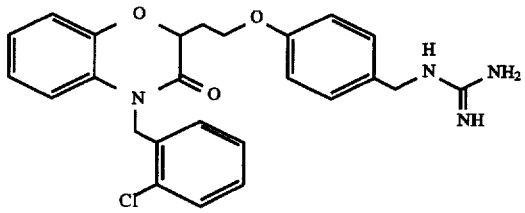

Prepared by method L using intermediate 9086-189-1 (Reference Example 42) and N,N'-di-t-butoxycarbonyl-(4-hydroxyphenyl)methylguanidine and method K with the following modifications. The bis-Boc-protected Mitsunobu coupling product was isolated by dissolving the crude product residue in aqueous methanol and treating with a dropwise addition of 2N NaOH until basic. The product oiled out of solution and removal of solvent by decantation afforded a viscous oil which was dried under vacuum and used without further purification. The deprotection step afforded the product, after crystallization in $CH_2Cl_2$, in 71% overall yield as a white powder, mp 180°–182° C.; MS (CI) 465 (MH$^+$); IR (KBr) 3320, 3162, 1685, 1665, 1611, 1515, 1503, 1468, 1447, 1401, 1333, 1302, 1281, 1243, 1181, 1113, 1048, 824, 749, 687, 565, 428, 401 cm$^{-1}$; $^1$H NMR (DMSO-d$_6$) δ8.07 (br t, J=5.9 Hz, 1H), 7.53 (dd, J=8.0 Hz, 1H), 7.8–6.7 (v brs, 4H), 7.35–7.15 (m, 3H), 7.26 (d, J=9.0 Hz, 2H), 7.1–6.93 (m, 3H), 6.99 (d, J=9.0 Hz, 2H), 5.22 (d, J=17.9 Hz, 1H), 5.11 (d, J=17.9 Hz, 1H), 5.04 (dd, J=8.8, 4.2 Hz, 1H), 4.3 (apparent d, J=6 Hz, 2H), 4.23 (m, 2H), 2.41 (m, 1H), 2.28 (m, 1H). Anal. Calc'd for $C_{25}H_{25}ClN_4O_3 \cdot HCl$: C 59.89, H 5.23, N 11.17. Found: C 59.57, H 5.13, N 10.99.

Compound 20

4-(2-Chlorobenzyl)-2-[2-[4-(2-guanidinoethyl)phenoxy]ethyl]-3,4-dihydro-3-oxo-2H-1,4-benzoxazine

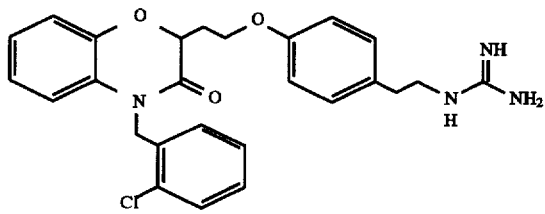

Prepared by method L using intermediate 9086-189-1 (Reference Example 42) and N,N'-di-t-butoxycarbonyl-2-(4-hydroxyphenyl)ethyl guanidine and method K with the following modifications. The bis-Boc-protected Mitsunobu coupling product was isolated, after flash chromatography and crystallization, in 36% yield. The deprotected product was isolated as the carbonate salt (tan solid) in 88% yield; mp 90° C. (dec); MS (CI) 479 (MH$^+$); IR (KBr) 3600, 3350, 2939, 1688, 1515, 1501, 1401, 1243, 1111, 1050, 834, 749, 522 cm$^{-1}$; $^1$H NMR (DMSO-d$_6$) δ7.53 (dd, J=7.8, 1.6 Hz, 1H), 7.33 (dd, J=7.8, 1.6 Hz, 1H), 7.29 (m, 1H), 7.25 (dd, 7.4, 1.6 Hz, 1H), 7.18 (d, J=8.2 Hz, 2H), 7.12–6.93 (m, 4H), 6.9 (d, J=8.2 Hz, 2H), 6.82 (dd, J=7.4, 1.6 Hz, 1H), 5.21 (d, J=17.2 Hz, 1H), 5.11 (d, J=17.2 Hz, 1H) 5.2 (dd, J=8.5, 4.1 Hz, 1H), 4.2 (m, 2H), 3.7–2.8 (br s, 5H), 2.69 (m, 2H), 2.4 (m, 1H), 2.25 (m, 1H). Anal. Calc'd for $C_{26}H_{27}N_4O_3Cl \cdot H_2CO_3 \cdot 0.3\ H_2O$: C 59.35, H 5.46, N 10.25, Cl 6.49. Found: C 59.37, H 5.29, N 10.25, Cl 6.86.

Compound 21

4-(4-Chlorobenzyl)-2-[2-[4-(guanidinomethyl)phenoxy]ethyl]-3,4-dihydro-3-oxo-2H-1,4-benzoxazine

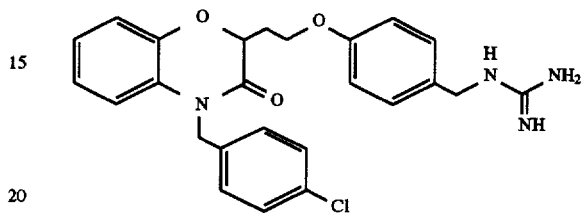

Prepared by method L using intermediate 10353-28-1 (Reference Example 41) and N,N'-di-t-butoxycarbonyl-(4-hydroxyphenyl)methyl guanidine and method K with the following modifications. The bis-Boc-protected Mitsunobu coupling product was isolated by dissolving the crude product residue in aqueous methanol and treating with a dropwise addition of 2N NaOH until basic. The product precipitated out of solution and was collected by filtration. The resulting white solid was air dried and used without further purification. The deprotected product was isolated as the carbonate salt (tan solid) in 24% overall yield as a tan solid, mp 90° C. (dec); MS (CI) 465 (MH$^+$); IR (KBr) 3330, 2940, 1685, 708, 1650, 1600, 1513, 1501, 1466, 1399, 1302, 1279, 1245, 1177, 1094, 1052, 799, 751 cm$^{-1}$; $^1$H NMR (DMSO-d$_6$) δ7.5–3.0 (v br s, 5H), 7.40 (d, J=8.4 Hz, 2H), 7.30 (d, J=8.4 Hz, 2H), 7.12 (d, J=8.8 Hz, 2H), 7.1–6.95 (m, 4H), 6.91 (d, J=8.8 Hz, 2H), 5.21 (d, J=17.4 Hz, 1H), 5.13 (d, J=17.4 Hz, 1H), 4.97 (dd, J=9.0, 4.2 Hz, 1H), 4.28 (m, 2H), 2.37 (m, 1H), 2.23 (m, 1H). Anal. Calc'd for $C_{25}H_{25}ClN_4O_3 \cdot CH_2O_3 \cdot 0.3\ H_2O$: C 58.66, H 5.23, N 10.52. Found: C 58.38, H 4.86, N 10.61.

REFERENCE EXAMPLE 89

Intermediate 10353-76

4-(2-Chlorobenzyl)-3,4-dihydro-2-(2-hydroxyethyl)-2H-1,4-benzoxazine

Method M: Intermediate 9086-189-1 (1 g, 1 eq, Reference Example 42) was dissolved in THF (5 ml) and treated with 1M Borane/THF (6.3 ml, 3 eq), and heated to reflux. After 3 h, the reaction mixture was concentrated under vacuum and the residue was partitioned between Et$_2$O and 1N HCl. The organic layer was washed with saturated Na$_2$CO$_3$, brine, dried over Na$_2$SO$_4$ and concentrated under vacuum. The product was isolated by flash chromatography, eluting with EtOAc/hexanes, to afford a 96% yield of a colorless oil.

REFERENCE EXAMPLE 90

Intermediate 10353-82

4-(3-Chlorobenzyl)-3,4-dihydro-2-(2-hydroxyethyl)-2H-1,4-benzoxazine

Prepared by Method M, from intermediate 10488-22 (Reference Example and isolated in 99% yield.

REFERENCE EXAMPLE 91

Intermediate 10353-83

4-(4-Chlorobenzyl)-3,4-dihydro-2-(2-hydroxyethyl)-2H-1,4-benzoxazine

Prepared by Method M from intermediate 10353-28-1 (Reference Example 41) and isolated in quanitative yield as a colorless oil.

REFERENCE EXAMPLE 92

Intermediate 10840-45

3,4-Dihydro-2-(2-hydroxyethyl)-4-(4-methylbenzyl)-2H-1,4-benzoxazine

Prepared by Method M from intermediate 10840-33 (Reference Example 46) in 80% yield and isolated as a green oil. IR (neat) 3371, 2921, 1607, 1500, 1247, 1221, 1052, 743 cm$^{-1}$; $^1$H NMR (CDCl$_3$) δ1.77-2.00 (m, 3H), 2.33 (s, H), 3.19 (dd, J=11.8, 7.7 Hz, 1H), 3.27 (dd, J=11.7, 2.6 Hz, 1H), 3.86-3.94 (m, 2H), 4.33-4.40 (m, 1H), 4.40 (s, 2H), 6.60-6.71 (m, 2H), 6.76-6.84 (m, H), 7.15 (br q, J$_{AB}$=8.2 Hz, 4H); Anal. Calc'd for C$_{18}$H$_{21}$NO$_2$.0.6H$_2$O: C, 73.49; H, 7.61; N, 4.76. Found: C, 73.33; H, 7.22; N, 4.84.

REFERENCE EXAMPLE 93

Intermediate 10840-46

3,4-Dihydro-2-(2-hydroxyethyl)-4-(3-methoxybenzyl)-2H-1,4-benzoxazine

Prepared by Method M from 10508-22-A (Reference Example 76) in quantitative yield and isolated as a green oil. IR 3350, 2948, 1605, 1505, 1283, 1262, 1050, 743 cm$^{-1}$; $^1$H NMR (CDCl$_3$) δ1.50-2.10 (v brs, 1H), 1.78-2.01 (m, 2H), 3.20 (dd, J=11.7, 7.8 Hz, 1H), 3.28 (dd, J=11.7, 2.6 Hz, 1H), 3.78 (s, 3H), 3.88 (t, J=5.6 Hz, 2H), 4.34-4.43 (m, 1H), 4.40 (s, 2H), 6.62-6.79 (m, 2H), 6.76-6.89 (m, 5H), 7.24 (t, J=7.7 Hz, 1H); MH$^+$ at m/z=300; Anal. Calc'd for C$_{18}$H$_{21}$NO$_3$.0.2H$_2$O; C, 71.36; H, 7.12; N, 4.62. Found: C, 71.25; H, 7.00; N, 4.62.

REFERENCE EXAMPLE 94

Intermediate 10840-8

4-(2,4-Dichlorobenzyl)-3,4-dihydro-2-(2-hydroxyethyl)-2H-1,4-benzoxazine

Prepared by Method M from 10005-181-1 (Reference Example 48) in 87% yield and was isolated as a colorless oil. IR (neat) 3348, 1607, 1501, 1247, 1221, 1046, 743 cm$^{-1}$; $^1$H NMR (CDCl$_3$) δ1.80-2.03 (m, 3H), 3.27-3.37 (m, 2H), 3.85-3.98 (m, 2H), 4.38-4.45 (m, 1H), 4.45 (s, 2H), 6.44 (dd, J=8.0., 1.4 Hz, 1H), 6.65 (td, J=7.6, 1.5 Hz, 1H), 6.77 (td, J=7.8, 1.6 Hz, 1H), 6.83 (dd, J=7.8, 1.6 Hz, 1H), 7.15-7.25 (m, 2H), 7.42 (d, J=1.8 Hz); MH$^+$ at m/z=338; Anal. Calc'd for C$_{17}$H$_{17}$Cl$_2$NO$_2$; C, 60.37; H, 5.07; N, 4.14. Found: C, 60.04; H, 4.98; N, 4.05.

Compound 22

4-(4-Chlorobenzyl)-2-[2-[4-(2-guanidinoethyl)phenoxy]ethyl]-3,4-dihydro-2H-1,4-benzoxazine

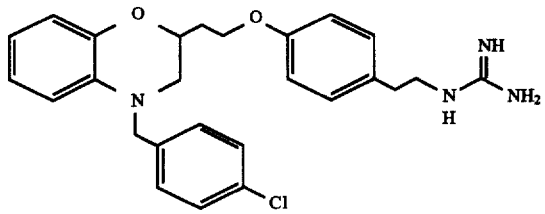

Prepared by method L using intermediate 10353-83 (Reference Example 91) and N,N'-di-t-butoxycarbonyl-2-(4-hydroxyphenyl)ethylguanidine and method K with the following modifications. The bis-Boc-protected Mitsunobu coupling product was isolated with satisfactory purity by flash chromatography (eluting with EtOAc/hexanes) in 58% yield. The deprotected product was isolated as the carbonate salt in 50% yield as a tan solid, single homogeneous peak by HPLC (PDA detection) 15 cm C$_{18}$ column, eluting with 55/45 H$_2$O (5% NH$_4$OH, 5% HOAC)/CH$_3$CN; MS (CI) 466 (MH$^+$); IR (KBr) 3475, 3321, 3064, 2931, 2875, 1698, 1638, 1608, 1581, 1513, 1502, 1467, 1696, 1358, 1303, 1288, 1244, 1178, 1116, 1047, 1013, 833, 743 cm$^{-1}$; $^1$H NMR (DMSO-d$_6$) δ 8.30-7.50 (br s, 2H), 7.40 (d, J=8.2 Hz, 2H), 7.35 (d, J=8.2 Hz, 2H), 7.19 (d, J=8.2 Hz, 2H), 6.90 (d, J=8.2 Hz, 2H), 6.77-6.60 (m, 3H), 6.55 (m, 1H), 4.53 (d, J=16.8 Hz, 1H), 4.45 (d, J=16.8 Hz, 1H), 4.35 (m, 1H), 4.12 (br d, J=11.4 Hz, 2H), 3.60-3.10 (br s, 5H), 3.49 (m, 2H), 2.73 (m, 2H), 2.05 (m, 2H).

Compound 23

4-(3-Chlorobenzyl)-2-[2-[4-(2-guanidinoethyl)phenoxy]ethyl]-3,4-dihydro-2H-1,4-benzoxazine

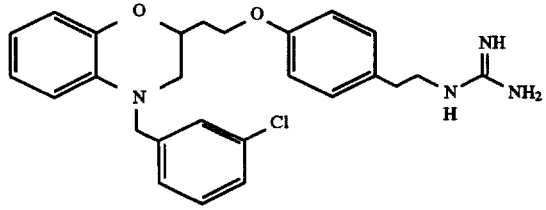

Prepared by method L using intermediate 10353-82 (Reference Example 90) and N,N'-di-t-butoxycarbonyl-2-(4-hydroxyphenyl)ethylguanidine and method K with the following modifications. The bis-Boc-protected Mitsunobu coupling product was isolated by flash chromatography (eluting with EtOAc/hexanes) in 94% yield. The deprotected product was isolated as the carbonate salt in 59% yield as a tan solid, single homogeneous peak by HPLC (PDA detection) 15 cm C$_{18}$ column, eluting with 55/45 H$_2$O (5% NH$_4$OH, 5% HOAC)/CH$_3$CN; MS (CI) 466 (MH$^+$); IR (KBr) 3473, 3316, 3064, 2931, 2876, 1698, 1638, 1608, 1580, 1512, 1503, 1468, 1431, 1393, 1359, 1303, 1243, 1221, 1178, 833, 742 cm$^{-1}$; $^1$H NMR (DMSO-d$_6$) δ 8.50-7.60 (br s, 2H), 7.42-7.20 (m, 4H), 7.19 (d, J=7.7 Hz, 2H), 6.90 (d, J=7.7 Hz, 2H), 6.78-6.70 (m, 3H), 6.58 (m, 1H), 4.55 (d, J=17.3 Hz, 1H), 4.48 (d, J=17.3 Hz, 1H), 4.15 (m, 2H), 3.80-3.10 (br s, 4H), 3.52 (br d, J=11.8 Hz, 2H), 3.25 (m, 2H), 2.73 (m, 2H), 2.08 (m, 2H).

Compound 24

4-(3-Chlorobenzyl)-3,4-dihydro-2-[2-[4-(2-guanidinoethyl)phenoxy]ethyl]-6-methyl-3-oxo-2H-1,4-benzoxazine

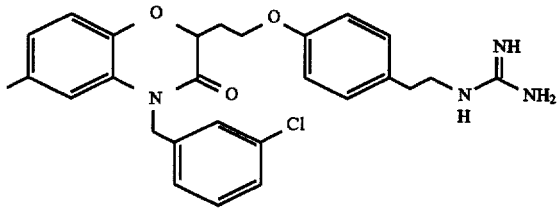

Prepared by method L using intermediate 12168-10-1 (Reference Example 39) and N,N'-di-t-butoxycarbonyl-2-(4-hydroxyphenyl)ethylguanidine and method K with the following modifications. The bis-Boc-protected Mitsunobu coupling product was isolated by flash chromatography (eluting with EtOAc/hexanes) in ~70% yield. The deprotected product was triturated from $Et_2O$ dissolved in $CH_2Cl_2$ and the solvent removed under vacuum to afford the product in 92% yield as a pale yellow solid. MS (CI) 493 ($MH^+$); IR (KBr) 3148, 1666, 1610, 1511, 1433, 1384, 1302, 1244, 1178, 1112, 1052, 817, 772, 680, 527 $cm^{-1}$; $^1H$ NMR (DMSO-$d_6$) δ 7.50 (br t, J=5.7 Hz, 1H), 7.40–6.85 (v br s, 5H), 7.35 (m, 3H), 7.20 (m, 3H), 6.94 (m, 4H), 6.81 (d, J=8.9 Hz, 1H), 5.20 (d, J=17.3 Hz, 1H), 5.12 (d, J=17.3 Hz, 1H), 4.94 (dd, J=9.1, 4.3 Hz, 1H), 4.18 (m, 2H), 3.31 (m, 2H), 2.72 (apparent t, J=7.3 Hz, 2H), 2.37 (m, 1H), 2.30–2.13 (m, 1H), 2.19 (s, 3H). Anal. Calc'd for $C_{27}H_{29}ClN_4O_3 \cdot HCl \cdot 1.0\ H_2O$: C 59.23, H 5.89, N 10.23. Found: C 59.47, H 5.60, N 10.11.

Compound 25

4-(3-Chlorobenzyl)-3,4-dihydro-2-[2-[4-(2-guanidinoethyl)phenoxy]ethyl]-3-oxo-2H-pyrido[3,2-b]-1,4-oxazine

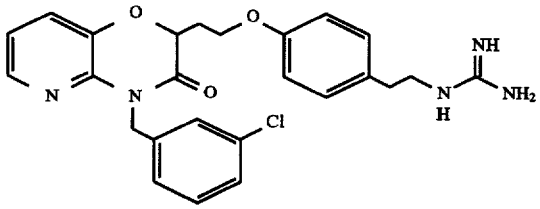

Prepared by method L using intermediate 10353-191-1 (Reference Example 40) and N,N'-di-t-butoxycarbonyl-2-(4-hydroxyphenyl)ethylguanidine and method K with the following modifications. The bis-Boc-protected Mitsunobu coupling product was isolated by flash chromatography (eluting with EtOAc/hexanes) in 77% yield. The deprotected product was isolated in 50% yield after trituration with $Et_2O$. mp 47°–54° C. (softens) 54–56° C.; MS (CI) 480 ($MH^+$); IR (KBr) 3326, 3150, 1666, 1599, 1513, 1459, 1398, 1331, 1278, 1229 $cm^{-1}$; $^1H$ NMR (DMSO-$d_6$) δ 8.0 (dd, J=4.9, 1.4 Hz, 1H), 7.53 (br t, J=7.3 Hz, 1H), 7.47 (dd, J=7.9, 1.2 Hz, 1H), 7.37 (s, 1H), 7.35–7.22 (m, 2H), 7.17 (d, J=8.6 Hz, 2H), 7.09 (dd, J=7.9, 4.8 Hz, 1H), 6.87 (d, J=8.6 Hz, 2H), 5.24 (d, J=16.3, Hz, 1H), 5.23 (d, J=16.3 Hz, 1H), 5.12 (dd, J=8.2, 4.2 Hz, 1H), 4.15 (m, 2H), 6.32 (m, 2H), 2.71 (m, 2H), 2.39 (m, 1H), 2.29 (m, 1H). Anal. Calc'd for $C_{25}H_{26}ClN_5O_3 \cdot 2HCl \cdot 0.8\ H_2O$: C 56.57, H 5.43, N 13.19. Found: C 56.84, H 5.65, N 13.04.

Compound 26

4-(4-Chlorobenzyl)-3,4-dihydro-2-[2-[4-(2-guanidinoethyl)phenoxy]ethyl]-3-oxo-2H-1,4-benzoxazine

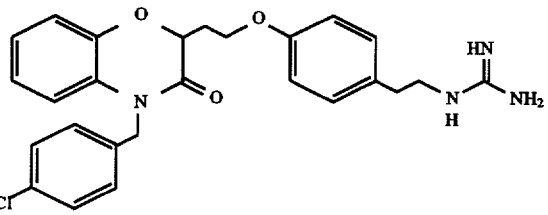

Prepared by method L using intermediate 10353-28-1 (Reference Example 41) and N,N'-di-t-butoxycarbonyl-2-(4-hydroxyphenyl)ethylguanidine and method K with the following modifications. The bis-Boc-protected Mitsunobu coupling product was isolated by dissolving the crude product residue in aqueous methanol and treating with 2N NaOH until basic. The product precipitated out of solution as a gummy semi-solid. The solvent was removed by decantation, the product was air dried and used without further purification. The deprotected product was isolated as the carbonate salt (tan solid) in 60% yield as a tan solid, single homogeneous peak by HPLC (PDA detection) 15 cm $C_{18}$ column, eluting with 55/45 $H_2O$ (5% $NH_4OH$, 5% HOAC)/$CH_3CN$; MS (CI) 479 ($MH^+$); IR (KBr) 3337, 3050, 2930, 2875, 1683, 1609, 1512, 1500, 1466, 1439, 1397, 1327, 1301, 1278, 1242, 1177, 1093, 750 $cm^{-1}$.

Compound 27

4-Benzyl-2-{2-[4-[2-(N,N-bis-tert-butoxycarbonylguanidinoethyl]phenoxy]ethyl}-3,4-dihydro-3-oxo-2H-1,4-benzoxazine

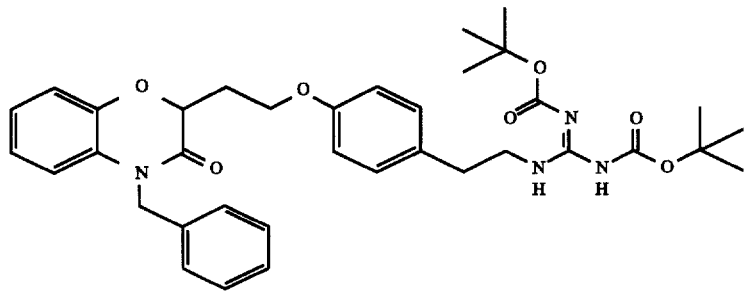

Prepared by Method L using intermediate 10508-23-A (Reference Compound 74) and isolated as a white powder in 28% yield after column chromatography (10% ether in hexane); IR (KBr) 3334, 2978, 1638, 1616, 1330, 1132, 750 cm$^{-1}$; $^1$H NMR (CDCl$_3$) δ 1.48 (s, 9H), 1.51 (s, 9H), 2.25–2.39 (m, 1H), 2.50–2.63 (m, 1H), 2.81 (t, J=7.2 Hz, 2H), 3.63 (q, J=7.9 Hz, 2H), 4.18–4.29 (m, 2H), 4.94 (dd, J=9.3, 3.8 Hz, 1H), 5.16 (s, 2H), 6.84–7.01 (m, 6H), 7.13 (d, J=8.4 Hz, 2H), 7.23–7.34 (m, 5H), 8.38 (br t, J=3.8 Hz, 1H), 11.49 (br s, 1H). Anal. Calc'd for C$_{36}$H$_{44}$N$_4$O$_7$: C, 67.06; H, 6.88; N, 8.69. Found: C, 66.80; H, 6.90; N, 8.63.

Compound 28

4-Benzyl-3,4-dihydro-2-{2-[4-[2-guanidinoethyl]phenoxy]ethyl}-3-oxo-2H-1,4-benzoxazine Hydrochloride 0.7 Hydrate

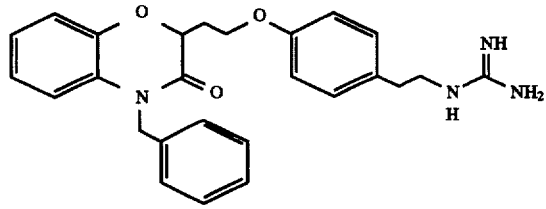

Prepared by Method K from Compound 27 and isolated as a white powder in 9.1% yield; IR (KBr) 3326, 3146, 1664, 1500, 1401, 1243, 827, 751 cm$^{-1}$; Anal. Calc'd for C$_{26}$H$_{28}$N$_4$O$_3$·HCl·0.7H$_2$O: C, 63.27; H, 6.21; N, 11.35. Found: C, 63.37; H, 5.98; N, 11.06.

Compound 29

3,4-Dihydro-2-{2-[4-(2-guanidinoethyl)phenoxy]ethyl}-4-(2-methoxybenzyl)-3-oxo-2H-1,4-benzoxazine

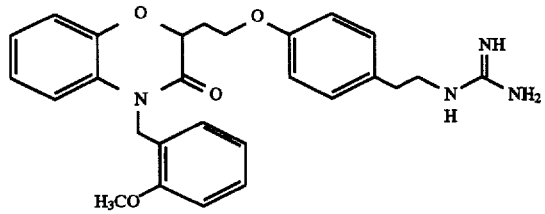

Prepared from 2-{2-[4-[2-(N,N-bis-tert-butoxycarbonylguanidino)ethyl]phenoxy]ethyl}-3,4-dihydro-4-(2-methoxybenzyl)-3-oxo-2H-1,4-benzoxazine by methods L and K to give an off-white powder in 25% yield; IR (KBr) 3164, 1663, 1501, 1405, 1245, 751 cm$^{-1}$; $^1$H NMR (CDCl$_3$) δ 2.20–2.33 (m, 1H), 2.37–2.52 (m, 1H), 2.76 (br s, 2H), 3.33 (br s, 2H), 3.87 (s, 3H), 4.08–4.21 (m, 2H), 4.87 (dd, J=8.6, 4.3 Hz, 1H), 5.09 (ABq, J$_{AB}$=18.0 Hz, 2H), 6.73–7.25 (v br s, 4H), 6.73–6.99 (m, 9H), 7.11 (d, J=7.7 Hz, 2H), 7.21 (t, J=7.2 Hz, 1H), 7.67 (br s, 1H); MH$^+$ at m/z=475; Anal. Calc'd for C$_{27}$H$_{30}$N$_4$O$_4$·HCl·0.75H$_2$O: C, 61.83; H, 6.25; N, 10.68. Found: C, 61.82; H, 6.26; N, 10.61.

Compound 30

2-{2-[4-[2-(N,N-Bis-tert-butoxycarbonylguanidino)ethyl]phenoxy]ethyl}-3,4-dihydro-4-(3-fluorobenzyl)-3-oxo-2H-1,4-benzoxazine

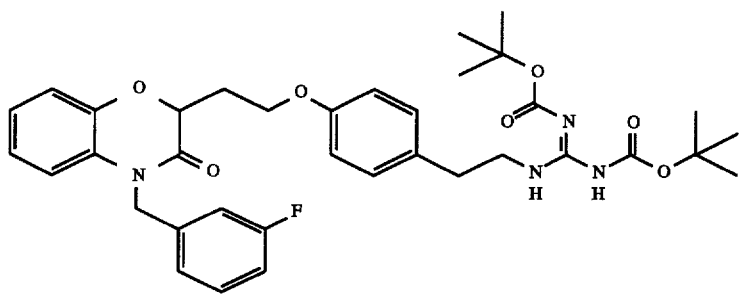

Prepared from 10508-24-A (Reference Example 45) by Method L and isolated as a white foam in 17% yield after chromatography using 20% EtOAc in hexane; IR (KBr) 3330, 2979, 1723, 1688, 1638, 1132, 1059, 751 cm$^{-1}$; $^1$H NMR (CDCl$_3$) δ 1.48 (s, 9H), 1.50 (s, 9H), 2.27–2.38 (m, 1H), 2.53–2.64 (m, 1H), 2.81 (t, J=7.2 Hz, 2H), 3.64 (q, J=6.8 Hz, 2H), 4.15–4.29 (m 2H), 4.94 (dd, J=9.0, 4.0 Hz, 1H), 5.15 (ABq, J$_{AB}$=15.2 Hz, 2H), 6.81–7.04 (m, 8H), 7.13 (d, J=8.6 Hz, 2H), 7.28–7.92 (m, 2H), 8.36 (t, J=4.8 Hz, 1H), 11.47 (s, 1H); Anal. Calc'd for C$_{36}$H$_{43}$FN$_4$O$_7$: C, 65.24; H, 6.54; N, 8.45. Found: 0, 65.03; H, 6.43; N, 8.31.

Compound 31

3,4-Dihydro-4-(3-fluorobenzyl)-2-{2-[4-(2-guanidinoethyl)phenoxy]ethyl}-3-oxo-2 H-1,4-benzoxazine

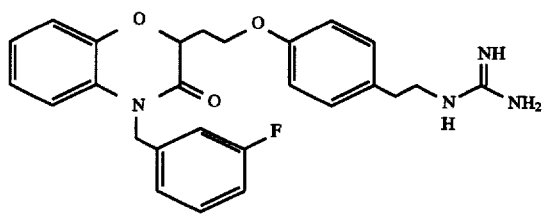

Prepared form Compound 30 by Method K and isolated as a white foam in 97% yield; IR (KBr) 3153, 1654, 1501, 753 cm$^{-1}$; $^1$H NMR (CDCl$_3$) δ 2.18–2.33 (m, 1H), 2.37–2.52 (m, 1H), 2.78 (br s, 2H), 3.34 (v br s, 2H), 4.05–4.22 (m, 2H), 4.86 (dd, J=8.7, 4.2 Hz, 1H), 5.07 (s, 2H), 6.75–7.25 (br s, 4H), 6.80 (d, J=7.6 Hz, 2H), 6.84–7.00 (m, 6H), 7.12 (d, J=7.7 Hz, 2H), 7.22–7.30 (m, 2H), 7.71 (br s, 1H); Anal. Calc'd for C$_{26}$H$_{27}$FN$_4$O$_3$.HCl.H$_2$O.0.1C$_3$H$_8$O: C, 60.40; H, 5.94; N, 10.71. Found: C, 60.11; H, 5.86; N, 10.42.

Compound 32

2-{2-[4-[2-(N,N-Bis-tert-butoxycarbonylguanidino)ethyl]phenoxy]ethyl}-3,4-dihydro-4-(3-methoxybenzyl)-3-oxo-2H-1,4-benzoxazine

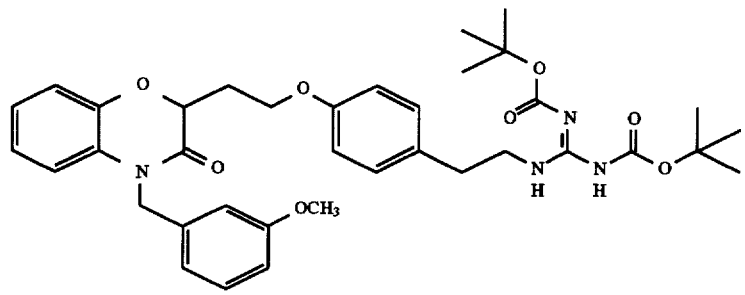

Prepared from intermediate 10508-22-A (Reference Example 76) by Method L and isolated as a white foam in 30% yield; IR (KBr) 3334, 2979, 1723, 1686, 1645, 1615, 1329, 1246, 1156, 1132, 1059, 751 cm$^{-1}$; $^1$H NMR (CDCl$_3$) δ 1.48 (s, 9H), 1.51 (s, 9H), 2.26–2.38 (m, 1H), 2.51–2.63 (m, 1H), 2.81 (t, J=7.2 Hz, 2H), 3.64 (q, J=6.79 Hz, 2H), 3.77 (s, 3H), 4.15–4.29 (m, 2H), 4.94 (dd, J=9.2, 4.0 Hz, 1H), 5.13 (s, 2H), 6.76–7.02 (m, 8H), 7.12 (d, J=8.6 Hz, 2H), 7.21–7.26 (m, 2H), 8.37 (t, J=4.8 Hz, 1H), 11.47 (s, 1H); Anal. Calc'd for C$_{37}$H$_{46}$N$_4$O$_8$.0.1H$_2$O: C, 65.68; H, 6.88; N, 8.28. Found: C, 65.40; H, 6.83; N, 8.10.

Compound 33

3,4-Dihydro-2-{2-[4-(2-guanidinoethyl)phenoxy]ethyl}-4-(3-methoxybenzyl)-3-oxo-2H-1,4-benzoxazine

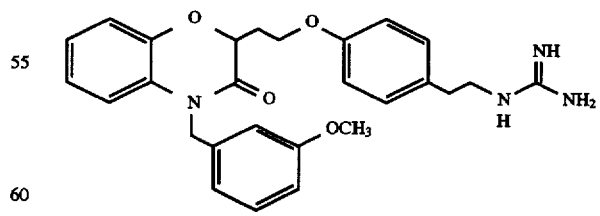

Prepared from Compound 32 by Method K and isolated as a CHCl$_3$ soluble white foam in 21% yield; IR (neat) 3020, 1671, 1513, 1501, 1407, 1217, 758 cm$^{-1}$; $^1$H NMR (CDCl$_3$) 2.15–2.28 (m, 1H), 2.35–2.48 (m, 1H), 2.70–2.87 (m, 3H), 3.34 (br s, 2H), 3.71 (s, 3H), 4.02–4.17 (m, 2H), 4.85 (dd, J=8.8, 4.0 Hz, 1H), 5.03 (ABq, J$_{AB}$=16.8 Hz, 2H), 6.72–7.23 (m, 16H), 7.64 (br s, 1H); Anal. Calc'd for C$_{27}$H$_{30}$N$_4$O$_4$·HCl·H$_2$O: C, 61.30; H, 6.29; N, 10.59. Found: C, 61.20; H, 6.04; N, 10.45.

Compound 34

4-(3-Benzyloxybenzyl)-2-{2-[4-[2-(N,N-Bis-tert-butoxycarbonylguanidino)ethyl]phenoxy]ethyl}-3,4-dihydro-3-oxo-2H-1,4-benzoxazine

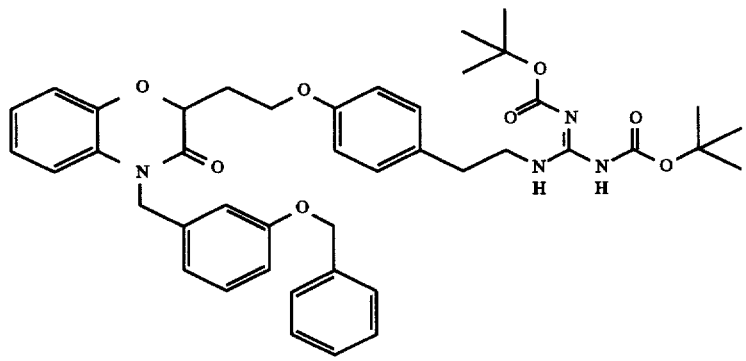

Prepared from 10508-82-A (Reference Example 77) by Method L and isolated as a white foam in 35% yield after chromatography (eluting with CH$_2$Cl$_2$); IR (KBr) 3331, 2977, 1722, 1687, 1638, 1613, 1501, 1410, 1329, 1245, 1156, 1131, 749 cm$^{-1}$; $^1$H NMR (CDCl$_3$) δ 1.48 (s, 9H), 1.51 (s, 9H), 2.24–2.37 (m, 1H), 2.50–2.63 (m, 1H), 2.81 (t, J=7.2 Hz, 2H), 3.63 (q, J=7.1 Hz, 2H), 4.15–4.30 (m, 2H), 4.92 (dd, J=9.4, 3.9 Hz, 1H), 5.02 (s, 2H), 5.12 (ABq, J$_{AB}$=15.4 Hz, 2H), 6.84–7.00 (m, 9H), 7.12 (d, J=8.6 Hz, 2H), 7.23–7.27 (m, 1H), 7.32–7.42 (m, 5H), 8.37 (br t, J=4.3 Hz, 1H), 11.5 (s, 1H); Anal. Calc'd for C$_{43}$H$_{50}$N$_4$O$_8$: C, 68.78; H, 6.71; N, 7.46. Found: C, 68.50; H, 6.78; N, 7.41.

Compound 35

4-(3-Benzyloxybenzyl)-3,4-dihydro-2-{2-[4-(2-guanidinoethyl)phenoxy]ethyl}-3-oxo-2H-1,4-benzoxazine

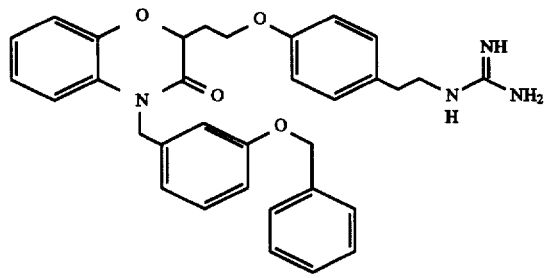

Prepared from Compound 34 by Method K and isolated as a white foam in 53% yield after repeated ether triturations, mp 100°–105° C.; IR (KBr) 3338, 3155, 1676, 1610, 1513, 1500, 1400, 1243, 751 cm$^{-1}$; $^1$H NMR (CDCl$_3$) δ 2.10–2.23 (m, 1H), 2.30–2.44 (m, 1H), 2.74 (br s, 2H), 3.32 (br s, 2H), 3.97–4.15 (m, 2H), 4.81 (dd, J=8.7, 4.1 Hz, 1H), 4.96 (s, 2H), 5.01 (s, 2H), 6.75–7.33 (m, 23H), 7.63 (br s, 1H); Anal. Calc'd for C$_{33}$H$_{34}$N$_4$O$_4$·HCl·H$_2$O: C, 65.50; H, 6.16; N, 9.26. Found: C, 65.77; H, 5.98; N, 9.06.

Compound 36

3,4-Dihydro-2-{2-[4-(2-guanidinoethyl)phenoxy]ethyl}-4-(3-hydroxybenzyl)-3-oxo-2H-1,4-benzoxazine

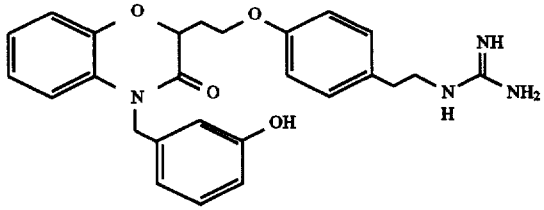

Compound 35 (0.5 g, 0.83 mmol) was reacted with H$_2$ at 50 psi in a Parr shaker containing containing 10% Pd/C (200 mg) in MeOH. After 2h, the catalyst was removed and the filtrate was concentrated in vacuum. The product was isolated as a white powder in 40% yield after ether trituration; IR (KBr) 3159, 1661, 1613, 1512, 1500, 1242, 752 cm$^{-1}$; $^1$H NMR (DMSO-d$_6$ plus CDCl$_3$) δ 2.28–2.38 (m, 1H), 2.45–2.58 (m, 1H), 2.82 (t, J=7.4 Hz, 2H), 3.01 (s, HDO), 3.40 (q, J=6.8 Hz, 2H), 4.15–4.30 (m, 2H), 4.91 (dd, J=9.1, 4.3 Hz, 1H), 5.08 (s, 2H), 6.69–6.75 (m, 3H), 6.87–7.02 (m, 8H), 7.11–7.30 (m, 5H), 7.54 (br t, J=5.1 Hz, 1H), 9.05 (s, 1H); MH$^+$ at m/z=461; Anal. Calc'd for C$_{26}$H$_{28}$N$_4$O$_4$·2HCl·H$_2$O: C, 56.63; H, 5.85; N, 10.16. Found: C, 56.46; H, 5.61; N, 9.85.

Compound 37

3,4-Dihydro-2-{2-[4-(2-guanidinoethyl)phenoxy]ethyl}-4-(4-methoxybenzyl)-3-oxo-2H-1,4-benzoxazine

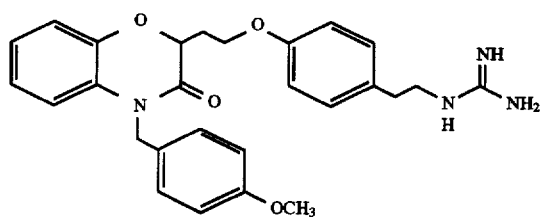

Prepared by method L using intermediate 10508-19 (Reference Example 47) and N,N'-di-t-butoxycarbonyl-2-(4-hydroxyphenyl)ethylguanidine and method K to give a white foam in 53% yield; IR (KBr) 3411, 1654, 1617, 1515, 1501, 1248, 750 cm$^{-1}$; $^1$H NMR (CDCl$_3$) δ 2.20 (m, 1H), 2.31–2.44 (m, 1H), 2.72 (br t, J=6.4 Hz, 2H), 3.29 (br t, J=6.4 Hz, 2H), 3.68 (s, 3H), 3.96– 4.12 (m, 2H), 4.79 (dd, J=8.8, 4.0 Hz, 1H), 4.97 (s, 2H), 6.70–7.30 (v br s, 4H), 6.71–6.93 (m, 8H), 7.05–7.13 (m, 4H), 7.70 (br s, 1H); MH$^+$ at m/z=475; Anal. Calc'd for C$_{27}$H$_{30}$N$_4$O$_4$·HCl·H$_2$O: C, 61.30; H, 6.29; N, 10.59. Found: C, 61.17; H, 6.10; N, 10.25.

Compound 38

3,4-Dihydro-2-{2-[4-(2-guanidinoethyl)phenoxy]ethyl}-3-oxo-4-(4-phenylbenzyl)-2H-1,4-benzoxazine

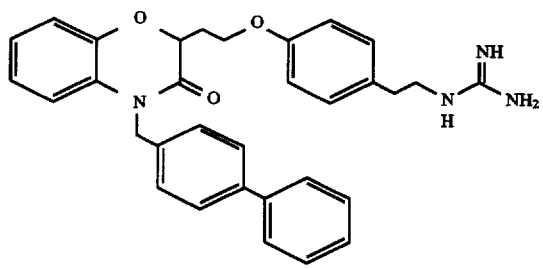

Prepared by method L using intermediate 11578-99 (Reference Example 59) and N,N'-di-t-butoxycarbonyl-2-(4-hydroxyphenyl)ethylguanidine and method K to give a white foam in 18% overall yield; IR (KBr) 3157, 1681, 1500, 1398, 1243, 759 cm$^{-1}$; $^1$H NMR (CDCl$_3$) δ 2.20–2.33 (m, 1H), 2.38–2.54 (m, 1H), 2.73–2.82 (m, 2H), 3.27–3.39 (m, 2H), 4.05–4.22 (m, 2H), 4.88 (dd, J=8.9, 4.4 Hz, 1H), 5.12 (s, 2H), 6.65–7.57 (v br s, 4H), 6.80 (d, J=8.4 Hz, 2H), 6.88–6.97 (m, 3H), 7.11 (d, J=8.3 Hz, 2H), 7.25–7.32 (m, 4H), 7.39 (t, J=7.1 Hz, 2H), 7.51 (d, J=8.0 Hz, 4H), 7.71 (br s, 1H); MH$^+$ at m/z=521; Calc'd for C$_{32}$H$_{32}$N$_4$O$_3$·HCl·H$_2$O: C, 66.83; H, 6.13; N, 9.74. Found: C, 67.01; H, 5.99; N, 9.53.

Compound 39

2-{2-[4-(2-Aminomethyl)phenoxy]ethyl}-4-(3,5-dichlorobenzyl)-3,4-dihydro-3-oxo-2H-1,4-benzoxazine

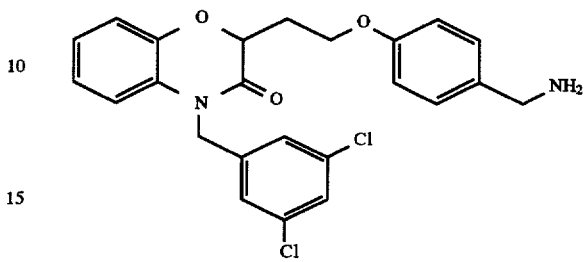

Prepared by method L using intermediate 10005-181-1 (Reference Example 48) and N,-t-butoxycarbonyl-(4-hydroxyphenyl)benzylamine and method K to give a white solid directly from the reaction in 73% yield, mp 228.5°–230° C.; IR (KBr) 2927, 1680, 1517, 1503, 1402, 1254, 752 cm$^{-1}$; $^1$H NMR (DMSO-d$_6$) δ 2.20–2.31 (m, 1H), 2.36–2.48 (m, 1H), 3.94 (s, 2H), 4.20–4.28 (m, 2H), 5.05 (dd, J=8.5, 3.8 Hz, 1H), 5.18 (ABq, J$_{AB}$=16.7 Hz, 2H), 6.96–7.10 (m, 6H), 7.35 (d, J=1.8 Hz, 2H), 7.43 (d, J=8.6 Hz, 2H), 7.52 (t, J=1.8 Hz, 1H), 8.37 (br s, 3H); Anal. Calc'd for C$_{24}$H$_{22}$Cl$_2$N$_2$O$_3$·HCl·0.5H$_2$O: C, 57.33; H, 4.81; N, 5.57. Found: C, 57.33; H, 4.77; N, 5.37.

Compound 40

4-(3,5-Dichlorobenzyl)-3,4-dihydro-2-{2-[4-(2-guanidinoethyl)phenoxy]ethyl}-3-oxo-2H-1,4-benzoxazine

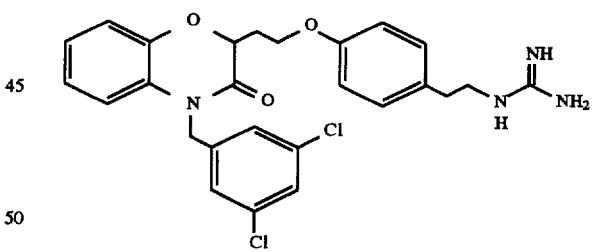

Prepared by method L using intermediate 10005-181-1 (Reference Example 48) and N,N'-di-t-butoxycarbonyl-2(4-hydroxyphenyl)ethylguanidine and method K to give a cream-colored solid in 48% yield, mp 115.5–117° C.; IR (KBr) 3328, 1665, 1515, 1501, 1399, 1245, 751 cm$^{-1}$; $^1$H NMR (DMSO-d$_6$) δ 2.17–2.30 (m, 1H), 2.33–2.47 (m, 1H), 2.72 (t, J=7.2 Hz, 2H), 3.28–3.48 (m, 3H), 4.15–4.24 (m, 2H), 5.02–5.06 (m, 1H), 5.18 (ABq, J$_{AB}$=16.7 Hz, 2H), 6.8–7.6 (v br s, 4H), 6.91 (d, J=8.5 Hz, 1H), 6.99–7.10 (m, 4H), 7.20 (d, J=8.5 Hz, 2H), 7.35 (s, 2H), 7.52 (s, 1H), 7.66 (t, J=5.5 Hz, 1H); Anal. Calc'd for C$_{26}$H$_{26}$Cl$_2$N$_4$O$_3$·HCl·0.25H$_2$O: C, 56.33; H, 5.00; N, 10.11. Found: C, 56.18; H, 5.26; N, 9.90.

Compound 41

2-{2-[4-[2-(N,N-Bis-tert-butoxycarbonylguanidino)ethyl]phenoxy]ethyl}-3,4-dihydro-4-(3-methoxybenzyl)-3-oxo-4-(4-picolyl)-2H-1,4-benzoxazine

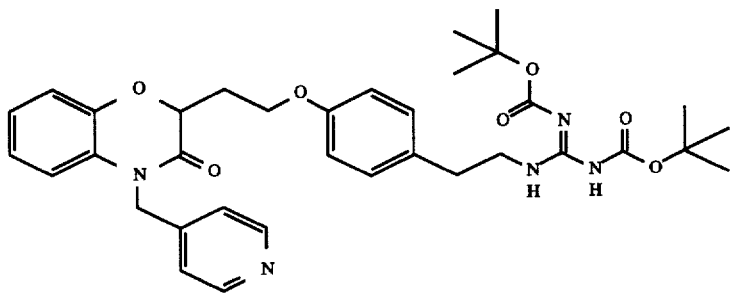

Prepared by method L using intermediate 10840-22 (Reference Example 58) and N,N'-di-t-butoxycarbonyl-2(4-hydroxyphenyl)ethyl guanidine to give an off-white powder in 20% yield; IR (KBr) 2979, 1723, 1690, 1638, 1501, 1416, 1368, 1333, 1246, 1158, 751 cm$^{-1}$; $^1$H NMR (CDCl$_3$) δ 1.48 (s, 9H), 1.50 (s, 9H), 2.28–2.40 (m, 1H), 2.53–2.64 (m, 1H), 2.81 (t, J=7.2 Hz, 2H), 3.63 (br q, J=7.2 Hz, 2H), 4.16–4.30 (m, 2H), 4.96 (dd, J=9.2, 4.0 Hz, 1H), 5.16 (ABq, J$_{AB}$=14 Hz, 2H), 6.73 (dd, J=8.4, 1.5 Hz, 1H), 6.85 (d, J=8.6 Hz, 2H), 6.93 (td, J=7.2, 2.0 Hz, 1H), 6.97–7.06 (m, 2H), 7.12–7.17 (m, 4H), 8.36 (br t, J=4.8 Hz, 1H), 8.56 (dd, J=4.5, 1.6 Hz, 2H), 11.47 (s, 1H); Anal. Calc'd for C$_{35}$H$_{43}$N$_5$O$_7$: C, 65.10; H, 6.71; N, 10.85. Found: C, 64.73; H, 6.69; N, 10.46.

Compound 42

3,4-Dihydro-2-{2-[4-(2-guanidinoethyl)phenoxy]ethyl}-3-oxo-4-(4-picolyl)-2H-1,4-benzoxazine

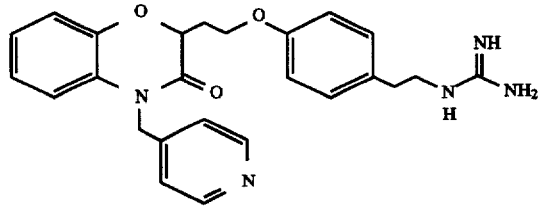

Prepared from Compound 41 by Method K and isolated as a white solid in 30% yield after trituration with ether, mp 244°–248° C.; IR (KBr) 3184, 1673, 1640, 1499, 1403, 1248, 760 cm$^{-1}$; $^1$H NMR (DMSO-d$_6$) δ 2.20–2.35 (m, 1H), 2.35–2.48 (m, 1H), 2.72 (t, J=7.2 Hz, 2H), 3.32 (q, J=6.6 Hz, 2H), 3.50–4.50 (v br s, 1H), 4.15–4.26 (m, 2H), 5.07 (dd, J=8.8, 4.1 Hz, 1H), 5.40 (ABq, J$_{AB}$=18.1 Hz, 2H), 6.80–7.55 (v br s, 4H), 6.87–7.13 (m, 6H), 7.21 (d, J=8.6 Hz, 2H), 7.66 (t, J=5.6 Hz, 1H), 7.78 (d, J=6.3 Hz, 2H), 8.78 (d, J=6.4 Hz, 2H); MH$_+$ at m/z=446; Anal. Calc'd for C$_{25}$H$_{27}$N$_5$O$_3$·2HCl·0.5H$_2$O: C, 56.93; H, 5.73; N, 13.28. Found: C, 56.87; H, 5.60; N, 13.06.

Compound 43

3,4-Dihydro-2-{2-[4-(2-guanidinoethyl)phenoxy]ethyl}-4-(1-naphthylmethyl)-3-oxo-2H-1,4-benzoxazine

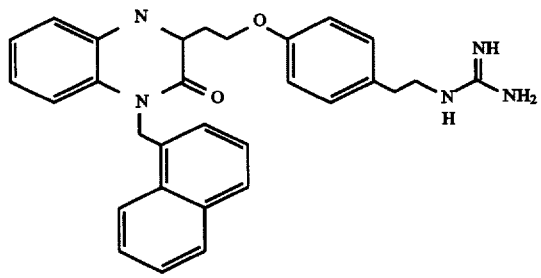

Prepared by method L using intermediate 10508-84-A1 (Reference Example 78) and N,N'-di4-butoxycarbonyl-2-(4-hydroxyphenyl)ethylguanidine and method K using trifluoroacetic acid with anisole present, instead of IPA/HCl. The crude material was treated with CH$_2$Cl$_2$/ether to give the title compound as a cream-colored solid in 72% yield; m.p. 75°–80° C.; IR (KBr) 3360, 1671, 1501, 1405, 1204, 1136, 799, 723 cm$^{-1}$; $^1$H NMR (DMSO-d$_6$) δ 2.29–2.37 (m, 1H), 2.37–2.50 (m, 1H), 2.72 (t, J=7.4 Hz, 2H), 3.28–3.48 (m, 2H), 3.31–3.39 (m, 2H), 3.48 (v br s, 1H), 4.16–4.29 (m, 2H), 5.08 (dd, J=8.8, 4.2 Hz, 1H), 5.62 (ABq, J$_{AB}$=17.4 Hz, 2H), 6.86–7.66 (v br s, 4H), 6.86–7.06 (m, 4H), 7.11 (d, J=8.1 Hz, 2H), 7.20 (d, J=8.6 Hz, 2H), 7.40 (t, J=7.7 Hz, 1H), 7.48–7.55 (m, 1H), 7.58–7.68 (m, 2H), 7.85 (d, J=8.2 Hz, 1H), 8.00 (d, J=9.1 Hz), 8.21 (d, J=8.1 Hz); MH$^+$ at m/z=495; Anal. Calc'd for C$_{30}$H$_{30}$N$_4$O$_3$·C$_2$HF$_3$O$_2$: C, 62.38; H, 5.06; N, 9.04. Found: C, 62.38; H, 5.06; N, 9.04.

Compound 44

2-{2-[4-[2-(N,N-Bis-tert-butoxycarbonylguanidino)ethyl]phenoxy]ethyl}-3,4-dihydro-4-(2-naphthylmethyl)-3-oxo-2H-1,4-benzoxazine

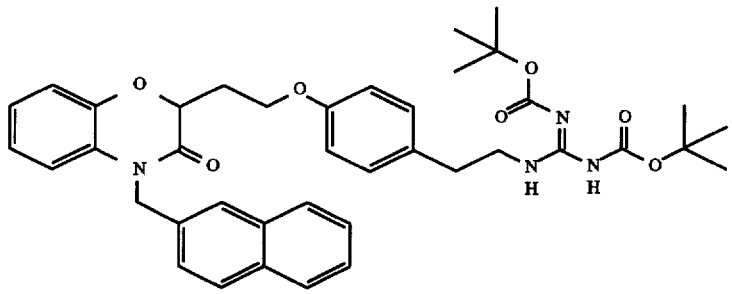

Prepared by method L using intermediate 10508-80-1 (Reference Example and N,N'-di-t-butoxycarbonyl-2(4-hydroxyphenyl)ethylguanidine. The crude material was purified by flash chromatography eluting with EtOAc/hexane to afford the product as a white foam in 24% yield; IR (KBr) 3330, 3053, 2977, 2931, 1722, 1638, 1614, 1512, 1501, 1366, 1330, 1244, 1156, 1131, 748 cm$^{-1}$; $^1$H NMR (CDCl$_3$) δ 1.48 (s, 9H), 1.51 (s, 9H), 2.31–2.44 (m, 1H), 2.55–2.68 (m, 1H), 2.82 (t, J=7.1 Hz, 2H), 3.65 (q, J=6 Hz, 2H), 4.20–4.33 (m, 2H), 5.00 (dd, J=9.4, 3.4 Hz, 1H), 5.32 (ABq, J$_{AB}$=15.4 Hz, 2H), 6.84–6.96 (m, 5H), 7.00 (t, J=6.8 Hz, 1H), 7.14 (d, J=8.5 Hz, 2H), 7.38 (d, J=8.4 Hz, 1H), 7.45–7.48 (m, 2H), 7.68 (s, 1H), 7.75–7.83 (m, 3H), 8.20 (br s, 1H), 11.48 (s, 1H); Anal. Calc'd for C$_{40}$H$_{46}$N$_4$O$_7$: C, 69.14; H, 6.67; N, 8.06. Found: C, 69.16; H, 6.88; N, 7.63.

Compound 45

3,4-Dihydro-2-{2-[4-(2-guanidinylethyl)phenoxy]ethyl}-4-(2-naphthylmethyl)-3-oxo-2H-1,4-benzoxazine

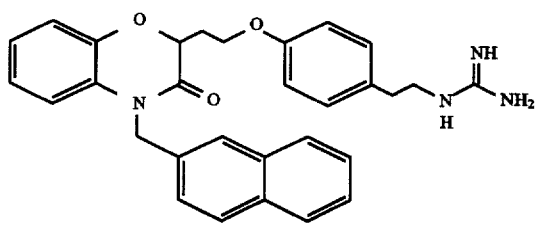

Prepared from Compound 44 by Method K and triturated with ether to afford the title compound as a white solid in 80% yield, mp 173°–178° C.; IR (KBr) 3154, 1680, 1501, 1400, 1241, 752 cm$^{-1}$; $^1$H NMR (DMSO-d$_6$) 2.22–2.35 (m, 1H), 2.38–2.48 (m, 1H), 2.72 (t, J=7.3 Hz, 2H), 3.28–3.38 (m, 2H), 4.17–4.26 (m, 2H), 5.05 (dd, J=8.7, 4.0 Hz, 1H), 5.34 (ABq, J$_{AB}$=16.2 Hz, 2H), 6.80– 7.80 (v br s, 4H), 6.92–7.01 (m, 4H), 7.08 (t, J=7.3 Hz, 2H), 7.20 (d, J=8.4 Hz, 2H), 7.43 (d, J=8.4 Hz, 1H), 7.48–7.51 (m, 2H), 7.59 (br t, J=5.1 Hz, 1H), 7.78 (s, 1H), 7.83–7.91 (m, 3H); MH$^+$ at m/z=495; Anal. Calc'd for C$_{30}$H$_{30}$N$_4$O$_3$.HCl.0.7H$_2$O: C, 66.28; H, 6.01; N, 10.31. Found: C, 66.30; H, 5.88; N, 10.06.

Compound 46

3,4-Dihydro-2-{2-[4-(2-guanidinylethyl)phenoxy]ethyl}-3-oxo-2H-4-(3-thienylmethyl)-1,4-benzoxazine

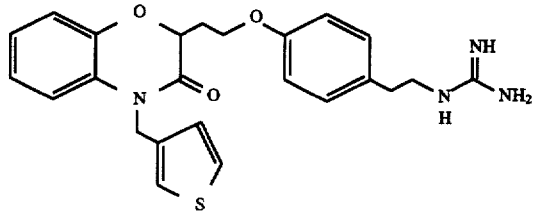

Prepared by method L using intermediate 11721-108-1 (Reference Intermediate 85) and N,N'-di-t-butoxycarbonyl-2(4-hydroxyphenyl)ethyl guanidine and method K using trifluoroacetic acid with anisole present, instead of IPA/HCl. The crude product was purified by flash chromatography using 1% MeOH in CH$_2$Cl$_2$ to 6% MeOH/1% NH$_4$OH in CH$_2$Cl$_2$, and isolated in 48% yield as a tan foam, mp 66°–71° C.; IR (KBr) 3364, 1655, 1500, 1246, 1203, 1136, 751 cm$^{-1}$; $^1$H NMR (DMSO-d$_6$) δ 2.11–2.26 (m, 1H), 2.3–2.43 (m, 1H), 2.73 (t, J=6.9 Hz, 2H), 3.28–3.39 (m, 1H), 4.13–4.22 (m, 2H), 4.93 (dd, J=8.8, 4.1 Hz, 1H), 5.12 (ABq, J$_{AB}$=17.2 Hz, 2H), 6.91 (d, J=8.6 Hz, 3H), 6.99–7.04 (m, 5H), 7.12–7.22 (m, 2H), 7.19 (d, J=8.6 Hz, 2H), 7.40 (d, J=2.3 Hz, 1H), 7.52 (dd, J=4.6, 2.3 Hz, 1H), 7.62 (t, J=5.75 Hz, 1H); MH$^+$ at m/z=451; Anal. Calc'd for C$_{24}$H$_{26}$N$_4$O$_3$S.C$_2$HF$_3$O$_2$: C, 51.61; H, 4.39; N, 8.85. Found: C, 51.34; H, 4.60; N, 8.85.

Compound 47

2-{2-[4-[2-(N,N-Bis-tert-butoxycarbonylguanidino)ethyl]phenoxy]ethyl}-4-(2-chloro-4-thienylmethyl)-3,4-dihydro-3-oxo-2H-1,4-benzoxazine

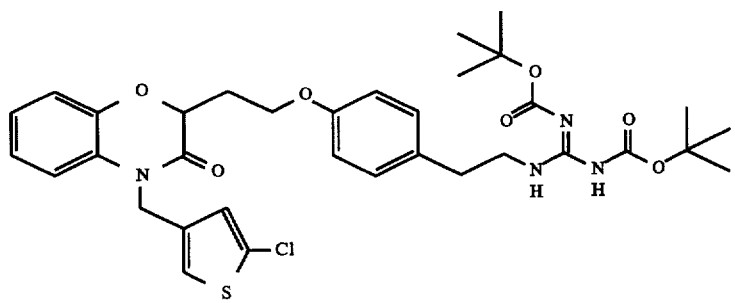

Compound 48

4-(2-Chloro-4-thienylmethyl)-3,4-dihydro-2-{2-[4-(2-guanidinoethyl)phenoxy]ethyl}-3-oxo-2H-1,4-benzoxazine

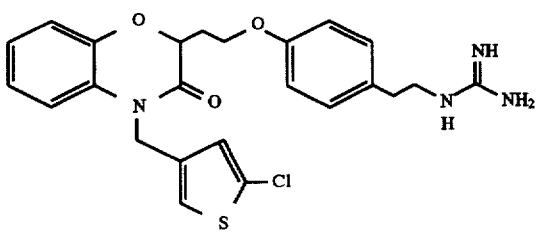

Prepared from Compound 47 by method K in 88% crude yield. This crude material was leached with EtOAc to remove the impurities to afford the product as a white foam; IR (KBr) 3148, 1667, 1500, 1450, 1399, 1243, 1058, 749 cm$^{-1}$; $^1$H NMR (CDCl$_3$) δ 2.04–2.23 (m, 3H), 2.30–2.41 (m, 1H), 2.72–2.83 (m, 2H), 3.28–3.40 (m, 2H), 3.97–4.15 (m, 2H, ), 4.77 (dd, J=7.7, 3.4 Hz, 1H), 5.06 (ABq, J$_{AB}$=14.5 Hz, 2H), 6.69–7.20 (v br s, 4H), 6.69–6.80 (m, 3H), 6.92–7.06 (m, 5H), 7.11 (d, J=8.1 Hz, 2H), 7.64 (br s, 1H); Anal. Calc'd for C$_{24}$H$_{25}$ClN$_4$O$_3$S.HCl.H$_2$O: C, 53.43; H, 5.23; N, 10.39. Found: C, 53.08; H, 5.27; N, 10.32.

Compound 49

2-{2-[4-[2-(N,N-Bis-tert-butoxycarbonylguanidino)ethyl]phenoxy]ethyl}-6-chloro-4-(3-chlorobenzyl)-3,4-dihydro-3-oxo-2H-1,4-benzoxazine

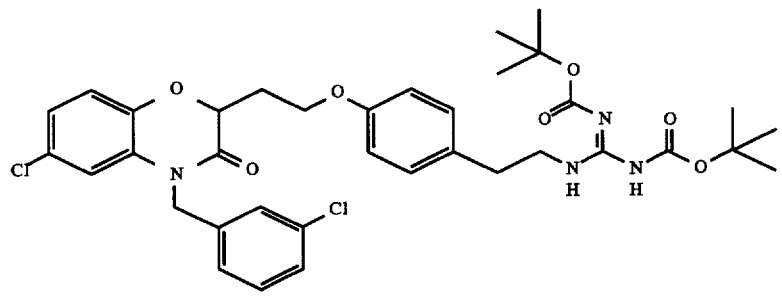

Prepared from 11578-71 (Reference Example 49) by Method L using equal equivalents of reagents to starting material and isolated in 34% yield as a colorless oil after chromatography (eluting with CH$_2$Cl$_2$); IR (neat) 3332, 2978, 1721, 1694, 1638, 1615, 1498, 1415, 1367, 1132, 811, 777 cm$^{-1}$; $^1$H NMR (CDCl$_3$) δ 1.48 (s, 9H), 1.51 (s, 9H), 2.25–2.37 (m, 1H), 2.54–2.66 (m, 1H), 2.82 (t, J=7.2 Hz, 2H), 3.63 (q, J=5.6 Hz, 2H), 4.16–4.25 (m, 2H), 4.94 (dd, J=9.3, 3.9 Hz, 1H), 5.09 (ABq, J$_{AB}$=16.1 Hz, 2H), 6.80 (s, 1H), 6.85 (d, J=8.5 Hz, 2H), 6.95 (s, 2H), 7.13 (d, J=8.5 Hz, 3H), 7.23–7.31 (m, 3H), 8.37 (br t, J=2Hz, 1H), 11.47 (s, 1H); Anal. Calc'd for C$_{36}$H$_{42}$Cl$_2$N$_4$O$_7$: C, 60.59; H, 5.93; N, 7.85. Found: C, 60.65; H, 6.04; N, 7.65.

Compound 50

6-Chloro-4-(3-chlorobenzyl)-2-{2-[4-(2-guanidinoethyl)phenoxy]ethyl}-3,4-dihydro-3-oxo-2H-1,4-benzoxazine

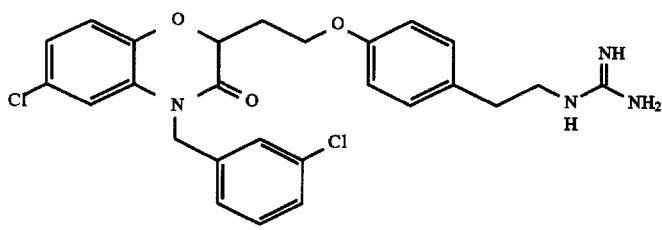

Prepared from Compound 49 by Method K where the product was isolated as a white foam from $CH_2Cl_2$ in 28% yield; IR (KBr) 3154, 1684, 1668, 1496, 1376, 1264, 1243, 1092 $cm^{-1}$; $^1H$ NMR ($CDCl_3$) δ 2.13–2.27 (m, 1H), 2.35–2.50 (m, 1H), 2.74 (br s, 2H), 3.31 (br s, 2H), 4.00–4.14 (m, 2H), 4.84 (dd, J=9.0, 4.2 Hz, 1H), 4.98 (ABq, $J_{AB}$=17.5 Hz, 2H), 6.73–7.29 (m, 15H), 7.61 (br s, 1H); $MH^+$ at m/z=513; Anal. Calc'd for $C_{26}H_{26}Cl_2N_4O_3 \cdot HCl \cdot 0.7H_2O \cdot 0.2C_3H_8O$: C, 55.61; H, 5.26; N, 9.75. Found: C, 55.83; H, 5.01; N, 9.51.

Compound 51

2-{2-[4-[2-(N,N-Bis-tert-butoxycarbonylguanidino)ethyl]phenoxy]ethyl}-4-(3-chlorobenzyl)-3,4-dihydro-3-oxo-6-phenyl-2H-1,4-benzoxazine

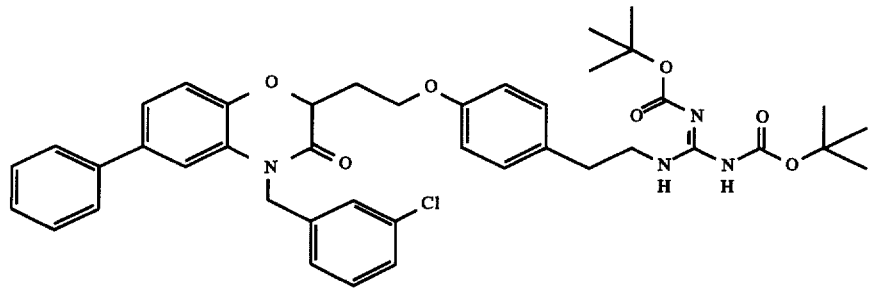

Prepared from 11578-41 (Reference Example 44) by Method L and isolated as an oil in 46% yield. This material was crystallized from ether/hexane to afford a white crystalline solid, mp 115°–116° C.; IR (KBr) 2976, 2931, 1724, 1689, 1642, 1614, 1430, 1336, 1135, 766 $cm^{-1}$; $^1H$ NMR ($CDCl_3$) δ 1.48 (s, 9H), 1.50 (s, 9H), 2.30–2.43 (m, 1H), 2.35–2.46 (m, 1H), 2.81 (t, J=7.3 Hz, 2H), 3.63 (q, J=7.1Hz, 2H), 4.17–4.32 (m, 2H), 4.99 (dd, J=9.3, 3.9 Hz, 1H), 5.18 (ABq, $J_{AB}$=25.7 Hz, 2H), 6.87 (d, J=8.5 Hz, 2H), 7.04–7.40 (m, 14H), 8.38 (t, J=4.3 Hz, 1H), 11.47 (br s, 1H); Anal. Calc'd for $C_{42}H_{47}ClN_4O_7$: C, 66.79; H, 6.27; N, 7.42. Found: C, 66.49; H, 6.20; N, 7.34.

Compound 52

4-(3-Chlorobenzyl)-3,4-dihydro-2-{2-[4-(2-guanidinoethyl)phenoxy]ethyl}-3-oxo-6-phenyl-2H-1,4-benzoxazine

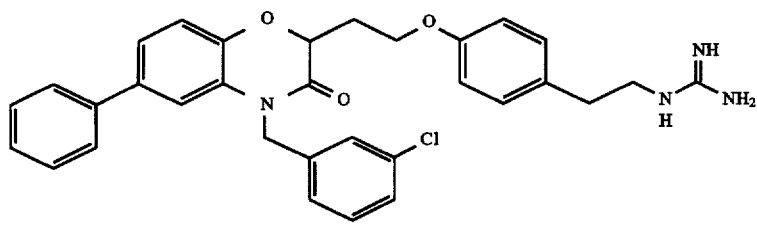

Prepared from Compound 51 by Method K and isolated as a yellow powder in 20% yield; IR (KBr) 3149, 1666, 1609, 1512, 1241, 1076, 1051, 761 cm$^{-1}$; $^1$H NMR (CD$_3$OD) δ 2.31–2.40 (m, 1H), 2.43–2.54 (m, 1H), 2.81 (t, J=7.2 Hz, 2H), 3.41 (t, J=7.0 Hz, 2H), 4.20–4.31 (m, 2H), 4.85 (s, 5H plus CD$_3$OH), 4.99 (dd, J=11.1, 4.5 Hz, 1H), 5.28 (s, 2H), 6.91 (d, J=8.6 Hz, 2H), 7.08 (d, J=8.3 Hz, 1H), 7.12–7.43 (m, 13H); Anal. Calc'd for C$_{32}$H$_{31}$ClN$_4$O$_3$.HCl.1.4H$_2$O: C, 62.32; H, 5.69; N, 9.08. Found: C, 61.95; H, 5.51; N, 9.27.

Compound 53

2-{2-[4-[2-(N,N'-Bis-tert-butoxycarbonylguanidino)ethyl]phenoxy]ethyl}-4-(3-chlorobenzyl)-3,4-dihydro-3-oxo-6-trifluoromethyl-2H-1,4-benzoxazine a colorless oil in 18% yield after SiO$_2$ column chromatography (CH$_2$Cl$_2$); IR (KBr) 3333, 2979, 1723, 1696, 1639, 1617, 1453, 1330, 1303, 1165, 1129, 824 cm$^{-1}$; $^1$H NMR (CDCl$_3$) δ 1.48 (s, 9H), 1.51 (s, 9H), 2.26–2.40 (m, 1H), 2.55–2.67 (m, 1H), 2.82 (t, J=7.1 Hz, 2H), 3.63 (q, J=5.4 Hz, 2H), 4.06–4.27 (m, 2H), 5.02 (dd, J=9.2, 3.9 Hz, 1H), 5.14 (ABq, J$_{AB}$=16.1 Hz, 2H), 6.84 (d, J=8.5 Hz, 2H), 7.05–7.17 (m, 3H), 7.13 (d, J=8.5 Hz, 2H), 7.23–7.30 (m, 4H), 8.37 (br t, J=4.3 Hz, 1H), 11.48 (s, 1H); Anal. Calc'd for C$_{37}$H$_{42}$ClF$_3$N$_4$O$_3$: C, 59.48; H, 5.67; N, 7.50. Found: C, 59.60; H, 5.67; N, 7.39.

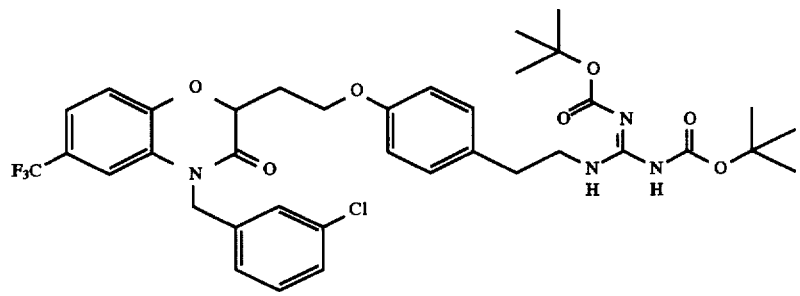

Prepared from 11578-56 (Reference Example 50) by method L using equal equivalents of reagents and isolated as Compound 54

4-(3-Chlorobenzyl)-3,4-dihydro-2-{2-[4-(2-guanidinoethyl)phenoxy]ethyl}-3-oxo-6-trifluoromethyl-2H-1,4-benzoxazine

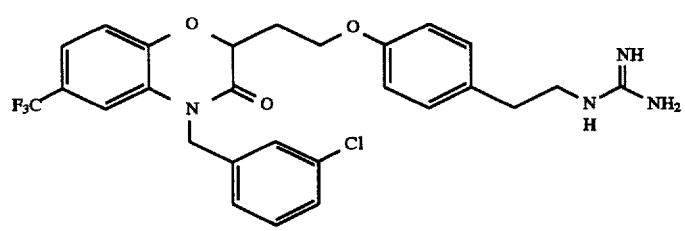

81

Prepared from Compound 53 by Method K and isolated as a white foam in 27% yield; IR (KBr) 3336, 3159, 1667, 1453, 1304, 827 cm$^{-1}$; $^1$H NMR (CDCl$_3$) δ 2.20–2.39 (m, 1H), 2.48 (br s, 3H), 2.77 (br s, 2H), 3.35 (br s, 2H), 4.08 (br s, 2H), 4.93 (dd, J=8.6, 4.0 Hz, 1H), 5.06 (ABq, J$_{AB}$=16.8 Hz, 2H), 6.75–7.30 (v br s, 4H), 6.77 (d, J=7.7 Hz, 2H), 7.01–7.26 (m, 7H), 7.25 (d, J=7.1 Hz, 2H), 7.64 (v br s, 1H);

MH$^+$ at m/z=547; Anal. Calc'd for C$_{27}$H$_{26}$ClF$_3$N$_4$O$_3$.HCl.0.7H$_2$O: C, 54.41; H, 4.80; N, 9.40. Found: C, 54.49; H, 4.74; N, 9.32.

Compound 55

4-(3-Chlorobenzyl)-3,4-dihydro-7-fluoro-2-{2-[4-(2-guanidinoethyl)phenoxy]ethyl}-3-oxo-2H-1,4-benzoxazine

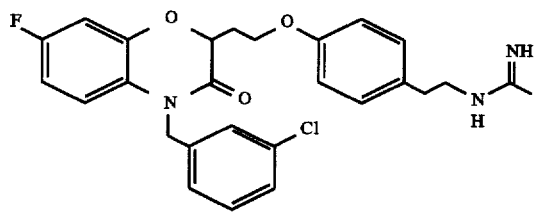

Prepared from 11578-47 (Reference Example 52) and N,N'-di-t-butoxycarbonyl-2(4-hydroxyphenyl) ethylguanidine by Method L using equal equivalents of reagents and by Method K. The product was isolated in 17% overall yield as a white foam; IR (KBr) 2877, 1664, 1509, 1405, 1243, 1154, 852 cm$^{-1}$; $^1$H NMR (CD$_3$OD) 2.26–2.37 (m, 1H), 2.42–2.53 (m, 1H), 2.83 (t, J=6.8 Hz, 2H), 3.42 (t, J=6.8 Hz, 2H), 4.17–4.29 (m, 2H), 4.84 (s, 6.4H plus CD$_3$OH), δ 4.98 (dd, J=8.4, 4.4 Hz, 1H), 5.18 (s, 2H), 6.73 (td, J=8.8, 2.6 Hz, 1H), 6.83 (dd, J=9.2, 2.8 Hz, 1H), 6.92 (d, J=8.0 Hz, 2H), 6.97 (dd, J=8.8, 5.2 Hz, 1H), 7.17 (d, J=8 Hz, 2H), 7.17–7.22 (m, 1H), 7.25–7.35 (m, 3H); MH$^+$ at m/z= 497; Anal. Calc'd for C$_{26}$H$_{26}$ClFN$_4$O$_3$.HCl.0.7H$_2$O: C, 57.19; H, 5.24; N, 10.26. Found: C, 56.81; H, 5.36; N, 10.26.

Compound 56

2-{2-[4-[2-(N,N'-Bis-tert-butoxycarbonylguanidino) ethyl]phenoxy]ethyl}-4-(3-chlorobenzyl)-6,8-dichloro-3,4-dihydro-3-oxo-2H-1,4-benzoxazine

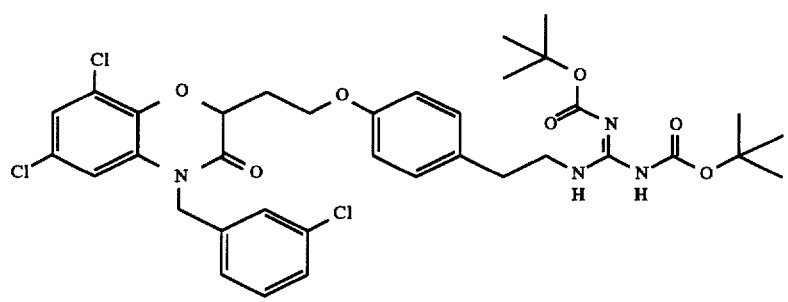

Prepared from 11578-33 (Reference Example 56) and N,N'-di-t-butoxycarbonyl-2(4-hydroxyphenyl)ethyl guanidine by Method L using equal equivalents of reagents to starting material and isolated as white solid in 27% yield after SiO$_2$ column chromatography eluting with CH$_2$Cl$_2$, mp 115°–117° C.; IR (KBr) 2977, 1699, 1639, 1615, 1593, 1367, 1131, 1058, 810, 776 cm$^{-1}$; $^1$H NMR (CDCl$_3$) δ 1.48 (s, 9H), 1.51 (s, 9H), 2.25–2.37 (m, 1H), 2.52–2.67 (m, 1H), 2.82 (t, J=7.2 Hz, 2H), 3.63 (q, J=7.1 Hz, 2H), 4.13–4.24 (m, 1H), 4.27–4.35 (m, 1H), 5.05 (dd, J=9.7, 3.5 Hz, 1H), 5.10 (s, 2H), 6.71 (d, J=2.2 Hz, 1H), 6.86 (d, J=8.6 Hz, 2H), 7.05 (d, J=2.2 Hz, 1H), 7.13 (d, J=8.6 Hz, 2H), 7.13 (s, 1H), 7.26–7.29 (m, 3H), 8.37 (t, J=2.6 Hz, 1H), 11.48 (s, 1H); Anal. Calc'd for C$_{36}$H$_{41}$Cl$_3$N$_4$O$_7$: C, 57.80; H, 5.52; N, 7.49. Found: C, 57.64; H, 5.39; N, 7.77.

Compound 57

4-(3-Chlorobenzyl)-6,8-dichloro-2-{2-[4-(2-guanidinoethyl)phenoxy]ethyl}-3,4-dihydro-3-oxo-2H-1,4-benzoxazine

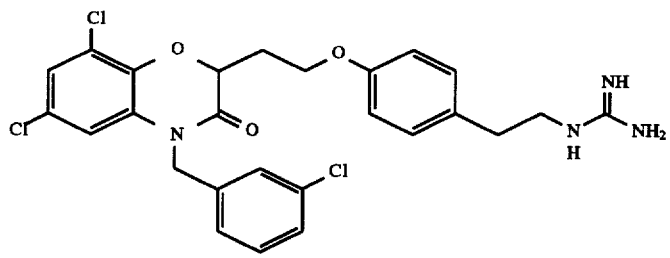

Prepared from Compound 56 by method K and isolated as a white foam in 75% yield; IR (KBr) 3150, 1666, 1591, 1479, 1242, 743 cm$^{-1}$; $^1$H NMR (DMSO-d$_6$) δ 2.23–2.37 (m, 1H), 2.50–2.61 (m, 1H), 2.84 (t, J=7.1 Hz, 2H), 3.39 (q, J=5.9 Hz, 2H), 4.15–4.23 (m, 1H), 4.25–4.35 (m, 1H), 5.04 (dd, J=9.8, 3.8 Hz, 1H), 5.11 (ABq, J$_{AB}$=16.3 Hz, 2H), 6.75 (d, J=2.2 Hz, 1H), 6.87 (d, J=8.4 Hz, 2H), 7.07–7.21 (m, 9H), 7.26–7.35 (m, 2H), 7.67 (br t, J=5.1 Hz, 1H); MH$^+$ at m/z=547; Anal. Calc'd for C$_{26}$H$_{25}$Cl$_3$N$_4$O$_3$.HCl.0.7H$_2$O: C, 52.31; H, 4.63; N, 9.39. Found: C, 52.37; H, 4.59; N, 9.37.

Compound 58

4-(3-Chlorobenzyl)-2-{2-[4-(2-guanidinoethyl)phenoxy]ethyl}-3,4-dihydro-7-methyl-3-oxo-2H-1,4-benzoxazine

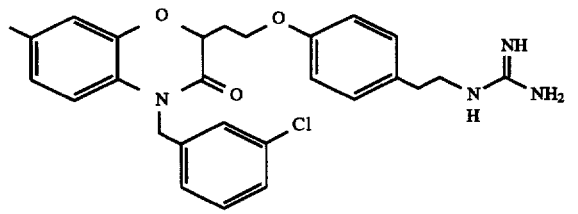

Prepared by method L using intermediate 11578-52 (Referenced Example 55) and N,N'-di-t-butoxycarbonyl-2-(4-hydroxyphenyl)ethylguanidine and method K in 2.5% overall yield as a white foam; IR (KBr) 3340, 3161, 1668, 1402, 1244, 1178, 1146, 1107, 1056 cm$^{-1}$; $^1$H NMR (CDCl$_3$) δ 2.15–2.28 (m, 1H), 2.20 (s, 3H), 2.34–2.47 (m, 3H), 2.76 (t, J=6.4 Hz, 2H), 3.30–3.40 (m, 2H), 4.00–4.18 (m, 2H), 4.83 (dd, J=8.9, 4.3 Hz, 1H), 5.01 (s, 2H), 6.63–7.27 (v br s, 4H), 6.63–6.70 (m, 2H), 6.75–6.83 (m, 2H), 7.03–7.23 (m, 7H), 7.63 (br s, 1H); MH$^+$ at m/z=493; Anal. Calc'd for C$_{27}$H$_{29}$ClN$_4$O$_3$.HCl.H$_2$O: C, 59.23; H, 5.89; N, 10.23. Found: C, 58.84; H, 5.60; N, 10.07.

Compound 59

2-{2-[4-[2-(N,N'-Bis-tert-butoxycarbonylguanidino)ethyl]phenoxy]ethyl}-3,4-dihydro-4-methyl-3-oxo-2H-1,4-benzoxazine

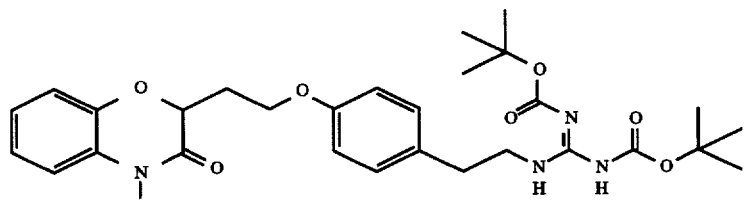

Prepared from 10840-117-1 (Reference Example 88) by Method L and isolated as a white foam in 13% yield; IR (KBr) 3334, 2978, 2933, 1722, 1686, 1639, 1614, 1513, 1504, 1417, 1131, 750 cm$^{-1}$; $^1$H NMR (CDCl$_3$) δ 1.48 (s, 9H), 1.50 (s, 9H), 2.19–2.31 (m, 1H), 2.45–2.56 (m, 1H), 2.81 (t, J=7.2 Hz, 2H), 3.38 (s, 3H), 3.63 (q, J=5.3 Hz, 2H), 4.10–4.26 (m, 2H), 4.83 (dd, J=8.8, 4.0 Hz, 1H), 6.84 (d, J=6.84 Hz, 2H), 6.95–7.07 (m, 4H), 7.12 (d, J=8.6 Hz, 2H), 8.36 (br t, J=4.0 Hz, 1H), 11.47 (s, 1H); Anal. Calc'd for C$_{30}$H$_{40}$N$_4$O$_7$.0.2H$_2$O: C, 62.96; H, 7.12; N, 9.79. Found: C, 62.88; H, 7.20; N, 9.71.

Compound 60

3,4-Dihydro-2-{2-[4-(2-guanidinoethyl)phenoxy]ethyl}-4-methyl-3-oxo-2H-1,4-benzoxazine

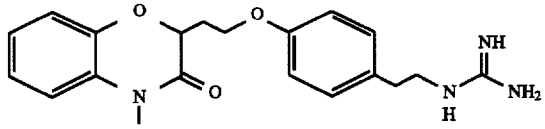

Prepared by dissolving Compound 59 in CH$_2$Cl$_2$ and treating with TFA. Solvent removal and purification by SiO$_2$ chromatography (2–6% MeOH in CH$_2$Cl$_2$) followed by crystallization from MeOH/CH$_2$Cl$_2$/ether afforded an 82% yield of a cream colored solid, mp 80° (shrinks) 82°–85° C.; IR (KBr) 3339, 3176, 1682, 1515, 1505, 1383, 1249, 1137, 755 cm$^{-1}$; $^1$H NMR (DMSO-d$_6$) δ 2.08–2.16 (m, 1H), 2.27–2.33 (m, 1H), 2.71 (t, J=7.5 Hz, 2H), 3.27–3.35 (m, 2H), 3.30 (s, 3H), 4.10–4.18 (m, 2H), 4.81 (dd, J=8.8, 4.2 Hz, 1H), 6.83–7.50 (v br s, 4H), 6.90 (d, J=8.6 Hz, 2H), 7.00–7.12 (m, 4H), 7.18 (d, J=8.7 Hz, 2H), 7.56 (br t, J=5.7 Hz, 1H); MH$^+$ at m/z=369.

Compound 61

3,4-Dihydro-2-{2-[4-(2-guanidinoethyl)phenoxy]ethyl}-3-oxo-4-pentyl-2H-1,4-benzoxazine

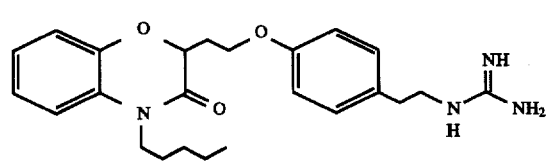

Prepared from intermediate 10840-185 (Reference Example 60) by Method K and isolated as a colorless glass in 98% yield; IR (KBr) 3154, 1661, 1513, 1500, 1244, 751 cm$^{-1}$; $^1$H NMR (CDCl$_3$) δ 0.88 (t, J=6.5 Hz, 3H), 1.19 (d, isopropanol), 1.25–1.37 (m, 4H), 1.52–1.68 (m, 2H), 2.09–2.21 (m, 1H), 2.30–2.40 (m, 1H), 2.79 (br s, 2H), 3.38 (br s, 2H), 3.84 (t, J=6.7 Hz, 2H), 4.00–4.15 (m, 2H plus isopropanol), 4.71 (dd, J=8.7, 4.0 Hz, 1H), 6.70–7.17 (v br s, 4H), 6.78 (d, J=7.5 Hz, 2H), 6.93–7.07 (m, 4H), 7.13 (d, J=7.4, 2H), 7.67 (br d, 1H); MH$^+$ at m/z=425; Anal. Calc'd for C$_{24}$H$_{32}$N$_4$O$_3$·HCl·0.1C$_3$H$_8$O·0.6H$_2$O: C, 61.00; H, 7.38; N, 11.73. Found: C, 61.04; H, 7.27; N, 11.67.

Compound 62

4-(3-Chlorobenzyl)-3,4-dihydro-2-[2-[4-(2-guanidinoethyl)phenoxy]ethyl]-3-oxo-2H-pyrido[4,3-b]-1,4-oxazine

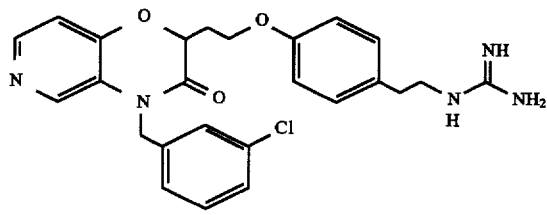

Prepared by method L using intermediate 11578-190 (Reference Example 84) and N,N'-di-t-butoxycarbonyl-2-(4-hydroxyphenyl)ethyl guanidine and method K in 35% as an off-white foam; IR (KBr) 3134, 1701, 1669, 1642, 1508, 1240, 1178, 1161, 1055, 824 cm$^{-1}$; $^1$H NMR (DMSO-d$_6$) δ 2.50 (m, 1H plus DMSO-d$_5$), 2.71 (t, J=7.5 Hz, 2H), 3.28–3.35 (m, 3H), 4.17 (t, J=5.6 Hz, 2H), 5.25 (ABq, J$_{AB}$=16.5 Hz, 2H), 5.52 (t, J=6.9, 1H), 6.70–7.60 (v br s, 5H), 6.83 (d, J=8.4 Hz, 2H), 7.18 (d, J=8.4 Hz, 2H), 7.28–7.40 (m, 3H), 7.48 (s, 1H), 7.50 (s, 1H), 7.67 (t, J=5.4 Hz, 1H), 8.39 (s, 1H), 8.40 (s, 1H); MH$^+$ at m/z=480; Anal. Calc'd for C$_{25}$H$_{26}$ClN$_5$O$_3$·2HCl·1.5H$_2$O: C, 51.78; H, 5.39; N, 12.08. Found: C, 51.78; H, 5.39; N, 12.08.

Compound 63

2-{2-[3-[2-(N,N-Bis-tert-butoxycarbonylguanidino)ethyl]phenoxy]ethyl}-4-(3,5-dichlorobenzyl)-3,4-dihydro-3-oxo-2H-1,4-benzoxazine

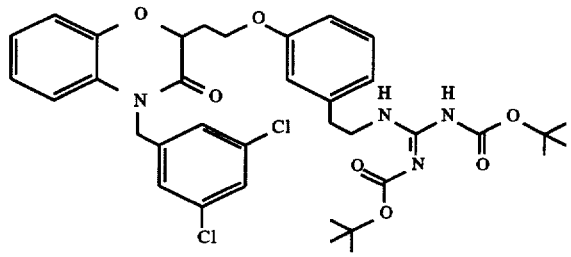

Prepared from 10005-181-1 (Reference Example 48) by Method L and isolated in 84% yield as a white solid after flash chromatography eluting with 2.5–10% EtOAc in CH$_2$Cl$_2$ and crystallization from CH$_2$Cl$_2$/ether/hexane, mp 116°–118° C.; IR (KBr) 3359, 1688, 1505, 1256, 1171, 752 cm$^{-1}$; $^1$H NMR (CDCl$_3$) δ 1.44 (s, 9H), 2.28–2.39 (m, 1H), 2.52–2.62 (m, 1H), 2.77 (t, J=9Hz, 2H), 3.33–3.41 (m, 2H), 4.16–4.30 (m, 2H), 4.54 (br s, 1H), 4.94 (dd, J=10.5, 3 Hz, 1H), 5.09 (ABq, J$_{AB}$=18 Hz, 2H), 6.75–6.83 (m, 4H), 6.93–7.06 (m, 3H 7.13 (d, J=1.8 Hz, 2H), 7.20–7.27 (m, 2H); Anal. Calc'd for C$_{30}$H$_{32}$Cl$_2$N$_2$O$_5$: C, 63.05; H, 5.64; N, 4.90. Found: C, 63.24; H, 5.60; N, 4.71.

Compound 64

2-{2-[3-(2-Aminoethyl)phenoxy]ethyl}-4-(3,5-dichlorobenzyl)-3,4-dihydro-3-oxo-2H-1,4-benzoxazine

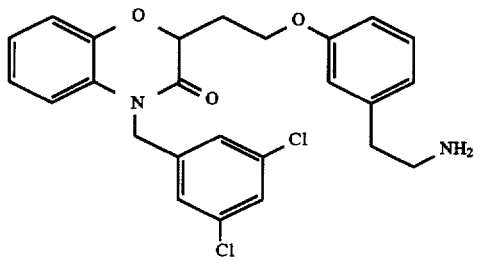

Prepared by methods J using intermediate 10005-181-1 (Reference Example 48) and 4-[2-(N-t-butoxycarbonylamino)ethyl]phenol as well as method K to give a white solid, 58% yield. mp 173.5°–176° C.; IR (KBr) 2942, 1684, 1592, 1501, 1399, 1265, 752 cm$^{-1}$; $^1$H NMR (DMSO-d$_6$) δ 2.19–2.32 (m, 1H), 2.35–2.47 (m, 1H), 3.84–3.89 (m, 2H), 3.01–3.06 (m, 2H), 4.19–4.24 (m, 2H), 5.03–5.08 (m, 1H), 5.18 (ABq, J$_{AB}$=16.7 Hz, 2H), 6.83–6.87 (m, 3H), 6.99–7.09 (m, 4H), 7.25 (t, J=7.6 Hz, 1H), 7.35 (d, J=1.8 Hz, 2H), 7.52 (t, J=1.8 Hz, 1H), 8.06 (br s, 3H); Anal. Calc'd for C$_{25}$H$_{24}$Cl$_2$N$_2$O$_3$·HCl·0.25·H$_2$O: C, 58.61; H, 5.02; N, 5.47. Found: C, 58.47; H, 4.88; N, 5.33.

Compound 65

2-{2-[4-[2-(N,N'-Bis-tert-butoxycarbonylguanidino)ethyl]phenoxy]ethyl}-3,4-dihydro-4-(4-methylbenzyl)-2H-1,4-benzoxazine

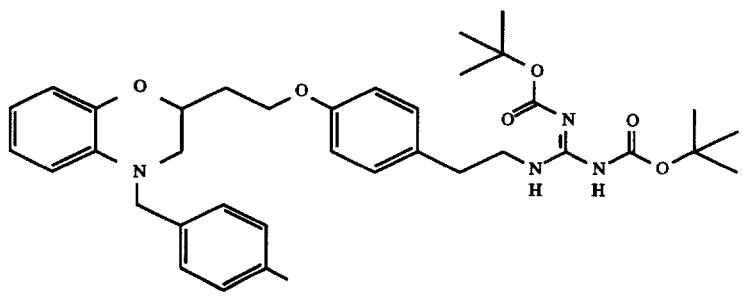

Intermediate 10840-45 (1 eq, Reference Example 92) was dissolved in 7 mL CH$_2$Cl$_2$/ether (3/1) under nitrogen and treated with triethylamine (1.2 eq) followed by methanesulfonyl chloride (1.2 eq), The mixture was stirred for 0.5 h and filtered. The filtrate was concentrated under vacuum and the residue was redissolved in ether and washed with $H_2O$ and dried over $MgSO_4$. Ether removal produced the desired methanesulfonate product. This crude material (1 eq) was dissolved in DMSO (1.7 mL) and treated with the corresponding phenol (1 eq) plus NaOH pellets (3 eq). This solution was stirred at 50° C. for 24 h under nitrogen and then diluted with $H_2O$. A $CH_2Cl_2$/EtOAc solution of the precipitate was washed with $H_2O$ and dried over $MgSO_4$. Solvent removal produced the crude material which was purified by flash chromatography to afford the product in 16% overall yield and isolated as a white powder; IR (KBr) 2979, 1723, 1650, 1625, 1513, 1246, 1156, 1133, 743 cm$^{-1}$; $^1$H NMR (CDCl$_3$) δ 1.47 (s, 9H), 1.50 (s, 9H), 2.03–2.17 (m, 2H), 2.33 (s, 3H), 2.81 (t, J=7.2 Hz, 2H), 3.18 (dd, J=11.9, 7.2 Hz, 1H), 3.34 (dd, J=11.9, 2.5, 1H), 3.63 (q, J=6.8 Hz, 2H), 4.08–4.23 (m, 2H), 4.38–4.45 (m, 3H), 6.62 (dt, J=7.5, 1.5 Hz, 1H), 6.69 (dd, J=7.5, 1.5 Hz, 1H), 6.75–6.84 (m, 2H), 6.82 (d, J=8.7 Hz, 2H), 7.12 (d, J=8.7 Hz, 2H), 7.16 (br q, J$_{AB}$=8.1 Hz, 4H), 8.36 (br t, J=4.8 Hz, 1H), 11.46 (s, 1H); Anal. Calc'd for C$_{37}$H$_{48}$N$_4$O$_6$: C, 68.92; H, 7.50; N, 8.69. Found: C, 68.65; H, 7.24; N, 8.56.

Compound 66

3,4-Dihydro-2-{2-[4-[2-guanidinoethyl]phenoxy]ethyl}-4-(4-methylbenzyl)-2H-1,4-benzoxazine

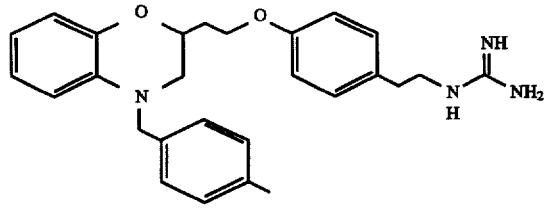

Prepared from Compound 65 by Method K in 3% yield and isolated as a green powder after trituration with CHCl$_3$; IR (KBr) 3157, 1663, 1611, 1513, 1300, 1241, 743 cm$^{-1}$; $^1$H NMR (CD$_3$OD) δ 2.04–2.14 (m, 2H), 2.30 (s, 3H), 2.81 (t, J=7.2 Hz, 2H), 3.18 (dd, J=12.0, 8.0 Hz, 1H), 3.36–3.49 (m, 3H), 4.07–4.2 (m, 2H), 4.37–4.46 (m, 1H), 4.50 (s, 2H), 6.70–6.95 (m, 7H), 7.05–7.40 (m, 9H); Anal. Calc'd for C$_{27}$H$_{32}$N$_4$O$_2$·HCl·1.75H$_2$O: C, 63.37; H, 7.31; N, 11.26. Found: C, 63.40; H, 7.14; N, 11.21.

Compound 67

2-{2-[4-[2-(N,N'-Bis-tert-butoxycarbonylguanidino)ethyl]phenoxy]ethyl}-4-(2,4-dichlorobenzyl)-3,4-dihydro-2H-1,4-benzoxazine

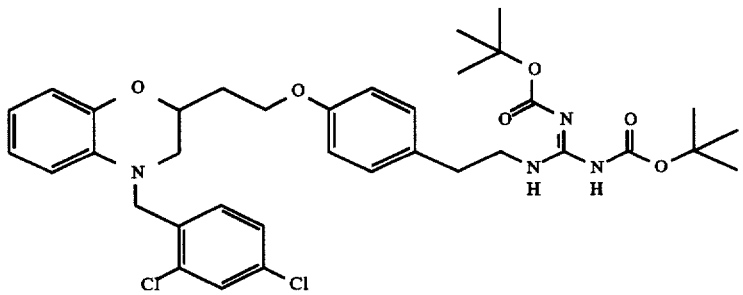

Prepared from 10840-8 (Reference Example 94) by Method L in 20% yield and isolated as a white foam; IR (KBr) 3336, 2979, 2932, 1723, 1640, 1617, 1366, 1133 cm$^{-1}$; $^1$H NMR (CDCl$_3$) δ 1.48 (s, 9H), 1.50 (s, 9H), 2.08–2.20 (m, 2H), 2.81 (t, J=7.2 Hz, 2H), 3.31 (dd, J=11.7, 7.5 Hz, 1H), 3.41 (dd, J=11.6, 2.6 Hz, 1H), 3.64 (q, J=6.5 Hz, 2H), 4.10–4.27 (m, 2H), 4.44–4.53 (m,1H), 4.46 (s, 2H), 6.45 (dd, J=8.0, 1.3 Hz, 1H), 6.65 (td, J=7.6, 1.4 Hz, 1H), 6.76 (td, J=7.8, 1.6 Hz, 1H), 6.80–6.87 (m, 3H), 7.10–7.24 (m, 4H), 7.42 (d, J=1.9 Hz, 1H), 8.35 (t, J=4.1 Hz, 1H), 11.46 (s, 1H); Anal. Calc'd for C$_{36}$H$_{44}$Cl$_2$N$_4$O$_6$·0.5H$_2$O: C, 61.01; H, 6.40; N, 7.91. Found: C, 61.14; H, 6.37; N, 7.83.

Compound 68

(2,4-Dichlorobenzyl)-3,4-dihydro-2-{2-[4-(2-guanidinoethyl)phenoxy]ethyl}-4-2H-1,4-benzoxazine

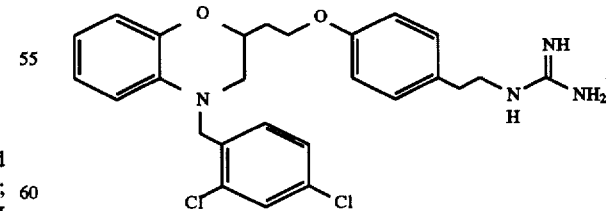

Prepared from Compound 67 by Method K in 4.5% yield and isolated as a green glass; IR (neat) 3334, 3166, 1665, 1611, 1513, 1246, 1219, 1046, 830 cm$^{-1}$; $^1$H NMR (CDCl$_3$) δ 1.74 (br s, 2H), 1.94–2.15 (m, 2H), 2.80 (br t, J=5.6 Hz, 2H), 3.20–3.38 (m, 4H), 4.02–4.18 (m, 2H), 4.32–4.47 (m, 1H), 4.42 (s, 2H), 6.35–7.40 (v br s, 4H), 6.41 (dd, J=8.0, 1.1 Hz, 1H), 6.61 (td, J=7.6, 1.2 Hz, 1H), 6.73 (td, J=7.9, 1.5 Hz, 1H), 6.80 (d, J=7.9 Hz, 2H), 7.10–7.20 (m, 5H), 7.39 (d, J=1.8 Hz, 1H), 7.80 (br s, 1H); MH⁺ at m/z=499; Anal. Calc'd for $C_{26}H_{28}Cl_2N_4O_2 \cdot HCl \cdot H_2O$: C, 56.38; H, 5.64; N, 10.11. Found: C, 56.68; H, 5.41; N, 9.97.

Compound 69

2-{2-[3-(2-(t-Butoxycarbonylamino)ethyl)phenoxy]ethyl}-4-(3-chlorobenzyl)-3,4-dihydro-3-oxo-2H-1,4-benzoxazine

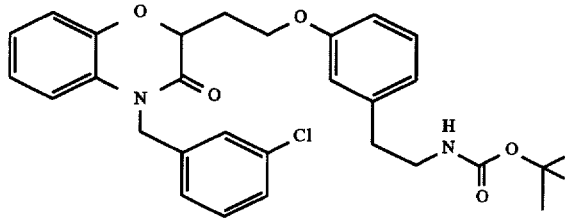

Prepared from 10488-22 (Reference Example 66) and 3-[2-(N-t-butoxycarbonylamino)ethyl]phenol by method J. The product was isolated in 82% yield after chromatography, to afford an oil which crystallized on standing, mp 107°–108° C.; MS (CI) MH⁺ no peak found; IR (KBr) 3319, 2986, 1597, 1532, 1505, 1468, 1445, 1402, 1368, 1323, 1271, 1171, 1061, 787, 752 cm⁻¹; ¹H NMR (CDCl₃) δ 7.23 (m, 5H), 7.13 (m, 1H), 7.00 (m, 2H), 6.94 (m, 1H), 6.78 (m, 3H), 5.18(d, 1H, J=16.0 Hz), 5.08 (d, 1H, J=16.0 Hz), 4.94 (dd, 1H, J=3.9, 9.2 Hz), 4.55 (br. s., 1H), 4.24 (m, 2H), 3.38 (m, 2H), 2.76 (t, 2H, J=6.9 Hz), 2.58 (m, 1H), 2.34 (m, 1H), 1.43 (s, 9H). Anal. Calc'd for $C_{30}H_{33}ClN_2O_5 \cdot 0.4H_2O$: C 66.21, H 6.26, N 5.15. Found: C 66.28, H 6.13, N 5.02.

Compound 70

2-{2-[3-(2-Aminoethyl)phenoxy]ethyl}-4-(3-chlorobenzyl)-3,4-dihydro-3-oxo-2H-1,4-benzoxazine

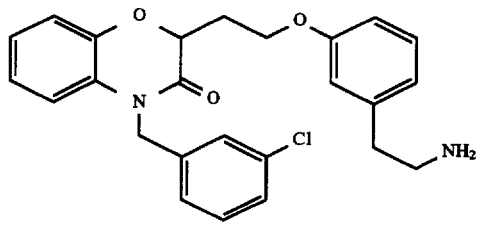

Prepared from Compound 69 by method K in quantitative yield, mp: 163° C. darkens, 169°–171° C. melts; MS (CI) MH⁺437; IR (KBr) 2948, 1678, 1599, 1503, 1468, 1447, 1402, 1321, 1265, 1171, 1115, 1051, 939, 866 cm⁻¹; ¹H NMR (DMSO-d₆) δ 8.80–8.00 (v br s, 2H), 7.22 (m, 4H), 7.10 (m, 1H), 6.95 (m, 3H), 6.80 (m, 4H), 5.13 (d, 1H, J=16.3Hz), 5.05 (d, 1H, J=16.3Hz), 4.89 (dd, 1H, J=3.8, 8.8Hz), 4.19 (m, 2H), 3.28 (br s, 2H), 3.08 (br s, 2H), 2.49 (m, 1H), 2.27 (m, 1H), 2.52–1.50 (v br s, 1H). Anal. Calc'd for $C_{25}H_{25}ClN_2O_3 \cdot HCl$: C 63.43, H 5.54, N 5.92. Found: C 63.16, H 5.40, N 5.73.

Compound 71

2-{2-[4-[2-(N,N'-Bis-tert-butoxycarbonylguanidino)ethyl]phenoxy]ethyl}-4-(3-chlorobenzyl)-3,4-dihydro-3-oxo-2H-1,4-benzoxazine

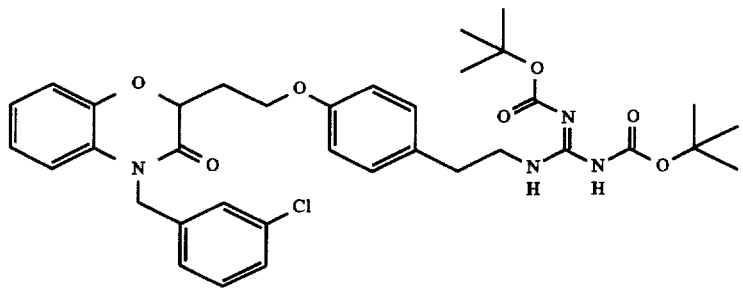

Prepared from 10488-22 (Reference Example 66) and N,N'-di-t-butoxycarbonyl-2(4-hydroxyphenyl)ethyl guanidine by method J in 31% yield, mp: 74°–78° C.; MS (FAB) MH⁺679; IR (KBr) 3332, 2979, 1723, 1688, 1501, 1414, 1368, 1329, 1246, 1132, 1059, 750 cm⁻¹; ¹H NMR (CDCl₃) δ 11.47 (br s, 1H),8.36 (br t, 1H), 7.25 (s, 2H), 7.14 (d, 2H, J=3.7Hz), 7.06 (m, 2H), 6.92 (m, 4H), 6.84 (m, 2H), 5.19 (d, 1H, J=16.0 Hz), 5.08 (d, 1H, J=16.0 Hz), 4.94 (dd, 1H, J=3.9, 9.3 Hz), 4.22 (m, 2H), 3.63 (m, 2H), 2.81 (t, 2H, J=7.2 Hz), 2.58 (m, 1H), 2.34 (m, 1H), 1.50 (s, 9H), 1.48 (s, 9H). Anal. Calc'd for $C_{36}H_{43}ClN_4O_7 \cdot 0.4H_2O$: C 62.99, H 6.43, N 8.16. Found: C 62.96, H 6.37, N 8.09.

Compound 72

4-(3-Chlorobenzyl)-3,4-dihydro-2-{2-[4-(2-guanidinoethyl)phenoxy]ethyl}-3-oxo-2H-1,4-benzoxazine

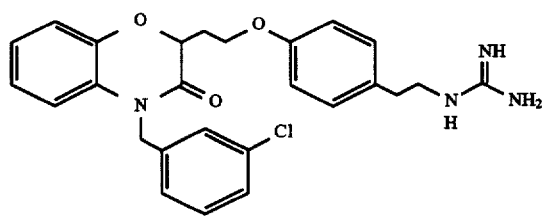

Prepared from Compound 71 by method K in 34% yield, mp 90°–101° C.; IR (KBr) 3355, 1501, 1468, 1402, 1244, 750 cm⁻¹; ¹H NMR (DMSO-d₆) δ 7.68 (br t, 1H), 7.50–6.80(v br s, 1H), 7.35 (d, 1H, J=7.3Hz), 7.20 (m, 4H), 7.03 (m, 4H), 6.92 (d, 2H, J=8.4Hz), 5.22 (d, 1H, J=16.5Hz), 5.13 (d, 1H, J=16.5Hz), 5.00 (dd, 1H, J=4.2, 8.7Hz), 4.21 (m, 2H), 2.72 (br t, 2H), 2.51 (m, 2H), 2.38 (br s, 1H), 2.24 (br s, 1H). Anal. Calc'd for C₂₆H₂₇ClN₄O₃·2.5HCl: C 54.77, H 5.22, N 9.83. Found: C 54.99, H 5.34, N 9.79.

Compound 73

2-{2-[3-(t-Butoxycarbonylaminomethyl)phenoxy]ethyl}-4-(3-chlorobenzyl)-3,4-dihydro-3-oxo-2H-1,4-benzoxazine

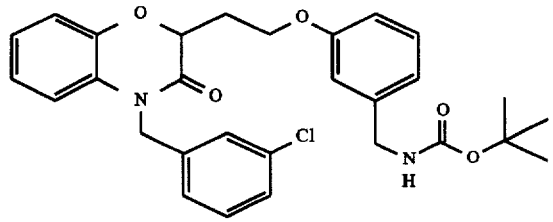

Prepared from 10488-22 (Reference Example 66) by method J in 48% yield, mp 98°–100° C.; MS (CI) M⁺522, one Cl present; IR (KBr) 3351, 2927, 1599, 1530, 1505, 1447, 1402, 1279, 1175, 1111, 1055, 939, 864 cm⁻¹; ¹H NMR (CDCl₃) δ 7.24 (m, 5H), 7.13 (m, 1H), 7.00 (m, 2H), 6.92 (m, 1H), 6.83 (m, 3H), 5.18 (d, 1H, J=16.0Hz), 5.07 (d, 1H, J=16.0Hz), 4.93 (dd, 1H, J=3.9 9.2Hz), 4.83 (br. s, 1H), 4.37–4.14 (brm, 4H), 2.58 (m, 1H), 2.34 (m, 1H), 1.46 (s, 9H). Anal. Calc'd for C₂₉H₃₁ClN₂O₅·0.3 H₂O: C 65.92, H 6.03, N 5.30. Found: C 65.95, H 5.99, N 5.22.

Compound 74

2-{2-[3-(Aminomethyl)phenoxy]ethyl}-4-(3-chlorobenzyl)-3,4-dihydro-3-oxo-2H-1,4-benzoxazine

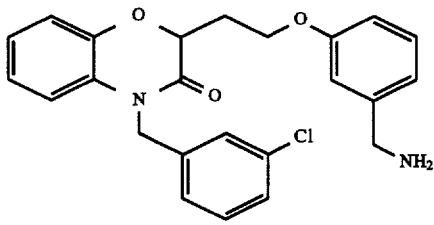

Prepared from Compound 73 by method K in quantitative yield, mp 124°–129° C.; MS (CI) MH⁺423; IR (KBr) 2886, 1599, 1501, 1402, 1265, 1171, 1080, 1051, 885, 470 cm⁻¹; ¹H NMR (DMSO-d₆) δ 7.27 (m, 5H), 7.13 (m, 1H), 7.00 (m, 2H), 6.95 (m, 2H), 6.90 (m, 2H), 6.83 (m, 2H), 5.17 (d, 1H, J=16.2Hz), 5.08 (d, 1H, J=16.2Hz), 4.94 (dd, 1H, J=4.0, 9.2Hz), 4.26 (m, 2H), 3.82 (s, 2H), 2.59 (m, 1H), 2.34 (m, 1H). Anal. Calc'd for C₂₄H₂₃ClN₂O₃·HCl 0.4 H₂O: C 61.78, H 5.36, N 6.00. Found: C 61.78, H 5.36, N 5.83.

Compound 75

2-{2-[4-(3-(t-Butoxycarbonylamino)propyl)phenoxy]ethyl}-4-(3-chlorobenzyl)-3,4-dihydro-3-oxo-2H-1,4-benzoxazine

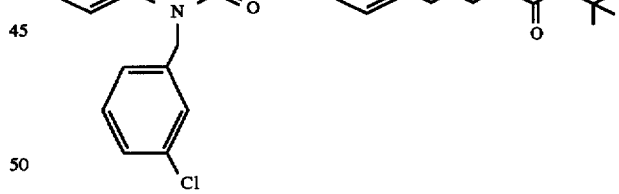

Prepared from 10488-22 (Reference Example 66) and 4-[3-(N-t-butoxycarbonylamino)propyl]phenol by method L in 58% yield, mp 75°–81° C.; MS (FAB) MH⁺551; IR (KBr) 3365, 2979, 2934, 1611, 1512, 1503, 1468, 1398, 1366, 1302, 1279, 1242, 1022, 997, 922 cm⁻¹; ¹H NMR (CDCl₃) δ 7.24 (d, 4H, J=6.4Hz), 7.12 (m, 2H), 7.08 (d, 1H, J=8.6Hz), 7.00 (m, 2H), 6.92 (m, 1H), 6.84 (m, 2H), 5.17 (d, 1H, J=16.0Hz), 5.08 (d, 1H, J=16.0Hz), 4.94 (dd, 1H, J=3.9, 9.2Hz), 4.21 (m, 2H), 3.14 (m, 2H), 2.59 (m, 2H), 2.32 (m, 1H), 1.78 (m, 2H), 1.44 (s, 9H). Anal. Calc'd for C₃₀H₃₃ClN₂O₅: C 67.09, H 6.19, N 5.22. Found: C 67.46, H 6.54, N 4.93.

Compound 76

2-{2-[4-(3-Aminopropyl)phenoxy]ethyl}-4-(3-chlorobenzyl)-3,4-dihydro-3-oxo-2H-1,4-benzoxazine

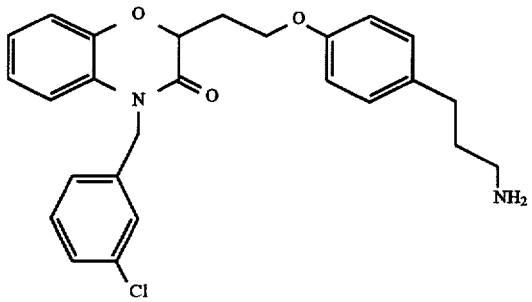

Prepared from Compound 75 by method K, mp 109°–111° C.; MS (CI) MH$^+$451; IR (KBr) 2936, 1674, 1609, 1514, 1466, 1400, 1302, 1111, 1049, 800, 681 cm$^{-1}$; $^1$H NMR (DMSO-d$_6$) δ 7.95 (brs, 2H), 7.36 (m, 4H), 7.21 (d, 1H, J=6.8Hz), 7.13 (d, 2H, J=8.5Hz), 7.02 (m, 4H), 6.90 (d, 2H, J=8.5Hz), 5.19 (d, 1H, J=16.2Hz), 5.13 (d, 1H, J=16.2Hz), 5.00 (dd, 1H, J=4.2, 8.7Hz), 4.19 (m, 2H), 2.75 (brs, 2H), 2.58 (brt, 2H, J=7.4Hz), 2.39 (m, 1H), 2.23 (m, 1H), 1.82 (m, 2H). AnalCalc'd for C$_{26}$H$_{27}$ClN$_2$O$_3$.HCl.H$_2$O: C 61.78, H 5.98, N 5.54. Found: C 61.91, H 6.07, N 5.62.

Compound 77

2-{2-[4-[(N,N'-Bis-tert-butoxycarbonyl)guanidinomethyl]phenoxy]ethyl}-4-(3-chlorobenzyl)-3,4-dihydro-3-oxo-2H-1,4-benzoxazine

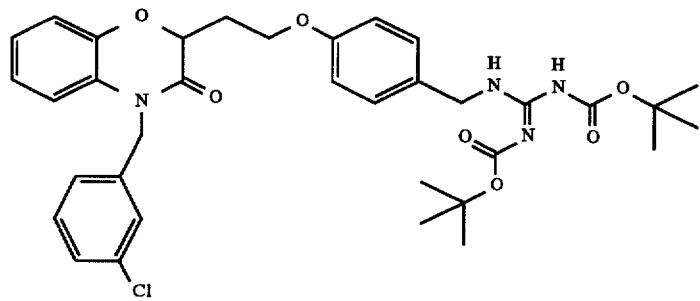

Prepared by method L using intermediate 10488-22 (Reference Example 66) and N,N'-di-t-butoxycarbonyl-2-(4-hydroxyphenyl)methyl guanidine in 52% yield, mp 74° C. shrinks, 89°–95° C. melts; MS (FAB) MH$^+$ 665; IR (KBr) 3334, 2979, 1723, 1690, 1501, 1396, 1368, 1325, 1248, 1057, 810 cm$^{-1}$; $^1$H NMR (CDCl$_3$) δ 11.52 (s, 1H), 8.49 (br t, 1H), 7.24 (m, 4H), 7.13 (m, 1H), 6.99 (m, 3H), 6.92 (m, 2H), 6.89 (d, 1H, J=8.5Hz), 6.82 (d, 1H, J=7.5Hz), 5.18 (d, 1H, J=16.0Hz), 5.08 (d, 1H, J=16.0Hz), 4.93 (dd, 1H, J=3.9, 9.3Hz), 4.54 (d, 2H, J=4.9Hz), 4.25 (m, 2H), 2.59 (m, 1H), 2.34 (m, 1H), 1.52 (s, 9H), 1.47 (s, 9H). Anal. Calc'd for C$_{35}$H$_{41}$ClN$_4$O$_7$.H$_2$O: C 61.53, H 6.34, N 8.20. Found: C 61.50, H 6.26, N 8.03.

Compound 78

4-(3-Chlorobenzyl)-3,4-dihydro-2-{2-[4-(guanidinylmethyl)phenoxy]ethyl}-3-oxo-2H-1,4-benzoxazine

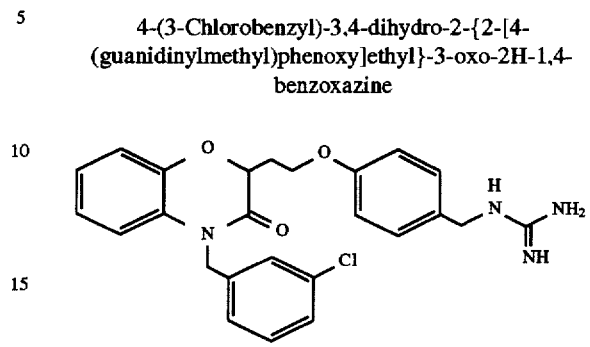

Prepared from Compound 77 by method K in 37% yield, mp decomposes >61° C.; MS (CI) MH$^+$465; IR (KBr) 3338, 1501, 1398, 1246, 1051, 750 cm$^{-1}$; $^1$H NMR (DMSO-d$_6$) δ 8.03 (br t, 1H, J=5.9Hz), 7.35 (m, 5H), 7.23 (m, 5H), 7.02 (m, 6H), 5.23 (d, 1H, J=16.5Hz), 5.12 (d, 1H, J=16.5Hz), 5.00 (dd, 1H, J=4.2, 8.7Hz), 4.29 (d, 2H, J=5.9Hz), 4.22 (m, 2H), 2.40 (m, 1H), 2.25 (m, 1H). Anal. Calc'd for C$_{25}$H$_{25}$ClN$_4$O$_3$.HCl. H$_2$O.0.1C6H14: C 58.23, H 5.61, N 10.61. Found: C 58.51, H 5.40, N 10.81.

Compound 79

2-{2-[4-(2-Aminoethyl)phenoxy]ethyl}-4-(3-chlorobenzyl)-3,4-dihydro-3-oxo-2H-1,4-benzoxazine

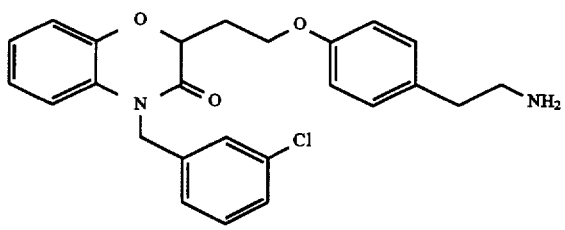

Prepared from 10488-22 (Reference Example 66) and 4-[2-(N-t-butoxycarbonylamino)ethyl]phenol by method J followed by method K in quantitative yield mp 140.5°–143° C.; MS (CI) MH⁺437; IR (KBr) 2930, 1885, 1591, 1503, 1466, 1437, 1398, 1323, 1182, 1138, 991, 879 cm⁻¹; ¹H NMR (DMSO-d₆) δ 8.00 (br s, 3H), 7.35 (m, 3H), 7.20 (m, 3H), 7.03 (m, 4H), 6.92 (d, 2H, J=8.6Hz), 5.23 (d, 1H, J=16.5Hz), 5.13 (d, 1H, J=16.4Hz), 5.00 (dd, 1H, J=4.2, 8.7Hz), 4.19 (m, 2H), 2.98 (m, 2H), 2.82 (m, 2H), 2.39 (m, 1H), 2.22 (m, 1H). Anal. Calc'd for C₂₅H₂₅ClN₂O₃·HCl: C 63.43, H 5.54, N 5.92. Found: C 63.26, H 5.46, N 5.86.

Compound 80

2-{2-[4-(2-(N,N-'Bis-tert-butoxycarbonylguanidino)ethyl)phenoxy]ethyl}-4-(3-chlorobenzyl)-3,4-dihydro-7-nitro-3-oxo-2H-1,4-benzoxazine

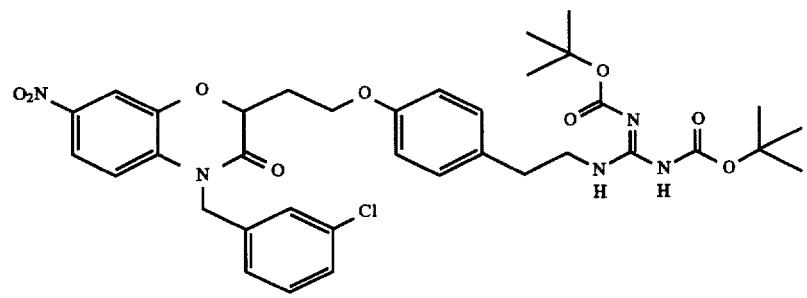

Prepared from intermediate 11653-356 (Reference Example 87) and N,N'-di-t-butoxycarbonyl-2-(4-hydroxyphenyl)ethyl guanidine by method J in 57% yield, mp (dec) >69° C.; MS (FAB) MH⁺724; IR (KBr) 3329, 3119, 3090, 2977, 2933, 2420, 2287, 1575, 1475, 1080, 1057, 927, 855, 701, 576, 490 cm⁻¹; ¹H NMR (CDCl₃) δ 11.50 (br s, 1H), 8.37 (br s, 1H), 7.88 (d, 1H, J=2.4Hz), 7.82 (dd, 1H, J=2.6, 8.8Hz), 7.28 (d, 2H, J=5.1Hz), 7.22 (s, 1H), 7.12 (m, 3H), 6.90 (d, 1H, J=8.8Hz), 6.84 (d, 2H, J=8.5Hz), 5.23 (d, 1H, J=16.4Hz), 5.13 (d, 1H, J=16.3Hz), 5.06 (dd, 1H, J=3.4, 9.1Hz), 4.23 (m, 2H), 3.63(q, 2H, J=5.4Hz), 2.82 (t, 2H, J=7.2Hz), 2.65 (m, 1H), 2.37 (m, 1H), 1.50 (s, 9H), 1.48 (s, 9H). Anal. Calc'd for C₃₆H₄₂ClN₅O₉·0.5H₂O: C 58.97, H 5.91, N 9.55. Found: C 58.97, H 6.00, N 9.25.

Compound 81

2-{2-[4-[2-(tert-Butoxycarbonylamino)ethyl]phenoxy]ethyl}-4-(3-chlorobenzyl)-3,4-dihydro-7-nitro-3-oxo-2H-1,4-benzoxazine

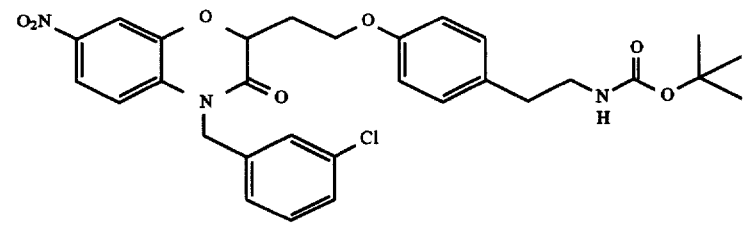

Prepared from intermediate 11653-35B (Reference Example 87) and N,N'-di-t-butoxycarbonyl-2-(4-hydroxyphenyl)ethyl guanidine by method J in 20% yield, mp 82°–85° C.; MS (CI) MH⁺582; IR (KBr) 3366, 3085, 2975, 2935, 1882, 1695, 1600, 1526, 1512, 1477, 1442, 1389, 1365, 1301, 1114, 999, 853, 665 cm⁻¹; ¹H NMR (CDCl₃) δ 7.88 (d, 1H, J=2.42 Hz), 7.84 (dd, 1H, J=8.82, 2.55 Hz), 7.28 (m, 4H), 7.22 (s, 1H), 7.12 (d, 2H, J=8.57 Hz), 6.90 (d, 1H, J=8.84 Hz), 6.85 (d, 1H, J=8.60 Hz), 5.23 (d, 1H, J=16.2 Hz), 5.13 (d, 1H, J=16.3 Hz), 5.06 (dd, 1H, J=9.03, 3.94 Hz), 4.53 (br s, 1H), 4.24 (m, 2H), 3.33 (m, 2H), 2.74 (t, 2H, J=6.86 Hz), 2.62 (m, 1H), 2.37 (m, 1H), 1.44 (s, 9H). Anal. Calc'd for C₃₀H₃₄ClN₃O₇: C 61.91, H 5.54 N 7.22. Found: C 61.58, H 5.80 N 7.36.

Compound 82

2-{2-[4-(2-Aminoethyl)phenoxy]ethyl}-4-(3-chlorobenzyl)-3,4-dihydro-7-nitro-3-oxo-2H-1,4-benzoxazine monohydrochloride

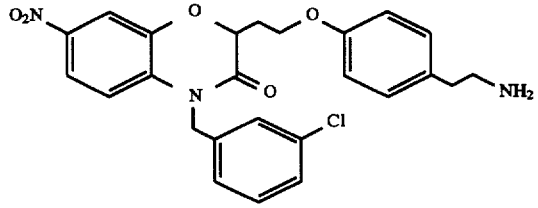

Prepared from Compound 81 by method K in 46% yield, mp 79° C.—shrinks, 92°–96° C.—melts; MS (CI) MH⁺ 482; IR (KBr) 3392, 2933, 2021, 1474, 1441, 1146, 1118, 928, 852, 701, 528 cm⁻¹; ¹H NMR (DMSO-d₆) δ 7.95 (br s, 2H), 7.92 (d, 1H, J=2.5Hz), 7.87 (m, 1H), 7.42 (s, 1H), 7.36 (m, 2H), 7.24 (d, 2H, J=8.8Hz), 7.16 (d, 2H, J=8.5Hz), 6.92 (d, 2H, J=8.5Hz), 5.30 (d, 1H, J=16.8Hz), 5.18 (m, 2H), 4.22 (m, 2H), 2.98 (t, 2H, J=8.6Hz), 2.80 (t, 2H, J=8.6Hz), 2.38 (m, 1H), 2.26 (m, 1H). Anal. Calc'd for $C_{25}H_{24}ClN_3O_5 \cdot HCl \cdot H_2O$: C 55.98, H 5.07, N 7.83. Found: C 55.92, H 4.80, N 7.82.

Compound 83

2-{2-[4-(N,N-'Bis-tert-butoxycarbonylguanidinomethyl)phenoxy]ethyl}-4-(3-chlorobenzyl)-3,4-dihydro-7-nitro-3-oxo-2H-1,4-benzoxazine

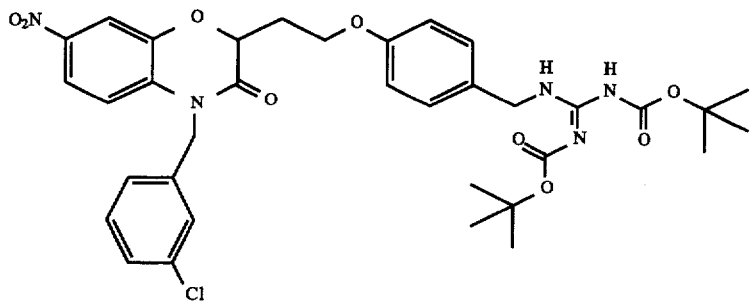

Prepared from intermediate 11653-35B (Reference Example 87) and N,N'-di-t-butoxycarbonyl-(4-hydroxyphenyl)methyl guanidine by method J in 65% yield, mp 67.5° C.—shrinks, 84°–88° C.—melts. MS (FAB) $MH^+$ 710; IR (KBr) 3730, 3326, 3122, 3089, 2978, 2932, 2413, 1720, 1640, 1615, 1503, 1476, 1081, 931, 558 $cm^{-1}$; $^1H$ NMR ($CDCl_3$) δ 11.55 (br s, 1H), 8.59 (br s, 1H), 7.90 (d, 1H, J=2.5Hz), 7.84 (dd, J=2.5, 8.8Hz), 7.25 (m, 4H), 7.10 (m, 1H), 6.86 (m, 4H), 5.22 (d, 1H, J=16.3Hz), 5.30 (d, 1H, J=16.3Hz), 5.10 (dd, 1H, J=3.4, 9.1Hz), 4.60 (m, 2H), 4.23 (m, 2H), 2.66 (m, 1H), 2.38 (m, 1H), 1.51 (s, 9H), 1.47 (s, 9H). Anal. Calc'd for $C_{35}H_{40}ClN_5O_9$: C 59.19, H 5.68, N 9.86. Found: C 59.10, H 6.07, N 9.74.

Compound 84

3,4-Dihydro-4-(3-chlorobenzyl)-2-{2-[4-(2-guanidinoethyl)phenoxy]ethyl}-7-nitro-3-oxo-2H-1,4-benzoxazine Monohydrochloride

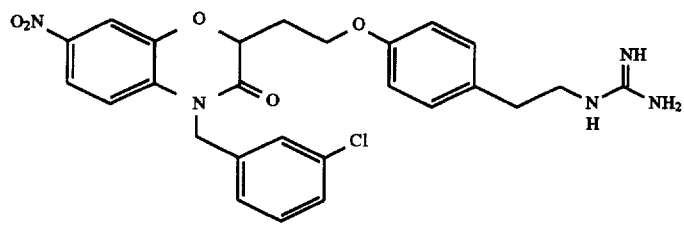

Prepared from Compound 83 by method K in quantitative yield, mp (dec) >101° C.; MS (FAB) $MH^+$524; IR (KBr) 3326, 3156, 2968, 2878, 1695, 1665, 1599, 1513, 1473, 1441, 1389, 1178, 1148, 1022, 852, 472 $cm^{-1}$; $^1H$ NMR (DMSO-$d_6$) δ 7.93 (d, 0.5H, J=2.6Hz), 7.89 (m, 1.5H), 7.62 (br t, 1H), 7.43 (s, 1H), 7.40–6.65(v br s, 3H), 7.35 (m, 2H), 7.27 (d, 2H, J=8.6Hz), 7.21 (d, 2H, J=8.6Hz), 6.92 (d, 2H, J=8.6Hz), 5.33 (d, 1H, J=16.7Hz), 5.20 (d, m, 2H, J=16.5Hz), 4.22 (m, 2H), 3.32 (m, 2H), 2.73 (t, 2H, J=7.3Hz), 2.41 (m, 1H), 2.32 (m, 1H). Anal. Calc'd for $C_{26}H_{26}ClN_5O_5 \cdot HCl \cdot H_2O$: C 53.99, H 5.05, N 12.11. Found: C 54.11, H 4.95, N 12.01.

Compound 85

2-{2-[4-(2-(N,N-Bis-tert-butoxycarbonyl)guanidinoethyl)phenoxy]ethyl}-4-(2-chlorobenzyl)-3,4-dihydro-7-nitro-3-oxo-2H-1,4-benzoxazine

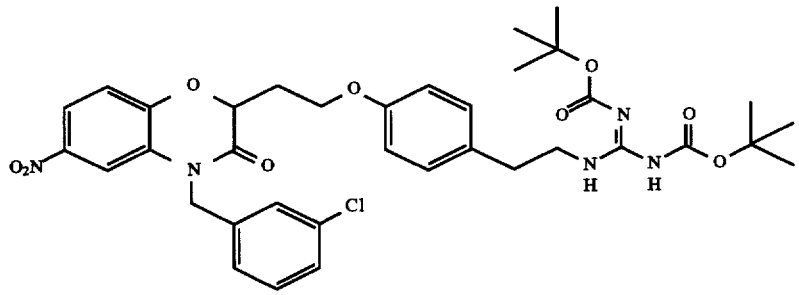

Prepared from intermediate 11653-58C (Reference Example 68) and N,N'-di-t-butoxycarbonyl-2(4-hydroxyphenyl)ethylguanidine in 85% yield, mp 69° C.—shrinks 90°–92° C.—melts; MS (FAB) MH$^+$724; IR (KBr) 3329, 3128, 2978, 2934, 1722, 1697, 1638, 1524, 1474, 1414, 1364, 1021, 933 cm$^{-1}$; $^1$H NMR (CDCl$_3$) δ 11.47 (br s, 1H), 8.37 (br s, 1H), 7.91 (dd, 1H, J=2.4, 8.8Hz), 7.77 (d, 1H, J=2.5Hz), 7.27 (m, 2H), 7.19 (brs, 1H), 7.10 (m, 4H), 6.83 (d, 2H, J=8.6Hz), 5.23 (d, 1H, J=17.9Hz), 5.14 (d, 1H, J=17.9Hz), 5.09 (dd, 1H, J=4.1, 9.1Hz), 4.20 (m, 2H), 3.63 (m, 2H), 2.82 (t, 2H, J=7.1Hz), 2.62 (m, 1H), 2.37 (m, 1H), 1.50 (s, 9H), 1.48 (s, 9H). Anal. Calc'd for C$_{36}$H$_{42}$ClN$_5$O$_9$: C 59.71, H 5.85, N 9.67. Found: C 59.38, H 6.04, N 9.63.

Compound 86

2-{2-[4-(2-(N,N'-Bis-tert-butoxycarbonyl)guanidino)ethyl)phenoxy]ethyl}-4-(2-chlorobenzyl)-3,4-dihydro-7-nitro-3-oxo-2H-1,4-benzoxazine

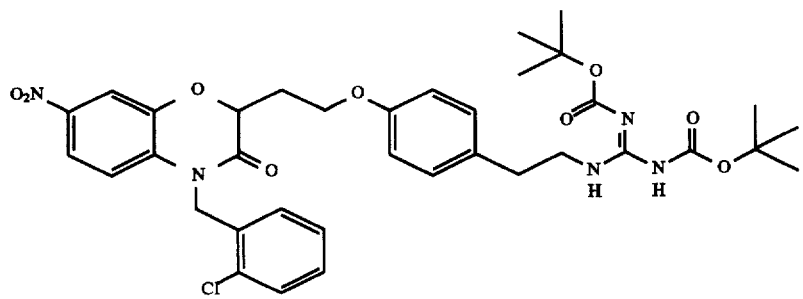

Prepared from intermediate 11653-24A (Reference Example 86) and N,N'-di-t-butoxycarbonyl-2-(4-hydroxyphenyl)ethyl guanidine by method L in 52% yield as a yellow foam, mp (dec) >85° C.; MS: FAB MH$^+$ 724; IR (KBr) 3335, 2979, 1637, 1527, 1390, 1341, 1156, 1059 cm$^{-1}$; $^1$H NMR (CDCl$_3$) δ 11.48 (br s, 1H), 7.90 (d, 1H, J=2.50), 7.83 (dd, 1H, J=2.52, 8.85), 7.45 (d, 1H, J=7.90), 7.26 (m, 1H), 7.19 (m, 2H), 7.14 (d, 1H, J=8.52), 6.94 (d, 1H, J=7.68), 6.85 (d, 2H, J=8.50), 6.80 (d, 1H, J=8.90), 5.30 (d, 2H, J=5.54), 5.08 (dd, 1H, J=5.02), 4.23 (m, 2H), 3.65 (m, 2H), 2.82 (t, 2H, J=7.2), 2.65 (m, 1H), 2.39 (m, 1H), 1.50 (s, 9H), 1.48 (s, 9H). Anal. Calc'd for C$_{36}$H$_{42}$ClN$_5$O$_9$: C 59.71, H 5.85, N 9.67. Found: C 59.48, H 5.89, N 9.52.

Compound 87

4-(2-Chlorobenzyl)-3,4-dihydro-2-{2-[4-(2-guanidinoethyl)phenoxy]ethyl}-7-nitro-3-oxo-2H-1,4-benzoxazine Monohydrochloride

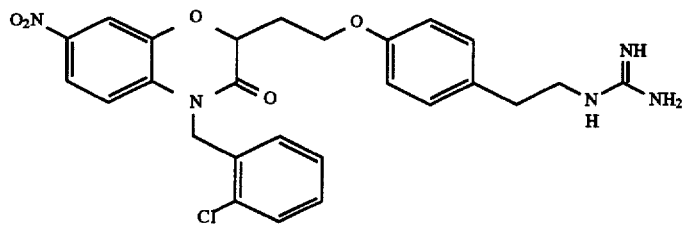

Prepared from Compound 86 by method K in 79% yield, mp 120°–125° C.; MS (CI) MH⁺524; IR (KBr) 3368, 3322, 3168, 2932, 2878, 1694, 1502, 1334, 1234, 1028, 806 cm⁻¹; ¹H NMR (DMSO-d₆) δ 7.92 (m, 1.5H), 7.90 (d, 0.5H, J=7.9 Hz), 7.55 (m, 2H), 7.40–6.50(v br s., 3H), 7.34 (t, 1H, J=7.5Hz), 7.26 (t, 1H, J=7.5 Hz), 7.20 (d, 2H, J=8.6 Hz), 7.08 (m, 2H), 6.92 (d, 2H, J=8.6 Hz), 5.28 (d, 1H, J=17.4 Hz), 5.22 (m, 1H), 5.16 (d, 1H, J=17.4 Hz), 4.22 (m, 2H), 3.34 (m, 2H), 2.71 (t, 2H, J=7.6 Hz), 2.41 (m, 1H), 2.35 (m, 1H). Anal. Calc'd for $C_{26}H_{26}ClN_5O_5 \cdot HCl \cdot H_2O$: C 53.99, H 5.05, N 12.11. Found C 53.75, H 5.23, N 12.09.

Compound 88

2-{2-[4-(2-(N, N-Bis-tert-butoxycarbonylguanidino)ethyl)-phenoxy]ethyl}-4-(2-chlorobenzyl)-3,4-dihydro-6-nitro-3-oxo-2H-1,4-benzoxazine

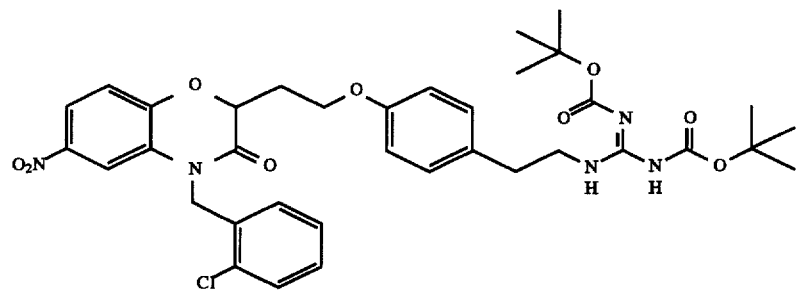

Prepared from intermediate 11653-44A (Reference Example 70) and N,N'-di-t-butoxycarbonyl-2-(4-hydroxyphenyl)ethyl guanidine by method L in 50% yield, mp 155° C.—shrinks, 160°–163° C.—melts. IR (KBr) 3345, 3108, 2980, 2934, 1723, 1701, 1529, 1338, 1126, 878 cm⁻¹; ¹H NMR (CDCl₃) δ 11.48 (br s, 1H), 8.38 (br s, 1H), 7.91 (dd, 1H, J=2.5, 8.8 Hz), 7.69 (d, 1H, J=2.5 Hz), 7.46 (dd, 1H, J=1.3, 9.1 Hz), 7.20 (m, 1H), 7.12 (m, 4H), 7.01 (d, 1H, J=7.6 Hz), 6.83 (d, 2H, J=8.6 Hz), 5.31 (s, 2H), 5.11 (dd, 1H, J=4.0, 8.9 Hz), 4.22 (m, 2H), 3.63 (m, 2H), 2.82 (t, 2H, J=7.2 Hz), 2.65 (m, 1H), 2.39 (m, 1H), 1.50 (s, 9H), 1.48 (s, 1H). Anal. Calc'd for $C_{36}H_{42}ClN_5O_9$: C 59.71, H 5.85, N 9.67. Found: C 59.89, H 5.84, N 9.61.

Compound 89

3,4-Dihydro-2-{2-[4-(2-guanidinoethyl)-phenoxy]ethyl}-6-nitro-4-(2-chlorobenzyl)-3-oxo-2H-1,4-benzoxazine

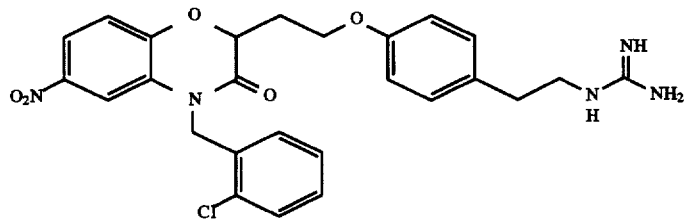

Prepared from Compound 88 by method K in 90% yield, mp (dec) >85° C.; MS (CI) MH$^+$524; IR (KBr) 3335, 3156, 1651, 1524, 1515, 1446, 1343, 1269, 1243, 1108, 746 cm$^{-1}$; $^1$H NMR (DMSO-d$_6$) δ 7.94 (dd, 1H, J=2.5, 8.9 Hz), 7.64 (d, 2H, J=2.6 Hz), 7.56 (d, 1H, J=7.8 Hz), 7.50–6.55(v. br. s., 3H), 7.30 (m, 4H), 7.19 (m, 3H), 6.90 (d, 2H, J=8.6 Hz), 5.31 (m, 2H), 5.21 (d, 1H, J=17.2 Hz), 4.19 (m, 2H), 3.29 (m, 2H), 2.71 (t, 2H, J=7.7 Hz), 2.44 (m, 1H) 2.35 (m, 1H). Anal. Calc'd for C$_{26}$H$_{26}$ClN$_5$O$_5$.HCl.0.5 H$_2$O: C 54.84 H 4.96, N 12.30. Found: C 54.87, H 4.94 N 12.02.

Compound 90

3,4-Dihydro-2-{2-[4-(2-(N,N'-Bis-tert-butoxycarbonylguanidino)ethyl)phenoxy]ethyl}-4-(3-nitrobenzyl)-7-nitro-3-oxo-2H-1,4-benzoxazine

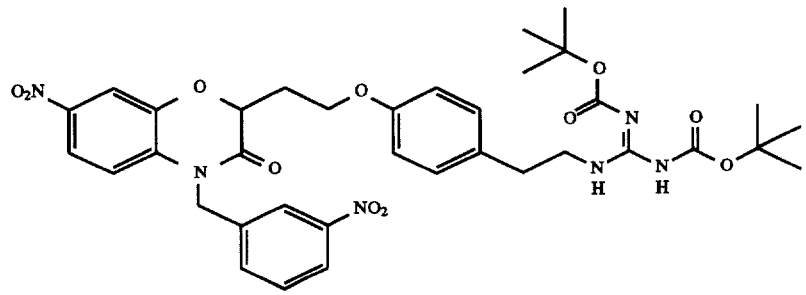

Prepared from intermediate 11653-85-B-1 (Reference Example 67) and N,N'-di-t-butoxycarbonyl-2-(4-hydroxyphenyl)ethyl guanidine by method L in 41% yield, mp (dec) >84° C.; MS (CI) MH$^+$735; IR (KBr) 3331, 2979, 2934, 1719, 1638, 1533, 1512, 1477, 1343, 1132, 812 cm$^{-1}$; $^1$H NMR (CDCl$_3$) δ 11.48 (s, 1H), 8.37 (br.t., 1H), 8.16 (m, 1H), 8.12 (s, 1H), 7.91 (d, 1H, J=2.4Hz), 7.85 (dd, 1H, J=2.5, 8.9 Hz), 7.54 (m, 2H), 7.13 (d, 2H, J=8.5 Hz), 6.89 (d, 1H, J=8.9 Hz), 6.83 (d, 1H, J=8.6 Hz), 5.34 (d, 1H, J=16.6 Hz) 5.27 (d, 1H, J=16.7 Hz), 5.10 (dd, 1H, J=4.0, 8.9 Hz), 4.24 (m, 2H), 3.63(q, 2H, J=7.0 Hz), 2.82 (t, 2H, J=7.2 Hz), 2.63 (m, 1H), 2.38 (m, 1H), 1.62 (br. s., 1H), 1.50 (s, 9H), 1.48 (s, 9H). Anal. Calc'd for C$_{36}$H$_{42}$N$_6$O$_{11}$: C 58.85, H 5.76, N 11.44. Found: C 58.73, H 5.77, N 11.34.

Compound 91

3,4-Dihydro-2-{2-[4-(2-guanidinoethyl)phenoxy]ethyl}-7-nitro-4-(3-nitrobenzyl)-3-oxo-2H-1,4-benzoxazine

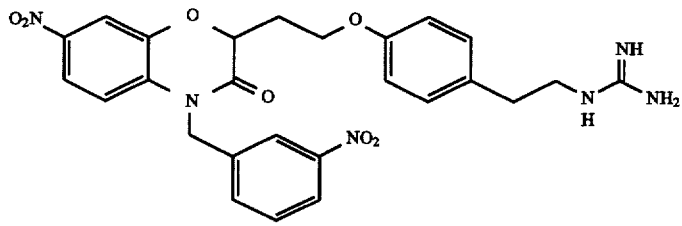

Prepared from Compound 90 by method K, mp (dec) >90° C.; MS (CI) MH⁺535; IR (KBr) 3336, 3155, 1696, 1602, 1528, 1390, 1343, 1244, 1179, 927, 743 cm⁻¹; ¹H NMR (DMSO-d₆) δ 8.23 (s, 1H), 8.15 (d, 1H, J=8.1 Hz), 7.89 (m, 2H), 7.72 (d, 1H, J=7.7 Hz), 7.63 (t, 1H, J=7.9 Hz), 7.55 (br t, 1H), 7.51–6.65(v br s., 3H), 7.31 (d, 1H, J=7.31 Hz), 7.20 (d, 2H, J=8.6 Hz), 6.91 (d, 2H, J=8.6 Hz), 5.43 (d, 1H, J=16.6 Hz), 5.34 (d, 1H, J=17.3 Hz), 5.23 (dd, 1H, J=4.1, 8.7 Hz), 4.21 (m, 2H), 3.30 (m, 2H), 2.71 (t, 2H, J=7.3 Hz), 2.41 (m, 1H), 2.30 (m, 1H). Anal. Calc'd for $C_{26}H_{26}N_6O_7 \cdot HCl \cdot 0.7\,H_2O$: C 53.51, H 4.91 N 14.40. Found: C 53.87, H 4.77, N 14.72.

Compound 92

6-Amino-4-(3-chlorobenzyl)-3,4-dihydro-2-{2-[4-(2-guanidinoethyl)phenoxy]ethyl}-3-oxo-2H-1,4-benzoxazine

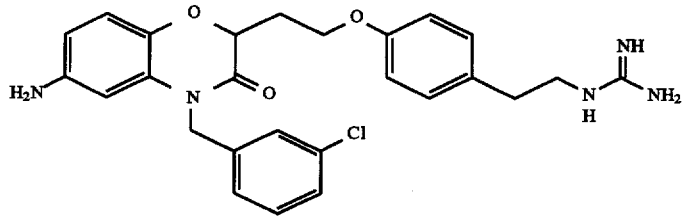

4-(3-Chlorobenzyl)-3,4-dihydro-2-{2-[4-(2-guanidinoethyl)phenoxy]ethyl}-6-nitro-3-oxo-2H-1,4-benzoxazine (0.3 g) was warmed in ethanol (5 ml) and H₂O (4 ml) until completely in solution. Iron powder (0.19 g, 6.8 eq) was stirred in followed by NH₄Cl (0.02 g, 0.7 eq) and the reaction continued at reflux for 5 hours. While still hot, the mixture was filtered through celite and the yellow filtrate concentrated down to a yellow oil. After drying in vacuo at 80° C., the product was collected as a yellow solid in 85% yield, mp (dec) >94° C.; MS (CI) MH⁺494; IR (KBr) 3332, 1667, 1614, 1512, 1467, 1396, 1243, 830, 774, 680 cm⁻¹; ¹H NMR (DMSO-d₆/CDCl₃) δ 7.66 (br s, 1H), 7.58–6.50 (v br s, 3H), 7.36 (m, 4H), 7.20 (m, 3H), 6.91 (d, 2H, J=8.6 Hz), 6.74 (d, 1H, J=8.4 Hz), 6.26 (d, 1H, J=2.2 Hz), 6.21 (dd, 1H, J=2.2, 8.4 Hz), 5.08 (d, 1H, J=16.7 Hz), 4.99 (d, 1H, J=16.5 Hz), 5.12–4.78(v br s., 1H), 4.79 (dd, 1H, J=4.0, 8.9Hz), 4.15 (m, 2H), 3.33 (m, 2H), 2.71 (t, 2H, J=7.5 Hz), 2.30 (m, 1H), 2.18 (m,1H). Anal. Calc'd for $C_{26}H_{28}ClN_5O_3 \cdot HCl \cdot 0.5H_2O$: C 57.89, H 5.61, N 12.98. Found: C 57.64, H 5.48, N 12.63.

Compound 93

2-{2-[4-(2-(N,N'-Bis-tert-butoxycarbonylguanidino
)ethyl)phenoxy]ethyl}-4-(4-nitrobenzyl)-3,4-
dihydro-3-oxo-2H-1,4-benzoxazine

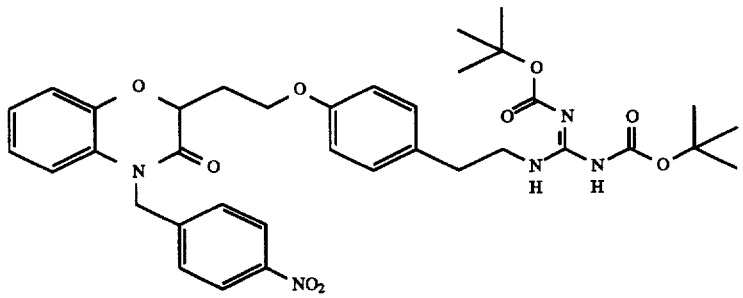

Prepared from intermediate 11653-173 (Reference Example 71) and and N,N'-di-t-butoxycarbonyl-2-(4-hydroxyphenyl)ethyl guanidine by method L in 61% yield, mp (dec) >78° C.; IR (KBr) 3331, 2977, 1722, 1689, 1638, 1513, 1500, 1467, 1278, 922, 859 cm$^{-1}$; $^1$H NMR (CDCl$_3$) δ 11.48 (br s., 1H), 8.37 (br t, 1H), 8.19 (d, 2H, J=8.8 Hz), 7.41 (d, 2H, J=8.8 Hz), 7.13 (d, 2H, J=8.6 Hz), 7.03 (m, 2H), 6.92 (m, 1H), 6.85 (d, 2H, J=8.6 Hz), 6.75 (d, 1H, J=7.9 Hz), 5.29 (d, 1H, J=16.7 Hz), 5.18 (d, 1H, J=16.7 Hz), 4.95 (dd, 1H, J=3.9, 9.3 Hz), 4.22 (m, 2H), 3.64 (m, 2H), 2.81 (t, 2H, J=7.3 Hz), 2.58 (m, 1H) 2.35 (m, 1H), 1.50 (s, 9H), 1.48 (s, 9H). Anal. Calc'd for C$_{36}$H$_{43}$N$_5$O$_9$·0.5H$_2$O: C 61.88, H 6.35, N 10.02. Found: C 62.07, H 6.32, N 9.85.

Compound 94

2-{2-[4-(2-(N,N'-Bis-tert-butoxycarbonylguanidino)
ethyl)phenoxy]ethyl}-3,4-dihydro-4-(3-nitrobenzyl)-
3-oxo-2H-1,4-benzoxazine

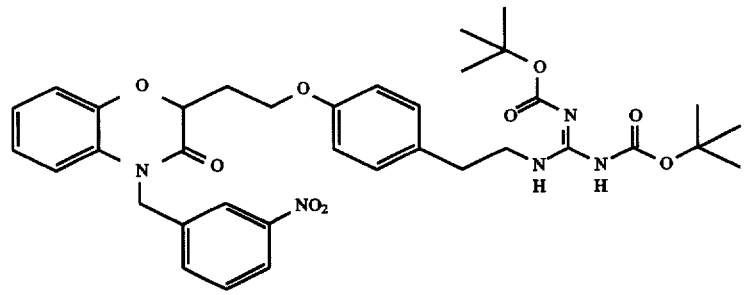

Prepared from intermediate 11653-180 (Reference Example 61) and N,N'-di-t-butoxycarbonyl-2-(4-hydroxyphenyl)ethyl guanidine by method L in 64% yield, mp (dec) >144° C.; MS (FAB) MH$^+$690; IR (KBr) 3333, 2979, 1769, 1720, 1684, 1641, 1613, 1582, 1526, 1512, 1501, 1467, 1403, 1303, 1279, 1208, 1020 cm$^{-1}$; $^1$H NMR (CDCl$_3$) δ 11.50 (br s, 1H), 8.37 (br t, 1H), 8.15 (s, 1H), 8.13 (s, 1H), 7.58 (d, 1H, J=7.7Hz), 7.54 (m, 1H), 7.12 (d, 2H, J=8.6Hz), 7.02 (m, 2H), 6.91 (m, 2H), 6.85 (d, 1H, J=8.6Hz), 6.79 (d, 1H, J=7.7Hz), 5.25 (s, 2H), 4.98 (dd, 1H, J=3.9, 9.4Hz), 4.22 (m, 2H), 3.63 (m, 2H), 2.81 (t, 2H, J=7.3Hz), 2.58 (m, 1H), 2.34 (m, 1H), 1.50 (s, 9H), 1.48 (s, 9H). Anal. Calc'd for C$_{36}$ H$_{43}$ N$_5$O$_9$·H$_2$O: C 61.09, H 6.41, N 9.89. Found: C 1.40, H 6.47, N 9.55.

Compound 95

3,4-Dihydro-2-{2-[4-(2-guanidinoethyl)phenoxy]
ethyl}-4-(3-nitrobenzyl)-3-oxo-2H-1,4-benzoxazine

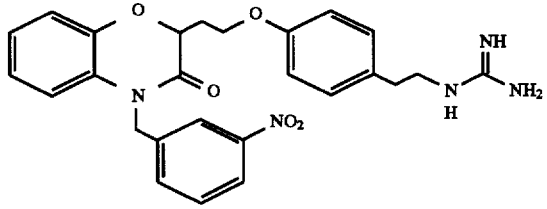

Prepared from Compound 94 by method K in 58% yield, mp (dec) >79° C.; MS (FAB) MH$^+$ 490; IR (KBr) 3321, 3146, 1665, 1529, 1500, 1466, 1399, 1349, 1322, 1279, 1249, 1154, 1097, 1063, 1022, 924, 810, 687, 468 cm$^{-1}$; $^1$H NMR (DMSO-d$_6$) δ 8.13 (s, 1H), 8.13 (d, 1H, J=7.9 Hz), 7.68 (m, 1H), 7.60–6.40 (v br s,3H), 7.39 (s, 1H), 7.20 (m, 2H), 7.08 (m, 3H), 6.98 (m, 3H), 6.92 (d, 1H, J=8.4 Hz), 5.36 (d, 1H, J=18.7 Hz), 5.28 (d, 1H, J=17.0 Hz), 5.02 (m, 1H), 4.28 (t, 1H, J=6.6 Hz), 4.18 (m, 1H), 3.35 (m, 3H), 2.72 (t, 2H, J=6.3 Hz), 2.40 (m, 1H), 2.27 (m, 1H). Anal. Calc'd for C$_{26}$H$_{27}$N$_5$O$_5$· 2.1 HCl: C 55.16, H 5.18, N 12.37. Found: C 55.08, H 5.23, N 12.21.

Compound 96

2-{2-[4-(2-(N,N'-Bis-tert-butoxycarbonylguanidino)
ethyl)phenoxy]ethyl}-7-nitro-4-(4-nitrobenzyl)-3,4-
dihydro-3-oxo-2H-1,4-benzoxazine

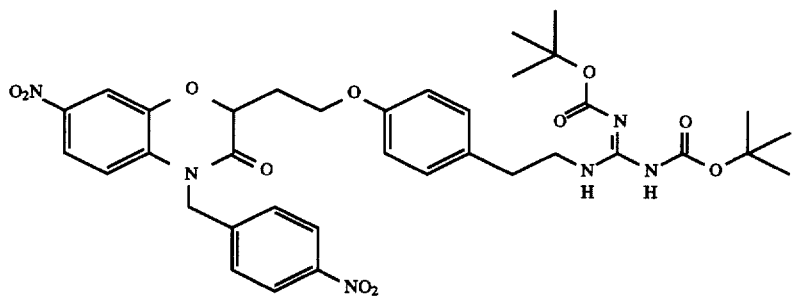

Prepared from 12279-11 (Reference Example 62) by method L in 43% yield and isolated as a yellow solid, mp (dec) >77° C.; MS (FAB) MH⁺ 735; IR (KBr) 3329, 3087, 2976, 2932, 2871, 1720, 1639, 1610, 1474, 1390, 1155, 1022, 882, 577, 461 cm⁻¹; ¹H NMR (CDCl₃) δ 11.49 (br s, 1H), 8.37 (br t, 1H), 8.21 (d, 2H, J=8.7 Hz), 7.91 (d, 1H, J=2.5 Hz), 7.84 (dd, 1H, J=2.5, 8.9), 7.40 (d, 2H, J=8.6 Hz), 7.14 (d, 2H, J=8.6 Hz), 6.83 (dd, 3H, J=2.5, 9.0 Hz), 5.35 (d, 1H, J=15.4 Hz), 5.25 (d, 1H, J=15.4 Hz), 5.08 (dd, 1H, J=4.0, 8.9 Hz), 4.22 (m, 2H), 3.63 (m, 2H), 2.82 (t, 2H, J=7.4 Hz), 2.63 (m, 1H), 2.38 (m, 1H), 1.50 (s, 9H), 1.48 (s, 9H). Anal. Calc'd for $C_{36}H_{42}N_6O_{11} \cdot C_3H_6O$: C 59.03, H 6.10, N 10.60. Found: C 58.96, H 6.17, N 10.54.

Compound 97

3,4-Dihydro-2-{2-[4-(2-guanidinoethyl)phenoxy]ethyl}-7-nitro-4-(4-nitrobenzyl)-3-oxo-2H-1,4-benzoxazine

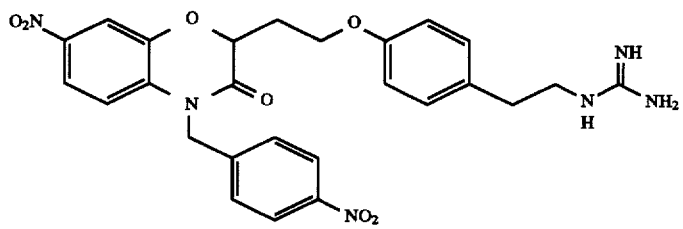

Prepared from Compound 96 by method K in quantitative yield, mp (dec) >141° C.; MS (FAB) MH⁺ 535; IR (KBr) 3323, 3158, 2948, 1702, 1667, 1598, 1470, 1434, 1396, 1182, 1144, 1107, 1012, 995, 898, 860, 826 cm⁻¹; ¹H NMR (DMSO-d₆) δ 8.22 (d, 2H, J=8.8 Hz), 7.92 (s, 1H), 7.89 (d, 1H, J=2.6 Hz), 7.61 (m, 3H), 7.60–6.65 (v br s, 2H), 7.23 (m, 4H), 6.94 (d, 2H, J=8.6 Hz), 5.47 (d, 1H, J=17.3 Hz), 5.36 (d, 1H, J=17.3 Hz), 5.27 (dd, 1H, J=8.8, 4.2 Hz), 4.23 (m, 2H), 3.35 (m, 2H), 2.74 (t, 2H, J=7.4 Hz), 2.45 (m, 1H), 2.38 (m, 1H). Anal. Calc'd for $C_{26}H_{26}N_6O_7 \cdot HCl \cdot 0.9H_2O \cdot 0.2$ IPA: C 53.32, H 5.11, N 14.02. Found: C 53.07, H 4.84, N 13.74.

Compound 98

2-{2-[4-(2-(N,N'-Bis-tert-butoxycarbonylguanidino)ethyl)phenoxy]ethyl}-4-(2-nitrobenzyl)-3,4-dihydro-3-oxo-2H-1,4-benzoxazine

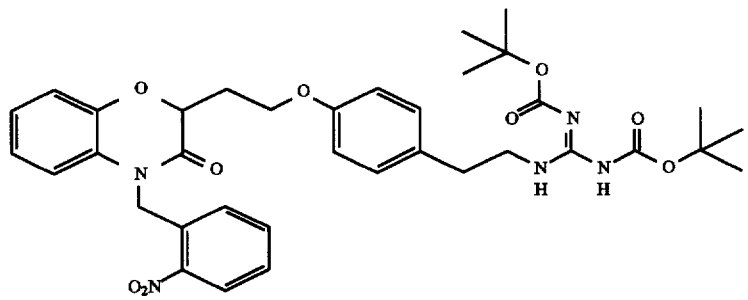

Prepared by method L using intermediate 11653-174-A (Reference Example 73) and N,N'-di-t-butoxycarbonyl-2-(4-hydroxyphenyl)ethyl guanidine in 40% yield as a yellow solid. mp (dec) >65° C.; MS (CI) MH$^+$ 690; IR (KBr) 3330, 3151, 2978, 2934, 1723, 1694, 1616, 1528, 1502, 1302, 1277, 1228, 1087, 1022, 933, 880, 562, 464 cm$^{-1}$; $^1$H NMR (CDCl$_3$) δ 11.40 (br s, 1H), 8.36 (br s, 1H), 8.18 (d, 1H, J=8.12 Hz), 7.42 (m, 2H), 7.10 (m, 2H), 6.96 (m, 4H), 6.85 (m, 1H), 6.73 (d,2H, J=8.27 Hz), 5.50 (d, 2H, J=17.95 Hz), 4.95 (dd, 1H, J=9.59, 4.21 Hz), 4.16 (m, 2H), 3.56 (m, 2H), 2.77 (m, 2H), 2.57 (m, 1H), 2.35 (m, 1H), 1.46 (s, 9H), 1.45 (s, 9H). Anal. Calc'd for C$_{36}$H$_{43}$N$_5$O$_9$·0.9 H$_2$O: C 61.25, H 6.40, N 9.92. Found: C 60.79, H 6.76, N 10.39.

Compound 99

2-{2-[4-(2-(N,N'-Bis-tert-butoxycarbonylguanidino)ethyl)phenoxy]ethyl}-3,4-dihydro-7-methoxy-4-(3-nitrobenzyl)-3-oxo-2H-1,4-benzoxazine

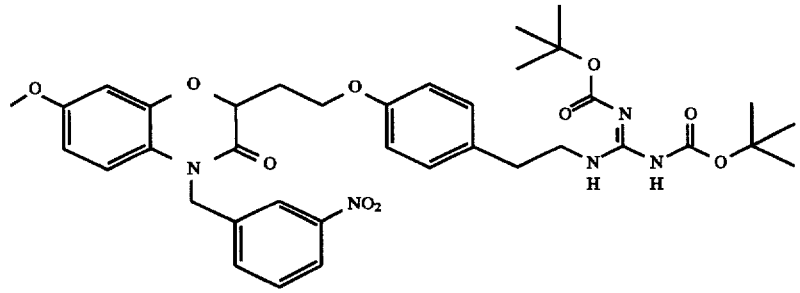

Prepared by method L using intermediate 12279-18-A (Reference Example 63) and N,N'-di-t-butoxycarbonyl-2-(4-hydroxyphenyl)ethyl guanidine in 83% yield, mp (dec) >71° C.; MS (FAB) MH+ 720; IR (KBr) 3329, 2977, 2934, 1722, 1683, 1639, 1532, 1413, 1350, 1330, 1247, 1164, 1057, 916, 729, 529 cm$^{-1}$; $^1$H NMR (CDCl$_3$) δ 11.48 (s, 1H), 8.37 (br s, 1H), 8.15 (s, 1H), 8.12 (s, 1H), 7.53 (m, 2H), 7.13 (d, 2H, J=8.62 Hz), 6.86 (d, 2H, J=8.62 Hz), 6.68 (d, 1H, J=8.88 Hz), 6.61 (d, 1H, J=2.72 Hz), 6.47 (dd, 1H, J=8.85, 2.70 Hz), 5.21 (s, 2H), 4.96 (dd, 1H, J=9.36, 3.95 Hz), 4.23 (m, 2H), 3.74 (s, 3H), 3.63 (m, 2H), 2.81 (t, 2H, J=7.22 Hz), 2.57 (m, 1H), 2.33 (m, 1H), 1.50 (s, 9H), 1.48 (s,9H). Anal. Calc'd for C$_{37}$H$_{45}$N$_5$O$_{10}$: C 61.74, H 6.30, N 9.73. Found: C 61.24, H 6.43, N 9.76.

Compound 100

3,4-Dihydro-2-{2-[4-(2-guanidinoethyl)phenoxy]ethyl}-7-methoxy-4-(3-nitrobenzyl)-3-oxo-2H-1,4-benzoxazine

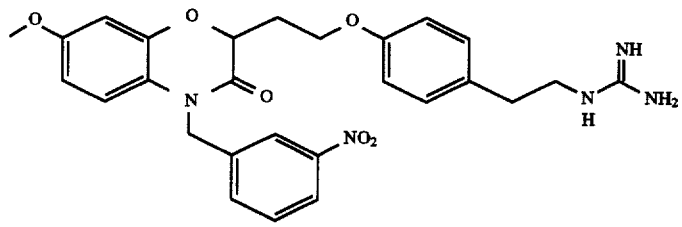

Prepared from Compound 99 by method K in 87% yield, mp (dec) >68° C.; MS (CI) MH+520; IR (KBr) 3317, 3147, 2930, 1466, 1407, 1357, 1324, 1309, 1163, 1135, 922, 798, 669, 530 cm$^{-1}$; $^1$H NMR (DMSO-d$_6$) δ 8.16 (s, 1H), 8.13 (d, 1H, J=8.28 Hz), 7.66 (m, 2H), 7.60 (t, 2H, J=7.30 Hz), 7.53–6.70(v br s, 2H), 7.20 (d, 2H, J=8.48 Hz), 7.01 (d, 1H, J=8.92 Hz), 6.92 (d, 2H, J=8.48 Hz), 6.69 (d, 1H, J=2.79 Hz), 6.55 (dd, 1H, J=2.70, 8.88 Hz), 5.28 (d, 2H, J=2.72 Hz), 4.98 (dd, 1H, J=4.05, 8.81 Hz), 4.20 (m, 2H), 3.68 (s, 3H), 3.32 (m, 2H), 2.71 (t, 2H, J=7.16 Hz)2.37 (m, 1H), 2.23 (m, 1H). Anal. Calc'd for C$_{27}$H$_{29}$N$_5$O$_6$·HCl·0.5H$_2$O: C 57.39, H 5.53, N 12.39. Found: C 57.71, H 5.90, N 11.99.

Compound 101

4-(3-Aminobenzyl)-2-{2-[4-(2-(N,N'-bis-tert-butoxycarbonylguanidino)ethyl)phenoxy]ethyl}-3,4-dihydro-3-oxo-2H-1,4-benzoxazine

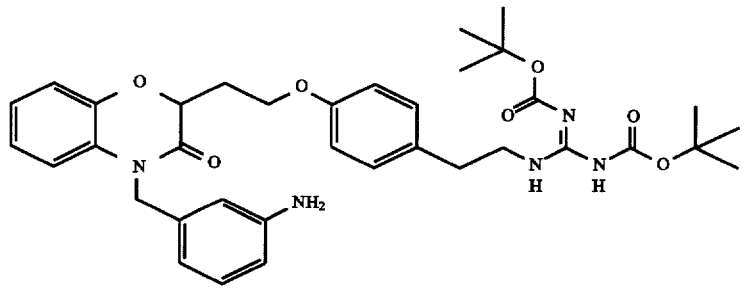

Prepared by method L using intermediate 12279-13-A (Reference Example 65) and N,N'-di-t-butoxycarbonyl-2(4-hydroxyphenyl)ethyl guanidine, and isolated by flash chromatography, eluting with acetone/hexane in 55% yield as a white solid, mp (dec) >68° C.; MS (FAB) MH$^+$660; IR (KBr) 3335, 2977, 1722, 1685, 1638, 1512, 1500, 1466, 1408, 1366, 1329, 1244, 1155, 1131, 1057, 809, 749, 688 cm$^{-1}$; $^1$H NMR (CDCl$_3$) δ 11.48 (s, 1H), 8.37 (br t, 1H), 7.12 (m, 3H), 6.95 (m, 2H), 6.87 (m, 4H), 6.85 (d, 1H, J=8.48 Hz), 6.64 (d, 1H, J=7.54 Hz), 6.56 (d, 1H, J=11.1 Hz), 5.07 (dd, 2H, J=15.97, 24.50 Hz), 4.93 (dd, 1H, J=3.83, 5.49 Hz), 4.23 (m, 2H), 3.62 (m, 4H), 2.81 (t, 2H, J=7.16 Hz), 2.56 (m, 1H), 2.33 (m, 1H), 1.50 (s, 9H), 1.48 (s, 9H). Anal. Calc'd for C$_{36}$H$_{45}$N$_5$O$_7$: C 65.54, H 6.87 N 10.61. Found: C 65.43, H 6.92, N 10.38.

Compound 102

2-{2-[4-(2-(N,N'-Bis-tert-butoxycarbonylguanidino)ethyl)phenoxy]ethyl}-3,4-dihydro-6-fluoro-4-(3-nitrobenzyl)-3-oxo-2H-1,4-benzoxazine

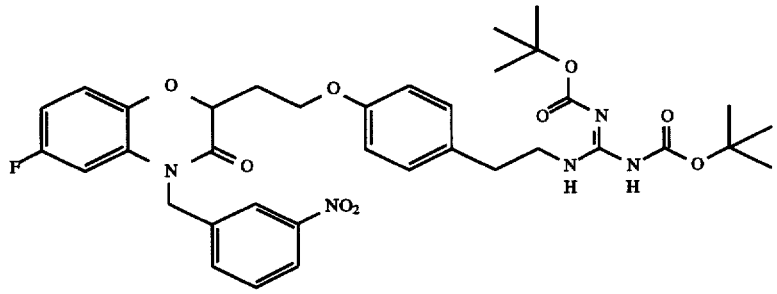

Prepared by method L using intermediate 12279-21 (Reference Example and N,N'-di-t-butoxycarbonyl-2(4-hydroxyphenyl)ethyl guanidine in 77% yield, mp (dec) >69° C.; MS (FAB) MH+708; IR (KBr) 3330, 2978, 1696, 1638, 1533, 1507, 1453, 1415, 1350, 1249, 1155, 948, 670 cm$^{-1}$; $^1$H NMR (CDCl$_3$) δ 11.47 (br s, 1H), 8.37 (br t, 1H), 8.16 (d, 1H, J=7.1 Hz), 8.11 (br s, 1H), 7.53 (m, 2H), 7.14 (d, 2H, J=8.6 Hz), 6.98 (dd, 1H, J=5.1, 8.9 Hz), 6.85 (d, 2H, J=8.6 Hz), 6.70 (m, 1H), 6.51 (dd, 1H, J=2.8, 9.4 Hz), 5.21 (d, 1H, J=16.4 Hz), 5.20 (d, 1H, J=16.4 Hz), 4.95 (dd, 1H, J=4.0, 9.3 Hz), 4.22 (m, 2H), 3.64 (m, 2H), 2.81 (t, 2H, J=7.1 Hz), 2.63 (m, 1H), 2.34 (m, 1H), 1.50 (s, 9H), 1.48 (s, 9H). Anal. Calc'd for C$_{36}$H$_{42}$FN$_5$O$_9$·1.5H$_2$O: C 60.41, H 6.34, N 9.78. Found: C 60.36, H 6.17, N 10.06.

Compound 103

2-[2-{4-[2-(t-Butoxycarbonylamino)ethyl]phenoxy}ethyl]-4-(4-carbomethoxybenzyl)-3,4-dihydro-3-oxo-2H-1,4-benzoxazine

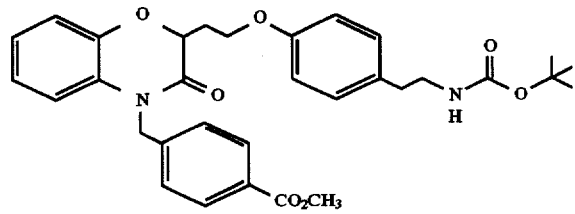

Prepared from intermediate 11758-71-2 (Reference Example 81) and 4-[2-(N-t-butoxycarbonylamino)-ethyl]phenol by method L to afford product as a white solid in 69% yield, mp 110°–112° C.; $^1$H NMR (CDCl$_3$) δ 8.00 (d, J=8.2 Hz, 2H), 7.30 (d, J=8.2 Hz, 2H), 7.10 (d, J=8.4 Hz, 2H), 6.98–7.04 (m, 2H), 6.89–6.95 (m, 3H), 6.78 (dd, J=1.3, 8.5 Hz, 1H), 5.21 (br s, 2H), 4.96 (dd, J=4.0, 9.5 Hz, 1H), 4.54 (br s with shoulders, 1H), 4.15–4.30 (m, 2H), 3.90 (s, 3H), 3.31–3.36 (m, 2H), 2.74 (t, J=6.7 Hz, 2H), 2.53–2.63 (m, 1H), 2.33 (ddt, J=14.1, 9.5, 4.8 Hz, 1H), 1.44 (s, 9H). $^{13}$C NMR (CDCl$_3$) δ 166.7, 166.4, 157.3, 155.9, 144.2, 141.3, 131.3, 130.2 (CH), 129.8 (CH), 129.5, 128.7, 126.5 (CH), 124.3 (CH), 122.9 (CH), 117.5 (CH), 115.3 (CH), 114.7 (CH), 76.6, 73.9 (CH), 63.1 (CH$_2$), 52.1 (CH$_3$), 45.2 (CH$_2$), 41.9 (CH$_2$), 35.3 (CH$_2$), 30.4 (CH$_2$), 28.4 (CH$_3$). IR 3376, 1713, 1684 cm$^{-1}$. MS (FAB) 561 (MH+), 461, 324 (base). Anal. Calc'd. for C$_{32}$H$_{36}$N$_2$O$_7$: C, 68.56; H, 6.47; N, 5.00. Found: C, 68.16; H, 6.45; N, 4.90.

Compound 104

2-{2-[4-(2-Aminoethyl)phenoxy]ethyl}-4-(4-carbomethoxybenzyl)-3,4-dihydro-3-oxo-2H-1,4-benzoxazine

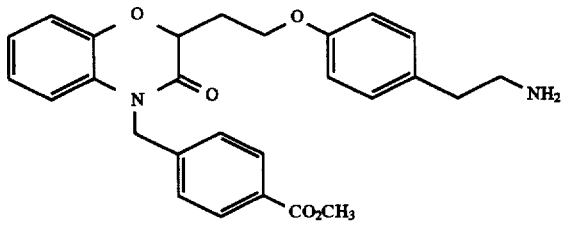

Prepared from Compound 103 by method K using trifluoroacetic acid with anisole present, instead of IPA/HCl. The resulting solid was triturated with ether to afford product as a white powder (182 mg; 88% yield; mp=164°–165° C.). $^1$H NMR (DMSO-d$_6$) δ 8.40 (br s, 3H), 7.98 (d, J=8.2 Hz, 2H), 7.32 (d, J=8.2 Hz, 2H), 7.13 (d, J=8.5 Hz, 2H), 6.77–7.01 (m, 6H), 5.21 (s, 2H), 4.94 (dd, J=4.0, 9.3 Hz, 1H), 4.19–4.27 (m, 2H), 3.90 (s, 3H), 3.06–3.12 (m, 2H), 2.90–2.96 (m, 2H), 2.51–2.60 (m, 1H), 2.29–2.37 (m, 1H). $^{13}$C NMR (DMSO-d$_6$) δ 165.9, 165.6, 157.0, 143.4, 140.7, 129.5 (CH), 129.2 (CH), 128.8, 128.5, 127.9, 125.8 (CH), 123.7 (CH), 122.3 (CH), 116.8 (CH), 114.7 (CH), 114.2 (CH), 73.1 (CH), 62.5 (CH$_3$), 51.5 (CH$_3$), 44.4 (CH$_2$), 40.4 (CH$_2$), 32.2 (CH$_2$), 29.6 (CH$_2$). IR 2700–3200 (br), 1722, 1705, 1680 cm$^{-1}$. MS 461 (MH+). Anal. Calc'd. for C$_{27}$H$_{28}$N$_2$O$_5$/C$_2$HF$_3$O$_2$: C, 60.62; H, 5.09; N, 4.88. Found: C, 60.31; H, 5.07; N, 4.78.

Compound 105

2-[2-{4-[2-(t-Butoxycarbonylamino)ethyl]
phenoxy}ethyl]-4-(3-carbomethoxybenzyl)-3,4-
dihydro-3-oxo-2H-1,4-benzoxazine

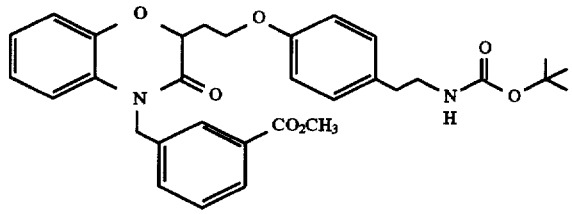

Prepared from intermediate 11758-93-2A (Reference Example 82) and 4-[2-(N-t-butoxycarbonylamino)ethyl] phenol, by method L and isolated as a white solid, 66.2% yield, mp 112°–113° C.; $^1$H NMR (CDCl$_3$) δ 7.93–7.95 (m, 2H), 7.38–7.41 (m, 2H), 7.10 (d, J=8.5 Hz, 2H), 6.88–7.02 (m, 3H), 6.86 (d, J=8.5 Hz, 2H), 6.81 (dd, J=1.5, 7.7 Hz, 1H), 5.20 (s, 2H), 4.96 (dd, J=4.0, 9.4 Hz, 1H), 4.51 (br s, 1H), 4.18–4.26 (m, 2H), 3.90 (s, 3H), 3.32–3.35 (br m, 2H), 2.73 (t, J=6.5 Hz, 2H), 2.55–2.60 (m, 1H), 2.32–2.38 (m, 1H), 1.43 (s, 9H). 3370, 1724, 1688 cm$^{-1}$. MS (FAB) 561 (MH$^+$), 324. Anal. Calc'd. for C$_{32}$H$_{36}$N$_2$O$_7$: C, 68.56; H, 6.47; N, 5.00. Found: C, 68.37; H, 6.63; N, 4.88.

Compound 106

2-{2-[4-(2-Aminoethyl)phenoxy]ethyl}-4-(3-
carbomethoxybenzyl)-3,4-dihydro-3-oxo-2H-1,4-
benzoxazine

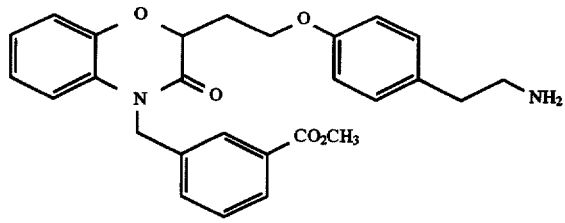

Prepared from Compound 105 by method K using trifluoroacetic acid with anisole present, instead of IPA/HCl and isolated as a cream-colored solid, 92% yield, mp=112°–114.5° C.; $^1$H NMR (DMSO-d$_6$) δ 7.90 (br s, 1H), 7.86 (d, J=7.5 Hz, 1H), 7.77 (br s, 3H), 7.47–7.54 (m, 2H), 7.19 (d, J=8.5 Hz, 2H), 7.00–7.08 (m, 4H), 6.95 (d, J=8.5 Hz, 2H), 5.26 (s, 2H), 5.00 (dd, J=4.0, 8.9 Hz, 1H), 4.19–4.23 (m, 2H), 3.84 (s, 3H), 3.02 (t, J=7.8 Hz, 2H), 2.79 (t, J=7.8 Hz, 2H), 2.35–2.40 (m, 1H), 2.23–2.28 (m, 1H). IR 2900–3100 (br), 1717, 1683 cm$^{-1}$. MS 461 (MH$^+$). Anal. Calc'd. for C$_{27}$H$_{28}$N$_2$O$_5$/C$_2$HF$_3$O$_2$: C, 60.62; H, 5.09; N, 4.88. Found: C, 60.27; H, 5.31; N, 4.68.

Compound 107

2-[2-{4-[2-(t-Butoxycarbonylamino)ethyl]
phenoxy}ethyl]-4-(2-carboethoxybenzyl)-3,4-
dihydro-3-oxo-2H-1,4-benzoxazine

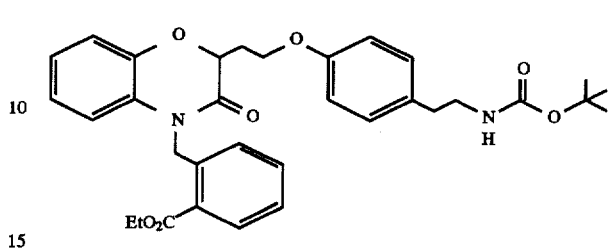

Prepared from intermediate 11758-82-2 (Reference Example 83) and 4-[2-(N-t-butoxycarbonylamino)-ethyl] phenol, by method L and isolated as a white solid in 76.9% yield, mp 103°–105° C.; $^1$H NMR (CDCl$_3$) δ 8.07 (dd, J=1.5, 7.6 Hz, 1H), 7.41 (dt, J=1.5, 7.6 Hz, 1H), 7.32 (dt, J=0.9, 7.6 Hz, 1H), 7.10 (d, J=8.6 Hz, 2H), 6.95–7.07 (m, 3H), 6.85–6.92 (m, 3H with a 2H doublet (J=8.6 Hz) at δ 6.87), 6.72 (dd, J=1.4, 8.0 Hz, 1H), 5.63 (d, J=17.9 Hz, 1H), 5.54 (d, J=17.9 Hz, 1H), 4.97 (dd, J=3.9, 9.4 Hz, 1H), 4.52 (br s, 1H), 4.41 (q, J=7.1 Hz, 2H), 4.20–4.28 (m, 2H), 3.32–3.36 (br m, 2H), 2.74 (t, J=6.8 Hz, 2H), 2.56–2.69 (m, 1H), 2.36 (ddt, J=14.4, 9.3, 4.8 Hz, 1H), 1.43 (t, J=7.1 Hz, 3H), 1.42 (s, 9H). $^{13}$C NMR δ 166.9, 166.4, 157.4, 155.9, 144.2, 137.7, 132.8 (CH), 131.5 (CH), 131.3, 129.8 (CH), 129.0, 128.5, 127.1 (CH), 125.6 (CH), 124.1 (CH), 122.9 (CH), 117.3 (CH), 115.6 (CH), 114.7 (CH), 73.7 (CH), 63.3 (CH$_2$), 61.2 (CH$_2$), 50.9, 44.5 (CH$_3$), 41.9 (CH$_2$), 35.3 (CH$_2$), 30.4 (CH$_2$), 28.4 (CH$_3$), 14.4 (CH$_3$).

Compound 108

2-{2-[4-(2-Aminoethyl)phenoxy]ethyl}-4-(2-
carboethoxybenzyl)-3,4-dihydro-3-oxo-2H-1,4-
benzoxazine

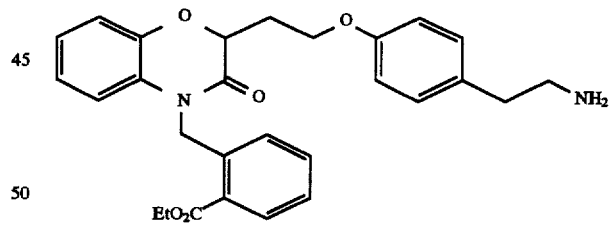

Prepared from Compound 107 by method K using trifluoroacetic acid with anisole present, instead of IPA/HCl and isolated as a white powder in 94.5% yield, mp 107.5°–109° C.; $^1$H NMR (DMSO-d$_6$) δ 7.99 (dd, J=1.5, 6.2 Hz, 1H), 7.75 (br s, 3H), 7.39–7.53 (m, 2H), 7.18 (d, J=8.6 Hz, 2H), 7.02–7.10 (m, 3H), 6.92–6.99 (m, 3H with a 2H doublet at a 6.94), 6.81 (d, J=8.0 Hz, 1H), 5.51 (d, J=17.5 Hz, 1H), 5.39 (d, J=17.5 Hz, 1H), 5.04 (dd, J=4.1, 8.7 Hz, 1H), 4.36 (q, J=7.1 Hz, 2H), 4.18–4.23 (m, 2H), 2.90–3.02 (m, 2H), 2.75–2.81 (m, 2H), 2.28–2.45 (m, 2H), 1.37 (t, J=7.1 Hz, 3H). IR 2975–3100 (br),1690 (sh), 1680 cm$^{-1}$. MS 475 (MH$^+$). Anal. Calc'd. for C$_{28}$H$_{30}$N$_2$O$_5$/1.0C$_2$HF$_3$O$_2$/1.5H$_2$O: C, 58.53; H, 5.57; N, 4.55. Found: C, 58.48; H, 5.44; N, 4.55.

Compound 109

4-{2-[2-(4-(2-(t-Butoxycarbonylamino)ethyl)phenoxy)]ethyl-3,4-dihydro-3-oxo-2H-1,4-benzoxazin-4-yl}methylbenzoic Acid

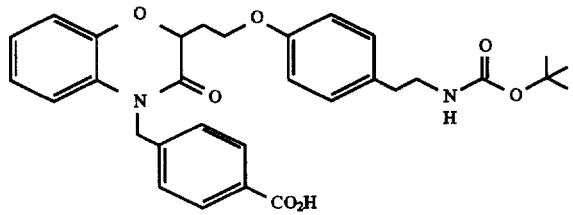

Method O: Compound 103 (150 mg, 1 eq) and 1N NaOH (2.5 eq) in methanol (10 mL) were heated in an oil bath at 50° C. for 26 h. After evaporation of the methanol, the residue was diluted with water (20 mL), cooled to 0° C., and acidified with 1N citric acid (1 mL). The precipitate was collected, washed with water and dried to give product as a white solid in 89% yield, mp=147°–148° C.; $^1$H NMR (DMSO-d$_6$) δ 8.04 (d, J=8.1 Hz, 2H), 7.34 (d, J=8.3 Hz, 2H), 7.10 (d, J=8.3 Hz, 2H), 6.75–7.04 (m, 6H), 5.22 (br s, 2H), 4.96 (dd, J=3.8, 9.0 Hz, 1H), 4.55 (br s, 1H), 4.10–4.28 (m, 2H), 3.31–3.36 (m, 2H), 2.73 (t, J=6.3 Hz, 2H), 2.55–2.61 (m, 1H), 2.34 (ddt, J=14.1, 9.8, 5.1 Hz, 1H), 1.43 (s, 9H). IR 3300–3350 (br), 1688 (br) cm$^{-1}$. MS (FAB) 547 (MH$^+$), 447 (M-Boc)$^+$, 310 (base). Anal. Calc'd. for C$_{31}$H$_{34}$N$_2$O$_7$: C, 68.12; H, 6.27; N, 5.12. Found: C, 67.71; H, 6.47; N, 5.00.

Compound 110

4-{3,4-Dihydro-2-[2-(4-(2-aminoethyl)phenoxy)]ethyl-3-oxo-2H-1,4-benzoxazin-4-yl}methylbenzoic Acid

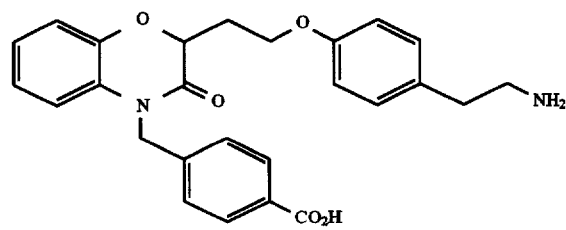

Prepared from Compound 109 by method K using trifluoroacetic acid with anisole present, instead of IPA/HCl and isolated a white powder in 98% yield, mp 195°–197° C.; $^1$H NMR (DMSO-d$_6$) δ 12.97 (br s, 1H), 7.90 (d, J=8.2 Hz, 2H), 7.77 (br s, 3H), 7.38 (d, J=8.2 Hz, 2H), 7.19 (d, J=8.3 Hz, 2H), 6.97–7.05 (m, 4H), 6.95 (d, J=8.3 Hz, 2H), 5.28 (d, J=16.3 Hz, 1H), 5.20 (d, J=16.3 Hz, 1H), 5.00 (dd, J=4.0, 8.7 Hz, 1H), 4.18–4.22 (m, 2H), 2.98–3.02 (m, 2H), 2.78 (t, J=7.8 Hz, 2H), 2.35–2.40 (m, 1H), 2.23–2.28 (m, 1H). $^{13}$C NMR δ 166.9, 165.8, 157.2, 143.6, 141.6, 129.8 (CH), 129.7 (CH), 129.3, 128.3, 126.6 (CH), 123.9 (CH), 122.8 (CH), 117.0 (CH), 115.7 (CH), 114.7 (CH), 73.0 (CH), 63.1 (CH$_2$), 43.7 (CH$_2$), 39.9 (CH$_2$), 31.9 (CH$_2$), 29.4 (CH$_2$). IR 3000–3200 (br), 1681, 1503 cm$^{-1}$. MS 447 (MH$^+$), 429 (M-OH)$^+$. Anal. Calc'd. for C$_{26}$H$_{26}$N$_2$O$_5$/C$_2$HF$_3$O$_2$/0.5H$_2$O: C, 59.05; H, 4.96; N, 4.92. Found: C, 58.96; H, 4.71; N, 4.76.

Compound 111

3-{3,4-Dihydro-2-[2-(4-(2-(-t-butoxycarbonylamino)ethyl)phenoxy)]ethyl-3-oxo-2H-1,4-benzoxazin-4-yl}methylbenzoic Acid

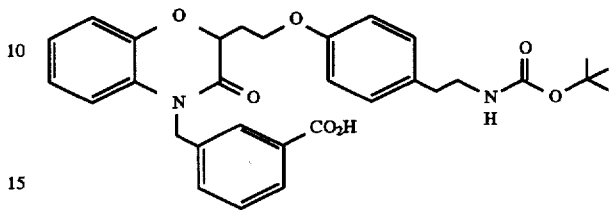

Prepared from Compound 105 by method O and isolated as a white glass in 92% yield, mp76–78° C.; $^1$H NMR (DMSO-d$_6$) δ 7.87 (br s, 1H), 7.82 (d, J=7.3 Hz, 1H), 7.51 (d, J=8.8 Hz, 1H), 7.47 (q, J=7.4 Hz, 1H), 7.10 (d, J=8.5 Hz, 2H), 6.97–7.07 (m, 4H), 6.87 (d, J=8.5 Hz, 2H), 6.85 (br s, 1H), 5.24 (s, 2H), 4.98 (dd, J=4.1, 8.8 Hz, 1H), 4.15–4.19 (m, 2H), 3.06–3.10 (br q, J=7.6 Hz, 2H), 2.61 (t, J=7.6 Hz, 2H), 2.32–2.37 (m, 1H), 2.20–2.25 (m, 1H), 1.36 (s, 9H). IR 2800–3100 (br), 1704, 1700 (sh) cm$^d$. MS 547 (MH$^+$), 473 (base). Anal. Calc'd. for C$_{31}$H$_{34}$N$_2$O$_7$/0.5 H$_2$O: C, 67.01; H, 6.35; N, 5.04. Found: C, 67.03; H, 6.44; N, 4.95.

Compound 112

3-{3,4-Dihydro-2-[2-(4-(2-aminoethyl)phenoxy)]ethyl-3-oxo-2H-1,4-benzoxazin-4-yl}methylbenzoic Acid

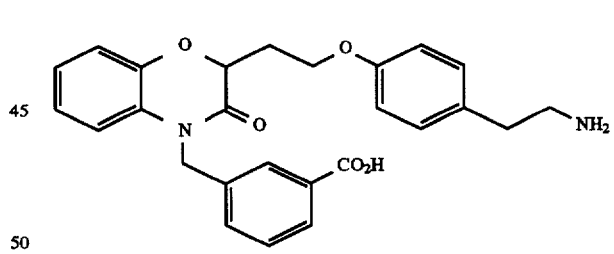

Prepared from Compound 111 by method K using trifluoroacetic acid with anisole present, instead of IPA/HCl and isolated as white crystals in 92% yield, mp 193°–195° C.; $^1$H NMR (DMSO-d$_6$) δ 13.03 (br s, 1H), 7.87 (br s, 1H), 7.83 (d, J=7.4 Hz, 1H), 7.77 (br s, 3H), 7.51 (d, J=7.9 Hz, 1H), 7.47 (q, J=7.5 Hz, 1H), 7.18 (d, J=8.5 Hz, 2H), 7.04–7.07 (m, 2H), 6.98–7.01 (m, 2H), 6.94 (d, J=8.5 Hz, 2H), 5.24 (s, 2H), 4.98 (dd, J=4.2, 8.8 Hz, 1H), 4.17–4.20 (m, 2H), 2.98–3.03 (m, 2H), 2.78 (t, J=7.8 Hz, 2H), 2.36–2.43 (m, 1H), 2.21–2.34 (m, 1H). IR 2800–3200 (br), 1677, 1636 cm$^{-1}$. MS 447 (MH$^+$), 429, 194 (base). Anal. Calc'd. for C$_{26}$H$_{26}$N$_2$O$_5$/C$_2$HF$_3$O$_2$/0.5H$_2$O: C, 59.05; H, 4.96; N, 4.92. Found: C, 58.74; H, 4.87; N, 4.69.

121

Compound 113

2-{2-[2-(4-(2-(-t-butoxycarbonylamino)ethyl)
phenoxy)]ethyl-3,4-dihydro-3-oxo-2H-1,4-
benzoxazin-4-yl}methylbenzoic Acid

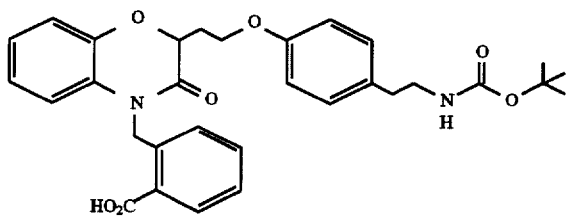

Prepared from Compound 107 by method O and isolated as a white powder in 93.5% yield, mp 156°–159° C.; $^1$H NMR (CDCl$_3$/DMSO-d$_6$) δ 8.13 (d, J=7.4 Hz, 1H), 7.32–7.40 (m, 3H with 1H exchangeable), 7.11 (d, J=8.0 Hz, 2H), 6.97–7.05 (m, 3H), 6.86 (d, J=8.0 Hz, 2H), 6.72–6.85 (m, 2H), 5.61 (d, J=18.1 Hz, 1H), 5.53 (d, J=18.1 Hz, 1H), 4.91 (dd, J=3.7, 9.3 Hz, 1H), 4.65 (br s, 1H), 4.14–4.22 (m, 2H), 3.23–3.28 (br m, 2H), 2.68 (t, J=7.0 Hz, 2H), 2.47–2.51 (m, 1H), 2.25–2.33 (m, 1H), 1.38 (s, 9H). IR 3350–3500 (br), 2950, 1687, 1512 cm$^{-1}$. MS (FAB) 547 (MH$^+$), 447 (base), 310. Anal. Calc'd. for C$_{31}$H$_{34}$N$_2$O$_7$/0.50H$_2$O: C, 67.01; H, 6.35; N, 5.04. Found: C, 67.24; H, 6.56; N, 5.02.

122

Compound 114

2-{2-[2-(4-(2-Aminoethyl)phenoxy)]ethyl-3,4-
dihydro-3-oxo-2H-1,4-benzoxazin-4-
yl}methylbenzoic Acid

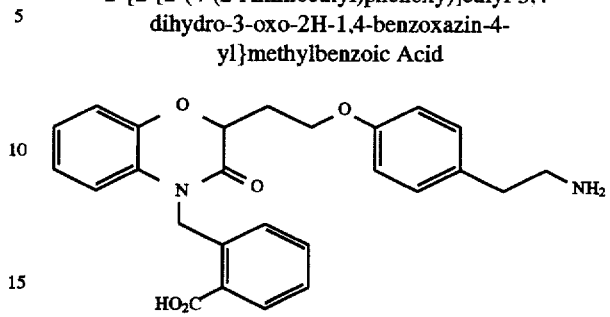

Prepared from Compound 113 by method K using trifluoroacetic acid with anisole present, instead of IPA/HCl and isolated as a white solid in 76.8% yield, mp 132°–133° C.; $^1$H NMR (DMSO-d$_6$) δ 8.00 (d, J=6.4 Hz, 1H), 7.74 (br s, 3H), 7.47 (t, J=6.5 Hz, 1H), 7.39 (t, J=7.7 Hz, 1H), 7.18 (d, J=8.5 Hz, 2H), 6.91–7.09 (m, 6H with a 2H doublet (J=8.5 Hz) at a 6.95), 6.79 (d, J=7.3 Hz, 1H), 5.53 (d, J=18.4 Hz, 1H), 5.42 (d, J=18.4 Hz, 1H), 5.04 (dd, J=4.0, 8.5 Hz, 1H), 4.18–4.24 (m, 2H), 2.95–3.09 (m, 2H), 2.75–2.81 (m, 2H), 2.23–2.42 (m, 2H). IR 2950–3200 (br), 1683, 1 51 4 cm$^{-1}$. MS 447 (MH$^+$), 138 (base). Anal. Calc'd. for C$_{26}$H$_{26}$N$_2$O$_5$/1.0C$_2$HF$_3$O$_2$/0.25H$_2$O: C, 59.52; H, 4.91; N, 4.96. Found: C, 59.43; H, 4.91; N, 4.80.

Compound 115

2-{2-[4-[2-(N,N-Bis-tert-butoxycarbonylguanidino)
ethyl]phenoxy]ethyl}-4-(4-carbomethoxybenzyl)-3,
4-dihydro-3-oxo-2H-1,4-benzoxazine

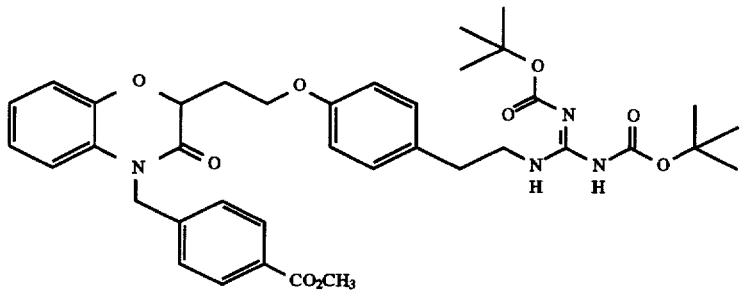

Prepared by by methods L using intermediate 11758-71-2 (Reference Example 81) and N,N'-di-t-butoxycarbonyl-2(4-hydroxyphenyl)ethyl guanidine and isolated, after chromatography (eluting with EtOAc/hexanes), as a white glass, mp 68°–71° C.; $^1$H NMR (CDCl$_3$) δ 11.45 (br s, 1H), 8.37 (br s, 1H), 7.99 (d, J=8.4 Hz, 2H), 7.30 (d, J=8.4 Hz, 2H), 7.13 (d, J=8.6 Hz, 2H), 6.74–7.01 (m, 6H with a 2H doublet (J=8.6 Hz) at δ 6.85), 5.23 (d, J=16.1 Hz, 1H), 5.16 (d, J=16.1 Hz, 1H), 4.95 (dd, J=3.8, 9.5 Hz, 1H), 4.19– 4.28 (m, 2H), 3.90 (s, 3H), 3.61–3.65 (m, 2H), 2.81 (t, J=7.2 Hz, 2H), 2.55–2.63 (m, 1H), 2.31–2.38 (m, 1H), 1.50 (s, 9H), 1.48 (s, 9H). IR 2950–3300 (br), 1724, 1688, 1639 cm$^{-1}$. MS (FAB) 703 (MH$^+$), 503 (base). Anal. Calc'd. for C$_{38}$H$_{46}$N$_4$O$_9$/ 0.5H$_2$O: C, 64.12; H, 6.66; N, 7.87. Found: C, 63.73; H, 6.87; N, 8.31.

Compound 116

2-{2-[4-[2-(t-Butoxycarbonylguanidino)ethyl] phenoxy]ethyl}-4-(4-carboxybenzyl)-3,4-dihydro-3-oxo-2H-1,4-benzoxazine

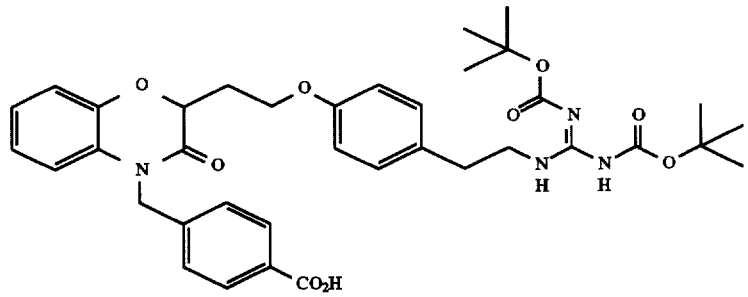

Prepared from Compound 115 by method O. The resulting white semisolid was collected, washed with water and dried. NMR shows ~10% methyl ester present. $^1$H NMR (DMSO-d$_6$) δ 7.89 (d, J=8.2 Hz, 2H), 7.37 (d, J=8.2 Hz, 2H), 6.88–7.08 (m, 8H), 5.27 (d, J=16.6 Hz, 1H), 5.19 (d, J=16.6 Hz, 1H), 5.00 (dd, J=4.0, 8.7 Hz, 1H), 3.50–3.61 (m, 2H), 2.65–2.69 (m, 2H), 2.35–2.45 (m, 1H), 2.21–2.30 (m, 1H), 1.37 (s, 9H). MS (FAB) 589 (MH$^+$), 489 (base).

Compound 117

4-(4-Carboxybenzyl)-2-{2-[4-[2-(guanidino)ethyl] Phenoxy]ethyl}-3,4-dihydro-3-oxo-2H-1,4-benzoxazine

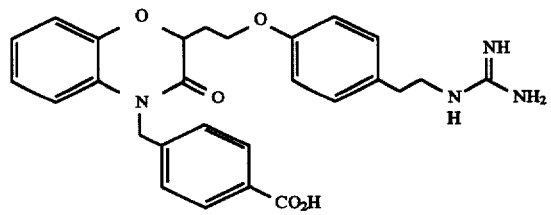

Prepared from Compound 116 by method K using trifluoroacetic acid with anisole present, instead of IPA/HCl and isolated to give an off-white solid, in yield mp 197°–199° C.; $^1$H NMR (DMSO-d$_6$) δ 7.91 (d, J=8.3 Hz, 2H), 7.76 (br s, 1H), 7.51 (br t, J=5 Hz, 1H), 7.40 (d, J=8.3 Hz, 2H), 7.19 (d, J=8.5 Hz, 2H), 6.92–7.09 (m, 9H), 5.29 (d, J=17.0 Hz, 1H), 5.23 (d, J=17.0 Hz, 1H), 5.01 (dd, J=4.1, 8.6 Hz, 1H), 4.18–4.23 (m, 2H), 3.30–3.39 (m, 2H), 3.01 (br s, 1H), 2.62–2.81 (m, 2H), 2.35–2.43 (m, 1H), 2.20–2.31 (m, 1H). IR 3000–3400 (br), 1676, 1501 cm$^{-1}$. MS (FAB) 489 (MH$^+$). Anal. Calc'd. for C$_{27}$H$_{28}$N$_4$O$_5$/1.0 C$_2$HF$_3$O$_2$/0.5 H$_2$O: C, 56.95; H, 4.94; N, 9.16. Found: C, 57.32; H, 4.96; N, 8.78.

Compound 118

Methyl 4-{2-[4-(3-chlorobenzyl)-3,4-dihydro-3-oxo-2H-1,4-benzoxazine-2-yl]ethoxy}phenyl Acetate

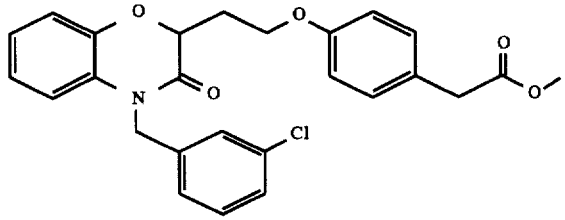

Prepared from method L, which was modified by coupling intermediate 10488-22 (Reference Example 66) with methyl-4-hydroxyphenylacetate at reflux overnight, and isolating a white solid in 38% yield, mp 94°–95° C.; $^1$H NMR (CDCl$_3$) δ 7.13–7.25 (m, 5H), 7.03–7.11 (m, 1H), 6.81–7.01 (m, 6H), 5.17 (d, J=16.2 Hz, 1H), 5.08 (d, J=16.2 Hz, 1H), 4.94 (dd, J=3.9, 9.4 Hz, 1H), 4.16–4.30 (m, 2H), 3.67 (s, 3H), 3.57 (s, 2H), 2.53–2.64 (m, 1H), 2.33 (ddt, J=9.6, 14.5, 4.8 Hz, 1H). IR 1736, 1673, 1502 cm$^{-1}$. MS 466 (MH$^+$), 300 (base). Anal. Calc'd. for C$_{26}$H$_{24}$ClNO$_5$: C, 67.02; H, 5.19; N, 3.01. Found: C, 66.78; H, 5.20; N, 2.94.

Compound 119

4-{2-[4-(3-Chlorobenzyl)-3,4-dihydro-3-oxo-2H-1,4-benzoxazine-2-yl]ethoxy}phenyl Acetic Acid

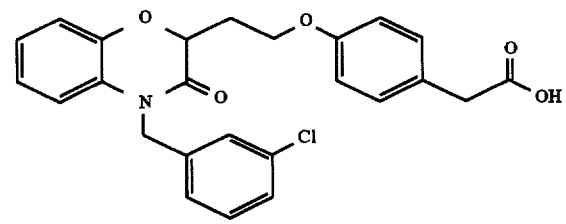

Prepared from Compound 118 by method O but was acidified with concentrated HCL to afford the acid as a white solid in 95% yield, mp 144°–145° C.; $^1$H NMR (DMSO-d$_6$) δ 7.19–7.24 (m, 5H), 7.11–7.13 (m, 1H), 6.88–7.01 (m, 5H), 6.83 (d, J=7.3 Hz, 1H), 5.16 (d, J=16.3 Hz, 1H), 5.07 (d, J=16.3 Hz, 1H), 4.93 (dd, J=5.4, 9.4 Hz, 1H), 4.19–4.23 (m, 2H), 3.61 (s, 2H), 2.51–2.58 (m, 1H), 2.31–2.34 (m, 1H). IR 3000–3200 (br), 1714, 1609 cm$^{-1}$. MS 452 (MH$^+$). Anal. Calc'd. for C$_{25}$H$_{22}$ClNO$_5$: C, 66.45; H, 4.91; N, 3.10. Found: C, 66.15; H, 4.66; N, 3.03.

Compound 120

Methyl 3-{4-{2-[4-(3-chlorobenzyl)-3,4-dihydro-3-oxo-2H-1,4-benzoxazin-2-yl]ethoxy}phenyl}propionate

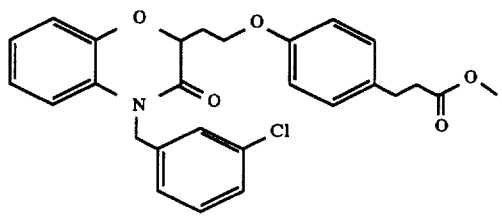

Prepared from method L, which was modified by coupling intermediate 10488-22 (Reference Example 66) with methyl-3-(4-hydroxyphenyl)propionate at reflux overnight, and isolating a white solid in yield, mp 88°–89° C.; $^1$H NMR (CDCl$_3$) δ 7.14–7.25 (m, 3H), 7.10 (d, J=8.6 Hz, 2H), 6.93–7.00 (m, 4H), 6.80–6.86 (m, 3H), 5.15 (d, J=16.3 Hz, 1H), 5.09 (d, J=16.3 Hz, 1H), 4.94 (dd, J=4.0, 9.8 Hz, 1H), 4.18–4.23 (m, 2H), 3.67 (s, 3H), 2.89 (t, J=7.8 Hz, 2H), 2.52–2.62 (m, 3H), 2.21–2.28 (m, 1H). IR 1734, 1677, 1502 cm$^{-1}$. MS 480 (MH$^+$). Anal. Calc'd. for C$_{27}$H$_{26}$ClNO$_5$/0.25 H$_2$O: C, 66.94; H, 5.51; N, 2.89. Found: C, 66.75; H, 5.36; N, 2.82.

Compound 121

3-{4-{2-[4-(3-chlorobenzyl)-3,4-dihydro-3-oxo-2H-1,4-benzoxazin-2-yl]ethoxy}phenyl}propionic Acid

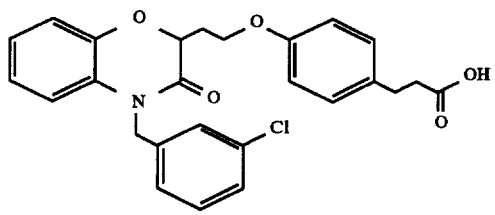

Prepared from Compound 120 by method O but was acidified with conc. HCL and isolated as a white solid in 90% yield, mp 141°–143° C.; $^1$H NMR (DMSO-d$_6$) δ 7.30–7.41 (m, 3H), 7.20–7.23 (m, 1H), 7.16 (d, J=8.1 Hz, 2H), 6.93–7.10 (m, 4H), 6.87 (d, J=8.1 Hz, 2H), 5.23 (d, J=16.0 Hz, 1H), 5.15 (d, J=16.0 Hz, 1H), 5.00 (dd, J=4.2, 8.9 Hz, 1H), 4.10–4.21 (m, 2H), 2.68–2.75 (m, 3H), 2.30–2.52 (m, 3H), 2.12–2.27 (m, 1H). IR 2900–3100 (br), 1721, 1686, 1502 cm$^{-1}$. MS 466 (MH$^+$), 300 (base). Anal. Calc'd. for C$_{26}$H$_{24}$ClNO5/0.5 H$_2$O: C, 65.75; H, 5.31; N, 2.95. Found: C, 65.97; H, 5.05; N, 2.89.

Compound 122

Methyl 3-{2-[4-(3-chlorobenzyl)-3,4-dihydro-3-oxo-2H-1,4-benzoxazine-2-yl]ethoxy}phenyl Acetate

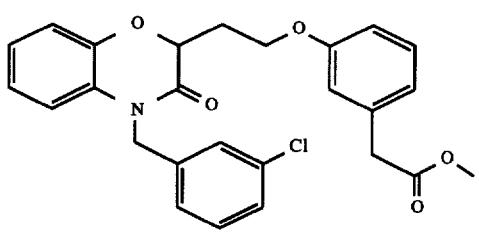

Prepared from method L, which was modified by coupling intermediate 10488-22 (Reference Example 66) with methyl 3-hydroxyphenylacetate at reflux overnight, to give a white solid in 48% yield, mp 80°–82° C.; $^1$H NMR (CDCl$_3$) δ 7.13–7.24 (m, 6H), 6.81–7.01 (m, 6H), 5.17 (d, J=16.2 Hz, 1H), 5.08 (d, J=16.2 Hz, 1H), 4.94 (dd, J=3.8, 9.3 Hz, 1H), 4.20–4.28 (m, 2H), 3.70 (s, 3H), 3.60 (s, 2H), 2.57–2.61 (m, 1H), 2.29–2.37 (m, 1H). IR 1735, 1680, 1503 cm$^{-1}$. MS 466 (MH$^+$). Anal. Calc'd. for C$_{26}$H$_{24}$ClNO$_5$: C, 67.02; H, 5.19; N, 3.01. Found: C, 66.66; H, 5.31; N, 2.90.

Compound 123

3-{2-[4-(3-Chlorobenzyl)-3,4-dihydro-3-oxo-2H-1,4-benzoxazine-2-yl]ethoxy}phenyl Acetic Acid

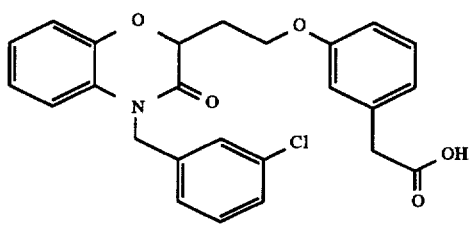

Prepared from Compound 122 by method O but was acidified with conc. HCL and isolated as a light pink amorphous solid in 87% yield. $^1$H NMR (DMSO-d$_6$) δ 7.22–7.29 (m, 4H), 7.10–7.13 (m, 1H), 6.80–7.03 (m, 7H), 5.17 (d, J=16.3 Hz, 1H), 5.07 (d, J=16.3 Hz, 1H), 4.94 (dd, J=3.9, 9.3 Hz, 1H), 4.20–4.28 (m, 2H), 3.63 (s, 2H), 2.53–2.59 (m, 1H), 2.33 (ddt, J=14.5, 9.5, 4.8 Hz, 1H). IR 2950–3100 (br), 1728, 1659, 1502 cm$^{-1}$. MS 452 (MH$^+$). Anal. Calc'd. for C$_{25}$H$_{22}$ClNO$_5$/0.6 H$_2$O: C, 64.89; H, 5.05; N, 3.03. Found: C, 64.62; H, 4.91; N, 2.95.

Compound 124

Methyl 4-{4-{2-[4-(3-chlorobenzyl)-3,4-dihydro-3-oxo-2H-1,4-benzoxazin-2-yl]ethoxy}phenyl}butyrate

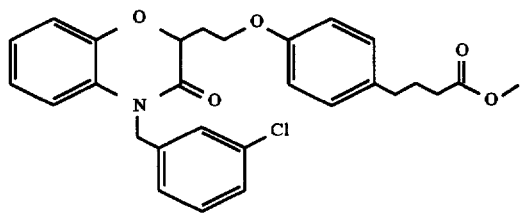

Prepared from method L, which was modified by coupling intermediate 10488-22 (Reference Example 66) with methyl 3-(4-hydroxyphenyl)butyrate at reflux overnight, and isolating a clear, amorphous solid in 46% yield; $^1$H NMR (CDCl$_3$) δ 7.10–7.20 (m, 3H), 6.99–7.08 (m, 3H with a 2H doublet (J=8.5 Hz) at δ 7.03), 6.83–6.94 (m, 3H), 6.75–6.80 (m, 3H with a 2H doublet (J=8.5 Hz) at δ 6.78), 5.09 (d, J=16.4 Hz, 1H), 5.00 (d, J=16.4 Hz, 1H), 4.94 (dd, J=3.9, 9.2 Hz, 1H), 4.10–4.25 (m, 2H), 3.60 (s, 3H), 2.41–2.52 (m, 3H), 2.20–2.35 (m, 3H), 1.89 (quintet, J=7.5 Hz, 2H). IR 1732, 1681, 1502 cm$^{-1}$. MS 494 (MH$^+$).

Compound 125

4-{4-{2-[4-(3-Chlorobenzyl)-3,4-dihydro-3-oxo-2H-1,4-benzoxazin-2-yl]ethoxy}phenyl}butyric Acid

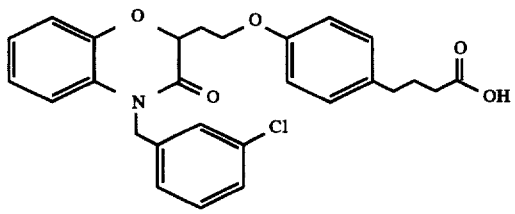

Prepared from Compound 124 by Method O but acidified with conc. HCL and isolated as a white solid in 83% yield, mp 129°–130° C.; $^1$H NMR (DMSO-d$_6$) δ 6.99–7.25 (m, 7H with a 2H doublet (J=8.5 Hz) at δ 7.10), 6.91–6.96 (m, 3H), 6.81–6.87 (m, 3H with a 2H doublet (J=8.5 Hz) at δ 6.84), 5.16 (d, J=16.3 Hz, 1H), 5.08 (d, J=16.3 Hz, 1H), 4.94 (dd, J=3.8, 9.4 Hz, 1H), 4.18–4.26 (m, 2H), 2.58–2.64 (m, 3H), 2.25–2.39 (m, 3H), 1.94 (quintet, J=7.5 Hz, 2H). IR 2900–3050 (br), 1697, 1678, 1503 cm$^{-1}$. MS 480 (MH$^+$), 422 (base). Anal. Calc'd. for C$_{27}$H$_{26}$ClNO$_5$: C, 67.57; H, 5.46; N, 2.92. Found: C, 67.19; H, 5.39; N, 2.78.

Compound 126

Methyl 3-[3-[2-{4-(3-chlorobenzyl)-3,4-dihydro-3-oxo-2H-1,4-benzoxazin-2-yl}ethoxy]phenyl] propionate

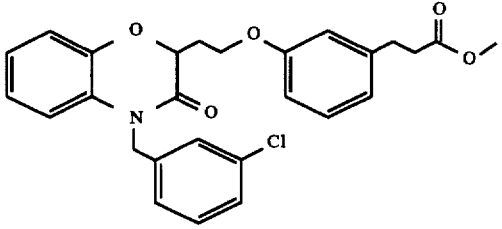

Prepared from method L, which was modified by coupling intermediate 10488-22 (Reference Example 66) with methyl 3-(3-hydroxyphenyl)propionate at reflux overnight, and isolating a white solid in 51% yield, mp 92°–94° C.; $^1$H NMR (CDCl$_3$) δ 6.91–7.24 (m, 8H), 6.76–6.83 (m, 4H), 5.18 (d, J=16.1 Hz, 1H), 5.08 (d, J=16.1 Hz, 1H), 4.94 (dd, J=3.9, 9.4 Hz, 1H), 4.21–4.28 (m, 2H), 3.68 (s, 3H), 2.93 (t, J=7.8 Hz, 2H), 2.63 (t, J=7.8 Hz, 2H), 2.53–2.59 (m, 1H), 2.33 (ddt, J=9.4, 14.2, 4.7 Hz, 1H). IR 1724, 1677, 1503 cm$^{-1}$. MS 480 (MH$^+$). Anal. Calc'd. for C$_{27}$H$_{26}$ClNO$_5$: C, 67.57; H, 5.46; N, 2.92. Found: C, 67.38; H, 5.51; N, 2.71.

Compound 127

3-[3-[2-{4-(3-Chlorobenzyl)-3,4-dihydro-3-oxo-2H-1,4-benzoxazin-2-yl}ethoxy]phenyl]propionic Acid

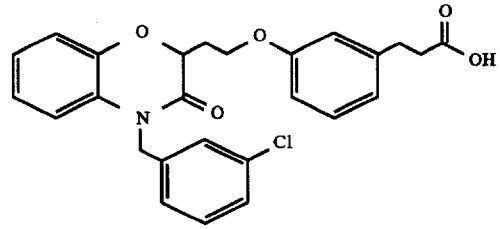

Prepared from Compound 126 by method O but acidified with conc. HCL and isolated as a white solid in 93% yield, mp 118°–119° C.; $^1$H NMR (DMSO-d$_6$) δ 7.18–7.24 (m, 4H), 7.10–7.12 (m, 1H), 6.90–7.04 (m, 3H), 6.77–6.83 (m, 4H), 5.16 (d, J=16.0 Hz, 1H), 5.07 (d, J=16.0 Hz, 1H), 4.95 (dd, J=3.8, 9.6 Hz, 1H), 4.21–4.29 (m, 2H), 2.94 (t, J=7.5 Hz, 2H), 2.67 (t, J=7.5 Hz, 2H), 2.53–2.57 (m, 1H), 2.32 (ddt, J=9.8, 14.5, 4.7 Hz, 1H). IR 3000–3200 (br), 1691, 1679, 1501 cm$^{-1}$. MS 466 (MH$^+$). Anal. Calc'd. for C$_{26}$H$_{24}$ClNO$_5$: C, 67.02; H, 5.19; N, 3.01. Found: C, 66.63; H, 5.17; N, 2.87.

Compound 128

Methyl 2-{2-[4-(3-chlorobenzyl)-3,4-dihydro-3-oxo-2H-1,4-benzoxazin-2-yl]ethoxy}phenylacetate

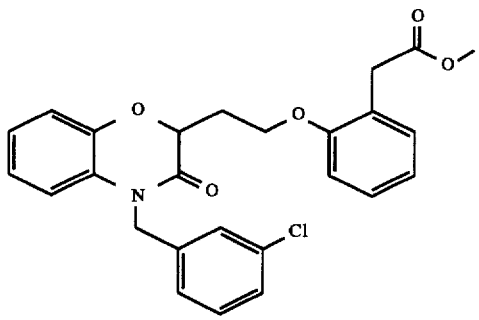

Prepared from method L, which was modified by coupling intermediate 10488-22 (Reference Example 66) with methyl 2-hydroxyphenylacetate at reflux overnight, and isolating a yellow oil. $^1$H NMR (CDCl$_3$) δ 7.09–7.39 (m, 6H), 6.81–7.04 (m, 6H), 5.18 (d, J=16.3 Hz, 1H), 5.07 (d, J=16.3 Hz, 1H), 4.92 (dd, J=3.8, 9.6 Hz, 1H), 4.21–4.32 (m, 2H), 3.60 (s, 2H), 2.54–2.62 (m, 2H), 2.33 (ddt, J=14.4, 9.6, 4.9 Hz, 1H).

Compound 129

2-{2-[4-(3-Chlorobenzyl)-3,4-dihydro-3-oxo-2H-1,4-benzoxazin-2-yl]ethoxy}phenylacetic Acid

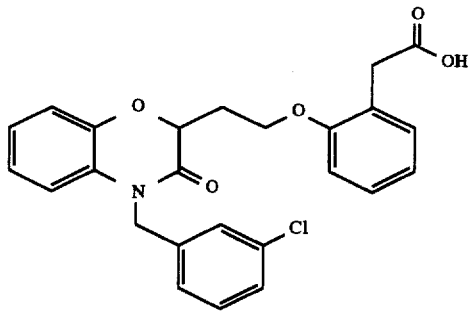

Prepared from Compound 128 by method O but acidified with conc. HCL and isolated as a white solid in 89% yield, mp 140°–142° C.; $^1$H NMR (DMSO-d$_6$) δ 7.07–7.25 (m, 6H), 6.84–7.00 (m, 6H), 5.13 (s, 2H), 5.01 (dd, J=4.0, 9.2 Hz, 1H), 4.20–4.34 (m, 2H), 3.68 (d, J=16.0 Hz, 1H), 3.59 (d, J=16.0 Hz, 1H), 2.40–2.59 (m, 1H), 2.28–2.38 (m, 1H). IR 3000–3200 (br), 1722, 1677, 1498 cm$^{-1}$. MS 452 (MH$^+$), 300 (base). Anal. Calc'd. for C$_{25}$H$_{22}$ClNO$_5$/0.2 H$_2$O: C, 65.92; H, 4.96; N, 3.07. Found: C, 65.75; H, 4.99; N, 2.88.

Compound 130

4-{2-[4-(3-Chlorobenzyl)-3,4-dihydro-3-oxo-2H-1,4-benzoxazin-2-yl]ethoxy}benzaldehyde

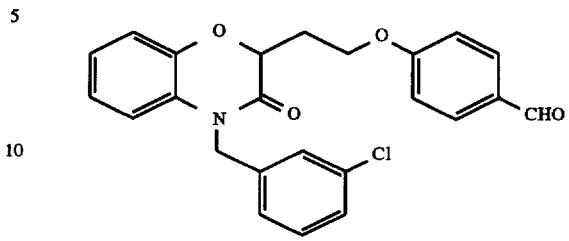

Prepared from method L, which was modified by coupling intermediate 10488-22 (Reference Example 66) with 4-hydroxybenzaldehyde at reflux overnight. The product was isolated as a white solid after chromatography in 30% yield, mp 130°–131° C.; $^1$H NMR (CDCl$_3$) δ 9.89 (s, 1H), 7.85 (d, J=8.8 Hz, 2H), 7.23–7.30 (m, 3H), 7.10–7.15 (m, 1H), 6.92–7.05 (m, 5H), 6.83 (dd, J=1.4, 8.7 Hz, 1H), 5.20 (d, J=16.2 Hz, 1H), 5.07 (d, J=16.2 Hz, 1H), 4.93 (dd, J=4.1, 9.1 Hz, 1H), 4.25–4.42 (m, 2H), 2.58–2.70 (m, 1H), 2.40 (ddt, J=10.0, 14.2, 5.0 Hz, 1H). IR 1700, 1674, 1598 cm$^{-1}$. MS 422 (MH$^+$). Anal. Calc'd. for O$_{24}$H$_{20}$ClNO$_4$: C, 68.33; H, 4.78; N, 3.32. Found: C, 68.01; H, 4.82; N, 3.27.

Compound 131

Methyl 2-[4-{2-[4-(3-chlorobenzyl)-3,4-dihydro-3-oxo-2H-1,4-benzoxazin-2-yl]ethoxy}phenyl] glycolate

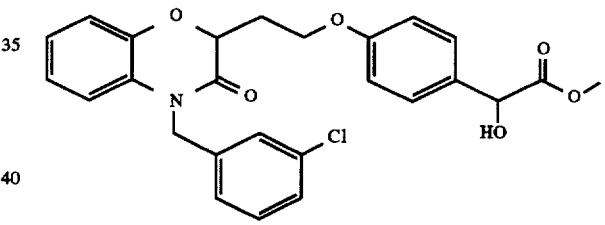

Bromoform (0.31 mL, 3.54 mmol) was added dropwise under a nitrogen atmosphere to Compound 130 (1.15 g, 2.73 mmol), lithium chloride (0.231 g, 5.45 mmol), potassium hydroxide (0.611 g, 10.9 mmol) and water (4 mL) in dioxane (4 mL). After heating in an oil bath at 40° C. overnight, the reaction was acidified to pH=1 with HCl (1N) and extracted with ethyl acetate (2×100 mL). The combined organic layers were washed with water (2×50 mL), dried (MgSO$_4$), filtered and evaporated to afford impure hydroxyacid as a yellow oil. A solution of acetyl chloride (0.4 mL) in methanol (10 mL) was added to the crude acid and the reaction stirred at room temperature under a nitrogen atmosphere overnight. The methanol was evaporated and the reside dissolved in ether (200 mL). This was washed with saturated NaHCO$_3$ (2×50 mL), dried (MgSO$_4$), filtered and evaporated. The α-hydroxyester was obtained after silica gel chromatgraphy (eluting with EtOAc/CH$_2$Cl$_2$), in 52% overall yield, $^1$H NMR (CDCl$_3$) δ 7.32 (d, J=8.7 Hz, 2H), 7.23–7.26 (m, 3H), 7.10–7.15 (m, 1H), 6.93–7.03 (m, 3H), 6.91 (d, J=8.7 Hz, 2H), 6.81–6.89 (m, 1H), 5.18 (d, J=16.2 Hz, 1H), 5.13 (d, J=5.6 Hz, 1H), 5.07 (d, J=16.2 Hz, 1H), 4.93 (dd, J=3.9, 9.4 Hz, 1H), 4.17–4.32 (m, 2H), 3.76 (s, 3H), 3.40 (d, J=5.6 Hz, 1H, exchangeable), 2.53–2.64 (m, 1H), 2.33 (ddt, J=14.4, 9.4, 4.8 Hz, 1H).

131

Compound 132

2-[4-{2-[4-(3-Chlorobenzyl)-3,4-dihydro-3-oxo-2H-1,4-benzoxazin-2-yl]ethoxy}phenyl]glycolic Acid

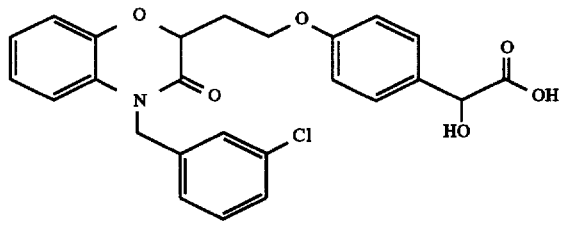

Prepared from Compound 131 by method O but acidified with conc. HCL and isolated as a pale yellow solid, in 85% yield, mp 54°–56° C.; $^1$H NMR (DMSO-d$_6$) δ 7.36 (d, J=8.6 Hz, 2H), 7.23–7.26 (m, 4H), 7.09–7.12 (m, 1H), 6.81–7.01 (m, 5H), 5.20 (s, 1H), 5.16 (d, J=16.6 Hz, 1H), 5.07 (d, J=16.6 Hz, 1H), 4.93 (dd, J=4.0, 9.2 Hz, 1H), 4.20–4.27 (m, 2H), 3.20 (br s, 1H, exchangeable), 2.53–2.62 (m, 1H), 2.30–2.38 (m, 1H). IR 3300–3400 (br), 2800–3150 (br), 1731, 1671, 1512 cm$^{-1}$. MS (FAB) 468 (MH$^+$), 300 (base). Anal. Calc'd. for C$_{25}$H$_{22}$ClNO$_6$/0.5 H$_2$O: C, 62.96; H, 4.86; N, 2.94. Found: C, 62.80; H, 4.99; N, 2.92.

Compound 133

Methyl 2-chloro-2-[4-{2-[4-(3-chlorobenzyl)-3,4-dihydro-3-oxo-2H-1,4-benzoxazin-2-yl]ethoxy}phenyl]acetate

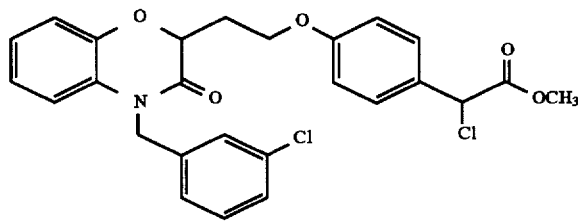

Thionyl chloride (0.091 mL, 1.24 mmol) was added to Compound 130 (0.460 g, 0.95 mmol) in benzene (10 mL), followed by pyridine (0.093 mL, 1.15 mmol) under a nitrogen atmosphere at room temperature. After stirring overnight, the solvent was evaporated and the residue poured into water (50 mL). This mixture was extracted with ethyl acetate (2×50 mL). The combined organic layers were washed with water (3×50 mL), dried (MgSO$_4$), filtered and evaporated to afford corresponding chloride as a clear gel in 82% yield; $^1$H NMR (DMSO-d$_6$) δ 7.42 (d, J=8.7 Hz, 2H), 7.23–7.29 (m, 3H), 7.11–7.15 (m, 1H), 6.99–7.03 (m, 2H), 6.90–6.97 (m, 3H with a 2H doublet (J=8.7 Hz) at δ 6.92), 6.82 (d, J=7.4 Hz, 1H), 5.34 (s, 1H), 5.18 (d, J=16.2 Hz, 1H), 5.08 (d, J=16.2 Hz, 1H), 4.93 (dd, J=4.0, 9.4 Hz, 1H), 4.19–4.33 (m, 2H), 3.78 (s, 3H), 2.54–2.65 (m, 1H), 2.34 (ddt, J=14.3, 9.4, 4.8 Hz, 1H).

Compound 134

5-[4-{2-[4-(3-Chlorobenzyl)-3,4-dihydro-3-oxo-2H-1,4-benzoxazin-2-yl]ethoxy}phenyl]thiazolidine-2,4-dione

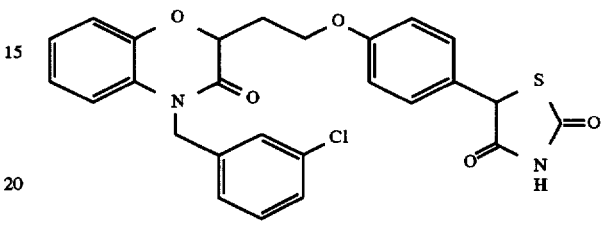

Thiourea (56 mg, 0.74 mmol) was added to Compound 133 (0.185 g, 0.37 mmol) in 2-methoxyethanol (3 mL). The reaction was heated in an oil bath at 110° C. for 3 h. After cooling, HCl (1N, 2.5 mL) was added the reaction heated at 100° C. overnight. The cooled reaction was diluted with water (50 mL) and extracted with ethyl acetate (2×50 mL). The organic layers were washed with water (3×50 mL), dried (MgSO$_4$), filtered and evaporated to afford the thiazolidindione as pale yellow foam in 64% yield, mp 70°–72° C.; $^1$H NMR (DMSO-d$_6$) δ 8.05 (br s, 1H), 7.35 (d, J=8.7 Hz, 2H), 7.23–7.25 (m, 3H), 7.11–7.15 (m, 1H), 6.81–7.02 (m, 5H with a 2H doublet (J=8.7 Hz) at δ 6.96), 6.83 (d, J=8.6 Hz, 1H), 5.36 (s, 1H), 5.19 (d, J=16.2 Hz, 1H), 5.07 (d, J=16.2 Hz, 1H), 4.94 (dd, J=4.0, 9.1 Hz, 1H), 4.22–4.30 (m, 2H), 2.54–2.62 (m, 1H), 2.32–2.40 (m, 1H). IR 1756, 1698, 1500 cm$^{-1}$. MS 509 (MH$^+$).

Compound 135

3,4-Dihydro-2-{2-[4-(2-guanidinoethyl)phenoxy]ethyl}-6-methylsulfonamido-4-(3-chlorobenzyl)-3-oxo-2H-1,4-benzoxazine

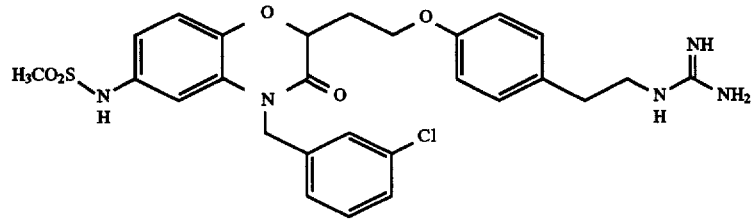

Method P: Compound 92 was heated at reflux for 10 hours with methanesulfonyl chloride (1.1 eq) DMAP (0.1 eq) in CH$_2$Cl$_2$ (10 mL). The resulting mixture was diluted with water and title compound was isolated by filtration, mp (dec) >121° C.; IR (KBr) 3240, 1667, 1613, 1512, 1475, 1349, 1245, 1178, 865 cm⁻¹; ¹H NMR (DMSO-d₆) δ 9.63 (br s, 1H), 8.07 (br s, 1H), 7.43 (br s, 2H), 7.35 (m, 4H), 7.20 (m, 3H), 7.01 (d, 1H, J=8.6 Hz), 6.89 (m, 2H), 6.82 (dd, 2H, J=2.2, 8.5 Hz), 5.16 (d, 1H, J=16.5 Hz), 5.03 (d, 1H, J=16.5 Hz), 4.97 (dd, 1H, J=4.2, 8.6 Hz), 4.16 (m, 2H), 3.25 (m, 2H), 2.79 (s, 3H), 2.70 (t, 2H, J=7.2 Hz), 2.35 (m, 1H), 2.22 (m, 1H). Anal. Calc'd for $C_{27}H_{30}ClN_5O_5S.1.7$ HCl: C 51.15, H 5.04, N 11.05. Found: 51.47, H 5.14, N 10.78.

Compound 136

2-{2-[4-(2-(N,N-Bis-tert-butoxycarbonylguanidino)ethyl)-phenoxy]ethyl}-3,4-dihydro-4-(3-methylsulfonamidobenzyl)-3-oxo-2H-1,4-benzoxazine

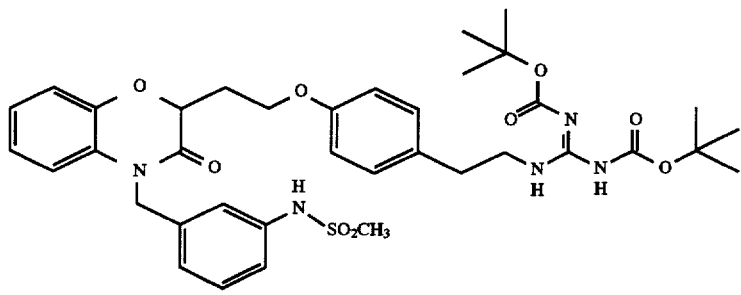

Prepared from Compound 101 by method P to give a tan solid (dec) >79° C.; MS (FAB) MH⁺738; IR (KBr) 3325, 2977, 1723, 1687, 1612, 1501, 1410, 1330, 1245, 1151, 1057, 971, 688 cm⁻¹; ¹H NMR (CDCl₃) δ 11.47 (br s, 1H), 8.37 (br t, 1H), 7.31 (m, 1H), 7.11 (m, 4H), 7.05–6.89 (m, 3H), 6.83 (m, 3H), 6.45 (br s, 1H), 5.14 (d, 2H, J=7.2 Hz), 4.94 (dd, 1H, J=4.0, 9.3 Hz), 4.20 (m, 2H), 3.62 (m, 2H), 2.94 (s, 3H), 2.81 (t, 2H, J=7.2 Hz), 2.55 (m, 1H), 2.34 (m, 1H), 1.60 (br s, 1H), 1.50 (s, 9H), 1.48 (s, 9H). Anal. Calc'd for $C_{37}H_{47}N_5O9S.0.9$ $H_2O$: C 58.93, H 6.52, N 9.29. Found C 59.19, H 6.58, N 9.00.

Compound 137

2-{2-[4-(2-Guanidinoethyl)-phenoxy]ethyl}-3,4-dihydro-4-(3-methylsulfonamidobenzyl)-3-oxo-2H-1,4-benzoxazine

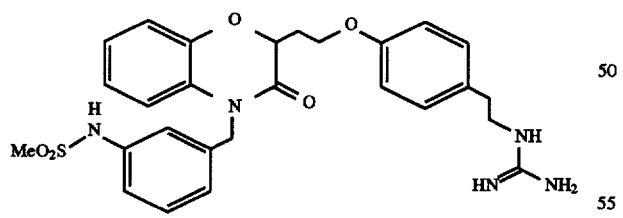

Prepared from Compoud 136 by method K in 94% yield, mp (dec) >95° C.; MS (FAB) MH⁺538; IR (KBr) 3156, 1664, 1500, 1468, 1402, 1327, 1243, 1147, 1052, 978, 751, 690, 514 cm⁻¹; ¹H NMR (DMSO-d₆) δ 9.82 (br s, 1H), 7.64 (br t, 1H), 7.55–6.85 (br s, 3H), 7.28 (t, 1H, J=7.8 Hz), 7.20 (d, 2H, J=8.5 Hz), 7.09 (s, 1H), 7.05 (m, 2H), 6.99 (m, 4H), 6.92 (d, 2H, J=8.5 Hz), 5.19 (d, 1H, J=16.6 Hz), 5.09 (d, 1H, J=16.6 Hz), 4.94 (dd, 1H, J=4.11, 9.0 Hz), 4.19 (m, 2H), 3.33

(m, 2H), 2.93 (s, 3H), 2.72 (t, 2H, J=7.4 Hz), 2.32 (m, 1H), 2.22 (m, 1H). Anal. Calc'd for $C_{27}H_{31}N_5O_5S$: C 55.32, H 5.93, N 11.32. Found: C 55.34, H 5.86, N 11.34.

Compound 138

2-{2-[4-[2-(N,N-Bis-tert-butoxycarbonylguanidino)ethyl]phenoxy]ethyl}-3,4-dihydro-3-oxo-4-pentyl-2H-1,4-benzoxazine

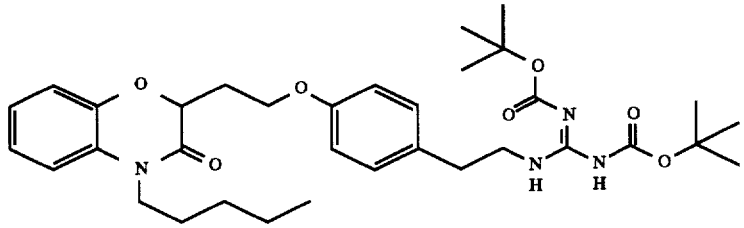

Prepared from 10840-185 (Reference Example 60) by method L using equal equivalents of reagents and was isolated in 42% yield as a white foam after SiO$_2$ chromatography (hexane/CH$_2$Cl$_2$, ⅓); IR (KBr) 3334, 2977, 2932, 2872, 1685, 1639, 1615, 1501, 1409, 1366, 1331, 1131, 1058, 748 cm$^{-1}$; $^1$H NMR (CDCl$_3$) δ 0.91 (t, J=6.8 Hz, 3H), 1.32–1.40 (m, 4H), 1.48 (s, 9H), 1.51 (s, 9H), 1.61–1.72 (m, 2H), 2.17–2.30 (m, 1H), 2.43–2.55 (m, 1H), 2.81 (t, J=7.2 Hz, 2H), 3.63 (q, J=7.1 Hz, 2H), 3.92 (t, J=6.8 Hz, 2H), 4.13–4.25 (m, 2H), 4.79 (dd, J=9.20, 4.0 Hz, 1H), 6.84 (d, J=8.5 Hz, 2H), 6.96–7.07 (m, 4H), 7.12 (d, J=8.6 Hz, 2H), 8.37 (br t, J=4.3 Hz, 1H), 11.48 (br s, 1H); Anal. Calc'd for $C_{34}H_{48}N_4O_7$: C, 65.36; H, 7.74; N, 8.97. Found: C, 65.23; H, 7.70; N, 8.98.

Compound 139

3,4-Dihydro-2-{2-[4-(2-guanidinoethyl)-phenoxy]ethyl}-4-(4-nitrobenzyl)-3-oxo-2H-1,4-benzoxazine

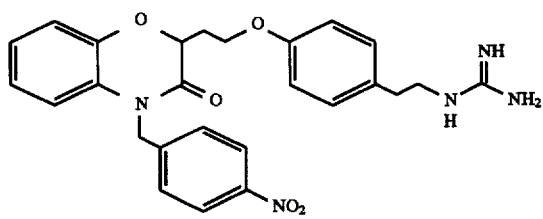

Prepared from Compound 93 by method K to give a solid: in 68% yield: mp: dec.>101° C.; MS: FAB MH$^+$ at 524; IR (KBr) 3433, 1671, 1600, 1525, 1501, 1468, 1398, 1344, 1253, 1065, 894, 810 cm$^{-1}$; $^1$H NMR (DMSO-d$_6$/TMS) δ 8.20(d, 2H, J=8.2 Hz), 7.54(d, 2H, J=8.5 Hz), 7.45–6.60(v. br. s., 4H), 7.38(s, 1H), 7.29(s, 1H), 7.18(m, 2H), 7.05(m, 2H), 6.97(m, 3H), 5.36(d, 1H, J=18.0 Hz), 5.22(1H, J=18.0 Hz), 4.99(m, 1H), 4.26(m, 2H), 3.35(m, 2H), 2.68(t, 2H, J=6.3 Hz), 2.40(m, 1H), 2.28(m, 1H).

Compound 140

2-{2-[4-[2-(N,N-Bis-tert-butoxycarbonylguanidino)ethyl]phenoxy]ethyl}-3,4-dihydro-4-(4-methoxybenzyl)-3-oxo-2H-1,4-benzoxazine

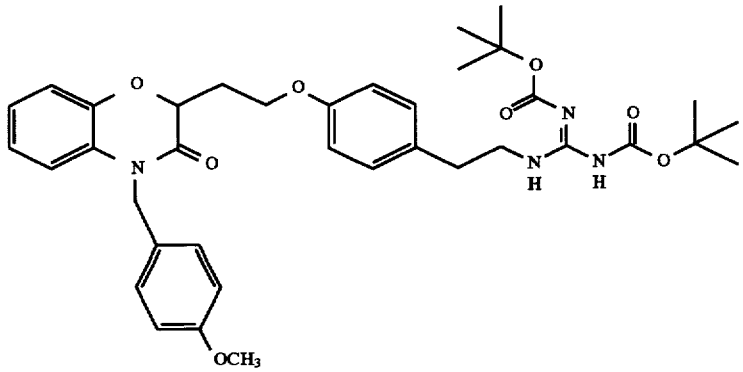

Prepared by method L using intermediate 10508-19 (Reference Example 47) and N,N'-di-t-butoxycarbonyl-2(4-hydroxyphenyl)ethyl guanidine to give the title compound as a white foam: Anal. Calc'd for $C_{27}H_{46}N_4O_8$: C, 65.86; H, 6.87; N, 8.3. Found: C, 65.51; H, 7.02; N, 8.27.

Compound 141

3,4-Dihydro-4-(2,4-dichlorobenzyl)-2-{2-[4-(2-guanidinoethyl)phenoxy]ethyl}-3-oxo-2H-1,4-benzoxazine

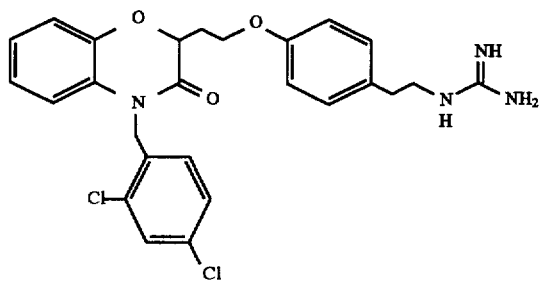

Prepared by method L using intermediate 10005-181-1 (Reference Example 48) and N,N'-di-t-butoxycarbonyl-2(4-hydroxyphenyl)ethyl guanidine and method K to give a solid: Anal. Calc'd for $C_{26}H_{426}Cl_2N_4O_3 \cdot HCl \cdot 0.75\ H_2O$: C, 55.43; H, 5.10; N, 9.94. Found: C, 55.43; H, 5.05; N, 9.75.

Compound 142

2-[2-[4-(3-Aminopropyl)phenoxy]ethyl]-4-(4-chlorobenzyl)-3,4-dihydro-3-oxo-2H-1,4-benzoxazine

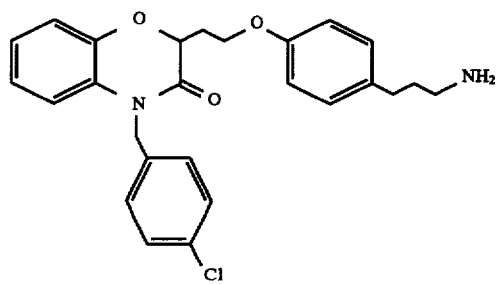

Prepared from intermediate 10353-28-1 (Reference Example 41) and 4-[3-(N-t-butoxycarbonylamino)propyl] phenol by methods J and K to give the title compound as a yellow solid (11% yield). m.p.=95°–97° C.; MS (FAB) MH+ 451; IR (Kbr) 1250, 1400, 1500, 1590, 1680, 2040, 2950, 3400 cm$^{-1}$; $^1$H (NMR) 7.40 (d, J=8.47 Hz, 2H), 7.30 (d, J=8.48 Hz,2H), 2.62 (t, J=7.54 Hz, 2H), 2.76 (t, J=7.52 Hz, 2H), 7.23 (t, J=8.12 Hz, 1H), 6.81 (d, J=7.37 Hz, 3H), 7.91 (br. s, 2H), 6.99–7.08 (m, 4H), 4.19–4.20 (m, 2H),2.33–2.49 (m, 1H), 2.19–2.30 (m, 1H), 1.82–1.87 (m, 2H), 5.18 (dd, J=16.48 and 23.23 Hz, 2H), 4.98 (dd, J=4.15 and 8.75 Hz, 1H). Anal. Calc'd for $C_{26}H_{28}N_2O_3Cl_2$: C 62.68, H 5.91, N 5.62. Found: C 62.97, H 5.78, N 5.37.

Compound 143

2-{2-[4-(2-(N,N-Bis-tert-butoxycarbonylguanidino) ethyl)phenoxy]ethyl}-3,4-dihydro-7-nitro-4-(2-nitrobenzyl) 3-oxo-2H-1,4-benzoxazine

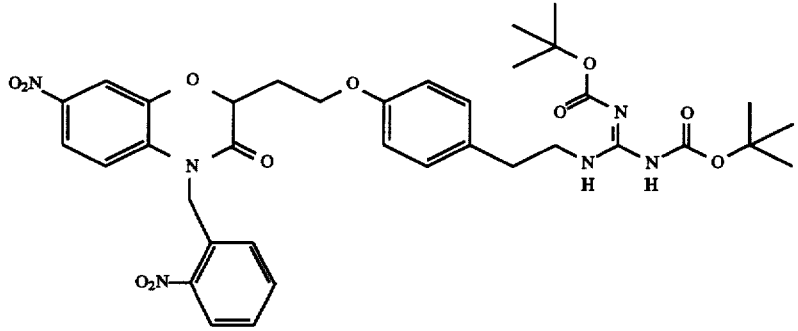

Prepared by method L using intermediate 11653-142 (Reference Example 69) and N,N'-di-t-butoxycarbonyl-2(4-hydroxyphenyl)ethyl guanidine, and method K to give the title compound as a solid in 13% yield; m.p.: dec.>128° C.; MS (FAB) MH+735; IR (KBr) 3323, 3087, 2977, 1723, 1690, 1641, 1613, 1530, 1513, 1476, 1418, 1395, 1240, 1154, 941 cm$^{-1}$; $^1$H NMR (CDCl$_3$/TMS) δ 11.43(s, 1H), 8.37(br. t., 1H), 8.24(dd, 1H, J=2.1, 7.4 Hz), 7.94(d, 1H, J=2.5 Hz), 7.84(dd, 1H, J=2.5, 8.9 Hz), 7.52(m, 2H), 7.14(d, 2H, J=8.6 Hz), 7.08(d, 1H, J=9.1 Hz), 6.84(d, 2H, J=8.6 Hz), 6.77(d, 1H, J=8.9 Hz), 5.68(d, 1H, J=18.1 Hz), 5.56(d, 1H, J=18.1 Hz), 5.10(dd, 1H, J=4.0, 8.9 Hz), 4.23(m, 2H), 3.64(m, 2H), 2.82(t, 2H, J=7.3 Hz), 2.63(m, 1H), 2.40(m, 1H), 1.50(s, 9H), 1.48(s, 9H).

Compound 144

2-[2-[4-(2-(t-Butoxycarbonylamino)ethyl)phenoxy]ethyl]-4-(3-chlorobenzyl)-3,4-dihydro-3-oxo-2H-1,4-benzoxazine

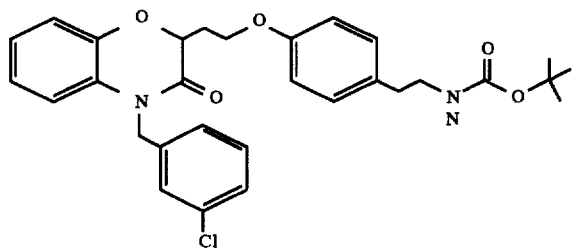

Methanesulfonyl chloride (0.8 ml, 1.5 eq.) was added in one portion to a solution of intermediate 10353-191-1 (2.0 g, 1 eq., Reference Example 40), DMAP (0.33 g, 0.4 eq.) and triethylamine (1.2 ml, 1.5 eq.) in 30 ml CH$_2$Cl$_2$. This mixture was stirred for 15 min and diluted with an equal part of water. The resulting organic layer was washed with brine, dried (MgSO$_4$) and concentrated in vacuo to give the mesylate. This mesylate was treated with 4-[2-(N-t-butoxycarbonylamino)ethyl]phenol following the procedures of method J to give the title compound as a solid: mp 91°–92° C.

following modifications. The bis-Boc-protected Mitsunobu coupling product was isolated by dissolving the crude product residue in aqueous methanol and treating with a dropwise addition of 2N NaOH until basic. The precipitate was collected by filtration. The resulting product was dissolved in ether, washed sequentially with 1N HCl, sat'd NaHCO$_3$, and brine, dired over Na$_2$SO$_4$ and concentrated under vacuum and used without further purification. The deprotected product was isolated the bicarbonate salt (light brown solid) in 22% yield as a tan solid, single homogeneous peak by HPLC (PDA detection) 15 cm C18 column, eluting with 55/45 H$_2$O (5% NH$_4$OH, 5% HOAC)/CH$_3$CN; MS (CI) 451 (MH$^+$); IR (KBr) 3314, 3036, 2923, 1682, 1608, 1581, 1511, 14658, 1443, 1392, 1352, 1302, 1244, 1223, 1175, 1046, 742 cm$^{-1}$.

Compound 146

2-{2-[4-(2-(N,N-Bis-tert-butoxycarbonylguanidino)ethyl)phenoxy]ethyl}-4-(3-chlorobenzyl)-3,4-dihydro-6-methoxy-3-oxo-2H-1,4-benzoxazine

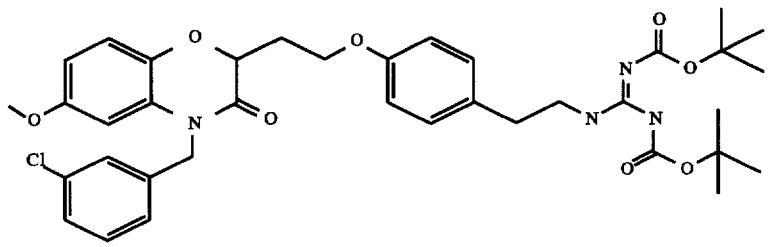

Compound 145

2-[2-[4-(2-guanidinomethyl)phenoxy]ethyl]-4-(2-chlorobenzyl)-3,4-dihydro-2H-1,4-benzoxazine

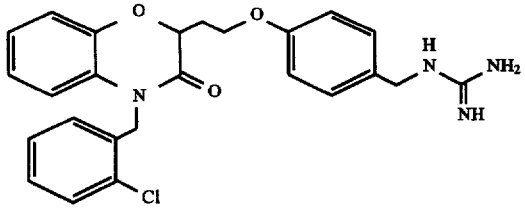

Prepared by method L using intermediate 10353-76 (Reference Example 89) and N,N'-di-t-butoxycarbonyl-2-(4-hydroxyphenyl)methyl guanidine and method K with the Prepared from intermediate 12168-25-1 (Reference Example 43) and N,N'-di-t-butoxycarbonyl-2(4-hydroxyphenyl)ethyl guanidine by method L in 92% yield. Crystallization from EtOH/H$_2$O afforded the pure product as a white solid. nmr (CDCl$_3$) δ 11.28 (s, 1H), 7.23 (m, 3H), 7.12 (m, 1H), 7.12 (d, J=9.0 Hz, 2H), 6.94 (d, J=8.9 Hz, 1H), 6.86 (d, J=9.0 Hz, 2H), 6.51 (dd, J=8.4, 2.9 Hz, 1H), 6.41 (d, J=2.1 Hz, 1H), 5.15 (d, J=16.9 Hz, 1H), 5.05 (d, J=16.9 Hz, 1H), 4.89 (dd, J=10.0, 4.1 Hz, 1H), 4.20 (m, 2H), 3.64 (m, 2H), 2.82 (apparent t, J=7.3 Hz, 2H), 2.55 (m, 1H), 2.32 (m, 1H), 1.52 (s, 9H), 1.50 (s, 9H).

Compound 147

4-(3-Chlorobenzyl)-3,4-dihydro-2-{2-[4-(2-guanidinoethyl)-phenoxy]ethyl}-6-methoxy-3-oxo-2H-1,4-benzoxazine

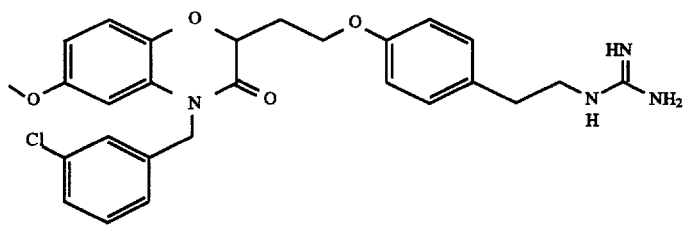

Prepared from Compound 146 by method K and isolated by trituration with Et$_2$O to afford a hydroscopic tan solid in 76% yield nmr (DMSO-d$_6$) δ 7.43 (br s, 1H), 7.4–6.5 (v br s, 4H), 7.35 (m, 3H), 7.22 (m, 1H), 7.19 (d, J=8.5 Hz, 2H), 6.98 (d, J=8.6 Hz, 1H), 6.96 (d, J=8.5 Hz, 2H), 6.61 (d, J=2.5 Hz, 1H) 2.58(dd, J=9.0, 3.1 Hz, 1H), 5.21 (d, J=17.0 Hz, 1H), 5.18 (d, J=17.0 Hz, 1H), 4.96 (dd, J=8.8, 4.1 Hz, 1H), 4.19 (m, 2H), 3.64 (s, 3H), 3.30 (m, 2H), 2.40 (apparent t, J=6.8 Hz, 2H), 2.39 (m, 1H), 2.23 (m, 1H).

Compound 148

2-{2-[4-(2-guanidinoethyl)-phenoxy]ethyl}-3,4-dihydro-6-fluoro-4-(3-nitrobenzyl)-3-oxo-2H-1,4-benzoxazine

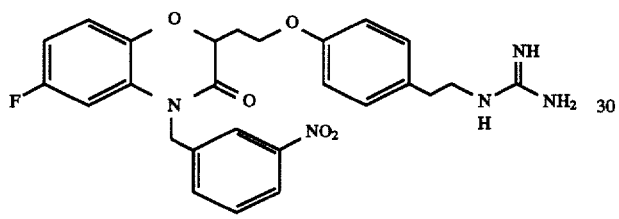

Prepared from Compound 102 by method K to give the title compound as a solid: MP: dec.>76° C.; MS (FAB) MH$^+$508; IR (KBr) 3349, 3180, 2932, 2872, 1621, 1531, 1506, 1469, 1296, 948, 838 cm$^{-1}$; $^1$H (NMR) δ 8.20 (s, 1H), 8.13 (d, 1H, J=7.9 Hz), 7.66 (m, 2H), 7.53 (br.s., 1H), 7.50–6.60 (v.br.s., 3H), 7.19 (d, 2H, J=8.4 Hz), 7.09 (m, 2H), 6.90 (d, 2H, J=8.4 Hz), 6.85 (m, 1H), 5.32 (s, 2H), 5.01 (dd, 1H, J=4.3, 8.7 Hz), 4.18 (m, 2H), 3.28 (m, 2H), 2.71 (t, 2H, J=7.2 Hz), 2.39 (m, 1H), 2.25 (m, 1H).

We claim:

1. A compound selected from those of Formula 1:

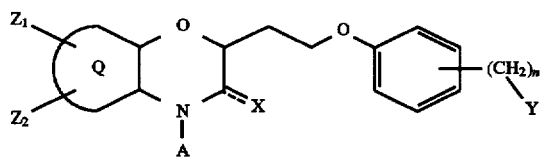

wherein the moiety Q is a fused phenyl moiety;

Z$_1$ is hydrogen, halogen, C$_1$–C$_6$ alkyl, C$_1$–C$_6$ alkoxy, phenyl, hydroxy, amino, nitro, sulfonylamino or trifluoromethyl;

Z$_2$ is hydrogen or a halogen;

X is hydrogen or oxygen;

A is C$_1$–C$_5$ alkyl, —CH$_2$phenyl, —CH$_2$thienyl, —CH$_2$pyridyl, —CH$_2$furyl, or -ethyl piperidine; wherein said phenyl, thienyl, pyridyl, furyl or piperidine moiety is optionally substituted with (C$_1$–C$_6$) alkyl, benzyl, oxybenzyl, phenoxy, hydroxy, alkoxy, halogen, dihalogen, nitro, amino, carboxyl or carbomethoxy;

n is an integer from 0–3;

Y is a moiety selected from:

(a) —NHR$_1$R$_2$, —N$^+$R$_1$R$_2$R$_3$;

(b)

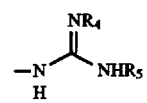

(c) —CO$_2$H, —CHO;

(d) —CH(R$_6$)CO$_2$H, —CH(R$_6$)CO$_2$CH$_3$, —CH=CHR$_7$, —CH=C(CO$_2$H)$_2$;

(e) a moiety of the formula:

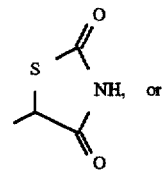

(f) 5-tetrazolyl;

wherein

R$_1$, R$_2$ and R$_3$ are independently hydrogen, C$_1$–C$_6$ alkyl, or t-butoxycarbonyl;

R$_4$ and R$_5$ are independently t-butoxycarbonyl or hydrogen or R$_4$ and R$_5$ may be joined together to form an imidazoline, imidazolyl or pyrimidine ring;

R$_6$ is hydrogen, hydroxy or chloro;

R$_7$ is CO$_2$H or C(O)NH(CH$_2$)$_p$OH wherein p is an integer from 1–4;

and the pharmaceutically acceptable salts, esters and prodrug forms thereof.

2. A compound according to claim 1 wherein the moiety Y is selected from:

(a) —NHR$_1$R$_2$, —N$^+$R$_1$R$_2$R$_3$;

(b)

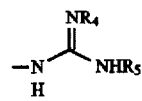

(c) —CO$_2$H;

(d) —CH(R$_6$)CO$_2$H, or

143

(e) a moiety of the formula:

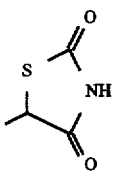

wherein

R₁, R₂ and R₃ are independently hydrogen, C₁-C₆ alkyl or t-butoxycarbonyl;

R₄ and R₅ are independently t-butoxycarbonyl or hydrogen;

R₆ is hydrogen or hydroxy;

and the pharmaceutically acceptable salts, esters and pro-drug forms thereof.

3. A compound according to claim 1 wherein:

the moiety Q is a fused phenyl;

Z₁ is hydrogen, halogen, C₁-C₆ alkyl, C₁-C₆ alkoxy, phenyl, hydroxy, amino, nitro, sulfonylamino or trifluoromethyl;

Z₂ is hydrogen or, where Z₁ is a halogen, Z₂ is also a halogen;

X is oxygen;

A is C₁-C₅ alkyl, —CH₂phenyl, —CH₂thienyl, —CH₂pyridyl, —CH₂furyl, or -ethyl piperidine; wherein said phenyl, thienyl, pyridyl, furyl or piperidine moiety is optionally substituted with (C₁-C₆) alkyl, benzyl, oxybenzyl, phenoxy, hydroxy, alkoxy, halogen, dihalogen, nitro, amino, carboxyl or carbomethoxy;

n is an integer from 0-3;

Y is a moiety selected from:
(a) —NHR₁R₂, —N⁺R₁R₂R₃;
(b)

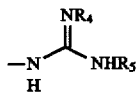

(c) —CO₂H;
(d) —CH(R₆)CO₂H, or
(e) a moiety of the formula:

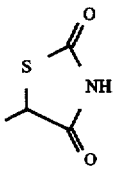

wherein

R₁, R₂ and R₃ are independently hydrogen, C₁-C₆ alkyl or t-butoxycarbonyl;

R₄ and R₅ are independently t-butoxycarbonyl or hydrogen;;

R₆ is hydrogen or hydroxy;

and the pharmaceutically acceptable salts, esters and pro-drug forms thereof.

4. The compound according to claim 1, 4-(2-Chlorobenzyl)-2-[2-[4-(guanidinomethyl)phenoxy]ethyl]-3,4-dihydro-3-oxo-2H-1,4-benzoxazine.

5. The compound according to claim 1, 4-(2-Chlorobenzyl)-2-[2-[4-(2-guanidinoethyl)phenoxy]ethyl]-3,4-dihydro-3-oxo-2H-1,4-benzoxazine.

144

6. The compound according to claim 1, 4-(3-Chlorobenzyl)-2-[2-[4-(2-guanidinoethyl)phenoxy]ethyl]-3,4-dihydro-2H-1,4-benzoxazine.

7. The compound according to claim 1, 2-{2-[4-(2-Aminomethyl) phenoxy]ethyl}-4-(3,5-dichlorobenzyl)-3,4-dihydro-3-oxo-2H-1,4-benzoxazine.

8. The compound according to claim 1, 4-(3,5-Dichlorobenzyl)-3,4-dihydro-2-{2-[4-(2-guanidinoethyl) phenoxy]ethyl}-3-oxo-2H-1,4-benzoxazine.

9. The compound according to claim 1, 6-Chloro-4-(3-chlorobenzyl)-2-{2-[4-(2-guanidinylethyl)phenoxy]ethyl}-3,4-dihydro-3-oxo-2H-1,4-benzoxazine.

10. The compound according to claim 1, 4-(3-Chlorobenzyl)-6,8-dichloro-2-{2-[4-(2-guanidinylethyl) phenoxy]-ethyl}-3,4-dihydro-3-oxo-2H-1,4-benzoxazine.

11. The compound according to claim 1, 4-(3-Chlorobenzyl)-2-{2-[4-(2-guanidinylethyl)phenoxy]-ethyl}-3,4-dihydro-7-methyl-3-oxo-2H-1,4-benzoxazene.

12. The compound according to claim 1, 2-{2-[3-(2-Aminoethyl)phenoxy]ethyl}-4-(3-chlorobenzyl)-3,4-dihydro-3-oxo-2H-1,4-benzoxazine.

13. The compound according to claim 1, 4-(3-Chlorobenzyl)-3,4-dihydro-2-{2-[4-(2-guanidinylethyl) phenoxy]ethyl}-2H-1,4-benzoxazine.

14. The compound according to claim 1, 2-{2-[4-(3-Aminopropyl)phenoxy]ethyl}-4-(3-chlorobenzyl)-3,4-dihydro-3-oxo-2H-1,4-benzoxazine.

15. The compound according to claim 1, 4-(3-Chlorobenzyl)-3,4-dihydro-2-{2-[4-(guanidinylmethyl) phenoxy]ethyl}-2H-1,4-benzoxazine.

16. The compound according to claim 1, 4-(2-Chlorobenzyl)-3,4-dihydro-2-{2-[4-(2-guanidinoethyl) phenoxy]ethyl}-7-nitro-3-oxo-2H-1,4-benzoxazine monohydrochloride.

17. The compound according to claim 1, 3,4-Dihydro-2-{2-[4-(2-guanidinoethyl)-phenoxy]ethyl}-6-nitro-4-(2-nitrobenzyl)-3-oxo-2H-1,4-benzoxazine.

18. The compound according to claim 1, 5-[4-{2-[4-(3-Chlorobenzyl)-3,4-dihydro-3-oxo-2H-1,4-benzoxazin-2-yl] ethoxy}phenyl]thiazolidine-2,4-dione.

19. The compound according to claim 1, 3,4-Dihydro-4-(2,4-dichlorobenzyl)-2-{2-[4-(2-guanidinoethyl)-phenoxy] ethyl}-3-oxo-2H-1,4-benzoxazine.

20. The compound according to claim 1, 2-[2-[4-(3-Aminopropyl)phenoxy]ethyl]-4-(4-chlorobenzyl)-3,4-dihydro-3-oxo-2H-1,4-benzoxazine.

21. A pharmaceutical composition for treating bacterial infections comprising an effective amount of a compound selected from claim 1 in association with a pharmaceutically acceptable carrier.

22. A method of treating bacterial infections in mammals by administering to a mammal suffering from such infection a therapeutically effective amount of a compound selected from claim 1.

23. A method of potentiating the activity of an antibacterial agent in mammals by administering said antibacterial agent in combination with a compound selected from claim 1.

24. A pharmaceutical composition for treating bacterial infections comprising an antibacterial agent and a compound selected from claim 1 in therapeutically effective amounts in association with a pharmaceutically acceptable carrier.

25. A method of preparing a compound of the Formula 1:

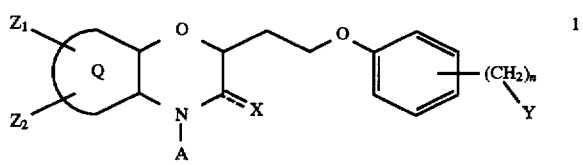

wherein the moiety Q is a fused phenyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or a halogen;

X is hydrogen or oxygen;

A is $C_1$–$C_5$ alkyl, —$CH_2$phenyl, —$CH_2$thienyl, —$CH_2$pyridyl, —$CH_2$furyl or -ethyl piperidine; wherein said phenyl, thienyl, pyridyl, furyl or piperidine moiety is optionally substituted with ($C_1$–$C_6$) alkyl, benzyl, oxybenzyl, phenoxy, hydroxy, alkoxy, halogen, dihalogen, nitro, amino, carboxyl or carbomethoxy;

n is an integer from 0–3;

Y is a moiety selected from:
(a) —$NHR_1R_2$, —$N^+R_1R_2R_3$;
(b)

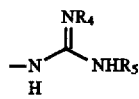

(c) —$CO_2H$, —CHO;
(d) —$CH(R_6)CO_2H$, —$CH(R_6)CO_2CH_3$, —CH=$CHR_7$, —CH=C($CO_2H$)$_2$;
(e) a moiety of the formula:

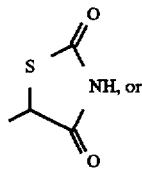

(f) 5-tetrazolyl;
wherein $R_1$, $R_2$ and $R_3$ are independently hydrogen, $C_1$–$C_6$ alkyl, or t-butoxycarbonyl;

$R_4$ and $R_5$ are independently t-butoxycarbonyl or hydrogen or $R_4$ and $R_5$ may be joined together to form an imidazoline, imidazolyl or pyrimidine ring;

$R_6$ is hydrogen, hydroxy or chloro;

$R_7$ is $CO_2H$ or C(O)NH($CH_2$)$_p$OH wherein p is an integer from 1–4;

and the pharmaceutically acceptable salts, esters and pro-drug forms thereof, which comprises reacting a compound of the formula:

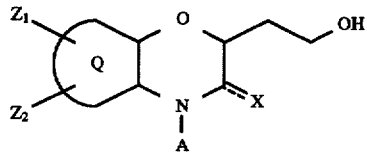

with a compound of the formula:

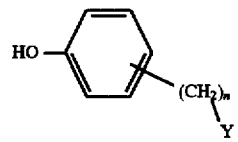

wherein the moiety Y is protected or unprotected, in a suitable solvent in the presence of an appropriate phosphine and azodicarbonyl reagent, and where Y is protected, removing the protecting group and recovering the compound of formula 1.

26. A compound of the formula:

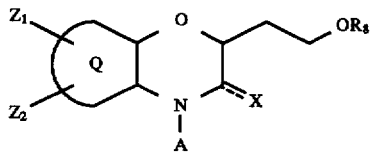

wherein the Q moiety is phenyl and $Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or a halogen, X is hydrogen or oxygen, A is —$CH_2$phenyl, —$CH_2$thienyl, —$CH_2$pyridyl, —$CH_2$furyl, or -ethyl piperidine; wherein said phenyl, thienyl, pyridyl, furyl or piperidine moiety is optionally substituted with ($C_1$–$C_6$)alkyl, benzyl, oxybenzyl, phenoxy, hydroxy, alkoxy, halogen, dihalogen, nitro, amino, carboxyl or carbomethoxy;

and $R_8$ is a hydroxy protecting group.

* * * * *